United States Patent
Burgoyne et al.

(10) Patent No.: US 6,706,701 B1
(45) Date of Patent: Mar. 16, 2004

(54) 6, 7-OXYGENATED STEROIDS AND USES RELATED THERETO

(75) Inventors: David L. Burgoyne, Delta (CA); Yaping Shen, Port Coquitlam (CA); John M. Langlands, Richmond (CA); Christine Rogers, Vancouver (CA); Joseph H.-L. Chau, Vancouver (CA); Edward Piers, Richmond (CA); Hassan Salari, Tswassen (CA)

(73) Assignees: Inflazyme Pharmaceuticals Ltd., Richmond (CA); University of British Columbia, Vancouver (CA); University of Alberta, Edmonton (CA)

( * ) Notice: Subject to any disclaimer, the term of this patent is extended or adjusted under 35 U.S.C. 154(b) by 0 days.

(21) Appl. No.: 09/471,827

(22) Filed: Dec. 23, 1999

Related U.S. Application Data

(63) Continuation of application No. 08/679,642, filed on Jul. 12, 1996, now abandoned.
(60) Provisional application No. 60/023,450, filed on Jul. 11, 1996.

(51) Int. Cl.$^7$ .............................. A61K 31/56; C07J 9/00; C07J 5/00
(52) U.S. Cl. ..................... 514/182; 514/178; 552/561; 552/552; 552/610
(58) Field of Search ................... 552/561, 552, 552/610; 514/182, 178

(56) References Cited

U.S. PATENT DOCUMENTS

| | | | |
|---|---|---|---|
| 3,026,320 A | 3/1962 | Djerassi et al. | 260/239.55 |
| 3,681,410 A | 8/1972 | Crabbe et al. | 260/397.3 |
| 3,818,054 A | 6/1974 | Bucourt et al. | 260/397.3 |
| 4,004,004 A | 1/1977 | von Daehne | 424/238 |
| 4,092,310 A | 5/1978 | Biollaz et al. | 260/239.55 |
| 5,002,961 A | * 3/1991 | Dage et al. | 514/392 |
| 5,017,573 A | * 5/1991 | Kon et al. | 514/218 |
| 5,079,239 A | 1/1992 | Sun et al. | 514/174 |
| 5,219,879 A | 6/1993 | Ko et al. | 514/438 |
| 5,506,221 A | 4/1996 | Andersen et al. | 514/172 |
| 5,763,435 A | * 6/1998 | Setchell | 514/182 |
| 5,942,248 A | * 8/1999 | Barnwell | 424/457 |

FOREIGN PATENT DOCUMENTS

| | | |
|---|---|---|
| CA | 2086221 A1 | 6/1994 |
| GB | 1 474 436 A | 5/1977 |
| GB | 2 228 482 | 8/1990 |
| JP | 41022178 B4 | 12/1966 |
| WO | WO 90/04398 | 5/1990 |
| WO | WO 94/14451 | 7/1994 |

OTHER PUBLICATIONS

Harris et al., Journal of Chromatography, vol. 131, pp. 437–441, 1977.*
Aggarwal et al., "Synthesis of 3α,6β,7α,12β– and 3α,6β,7β,12β–tetrahydroxy–5β–cholanoic acids," *Steroids* 57(3): 107–111, 1992.
Anastasia et al., "Synthesis of (2R, 3S, 22S, 23S)–2,3,22,23–Tetrahydroxy–B–homo–7–aza–5α–stigmastan–6–one, an Aza–analogue of Homobrassinolide," *J. Chem. Soc. Perkin Trans. 1*(12): 2117–2121, 1986.
Bramley et al., "Effect of a Novel Steroid Pneumocort on Ovalbumin Induced Hyperresponsiveness in Guinea Pigs," *American Journal of Respiratory and Critical Care Medicine* 149(4):Abstract No. 768, 1994.
Bramley et al., "Effects of IZP–94005 (contignasterol) on antigen–induced bronchial responsiveness in ovalbumin–sensitized guinea–pigs," *British Journal of Pharmacology* 115(8): 1433–1438, 1995.
Bramley et al., "IZP–94005. Contignasterol–Pneumocort®," *Drugs of the Future* 19(8):738–739, 1994.
Bramley et al., "Pharmocological Activity of Pneumocort: A Novel Naturally Occuring Steroid Anti–Asthma Therapy, Isolated from a Marine Sponge," *IBC Conference on Allergic Diseases and Asthma–New Approaches for Treatment*, Washington, D.C., 1993.
Brückner et al., "Darstellung und Eigenshaften monohalogenierter 3–Keto–Δ$^{4,6}$–dien–steroide," *Chemische Berichte Jahrg.* 94:1225–1240, 1961. (+ Chemical Abstracts, vol. 55, No. 22, col. 22376, Section A).
Bruno et al., "Isolation and Structure of New Polyhydroxylated Sterols from a Deep–Water Starfish of the Genus Rosaster," *Gazetta Chimica Italiana* 120(7):449–451, 1990.
Bruno et al., "Starfish Saponins, 38. Steroidal Glycosides From The Starfish *Pycnopodia helianthoides*," *Journal of Natural Products* 52(5): 1022–1026, 1989.
Burgoyne et al., "Contignasterol, a Highly Oxygenated Steroid with the "Unnatural" 14β Configuration from the Marine Sponge *Petrosia contignata* Thiele, 1899," *Journal of Organic Chemistry* 57(2):525–528, 1992.
Cambie et al., "Epoxidation of 3α,5–Cyclo–5α–androst–6–en–17–one," *J. Chem. Soc., Perkin Trans. I*(4): 323–326, 1975.
Canonica et al., "Structure of Calonysterone, an Unusually Modified Phytoecdysone," *J. Chem. Soc. Chem. Commun.* (19): 737–738, 1973.
D' Auria et al., "Starfish Sponins, Part 41. Structure Of Two New Steroidal Glycoside Sulfates (Miniatosides A and B) And Two New Polyhydroxysteroids From The Starfish *Patiria miniata*," *Journal of Natural Products* 53(1): 94–101, 1990.

(List continued on next page.)

*Primary Examiner*—Barbara P. Badio
(74) *Attorney, Agent, or Firm*—Seed IP Law Group PLLC

(57) ABSTRACT

Steroid compounds having various oxygen substitution on the steroid nucleus are disclosed. A specific functionality present on many of the steroid compounds is oxygen substitution at both of positions 6 and 7. Thus, certain steroids have oxygen substitution at C6 and C7, and some have specific stereochemistries such as 6α and 7β oxygen substitution, and an alpha hydrogen at the 5 position in addition to having 6α and 7β oxygen substitution. Steroids having 3,4-epoxy functionality are also disclosed. In addition, steroids having C17 pyran and δ-lactone functionality, with oxygen substitution at C6 and C7, or at C15, of the steroid nucleus, are disclosed.

30 Claims, No Drawings

OTHER PUBLICATIONS

Davey et al., "Hydroxy–steroids. Part XI. The Preparation and Infrared Spectra of Vicinal Cholestanediols," *J. Chem. Soc.* (C) (21): 2674–2682, 1968.

Fukunaga et al., "Gas Chromatography Of Dimethylalkylsilyl Ether Derivatives Of Bile Acid Methyl Esters," *Journal of Chromatography 190*(2): 339–345, 1980.

Hanson et al., "Steroechemistry of Hydroboronation and Osmylation of 3α,5–Cycloandrost–6–en–17–one," *J. Chem. Soc., Perkin Trans. I*(6): 1465–1468, 1988.

Higuchi et al., "$^1$H–NMR Spectroscopy and Biological Activities of Polyhydroxylated Steroids from the Starfish *Asterina pectinifera* Müller et Troschel," *Liebigs Ann. Chem. 12*:1185–1189, 1988.

Iida et al., "Capillary gas chromatographic behavior of stereoisomeric bile acids with a vicinal glycol structure by their "mixed" alkylboronate derivatives," *Journal of Chromatography 537*(1–2): 345–356, 1991.

Iida et al., "Potential bile acid metabolites. 14. Hyocholic and muricholic acid stereoisomers," *Journal of Lipid Research 30*(8): 1267–1279, 1989.

Iida et al., "Potential bile acid metabolites. 16. Synthesis of stereoisomeric 3α,6,7,12α–tetrahydroxy–5β–cholanoic acids," *Steroids 55*(12): 530–539, 1990.

Iida et al., "Potential bile acid metabolites. 19. The epimeric 3α,6,7β–trihydroxy– and 3α–6,7β,12α–tetrahydroxy–5α–cholanoic acids," *Steroids 58*(4): 148–152, 1993.

Iida et al., "Preparation of Glycine–conjugated Bile Acids and their Gas/Liquid Chromatographic Analysis on an Aluminum–clad Flexible Fused Silica Capillary Column," *Biomedical Chromatography 6*(1): 4–8, 1992.

Iorizzi et al., "Chemical And Biological Investigation Of The Polar Constituents Of The Starfish *Luidia clathrata*, Collected In The Gulf Of Mexico," *Journal of Natural Products 58*(5): 653–671, 1995.

Iorizzi et al., "Starfish Saponins, 48. Isolation Of Fifteen Sterol Constituents (Six Glycosides And Nine Polyhydroxysteroids) From The Starfish *Solaster borealis*," *Journal of Natural Products 55*(7): 866–877, 1992.

Iorizzi et al., "Starfish Saponins, Part 46. Steroidal Glycosides And Polyhydroxysteroids From The Starfish *Culcita novaeguineae*," *Journal of Natural Products 54*(5): 1254–1264, 1991.

Iorizzi et al., "Starfish Saponins, Part 53. A Reinvestigation Of The Polar Steroids From The Starfish *Oreaster reticulatus*: Isolation Of Sixteen Steroidal Oligoglycosides And Six Polyhydroxysteroids," *Journal of Natural Products 58*(1): 10–26, 1995.

Iorizzi et al., "Starfish Saponins. Part 39. Steroidal Oligoglycoside Sulphates and Polyhydroxysteroids from the Starfish *Asterina pectinifera*," *Gazzetta Chemica Italiana 120*(3): 147–153, 1990.

Janssen et al., "By–Products In The Analysis Of β–Muricholic Acid In Biological Samples As Methyl Ester Triacetate," *Steroids 53*(6): 677–693, 1989.

Kaise et al., "Structure of viridominic acids A and B, new chlorosis–inducing metabolites of a fungus," *Tetrahedron Letters 36*:3789–3792, 1972.

Kawata et al., "A New Product of Cholesterol by Metal–free Autoxidation in Aqueous Dispersion," *Chem. Pharm. Bull. 24*(12): 3109–3113, 1976.

Kicha et al., "Polyhydroxylated steroids from the starfish Patiria pectinifers," *Khim. Prir. Soedin.*(6):738–41, 1984. (+ Chemical Abstracts 102(15):Abstract No. 129131, 1985).

Kishi et al., "Synthesis of Brassinolide Analogs with a Modified Ring B and Their Plant Growth–promoting Activity," *Agric. Biol. Chem. 50*(7): 1821–1830, 1986.

Kitagawa et al., "Marine Natural Products. XV. Chemical Constituents of an Okinawan Soft Coral of Xenia sp. (Xeniidae)," *Chem. Pharm. Bull. 34*(11): 4590–4596, 1986.

Kobayashi et al., "Marine sterols. XXV. Isolation of 23–Demethylgorgost–7–ene–3β,5α,6β–triol and (24S)–Ergostane–3β,5α,6β,7β,15β–pentol from Soft Corals of the Andaman and Nicobar Coasts," *Chem. Pharm. Bull. 41*(1): 87–89, 1993.

Kocor et al., "Steroids. XV. Epoxidation of some steroidal 3–keto–1,4,6–trienes,", *Bull. Acad. Pol. Sci. Ser. Sci. Chim. 18*(10):595–599, 1970. (+ Chemical Abstracts 74(21): Abstract No. 112292, 1971).

Kocovský et al., "Stereo– and Regio–control of Electrophilic Additions to Cyclohexene Systems by Neighbouring Groups: Participation of Allylic and Homoallylic Ester Groups in Hypobromous Acid Addition to some 5–Unsaturated Cholestane Derivatives," *J. Chem. Soc. Perkin Trans. I*(8): 2297–2303, 1988.

Kuroki et al., "Bile salts of the West Indian manatee, *Trichechus manatus latirostris*: novel bile alcohol sulfates and absence of bile acids," *Journal of Lipid Research 29*(4): 509–522, 1988.

Marschall et al., "The Major Metabolites of Ursodeoxycholic Acid in Human Urine are Conjugated With N–acetylglucosamine," *Hepatology* (St. Louis) 20(4): 845–853, 1994.

McKee et al., "HIV–Inhibitory Natural Products. 11. Comparative Studies of Sulfated Sterols from Marine Invertebrates," *J. Med. Chem. 37*(6): 793–797, 1994.

Minale et al., "New Polyhydroxylated Sterols From the Starfish *Luidia maculata*," *Journal of Natural Products 47*(5): 784–789, 1984.

Minale et al., "Steroidal Oligoglycosides of Marine Origin," Nat. Prod. Biol. Act., Naito Found. Symp. (1986), Meeting Date 1984, 59–73. Editor(s): Imura, Hiroo. Publisher: Univ. Tokyo Press, Tokyo, Japan.

Njar et al., "Synthesis of 6α,7α– and 6β,7β–aziridinoandrost–4–ene–3,17–diones and related compounds: potential aromatase inhibitors," *J. Chem. Soc. Perkin Trans. I*(8): 985–991, 1995.

Numazawa and Tachibana, "The Solvolytic Ring Opening of a 4β,5β–Epoxy–3,6–dione Steroid: Preparation of Potential Aromatase Inhibitors," *J. Chem. Soc. Perkin Trans. 1*(23): 2975–2978, 1993.

Rashkes et al., "Mass Spectra of polyhydroxysteroids from the sea star *Patiria pectinifera*," *Khim. Prir. Soedin. 41*(3):361–7, 1985. (+ Chemical Abstracts 103(11):Abstract No. 85353, 1985).

Riccio et al., "A Novel Group of Highly Hydroxylated Steroids from the Starfish *Protoreaster nodosus*," *Tetrahedron 38*(24):3615–3622, 1982.

Riccio et al., "Highly Hydroxylated Marine Steroids from the Starfish *Archaster typicus*," *Journal of the Chemical Society, Perkin Transactions 1* 4:665–670, 1986.

Rodewald and Boncza–Tomaszewski, "Transformation of 3β–Acetoxycholesta–5,7–Diene Into 3β–Acetoxy–5α,6α,7α,8α–Tetrahydroxycholestane," *Polish Journal of Chemistry 53*(7–8): 1679–1682, 1979.

Setchell et al., "Hepatic Bile Acid Metabolism during Early Development Revealed from the Analysis of Human Fetal Gallbladder Bile," *Journal Of Biological Chemistry 263*(32): 16637–16644, 1988.

Shoji et al., "Two Unique Pentacyclic Steroids with Cis C/D Ring Junction from *Xestospongia bergquistia* Fromont, Powerful Inhibitors of Histamine Release," *The Journal of Organic Chemistry* 57:2996–2997, 1992.

Strandvik et al., "The urinary bile acid excretion in healthy premature and full–term infants during the neonatal period," *Scand. J. Clin. Lab. Invest.* 54(1): 1–10, 1994.

Takei et al., "Effect of Contignasterol on Histamine Release Induced by Anti–Immunoglobulin E from Rat Peritoneal Mast Cells," *Journal of Pharmaceutical Sciences* 83(9):1234–1235, 1994.

Tal, "6,7–Dihydroxy–6,7–Dihydrocanrenone Isomers: Improved Synthesis and Proton NMR Study," *Steroids* 54(1):113–122, 1989.

Thompson et al., "Taurine conjugate of 3α,6β,7β–trihydroxy–5β,22–cholen–24–oic acid (tauro–$\Delta^{22}$–α–muricholate): the major bile acid in the serum of female rats treated with β–naphthylisothiocyanate and its secretion by liver slices," *Journal of Lipid Research* 34(4): 553–561, 1993.

Twisk et al., "Structural aspects of bile acids involved in the regulation of cholesterol 7α–hydroxylase and sterol 27–hydroxylase," *Eur. J. Biochem* 228(3): 596–604, 1995.

Vose et al., "Lipophilic gel chromatography of steroids. Structure–standard elution volume relationships," *Journal of Chromatography* 179:187–191, 1979.

Warren et al., "Regioselective Synthesis Of Cholestane–3β, 5α,6α–Triol–7–One 3–Acetate And Eight Stereoisomeric Cholestane–3β,4,5α,6 And of 3β,5α,6,7–Tetrol Triacetates," *Organic Preparations And Procedure Int.* 21(2): 147–156, 1989.

Yoshii et al., "Synthesis of 5β–Cholestane–3α,6β, 7α,25, 26–pentol and Identification of a Novel Bile Alcohol, α–Trichechol, Present in the West Indian Manatee Bile," *Chem. Pharm. Bull.* 37(7): 1852–1854, 1989.

Yoshimura et al., "An efficient synthesis of 4β– and 6α–hydroxylated bile acids," *Steroids* 58(2): 52–58, 1993.

\* cited by examiner

6,7-OXYGENATED STEROIDS AND USES RELATED THERETO

CROSS-REFERENCE TO RELATED APPLICATIONS

This application claims priority from U.S. Provisional Application No. 60/023,450, filed Jul. 11, 1996, and is a continuation of U.S. patent application Ser. No. 08/679,642, filed Jul. 12, 1996, now abandoned, which applications are incorporated herein by reference in their entireties.

TECHNICAL FIELD

The invention is directed to steroid compounds and in particular to 6,7-oxygenated steroid compounds and therapeutic uses related thereto.

BACKGROUND OF THE INVENTION

Asthma and allergy are closely related with good evidence from clinical studies demonstrating a strong correlation between the severity of asthma and the degree of atopy (allergy). Sensitization to allergens is believed to be the most important risk factor for asthma in both children and adults, with approximately 90% of asthma cases exhibiting atopy.

Allergy is characterized by an increased blood serum IgE (antibody) level. Repeated exposure to allergens, in a process called sensitization, is normally required to elicit sufficient B cell production of IgE specific to a given allergen or series of allergens to trigger atopy and the subsequent asthmatic or allergic response. Once B cells are exposed to allergens they produce antibodies which bind to the surface of mast cells. The crosslinking of 2 antibodies by the antigen causes a series of reactions causing degranulation and the release of a number of mediators which modulate the inflammatory response. Mediators that are released or generated during the asthmatic and allergic response include histamine, leukotrienes, prostaglandins, cytokines and tryptase.

Asthma is characterized by hyperresponsiveness of the airways, episodic periods of bronchospasm and chronic inflammation of the lungs. Obstruction of the airways is reversible with time or in response to drug therapies. Patients exhibiting normal airflow may be hyperreactive to a variety of naturally occurring stimuli, e.g., cold air, exercise, chemicals and allergen. The most common event initiating an asthmatic response is an immediate hypersensitivity to common allergens including ragweed pollen, grass pollen, various fungi, dust mites, cockroaches and domestic animals. The symptoms of the disease include chest tightness, wheezing, shortness of breath and coughing. Mild forms of the disease occur in up to 10% of the U.S. population, while the U.K., Australia and New Zealand report higher prevalences. Asthma incidence and mortality has been increasing worldwide, doubling over the past 20 years despite modern therapies.

The response of the airways to allergen is complex and consists of an early asthmatic response (EAR) which peaks 20–30 min after exposure to the stimuli, is characterized by bronchoconstriction and normally resolves after 1½ to 2 hours. The late asthmatic response (LAR) generally occurs 3–8 hours after initial exposure, and involves both bronchoconstriction and the development of inflammation and edema in the lung tissue. This inflammation often becomes chronic, with epithelial damage occurring and infiltration of the lungs with inflammatory cells such as eosinophils and neutrophils.

Current Treatments for Asthma

Glucocorticosteroids (steroids) are the most effective long-term therapy for the treatment of asthma. Oral steroids are not very useful for the control of acute asthma attacks and their chronic use in the control of asthma is minimal due to the introduction of inhaled steroids. Due to the presence of airway inflammation even in mild asthma, inhaled steroids are used even in early stage drug therapy. As effective as inhaled steroids are, side effects limit their use and combination therapy is often employed. Combination therapy is divided into the following areas: anti-inflammatory drugs (e.g., inhaled and oral steroids), bronchodilators, (e.g., $\beta_2$-agonists, xanthines, anticholinergics), and mediator inhibitors (e.g., cromolyns and leukotriene antagonists).

Cromolyns (e.g., disodium cromoglycate and nedocromil) inhibit the release of histamine in vitro and prevent bronchial hyperreactivity, while displaying few side effects. They are not effective orally and have no bronchodilator effect. Usually chronic treatment (several days) is required to achieve optimal anti-inflammatory effect, though cromolyns exhibit beneficial effects against exercise-induced asthma when administered only 10 minutes prior to exercise. Cromolyns are, at best, only marginally effective against moderate to severe asthma.

Glucocorticosteroids (steroids) have profound effects against lung inflammation, and are by far the most effective drugs for the treatment of asthma and allergies. In mast cells they inhibit the production of arachidonic acid metabolites (leukotrienes and prostaglandins) and cytokines. Responses to inhaled steroids or systemic steroids can occur within 4 hours but may take several days depending on the severity of the disease state. Symptoms often return without regular chronic treatment. Side effects of inhaled steroids used on a continual basis include dysphonia, local irritation and oral candidiasis (a fungal infection). Higher doses of inhaled steroids cause suppression of the HPA-axis which is responsible for the regulation of serum cortisol levels, metabolism, stress, CNS function and immunity. Continuous use of high dose inhaled steroids or oral steroids induce more severe side effects: severe suppression of the HPA axis, causing effects on the immune system, hypertension, osteoporosis, peptic ulcers, growth retardation in children, behavioral problems, reproductive problems, cataracts and hematological disorders.

Beta-agonists reverse the bronchospasm produced during an asthmatic attack and have a modest activity against the onset of the response. Their routes of administration and duration of action are variable. Prolonged use of these agents can cause decreased response to the therapy itself with the development of tolerance. These compounds have no effect on the inflammatory response itself.

Xanthines, which are cyclic AMP phosphodiesterase inhibitors, are also used in bronchodilator therapy. Though effective, xanthine activity is influenced by a number of factors including food, age, smoking, etc. The therapeutic window is relatively narrow and side effects include gastrointestinal disorders, CNS disturbances, headache, anxiety and cardiac arrhythmias. The importance of treatment of inflammation in asthma and allergy has led to a decline in the use of xanthines for therapy.

Anticholinergic agents such as ipratropium bromide are used to block the contraction of bronchial smooth muscle induced by acetylcholine released as a neurotransmitter. Some positive effects are reported in asthma, with these drugs being most effective against chronic obstructive pulmonary disease. A large number of side effects are seen with these drugs including urinary retention, dry mouth, tachycardia, nausea, vomiting, flushing and hypertension.

Inhibitors of 5-lipoxygenase inhibit the generation of leukotrienes, while leukotriene antagonists prevent the action of leukotrienes, which are potent bronchospastic mediators released during an asthmatic reaction. Use of leukotriene synthesis inhibitors has been associated with increased liver enzymes, indicating the need to monitor liver function closely in certain patient populations. Leukotriene inhibitors have shown comparative activity to the cromolyns, and activity equivalent to low dose corticosteroids.

In general, moderate to severe asthma patients are poorly served by the present armamentarium of drugs. Drugs that are safe are only marginally effective, while effective drugs have unacceptable side effects with extensive monitoring of patients required. There is a significant need for therapeutic agents that achieve safe and effective relief of asthma and allergy symptoms. The present invention provides these and related benefits as described herein.

SUMMARY OF THE INVENTION

One aspect of the invention provides compounds of the formula:

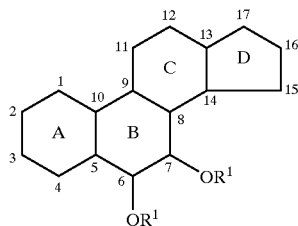

including pharmaceutically acceptable salts and solvates thereof, wherein:
- each of C1, C2, C3, C4, C11, C12, C15 and C16 is independently substituted according to any of (a) and (b):
  - (a) one of: $=O, =C(R^4)(R^4)$, $—C(R^4)(R^4)(C(R^4)(R^4))_n—$ and $—(O(C(R^4)(R^4))_nO)—$ wherein n ranges from 1 to about 6;
  - (b) two of: $—X, —R^4$ and $—OR^1$, each independently selected;
- each of C5, C6, C7, C8, C9, C10, C13 and C14 is independently substituted with one of $—X, —R^4$ or $—OR^1$;
- C17 is substituted according to any of (c), (d), (e), (f), (g), (h) and (i):
  - (c) $=C(R^2)(R^3)$ except when C14 is substituted with methyl;
  - (d) $—R^5$ and $—OR^6$ so long as the A and B rings are not aromatic, and when C10 is substituted with methyl then C5 is not bonded directly to oxygen, where $R^5$ and $R^6$ may together form a direct bond so C17 is a carbonyl group, or may together with C17 form a cyclic 3–6 membered ether or 4–6 membered lactone; otherwise $R^5$ is $R^4$ or $—OR^6$ and $R^6$ is $R^1$ or $R^4$;
  - (e) one of: $=O, =C(R^4)(R^4)$, $—C(R^4)(R^4)(C(R^4)(R^4))_n—$ and $—(O(C(R^4)(R^4))_nO)—$ wherein n ranges from 1 to about 6, as long as one of the following conditions i), ii), iii) or iv) apply:
    - i) C5 is substituted with a hydrogen in the alpha configuration, and C3 is not bonded to oxygen, and when C3 is substituted with two hydrogen atoms then C17 is not substituted with either $—CH(CH_3)(CH_2)_3CH(CH_3)_2$ or $—CH(CH_3)(CH_2)2C(=O)OCH_3$;
    - ii) C10 and C13 are not simultaneously substituted with methyl, and when C10 is substituted with methyl, then C14 is not substituted with a methyl, and the A ring is never aromatic;
    - iii) if C3 and C4 are bonded to oxygen atoms, and the C6-OR$^1$ substituent has the alpha configuration, and the C7-OR$^1$ substituent has the beta configuration, then C17 is not substituted with any of the following:

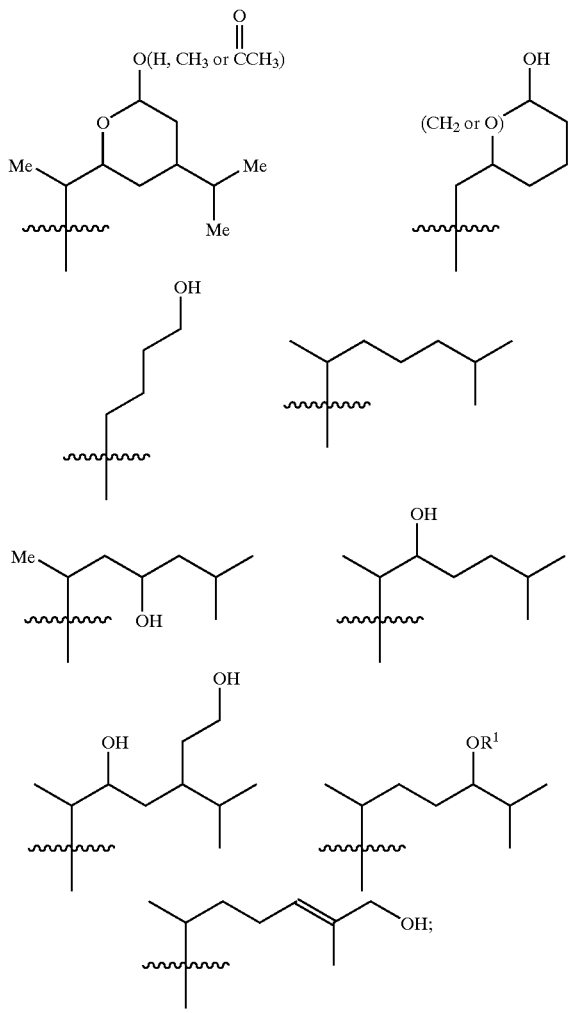

- iv) C3 and C4 are each bonded to the same oxygen atom so as to form an oxirane ring, with the proviso that C7 does not have carbonyl substitution when C5 has hydroxyl or $—OR^1$ substitution;
  - (f) two of the following substituents, which are independently selected: $—X, —R^4$ and $—OR^1$, as long as one of the above conditions i), ii), iii) or iv) apply;
  - (g) a cyclic structure of the formula

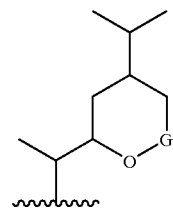

wherein G is $—C(=O)—, —CH(OR^1)—, —C(R^4)(OR^1)—$ or $—C(OR^1)(OR^1)—$, as long as C3 and C4 are not simultaneously substituted with hydroxyl or protected hydroxyl;
  - (h) two hydrogen atoms, as long as C3 is not substituted with a carbonyl group;

(i) one hydrogen atom and one group selected from C$_1$–C$_{30}$ hydrocarbyl groups and C$_1$–C$_{30}$ halogen substituted hydrocarbyl groups, excluding —CH(CH$_3$)(CH$_2$)$_3$CH(CH$_3$)$_2$;

the A, B, C and D rings may independently be fully saturated, partially saturated or fully unsaturated;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^2$, R$^3$ and R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and X represents fluoride, chloride, bromide and iodide.

In a preferred embodiment, the compounds have the formula

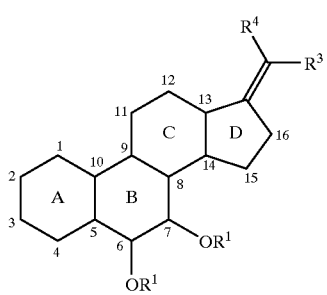

including pharmaceutically acceptable salts and solvates thereof, wherein:

each of C1, C2, C3, C4, C11, C12, C15 and C16 is independently substituted with
  (a) one of: =O, =C(R$^4$)(R$^4$), —C(R$^4$)(R$^4$)(C(R$^4$)(R$^4$))$_n$— and —(O(C(R$^4$)(R$^4$))$_n$O)— wherein n ranges from 1 to about 6; or
  (b) two of the following, which are independently selected: —X, —R$^4$ and —OR$^1$;

each of C5, C8, C9, C10 and C13 is independently substituted with one of —X, —R$^4$ or —OR$^1$;

C14 is substituted with —X, —OR$^1$, or —R$^4$ excluding methyl;

the A, B, C and D rings may independently be fully saturated, partially saturated or fully unsaturated;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^2$, R$^3$ and R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and X represents fluoride, chloride, bromide and iodide.

In another preferred embodiment, the compounds have the formula

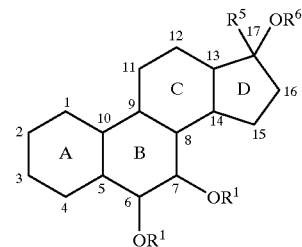

including pharmaceutically acceptable salts and solvates thereof, wherein:

each of C1, C2, C3, C4, C11, C12, C15 and C16 is independently substituted with
  (a) one of: =O, =C(R$^4$)(R$^4$), —C(R$^4$)(R$^4$)(C(R$^4$)(R$^4$))$_n$— and —(O(C(R$^4$)(R$^4$))$_n$O)— wherein n ranges from 1 to about 6; or
  (b) two of the following, which are independently selected: —X, —R$^4$ and —OR$^1$;

each of C5, C8, C9, C10, C13 and C14 is independently substituted with one of —X, —R$^4$ or —OR$^1$;

the A, B, C and D rings may independently be fully saturated, partially saturated or fully unsaturated, with the proviso that neither the A nor B ring is aromatic;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and R$^5$ and R$^6$ may together form a direct bond so C17 is a carbonyl group, or may together with C17 form a cyclic 3–6 membered ether or 4–6 membered lactone; otherwise R$^5$ is R$^4$ or —OR$^6$ and R$^6$ is R$^1$ or R$^4$; and X represents fluoride, chloride, bromide and iodide;

with the proviso that when C10 is substituted with methyl, then C5 is not directly bonded to an oxygen atom.

In another preferred embodiment, the compounds have the formula

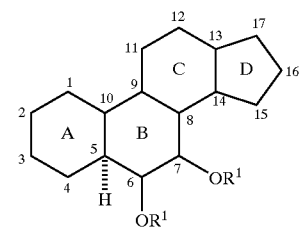

including pharmaceutically acceptable salts and solvates thereof, wherein:

each of C1, C2, C4, C11, C12, C15, C16 and C17 is independently substituted with (a) one of: =O, =C(R⁴)(R⁴), —C(R⁴)(R⁴)(C(R⁴)(R⁴))ₙ— and —(O(C(R⁴)(R⁴))ₙO)— wherein n ranges from 1 to about 6; or
(b) two of the following, which are independently selected: —X, —R⁴ and —OR¹;

each of C8, C9, C10, C13 and C14 is independently substituted with one of —X, —R⁴ or —OR¹;

C3 is substituted with one of =C(R⁴)(R⁴) and —C(R⁴)(R⁴)(C(R⁴)(R⁴))ₙ— wherein n ranges from 1 to about 6, or two of —X, and —R⁴ with the proviso that C3 is not bonded to an oxygen atom, and when C3 is substituted with two hydrogen atoms then C17 is not substituted with either —CH(CH₃)(CH₂)₃CH(CH₃)₂ or —CH(CH₃)(CH₂)2C(=O)OCH₃;

the A, B, C and D rings may independently be fully saturated, partially saturated or fully unsaturated;

R¹ is H or a protecting group such that —OR¹ is a protected hydroxyl group, where vicinal —OR¹ groups may together form a cyclic structure which protects vicinal hydroxyl groups, and where geminal —OR¹ groups may together form a cyclic structure which protects a carbonyl group, with the proviso that either or both of —OR¹ at C6 and C7 represent a carbonyl or protected carbonyl group;

R⁴ at each occurrence is independently selected from H and C₁₋₃₀ organic moiety that may optionally contain at least one heteroatom selected from the group consisting of boron, halogen, nitrogen, oxygen, silicon and sulfur; where two geminal R⁴ groups may together form a ring with the carbon atom to which they are both bonded; and X represents fluoride, chloride, bromide and iodide.

In another preferred embodiment, the compounds have the formula

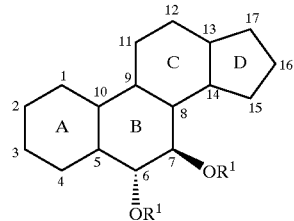

including pharmaceutically acceptable salts and solvates thereof, wherein:

each of C1, C2, C3, C4, C11, C12, C15, C16 and C17 is independently substituted with
(a) one of: =O, =C(R⁴)(R⁴), —C(R⁴)(R⁴)(C(R⁴)(R⁴))ₙ— and —(O(C(R⁴)(R⁴))ₙO)— wherein n ranges from 1 to about 6; or
(b) two of the following, which are independently selected: —X, —R⁴ and —OR¹;

each of C5, C8, C9, C10, C13 and C14 is independently substituted with one of —X, —R⁴ or —OR¹;

with the provisos that (a) C10 and C13 are not simultaneously substituted with methyl, and (b) when C10 is substituted with methyl, then C14 is not substituted with a methyl;

the A, B, C and D rings may independently be fully saturated, partially saturated or fully unsaturated with the proviso that the A ring is not aromatic;

R¹ is H or a protecting group such that —OR¹ is a protected hydroxyl group, where vicinal —OR¹ groups may together form a cyclic structure which protects vicinal hydroxyl groups, and where geminal —OR¹ groups may together form a cyclic structure which protects a carbonyl group, with the proviso that either or both of —OR¹ at C6 and C7 represent a carbonyl or protected carbonyl group;

R⁴ at each occurrence is independently selected from H and C₁₋₃₀ organic moiety that may optionally contain at least one heteroatom selected from the group consisting of boron, halogen, nitrogen, oxygen, silicon and sulfur; where two geminal R⁴ groups may together form a ring with the carbon atom to which they are both bonded; and X represents fluoride, chloride, bromide and iodide.

In another preferred embodiment, the compounds have the formula

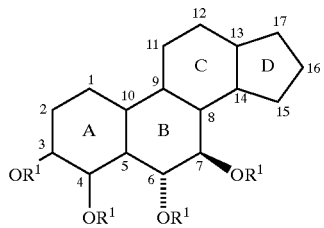

including pharmaceutically acceptable salts and solvates thereof, wherein:

each of C1, C2, C11, C12, C15, C16 and C17 is independently substituted with
(a) one of: =O, =C(R⁴)(R⁴), —C(R⁴)(R⁴)(C(R⁴)(R⁴))ₙ— and —(O(C(R⁴)(R⁴))ₙO)— wherein n ranges from 1 to about 6; or
(b) two of the following, which are independently selected: —X, —R⁴ and —OR¹;

with the proviso that C17 is not substituted with any of the following:

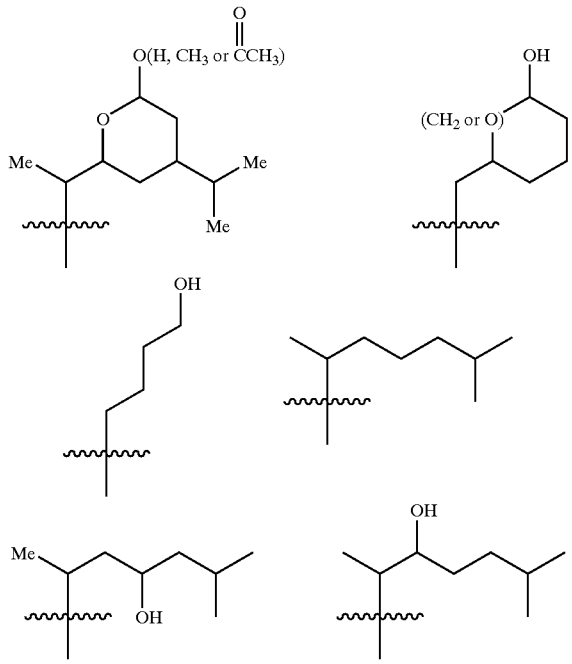

-continued

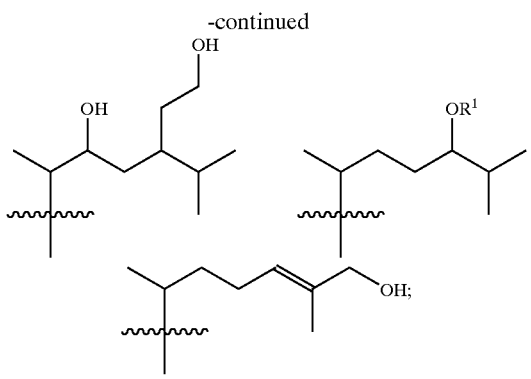

each of C5, C9, C10, C13 and C14 is independently substituted with one of —X, —$R^4$ or —$OR^1$;

C8 is substituted with —X or —$R^4$ and is preferably not bonded directly to oxygen;

the A, B, C and D rings may independently be fully saturated, partially saturated or fully unsaturated;

$R^1$ is H or a protecting group such that —$OR^1$ is a protected hydroxyl group, where vicinal —$OR^1$ groups may together form a cyclic structure which protects vicinal hydroxyl groups, and where geminal —$OR^1$ groups may together form a cyclic structure which protects a carbonyl group;

$R^4$ at each occurrence is independently selected from H and $C_{1-30}$ organic moiety that may optionally contain at least one heteroatom selected from the group consisting of boron, halogen, nitrogen, oxygen, silicon and sulfur; where two geminal $R^4$ groups may together form a ring with the carbon atom to which they are both bonded; and X represents fluoride, chloride, bromide and iodide.

In another preferred embodiment, the compounds have the formula

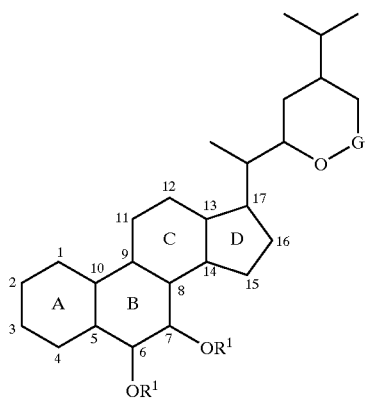

including pharmaceutically acceptable salts and solvates thereof wherein:

each of C1, C2, C3, C4, C11, C12, C15 and C16 is independently substituted with
(a) one of: =O, =C($R^4$)($R^4$), —C($R^4$)($R^4$)(C($R^4$)-($R^4$))$_n$— and —(O(C($R^4$)($R^4$))$_n$O)— wherein n ranges from 1 to about 6; or
(b) two of the following, which are independently selected; —X, —$R^4$ and —$OR^1$;

with the proviso that C3 and C4 are not simultaneously substituted with hydroxyl or protected hydroxyl, and are preferably not simultaneously substituted with oxygen atoms;

each of C5, C8, C9, C10, C13 and C14 is independently substituted with one of —X, —$R^4$ or —$OR^1$;

G is —C(=O)—, —CH($OR^1$)—, —C($R^4$)($OR^1$)— or —C($OR^1$)($OR^1$)—;

the A, B, C and D rings may independently be fully saturated, partially saturated or fully unsaturated;.

$R^1$ is H or a protecting group such that —$OR^1$ is a protected hydroxyl group, where vicinal —$OR^1$ groups may together form a cyclic structure which protects vicinal hydroxyl groups, and where geminal —$OR^1$ groups may together form a cyclic structure which protects a carbonyl group, with the proviso that either or both of —$OR^1$ at C6 and C7 represents a carbonyl or protected carbonyl group;

$R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and X represents fluoride, chloride, bromide and iodide.

In another preferred embodiment, the compounds have the formula

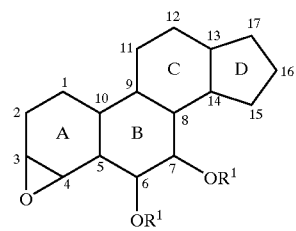

including pharmaceutically acceptable salts and solvates thereof, wherein:

each of C1, C2, C11, C12, C15, C16 and C17 is independently substituted with
(a) one of: =O, =C($R^4$)($R^4$), —C($R^4$)($R^4$)(C($R^4$)-($R^4$))$_n$— and —(O(C($R^4$)($R^4$))$_n$O)— wherein n ranges from 1 to about 6; or
(b) two of the following, which are independently selected: —X, —$R^4$ and —$OR^1$;

each of C5, C8, C9, C10, C13 and C14 is independently substituted with one of —X, —$R^4$ or —$OR^1$;

the A, B, C and D rings may independently be fully saturated, partially saturated or fully unsaturated;

$R^1$ is H or a protecting group such that —$OR^1$ is a protected hydroxyl group, where vicinal —$OR^1$ groups may together form a cyclic structure which protects vicinal hydroxyl groups, and where geminal —$OR^1$ groups may together form a cyclic structure which protects a carbonyl group, with the proviso that either or both of —$OR^1$ at C6 and C7 represents a carbonyl or protected carbonyl group;

$R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and X represents fluoride, chloride, bromide and iodide;

with the proviso that C7 does not have carbonyl substitution when C5 has hydroxyl or —$OR^1$ substitution.

In another preferred embodiment, the compounds have one of the formulas

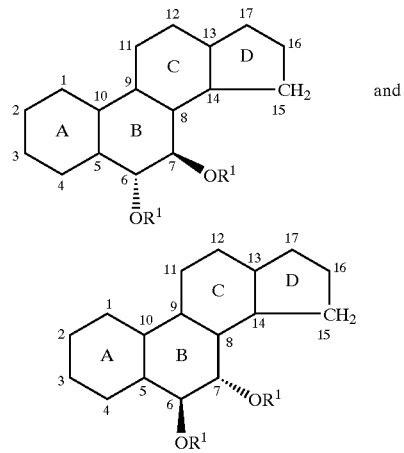

including pharmaceutically acceptable salts and solvates thereof, wherein:
each of C1, C2, C3, C4, C11, C12 and C16 is independently substituted according to (a) or (b):
(a) one of: =O, =C(R⁴)(R⁴), —C(R⁴)(R⁴)(C(R⁴)- (R⁴))$_n$— and —(O(C(R⁴)(R⁴))$_n$O)— wherein n ranges from 1 to about 6,
(b) two of: —X, —R⁴ and —OR¹, each independently selected;
C5 is substituted with a hydrogen atom;
each of C6, C7, C8, C9, C10, C13 and C14 is independently substituted with one of —X, —R⁴ or —OR¹; and
C17 is substituted according to (c), (d), (e) or (f):
(c) two substituents selected from hydrogen, halogen, $C_1$–$C_{30}$ saturated hydrocarbyl excluding —CH(CH₃)(CH₂)₃CH(CH₃)₂, halogen substituted $C_1$–$C_{30}$ saturated hydrocarbyl, $C_1$–$C_{30}$ unsaturated hydrocarbyl, and halogen substituted $C_1$–$C_{30}$ unsaturated hydrocarbyl;
(d) one substituent selected from =C(R⁴)(R⁴) with the proviso that C14 is not substituted with methyl;
(e) at least one oxygen atom-containing substituent selected from =O, —(O(C(R⁴)(R⁴))$_n$O)— wherein n ranges from 1 to about 6, —OH, and —OR¹;
(f) at least one nitrogen atom-containing substituent selected from —N(R⁴)(R⁴) wherein the two R⁴ groups may together with the nitrogen atom form one or more rings, so that the nitrogen atom-containing substituent includes nitrogen atom-containing heterocyclic groups; wherein
the A, B, C and D rings may independently be fully saturated, partially saturated or fully unsaturated;
R¹ is H or a protecting group such that —OR¹ is a protected hydroxyl group, where —OR¹ groups bonded to adjacent carbon atoms may together form a cyclic structure which protects both hydroxyl groups;
R⁴ at each occurrence is independently selected from H and R⁵;
R⁵ is a $C_{1-30}$ organic moiety that may optionally contain at least one heteroatom selected from the group consisting of boron, halogen, nitrogen, oxygen, silicon and sulfur; where two geminal R⁵ groups may together form a ring with the carbon atom to which they are both bonded; and X represents fluoride, chloride, bromide or iodide.
In another aspect, the invention provides a pharmaceutical composition comprising a compound according any of the descriptions provided above, in combination with a pharmaceutically acceptable carrier or diluent.
In another aspect, the invention provides a pharmaceutical composition comprising a compound in combination with a pharmaceutically acceptable carrier or diluent, the compound having the formula

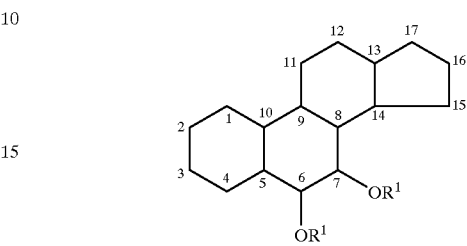

including pharmaceutically acceptable salts and solvates thereof, wherein:
each of C5, C6, C7, C8, C9, C10, C13 and C14 is independently substituted with —X, —R⁴ and —OR¹;
each of C1, C2, C3, C4, C11, C12, C15, C16 and C17 is independently substituted with a substituent selected from (a) or (b), wherein
(a) represents one of: =O, =C(R⁴)(R⁴), —C(R⁴)(R⁴) (C(R⁴)(R⁴))$_n$— and —(O(C(R⁴)(R⁴))$_n$O)—, wherein n ranges from 1 to about 6; and
(b) represents two of: —X, —R⁴ and —OR¹, which are independently selected at each occurrence;
the A, B, C and D rings may independently be fully saturated, partially saturated or fully unsaturated;
R¹ is H or a protecting group such that —OR¹ is a protected hydroxyl group, where the C6 and C7-OR¹ groups may together form a cyclic structure which protects both hydroxyl groups;
R⁴ at each occurrence is independently selected from H and R⁵;
R⁵ is a $C_{1-30}$ organic moiety that may optionally contain at least one heteroatom selected from the group consisting of boron, halogen, nitrogen, oxygen, silicon and sulfur; where two geminal R⁴ groups may together form a ring with the carbon atom to which they are both bonded; and
X represents fluoride, chloride, bromide or iodide;
with the proviso that C15 is not bonded to an oxygen atom.
In another aspect, the invention provides for the use of the above compounds (any one or mixture thereof) for manufacture of a medicament for the treatment of asthma, allergy, inflammation including arthritis, and/or thrombosis, or for treating a condition associated with an elevated level of NFκB.
In another aspect, the invention provides a process for treating asthma comprising administering to a subject in need thereof an effective amount of the compound or salt thereof, or a pharmaceutical composition, each as described above.
In another aspect, the invention provides a process for treating allergy comprising administering to a subject in need thereof an effective amount of the compound or salt thereof, or a pharmaceutical composition, each as described above.
In another aspect, the invention provides a process for treating inflammation due to arthritis comprising administering to a subject in need thereof an effective amount of the compound or salt thereof, or a pharmaceutical composition, each as described above.

In another aspect, the invention provides a process for treating thrombosis comprising administering to a subject in need thereof an effective amount of the compound or salt thereof, or a pharmaceutical composition, each as described above.

In another aspect, the invention provides a process for treating a condition associated with an elevated level of NFκB activity in a subject, comprising administering to a subject in need thereof an effective amount of the compound or salt thereof, or a pharmaceutical composition, each as described above.

In another aspect, the invention provides a process for introducing an exocyclic olefin group to the C17 position of a 6,7-dioxygenated steroid comprising providing a compound of Formula (10), reacting the compound of Formula (10) with a Wittig reagent of Formula (11) in the presence of a base, to provide an olefin compound of Formula (12)

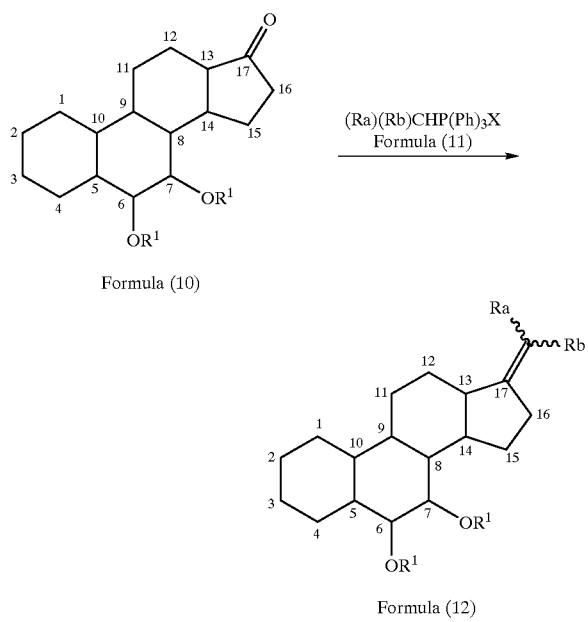

Formula (10)

(Ra)(Rb)CHP(Ph)$_3$X
Formula (11)

Formula (12)

wherein each of the compounds of Formulas (10) and (12) include pharmaceutically acceptable salts and solvates thereof, and wherein:

each of C1, C2, C3, C4, C11, C12, C15 and C16 is independently substituted according to any of (a) and (b):

(a) one of: =O, =C($R^4$)($R^4$), —C($R^4$)($R^4$)(C($R^4$)-($R^4$))$_n$— and —(O(C($R^4$)($R^4$))$_n$O)— wherein n ranges from 1 to about 6;

(b) two of: —X, —$R^4$ and —$OR^1$, each independently selected;

each of C5, C6, C7, C8, C9, C10, C13 and C14 is independently substituted with one of —X, —$R^4$ or —$OR^1$;

$R^1$ is H or a protecting group such that —$OR^1$ is a protected hydroxyl group, where vicinal —$OR^1$ groups may together form a cyclic structure which protects vicinal hydroxyl groups, and where geminal —$OR^1$ groups may together form a cyclic structure which protects a carbonyl group, with the proviso that either or both of —$OR^1$ at C6 and C7 represents a carbonyl or protected carbonyl group;

Ra, Rb and $R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and X represents fluoride, chloride, bromide and iodide, which is independently selected at each occurrence.

In another aspect, the invention provides a process for introducing 6α,7β-dioxygenation into a steroid, comprising providing a steroid of Formula (13) having a carbonyl group at C7 and a double bond between C5 and C6, comprising a reduction the carbonyl group to a hydroxyl group, followed by a hydroboration of the double bond to provide a hydroxyl group at C6, wherein the C6 hydroxyl group has the α-configuration and the C7 hydroxyl group has the β-configuration,

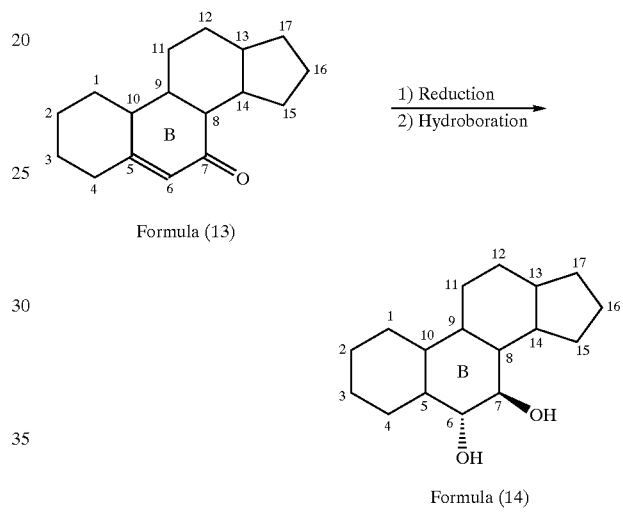

Formula (13)

1) Reduction
2) Hydroboration

Formula (14)

wherein each of the compounds of Formulas (13) and (14) include pharmaceutically acceptable salts and solvates thereof, and wherein:

each of C1, C2, C3, C4, C11, C12, C15, C16 and C17 is independently substituted according to any of (a) and (b):

(a) one of: =O, =C($R^4$)($R^4$), —C($R^4$)($R^4$)(C($R^4$)-($R^4$))$_n$— and —(O(C($R^4$)($R^4$))$_n$O)— wherein n ranges from 1 to about 6;

(b) two of: —X, —$R^4$ and —$OR^1$, each independently selected;

each of C8, C9, C10, C13 and C14 is independently substituted with one of —X, —$R^4$ or —$OR^1$;

$R^1$ is H or a protecting group such that —$OR^1$ is a protected hydroxyl group, where vicinal —$OR^1$ groups may together form a cyclic structure which protects vicinal hydroxyl groups, and where geminal —$OR^1$ groups may together form a cyclic structure which protects a carbonyl group, with the proviso that either or both of —$OR^1$ at C6 and C7 represents a carbonyl or protected carbonyl group;

$R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and X represents fluoride, chloride, bromide and iodide.

In another aspect, the invention provides a process for a stereocontrolled introduction of a hydroxyl group at C3 of a steroid nucleus, comprising providing a steroid compound of Formula (15) having a carbonyl group at C3, and reducing the carbonyl group to a hydroxyl group with a reducing agent so as to provide at least one compound of Formulas (16) and (17)

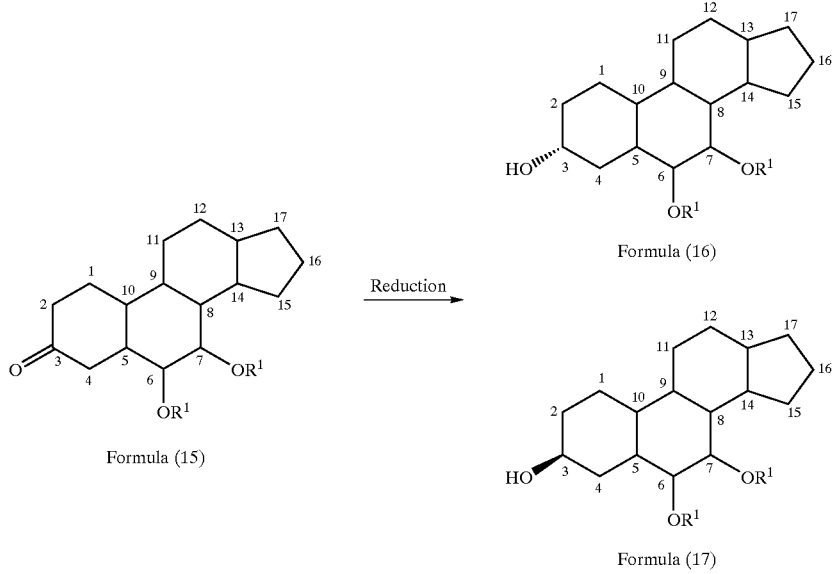

Formula (15)

Formula (16)

Formula (17)

wherein each of the compounds of Formulas (15), (16) and (17) include pharmaceutically acceptable salts and solvates thereof, and wherein:
  each of C1, C2, C4, C11, C12, C15, C16 and C17 is independently substituted according to any of (a) and (b):
    (a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6;
    (b) two of: —X, —R$^4$ and —OR$^1$, each independently selected;
  each of C5, C6, C7, C8, C9, C10, C13 and C14 is independently substituted with one of —X, —R$^4$ or —OR$^1$;
  R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;
  R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and
X represents fluoride, chloride, bromide and iodide.

DETAILED DESCRIPTION OF THE INVENTION

The invention is directed to various steroid derivatives having specific functionality as described in detail herein.

The compounds described herein demonstrate effectiveness as good controllers of the asthmatic and allergic responses in that they show efficacy against mast cell degranulation, inhibition of allergen-induced bronchospasm (acute phase) and inhibition of allergen-induced lung inflammation (late phase). This group of compounds represents a new series of agents which have potential therapeutic benefit in the treatment of asthma and allergies, with high potency, a broad spectrum of activity and the reduced probability of side effects.

For convenience in identifying the novel features of the invented compounds, an unsubstituted steroid nucleus having each ring carbon thereof identified with a unique number is shown below as Structure 1. This numbering system will be used consistently herein.

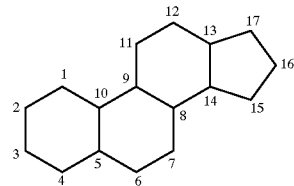

Structure 1

The compounds of the present invention contain at least two asymmetric carbon atoms and thus exist as enantiomers and diastereomers. Unless otherwise noted, the present invention includes all enantiomeric and diastereomeric forms of the compounds of the above formula. Pure stereoisomers, mixtures of enantiomers and/or diastereomers, and mixtures of different compounds of the above formulae are included within the present invention.

The synthesis procedures described herein, especially when taken with the general knowledge in the art, provide sufficient guidance to those of ordinary skill in the art to perform the synthesis, isolation, and purification of the preferred compounds described herein and other analogous compounds. Individual enantiomers may be obtained, if desired, from mixtures of the different forms by known methods of resolution, such as the formation of diastereomers, followed by recrystallization.

The compounds of the above formula may be in the form of a solvate or a pharmaceutically acceptable salt, e.g., an acid addition salt. Such salts include hydrochloride, sulfate, phosphate, citrate, fumarate, methanesulfonate, acetate, tartrate, maleate, lactate, mandelate, salicylate, succinate and other salts known in the art.

A compound of the present invention may be prepared as a composition by combining it with a pharmaceutically acceptable carrier or diluent. Suitable carriers or diluents include physiological saline. It will be evident to those of ordinary skill in the art that a composition of the present invention may contain more than one steroid compound or one or more steroid compounds in combination with one or more non-steroid compounds.

A specific functionality present on many of the steroid compounds of the invention is oxygen substitution at both of positions 6 and 7. Thus, certain steroids of the invention have the oxygen substitution pattern shown in Structure 2 below. Some of these steroids are additionally characterized by having specific stereochemistries. For example, steroids having 6α and 7β oxygen substitution, as shown in Structure 3, and steroids having an alpha hydrogen at the 5 position in addition to having 6α and 7β oxygen substitution, as shown in Structure 4 below, fall within the scope of the invention.

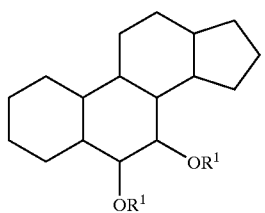

Structure 2

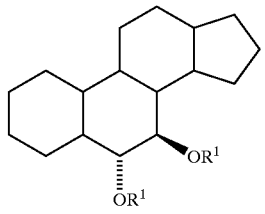

Structure 3

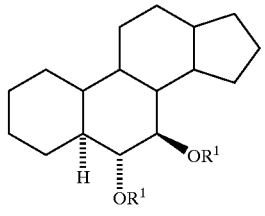

Structure 4

In Structures 2, 3 and 4, each of the oxygen atoms that are bonded to carbons 6 and 7 are simultaneously bonded to an "$R^1$" group. The $R^1$ group is hydrogen or a protecting group for an hydroxyl group. Suitable protecting groups are set forth in Greene, "Protective Groups in Organic Chemistry", John Wiley & Sons, New York N.Y. (1981). When a compound of Structures 2–4 contains vicinal —$OR^1$ groups (i.e., —$OR^1$ groups on neighboring carbon atoms), those vicinal —$OR^1$ groups may together form a cyclic structure which protects vicinal hydroxyl groups. A ketal is an example of protected vicinal —$OR^1$ group. Geminal —$OR^1$ groups (i.e., two —$OR^1$ groups on the same carbon atom) may together form a cyclic structure which protects a carbonyl group. A ketal is an example of such a cyclic structure. It should be understood that either or both of —$OR^1$ at C6 and C7 represents a carbonyl or protected carbonyl group, and thus at C6 and C7, R1 may be a direct bond between the oxygen atom and the carbon (C6 or C7) to which the oxygen atom is bonded.

Steroids of the invention may have substituents with either the α or stereochemistry at the C8 and/or C9 positions. A hydrogen atom at C8 of the steroids of the invention is typically in the β configuration. In addition, preferred steroids of the invention may have methyl substituents with p stereochemistry at the C10 and/or C13 positions. Compounds of the invention preferably have a C14 hydrogen with the α stereochemistry when C15 is not a ketone. In preferred steroids of the invention that have a substituent at C17, the C17 substituent has β stereochemistry.

Steroids having 6,7-dioxygenation in the B-ring according to Structure 2 can be synthesized from a number of commercially available steroidal precursors having an α,β-unsaturated carbonyl group in the A-ring, including 4-androsten-3,17-dione (compound 1 below) and dehydroisoandrosterone (compound 247 below). These specific steroid precursors are available from Steraloids Inc., Wilton, N.H. Other suitable steroid precursors having C3 oxygen functionalities and $\Delta^5$ carbon-carbon double bonds may be obtained from, e.g., Aldrich Chemical Co., Milwaukee, Wis.

An exemplary synthetic sequence to prepare a compound of Structure 2 from 4-androsten-3,17-dione is summarized in Scheme 1 below.

Scheme 1

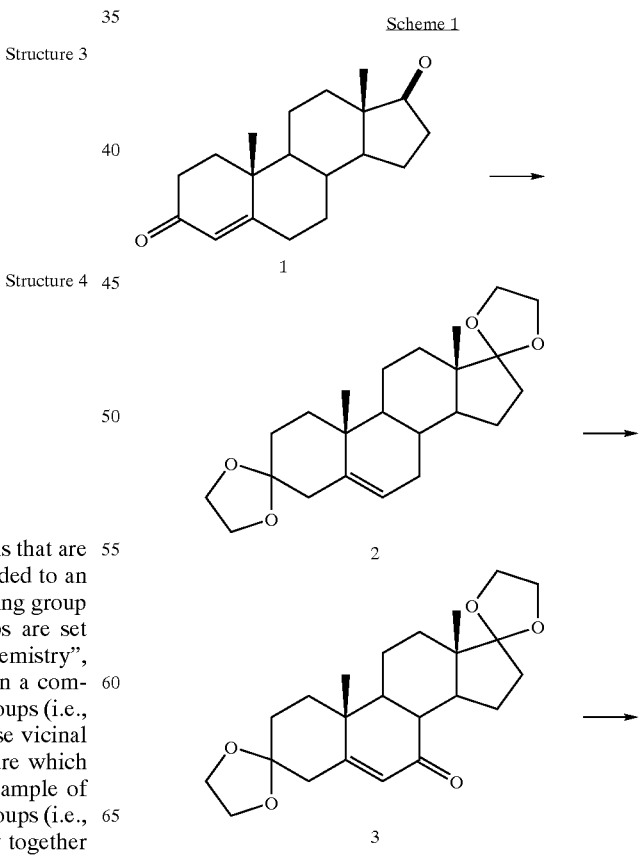

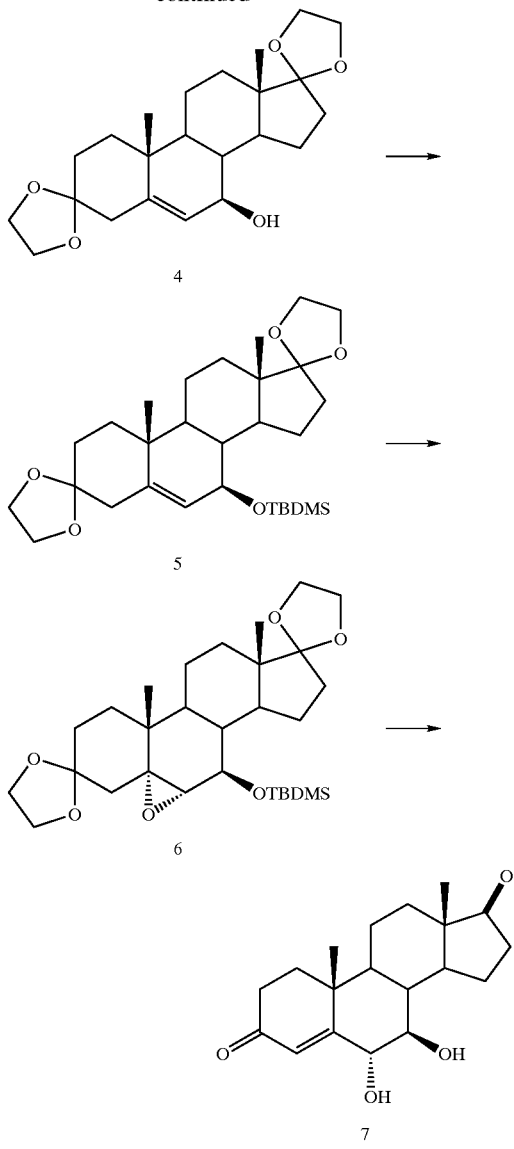

Initially, the carbonyl functionalities of 4-androsten-3,17-dione are protected by carbonyl protecting groups. As shown in Scheme 1, this may be accomplished by reacting compound 1 with a benzene solution of (CH$_2$OH)$_2$ and p-TsOH, thereby converting the carbonyl groups to ketal groups. Other suitable carbonyl protecting groups are listed in Greene, "Protective Groups in Organic Chemistry", John Wiley & Sons, New York, N.Y. (1981). Under the acidic conditions which form the protected ketone groups, there occurs concomitant migration of the C4–C5 carbon-carbon double bond to the C5–C6 position, to ultimately form compound 2.

Allylic oxidation of the C5–C6 carbon-carbon double bond of compound 2 introduces a carbonyl oxygen at C7, to thereby form compound 3. A number of oxidizing agents and experimental conditions can be used for this allylic oxidation, including chromium trioxide/3,5-dimethylpyrazole complex, pyridinium chlorochromate (PCC), pyridinium dichromate (PDC), or RuCl$_3$ and t-butylhydroperoxide.

Reduction of the resultant C7 ketone with an appropriate reducing agent gives the hydroxyl functionality at C7, as shown in compound 4. Any of several metal hydride reducing agents can be used for this task including sodium borohydride or lithium aluminum hydride. Generally, reduction of the C7 ketone produces the β-OH configuration by hydride attack from the least hindered face of the steroid. The C7 hydroxyl group is then preferably protected with an hydroxyl protecting group, e.g., t-butyldimethylsilane (TBDMS), to provide a protected allylic alcohol as in compound 5. Other suitable hydroxyl protecting groups are listed in Greene, supra.

Introduction of the C6 oxygen can be achieved, before or after protection of the C7 hydroxyl group, by methods such as hydroboration/oxidation or epoxidation followed by ring opening. For example, the Δ$^5$ carbon-carbon double bond of compound 5 can be epoxidized with any of a number of peracids including m-chloroperbenzoic acid, trifluoroperacetic acid or 3,5-dinitroperoxybenzoic acid, to provide an epoxide such as in compound 6. Generally, the epoxide introduced has the α-configuration arising from attack on the least hindered face of the steroid ring structure. Subsequent ring opening of the epoxide can be accomplished under acidic conditions, such as 80% aqueous acetic acid at 60° C. The crude mixture contains both compound 7 (having an allylic alcohol at the C6 position with the α-configuration) and the C7 silyl derivative thereof. This crude mixture can be treated with tetrabutylanmmonium fluoride (TBAF) in tetrahydrofuran (THF) to give a single compound (7). Alternatively, hydroboration of the Δ$^5$ double bond with an appropriate borane complex followed by oxidation using reagents such as basic hydrogen peroxide will also introduce an hydroxyl group in the α-configuration at C6.

Compound 7 is exemplary of compounds having the oxygenation pattern of Structures 2 and 3. The methodology by which compound 1 may be converted to a compound of Structures 2 and/or 3 is generally applicable to a wide variety of compounds having an α,β-unsaturated carbonyl group in the A-ring of a steroid. Additional compounds of Structures 2 and/or 3 may be prepared by modification of a dihydroxy compound such as compound 7. In such case, it may be necessary to protect each of the C6 and C7 hydroxyl groups, and methodology to achieve such protection is described later herein.

Compound 7 or an analog thereof may be converted to a compound of Structure 4. Essentially, this may be accomplished by protecting the C6 and C7 hydroxyl groups and the C17 carbonyl group, and then reducing the Δ$^4$ carbon-carbon double bond. Lithium in ammonia/THF is an example of a suitable reducing agent. Such a reduction provides an enolate, which may be trapped with a suitable electrophile, e.g., trimethylsilyl chloride or diethylchlorophosphate.

An example of such a conversion is shown in Scheme 2. Thus, protection of the C6 and C7 hydroxyl groups of compound 7 may be accomplished by treatment with 2,2-dimethoxypropane and a catalytic amount of (1S)-(+)-10-camphorsulfonic acid (CSA) to produce acetonide 8. The C17 carbonyl group of compound 8 may be protected by converting it to an hydroxyl group, and then protecting the hydroxyl group. Chemoselective reduction of the C17 carbonyl group may be accomplished by use of NaBH$_4$ in methanol to provide compound 9, which in turn is reacted with a suitable hydroxyl protecting group, e.g., t-butyldimethylsilyl chloride, to provide silyl ether compound 10. Compound 10 may be reacted with lithium in liquid ammonia/THF, followed by quenching with diethylchlorophosphate, to provide compound 11. Compound 11 has a 5α hydrogen, as well as C6 and C7 dihydroxylation, and thus is a representative compound of Structure 4.

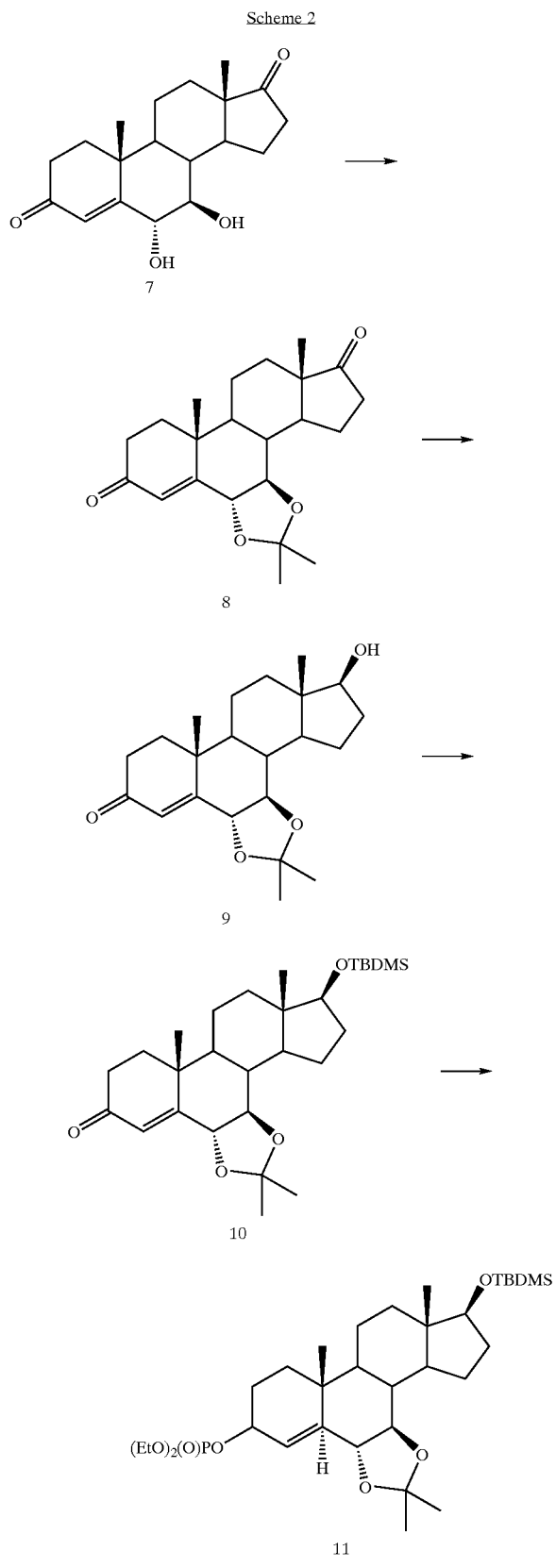

Scheme 2

In an aspect of the present invention, olefinic steroids having an exocyclic olefin at C17 and oxygen atoms at both C6 and C7 are provided. In one embodiment, the olefinic steroid has the Structure 5, including individual enantiomeric or geometric isomers thereof, and further including a solvate or pharmaceutically acceptable salt thereof. Structure 5 is defined as follows:

A compound of the formula

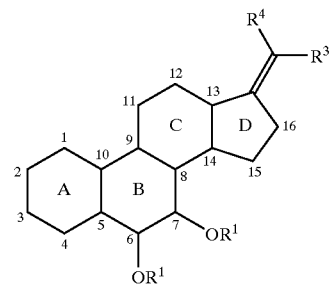

including pharmaceutically acceptable salts and solvates thereof, wherein:

each of C1, C2, C3, C4, C11, C12, C15 and C16 is independently substituted with
(a) one of: =O, =C($R^4$)($R^4$), —C($R^4$)($R^4$)(C($R^4$)-($R^4$))$_n$— and —(O(C($R^4$)($R^4$))$_n$O)— wherein n ranges from 1 to about 6; or
(b) two of the following, which are independently selected: —X, —$R^4$ and —O$R^1$;

each of C5, C8, C9, C10 and C13 is independently substituted with one of —X, —$R^4$ or —O$R^1$;

C14 is substituted with —X, —O$R^1$, or —$R^4$ excluding methyl;

the A, B, C and D rings may independently be fully saturated, partially saturated or fully unsaturated;

$R^1$ is H or a protecting group such that —O$R^1$ is a protected hydroxyl group, where vicinal —O$R^1$ groups may together form a cyclic structure which protects vicinal hydroxyl groups, and where geminal —O$R^1$ groups may together form a cyclic structure which protects a carbonyl group, with the proviso that either or both of —O$R^1$ at C6 and C7 represents a carbonyl or protected carbonyl group;

$R^2$, $R^3$ and $R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and X represents fluoride, chloride, bromide and iodide.

Providing an exocyclic double bond at C17 is readily accomplished by the Wittig reaction, starting with a C17 carbonyl compound. Steroids of the invention having C17 carbonyl functionality are readily available, e.g., in compound 7 as prepared according to Scheme 1, or by the synthetic sequence summarized in Scheme 3 below, which starts from compound 10 (as prepared in Scheme 2).

Scheme 3

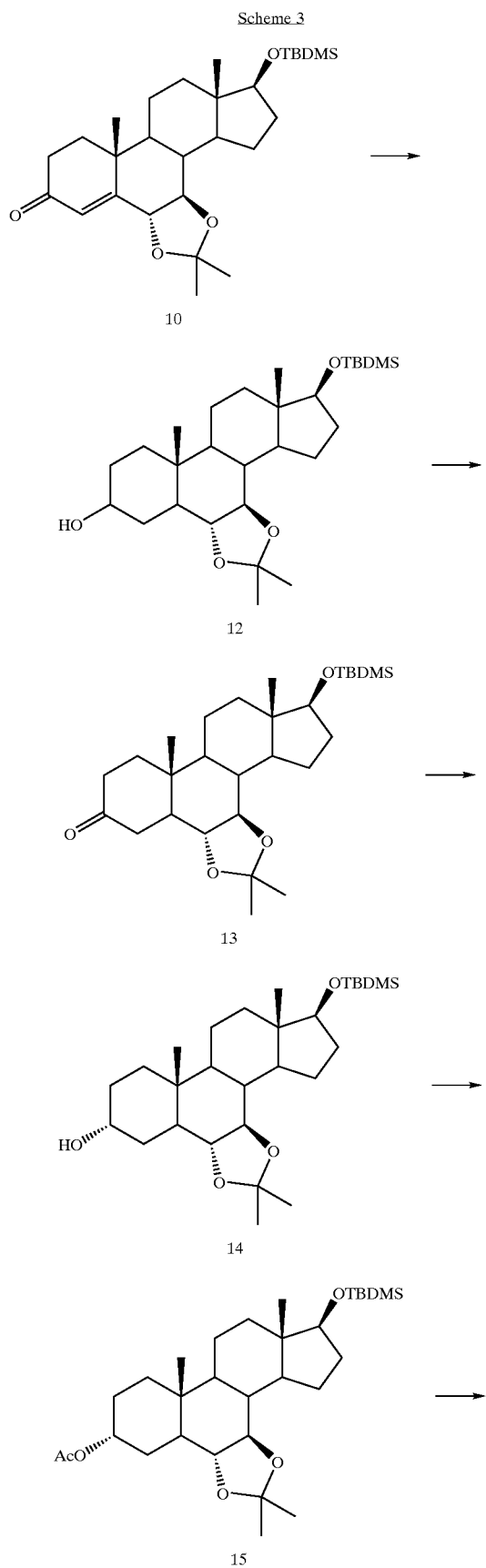

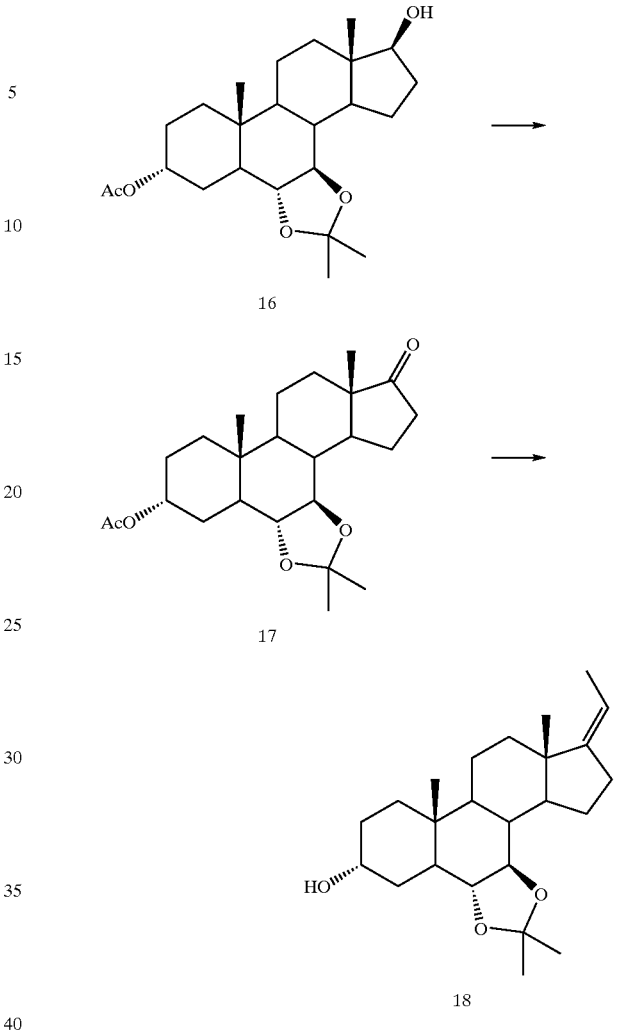

Thus, the A-ring of compound 10 can be reduced to afford a C3 carbonyl group as the only functionality in the A-ring. Scheme 3 illustrates a two-step sequence to achieve this reduction, wherein compound 10 is reduced with lithium in liquid ammonia and an ether solvent, e.g., diethyl ether or THF, to provide a mixture of compounds 12 and 13. This mixture may then be oxidized with a suitable oxidizing agent, for example PDC, to give exclusively compound 13. Compound 13 may then be reduced with LS-Selectride® (Aldrich Chemical Co., Milwaukee, Wis.) or other selective reducing agent, to provide compound 14 having the indicated stereochemistry.

The 3α-hydroxyl group of compound 14 may then be protected as the acetate using acetic anhydride and pyridine to give compound 15. Other suitable hydroxyl protecting groups could be used instead of the acetate group. Removal of the silyl protecting group at C17 can be achieved under standard conditions known in the art for removing this silyl protecting group, e.g., using tetrabutylammonium fluoride (TBAF), to afford a C17 hydroxyl compound such as compound 16. The C17 hydroxyl group can be oxidized to a carbonyl group under typical oxidation conditions, e.g., using oxalyl chloride in DMSO and Et$_3$N, to provide ketone compound 17.

Compound 17 can be used in a multitude of olefination reactions, including Wittig-type reactions, to provide compounds of Structure 5 having an olefin at C17. For example, compound 17 may be reacted with ethyltriphenylphosphonium bromide to provide the ethylidene compound 18. Other starting ketones may be used to provide other steroids having an exocyclic double bond at C17.

As described previously, compounds containing a carbonyl at C17 (or those that contain functionality that is readily converted to a carbonyl group) can be transformed into compounds containing a carbon-carbon double bond at C17 using Wittig chemistry. For example, as outlined in Scheme 4 below, compound 19 may be transformed into the corresponding C17 ethylidene compound 23 in a five step process. Thus, the 2α,3β-dihydroxy functionality of compound 19 may be protected with hydroxyl protecting groups, (e.g., using 2,2-dimethoxy propane and camphor sulfonic acid (CSA) in N,N-dimethylformamide (DMF) to give a compound such as compound 20. Deprotection of the C17 hydroxyl may be achieved using reaction conditions suitable for the particular hydroxyl protecting group (in this instance, TBAF in THF may be used) followed by oxidation of the resulting hydroxyl group (e.g., using PDC in $CH_2Cl_2$) yields the compound containing the C17 ketone (21). Reaction of compound 21 with a Wittig reagent, e.g., ethyl triphenyl phosphonium bromide and potassium t-butoxide in toluene, gives compound 22. Deprotection of the hydroxyl groups in olefin 22 affords the tetrahydroxy compound 23.

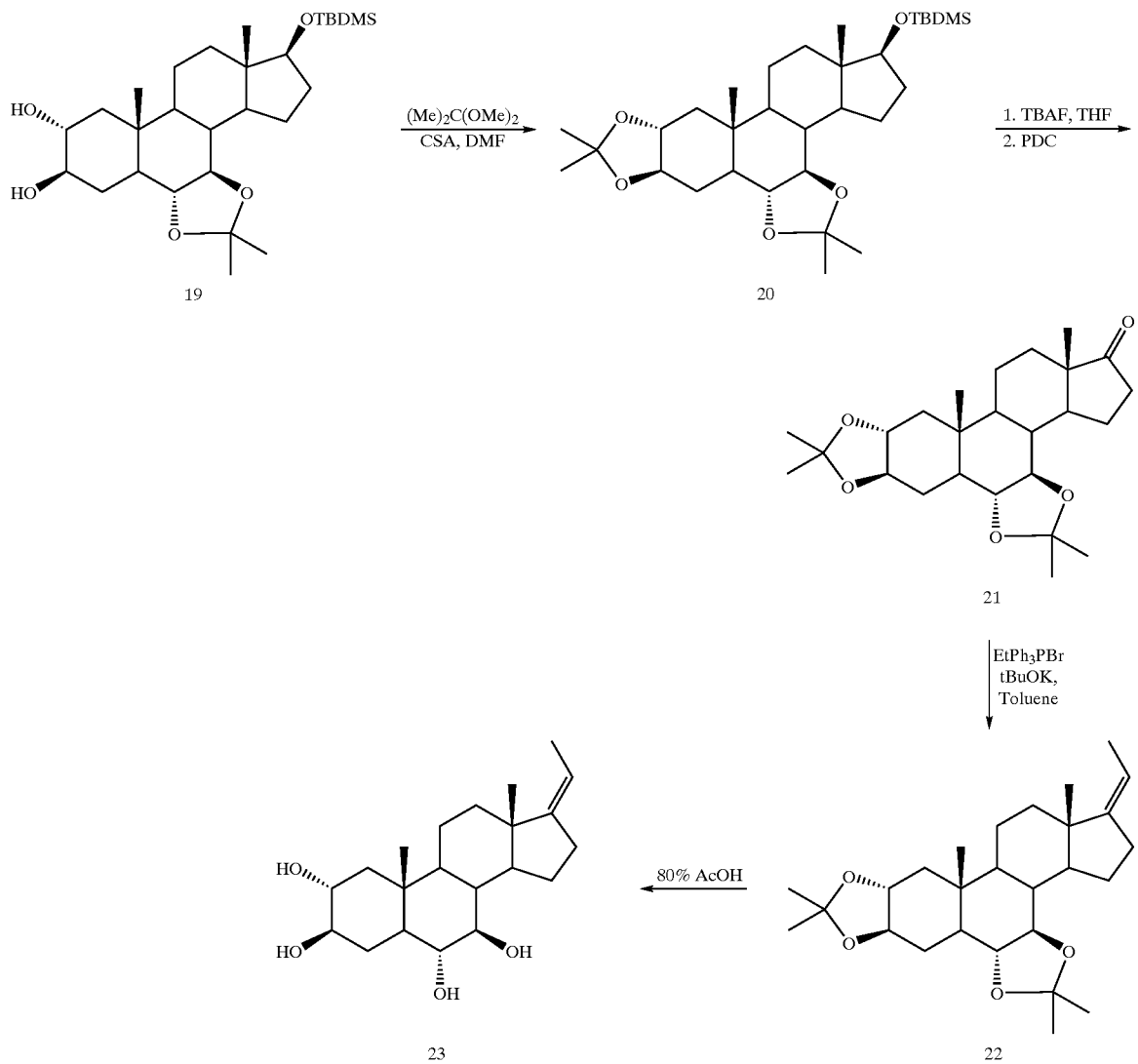

Scheme 4

Protection steps may be required prior to derivatization at C17 in some cases. For example, in compound 24 (prepared according to Scheme 14) the C3 ketone should first be protected before proceeding with the transformations at C17 (see Scheme 5 below). Thus, compound 24 may first be reduced (e.g., by reaction with $NaBH_4$ in ethanol) then acylated (e.g., using acetic anhydride in pyridine) to yield the C3,C5-acetoxy derivative 25. Deprotection, oxidation and Wittig chemistry at C17, analogous to that described in Scheme 4 may be used to provide compound 27. Subsequent deprotection of the C6 and C7 hydroxyl groups (80% acetic acid is conveniently used to remove the ketal group of compound 27) gives compound 28 which contains the exocyclic $\Delta^{17}$ olefin.

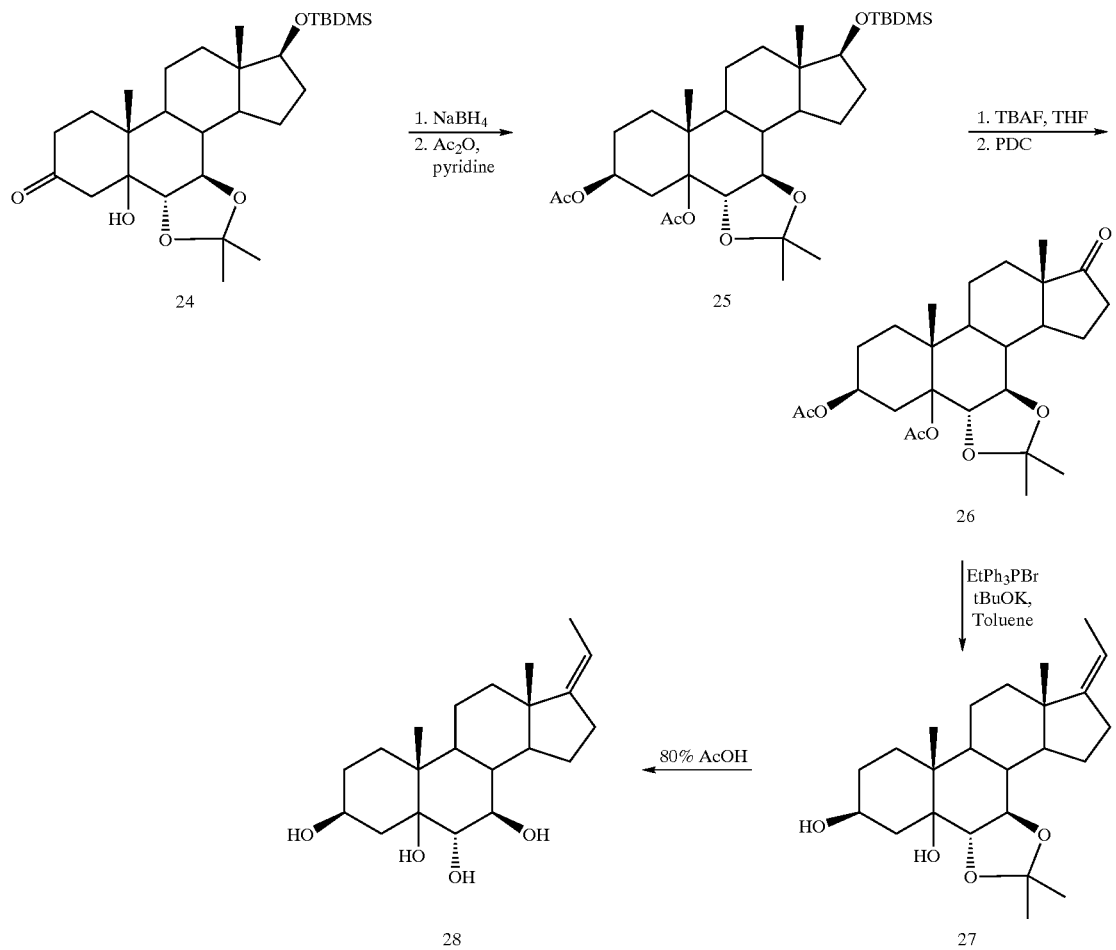

In an aspect of the present invention, steroids having C17 oxygenation as well as oxygenation at C6 and C7 are provided. In one embodiment, the steroid has the Structure 6, including individual enantiomeric or geometric isomers thereof, and further including a solvate or pharmaceutically acceptable salt thereof. Structure 6 is defined as follows:

A compound of the formula

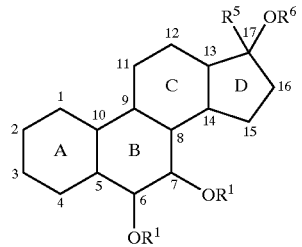

including pharmaceutically acceptable salts and solvates thereof, wherein:

each of C1, C2, C3, C4, C11, C12, C15 and C16 is independently substituted with
(a) one of: =O, =C(R$^4$)(R$^4$), —C(R$^4$)(R$^4$)(C(R$^4$)- (R$^4$))$_n$— and —(O(C(R$^4$)(R$^4$))$_n$O)— wherein n ranges from 1 to about 6; or
(b) two of the following, which are independently selected: —X, —R$^4$ and —OR$^1$;

each of C5, C8, C9, C10, C13 and C14 is independently substituted with one of —X, —R$^4$ or —OR$^1$;

the A, B, C and D rings may independently be fully saturated, partially saturated or fully unsaturated;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and $R^5$ and $R^6$ may together form a direct bond so C17 is a carbonyl group, or may together with C17 form a cyclic 3–6 membered ether or 4–6 membered lactone; otherwise $R^1$ is $R^4$ or —$OR^6$ and $R^6$ is $R^1$ or $R^4$; and X represents fluoride, chloride, bromide and iodide.

Preferably, neither the A nor B ring in compounds of Structure 6 is aromatic. In another preferred embodiment, when C10 is substituted with methyl, then C5 is not directly bonded to an oxygen atom.

Many examples of compounds of Structure 6 and their synthesis have already been provided above. For instance, compounds 7, 8, 9, 10, 11, 13, 14, 15, 16, 17, 19, 20, 21, 24, 25 and 26 are representative compounds of Structure 6. Many additional compounds of Structure 6, including the synthesis thereof, are provided herein in connection with other compounds of the invention. Therefore, one of ordinary skill in the art is able to prepare many compounds of Structure 6 in view of the disclosure herein.

Compounds of Structure 6 may have oxygen and/or hydrocarbon substitution at C1. Exemplary synthetic methodology to provide oxygen and/or hydrocarbon substitution at C1 for a compound of Structure 6 is provided below and outlined in Schemes 6, 7, and 8. It should be recognized that the same or analogous synthetic methodology can be applied to provide oxygen and/or hydrocarbon substitution at C1 for any compound of Structures 5–12 where C1 oxygen and/or hydrocarbon substitution is desired.

Introduction of an oxygen functionality at C1 of the steroid carbon skeleton can be accomplished by first generating the 1-ene-3-one functionalization pattern in the A-ring of a steroid, followed by Michael addition chemistry using any of a number of alkoxide anions, as outlined in Scheme 6. For example, the enone 29 may be produced from compound 13 using standard methodology. The benzyloxy compound 30 may then be produced by reacting the enone (29) with benzyl alcohol and KOH. Reduction of the C3 ketone of compound 30, and protection of the resultant secondary alcohol as the silyloxy derivative (to provide compound 31) may be followed by catalytic hydrogenation to yield the C1 hydroxyl functionality in compound 32. Oxidation of this secondary alcohol using, e.g., PDC in $CH_2Cl_2$ may produce compound 33 having a C1 ketone.

Scheme 6

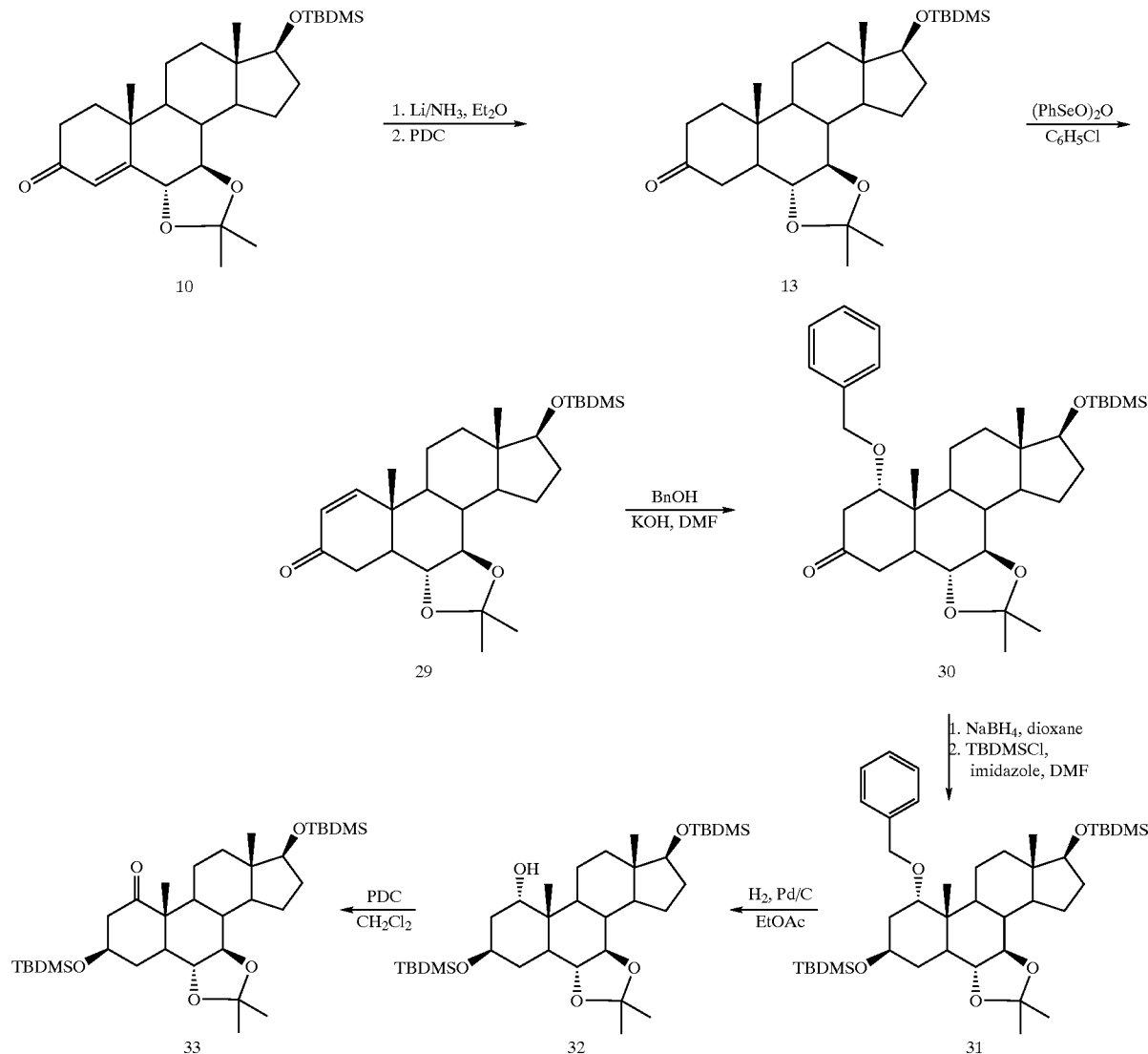

Compounds containing both an alkyl group and an hydroxyl group at C1 may be produced by reaction of compound 33 with an alkyl lithium reagent. For example, reaction of compound 33 with CH₃Li in ether will provide the tertiary alcohol in compound 34 (Scheme 7).

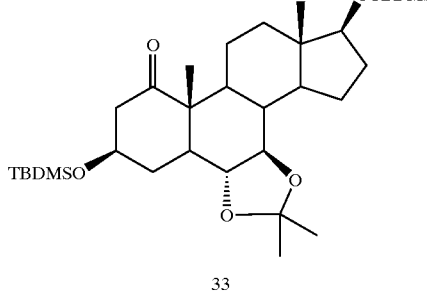

Michael addition chemistry similar to that described in Scheme 6 can be used to add an alkyl group to the C1 position. This can be accomplished using a number of reagents including R₂CuLi where R may be alkyl, vinyl or aryl. For example, compound 29 may be reacted with Me₂CuLi in ether to yield the C1 methyl substituted derivative 35 (Scheme 8).

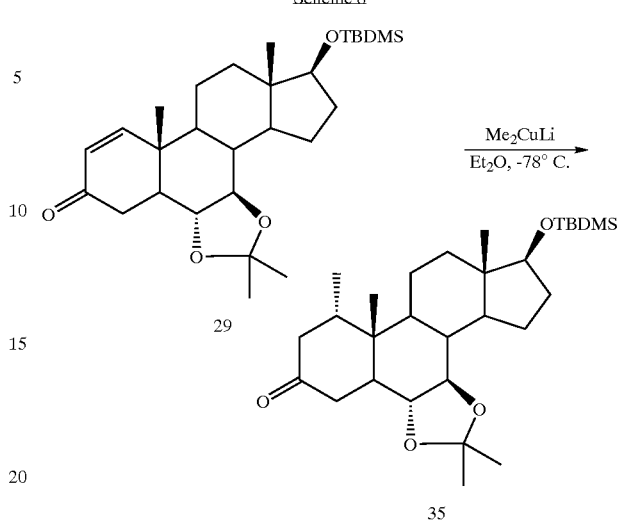

Compounds of Structure 6 may have oxygen and/or hydrocarbon substitution at C2. Exemplary synthetic methodology to provide oxygen and/or hydrocarbon substitution at C2 for a compound of Structure 6 is provided below. It should be recognized that the same or analogous synthetic methodology can be applied to provide oxygen and/or hydrocarbon substitution at C2 for any compound of Structures 5–12 where C2 oxygen and/or hydrocarbon substitution is desired.

Compounds containing oxygen at C2 may be prepared in a number of ways including hydroboration of a silyl enol ether as shown in Scheme 9. The silyl enol ether may be prepared from the enone 29 via Li/NH₃ reduction followed by trapping of the resultant enolate using TMSCl to yield compound 36 (or other R₃SiCl reagents to produce an analogous silyl enol ether). Hydroboration of the carbon-carbon double bond in 36 may give the 2α,3β-dihydroxy functionalization pattern (compound 19). Oxidation of this dihydroxy compound using PDC in CH₂Cl₂ may provide the diketone 38.

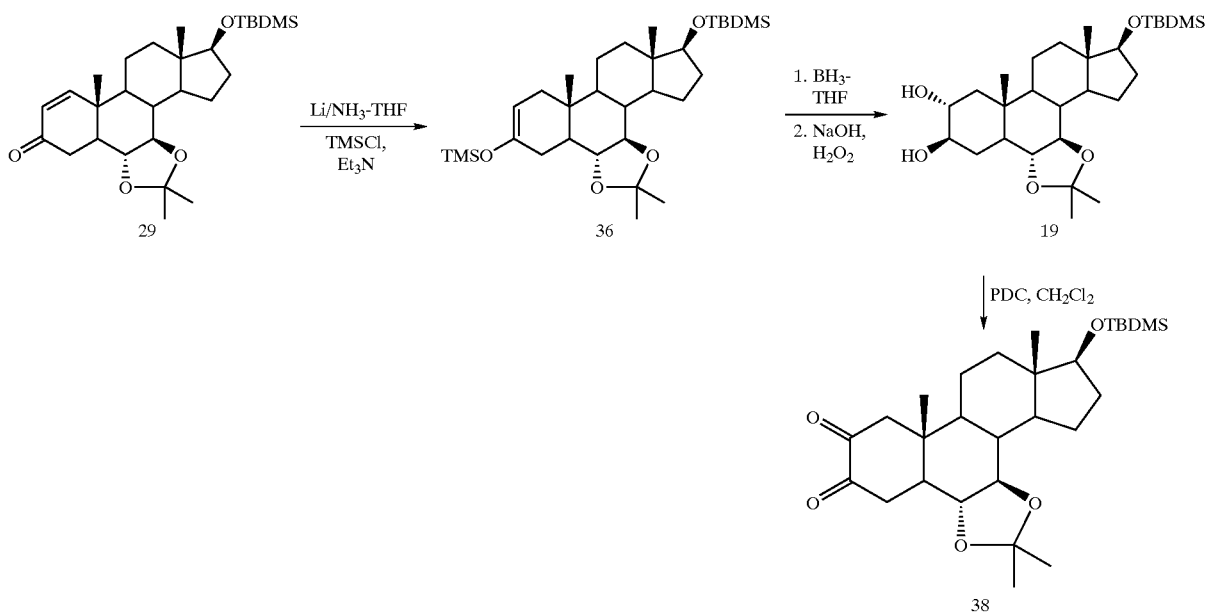

Preparation of C2 hydrocarbon substituted compounds can be produced, e.g., by α-alkylation of a compound containing a C3 ketone functionality. For example, Li/NH₃ reduction of the enone 29 followed by trapping the resultant anion with an alkylating agent provides C2 alkylation. Treatment of the resultant enolate with methyl iodide may yield the C2 methylated compound 39 (Scheme 10 below). This methodology can be applied to a variety of different compounds using a number of different alkyl halides.

Scheme 10

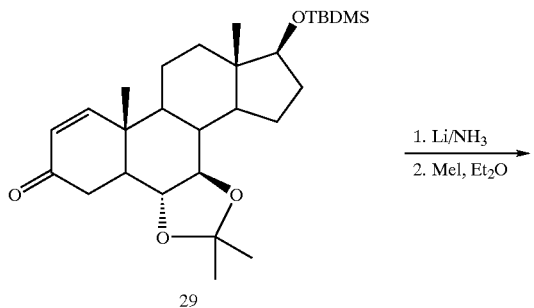

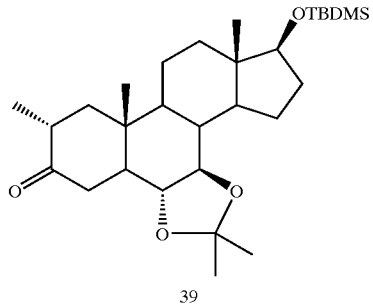

Compounds of Structure 6 may have hydrocarbon substitution at C3. Exemplary synthetic methodology to provide hydrocarbon substitution at C3 for a compound of Structure 6 is provided below. It should be recognized that the same or analogous synthetic methodology can be applied to provide hydrocarbon substitution at C3 for any compound of Structures 5–12 where C3 hydrocarbon substitution is desired.

Wittig chemistry on compound 13 followed by reduction of the double bond or alternative modifications will provide the alkyl or dialkyl derivative at C3. For example, reaction of compound 13 with methyl triphenylphosphonium bromide and tBuOK in toluene may be used to give compound 40 (Scheme 11). A Simmons-Smith reaction on compound 40 with $CH_2I_2$ and Zn—Cu followed by catalytic hydrogenolysis of the cyclopropane derivative 41 using $H_2$, Pd/C in ethanol can be used to give the dialkyl derivative 42 (Scheme 11).

Scheme 11

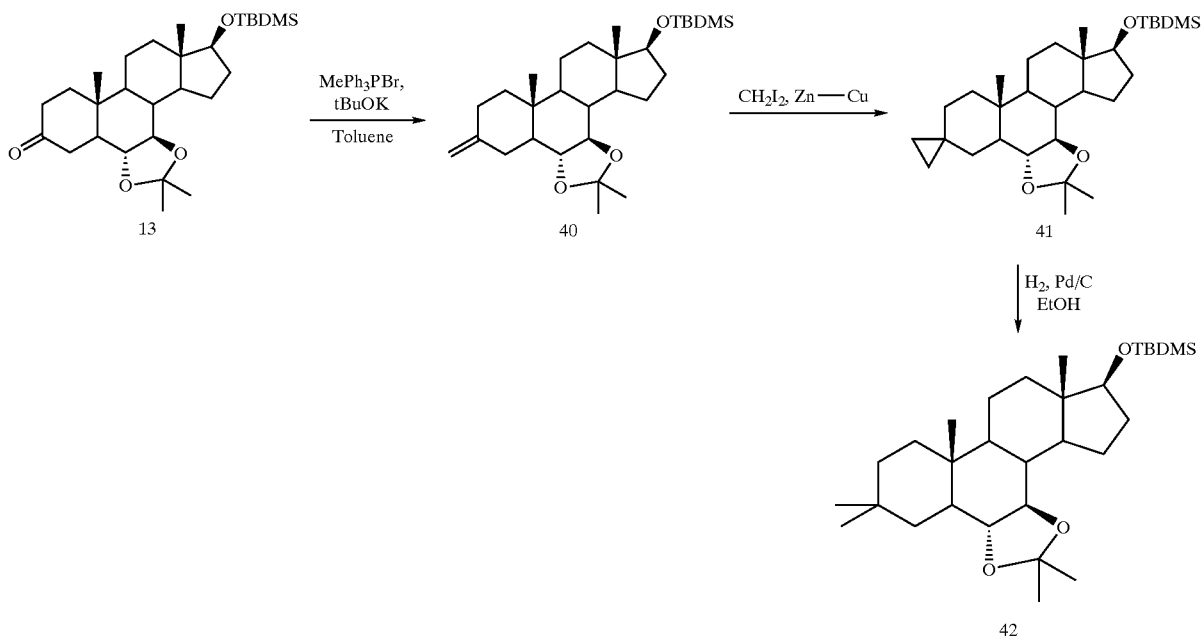

Compounds of Structure 6 may have hydrocarbon substitution at C4. Exemplary synthetic methodology to provide hydrocarbon substitution at C4 for a compound of Structure 6 is provided below. It should be recognized that the same or analogous synthetic methodology can be applied to provide hydrocarbon substitution at C4 for any compound of Structures 5–12 where C4 hydrocarbon substitution is desired.

Alkylation at C4 may be achieved by first producing the enolate anion from the enone in compound 10 (using, for example, reduction with lithium in liquid ammonia) followed by treatment with an appropriate alkyl halide as shown in Scheme 12.

Scheme 12

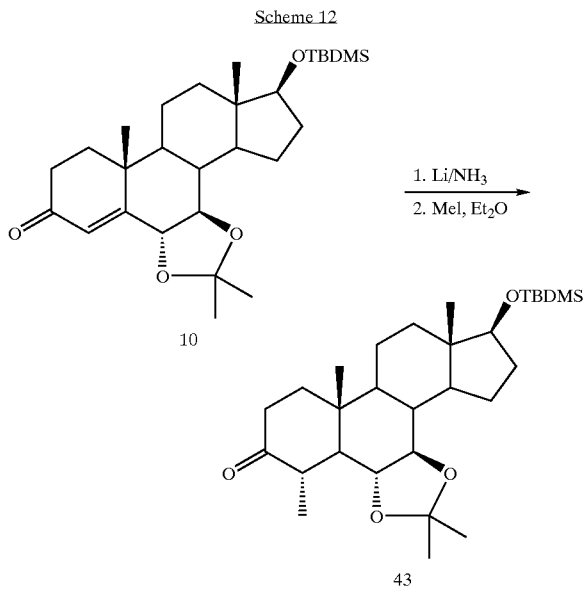

Alternatively, Compounds of Structure 6 may have carbonyl functionality at C4. Exemplary synthetic methodology to provide carbonyl functionality at C4 for a compound of Structure 6 is provided below. It should be recognized that the same or analogous synthetic methodology can be applied to provide carbonyl functionality at C4 for any compound of Structures 5–12 where a C4 carbonyl group is desired. As described below, the carbonyl functionality at C4 provides a convenient entry into compounds having a tertiary alcohol and a hydrocarbyl group at C4.

Compounds with a ketone (carbonyl) functionality at C4 may be prepared from compound 44 (which in turn is prepared from a deacetylation of acetate 147 from Scheme 44) by selectively tosylating, epoxidation and then epoxide ring opening followed by oxidation of the resultant 4β-hydroxyl functionality. For example, as illustrated in Scheme 13, treatment of the diol 44 with p-toluenesulfonyl-chloride in pyridine and DMF followed by reaction of the resultant tosylate 45 with tBuOK can introduce the 3β,4β-epoxide (compound 46). Treatment of the epoxide with Me₂CuLi gives the 3α-methyl derivative 47 and subsequent oxidation using, for example, PDC in CH₂Cl₂ gives the desired ketone (carbonyl) at C4 (compound 48). Epimerization to the 3β-methyl derivative can be achieved using tBuOK in tBuOH and subsequent treatment of the ketone with a methyl lithium in THF can provide the tertiary alcohol at C4 (compound 49).

Scheme 13

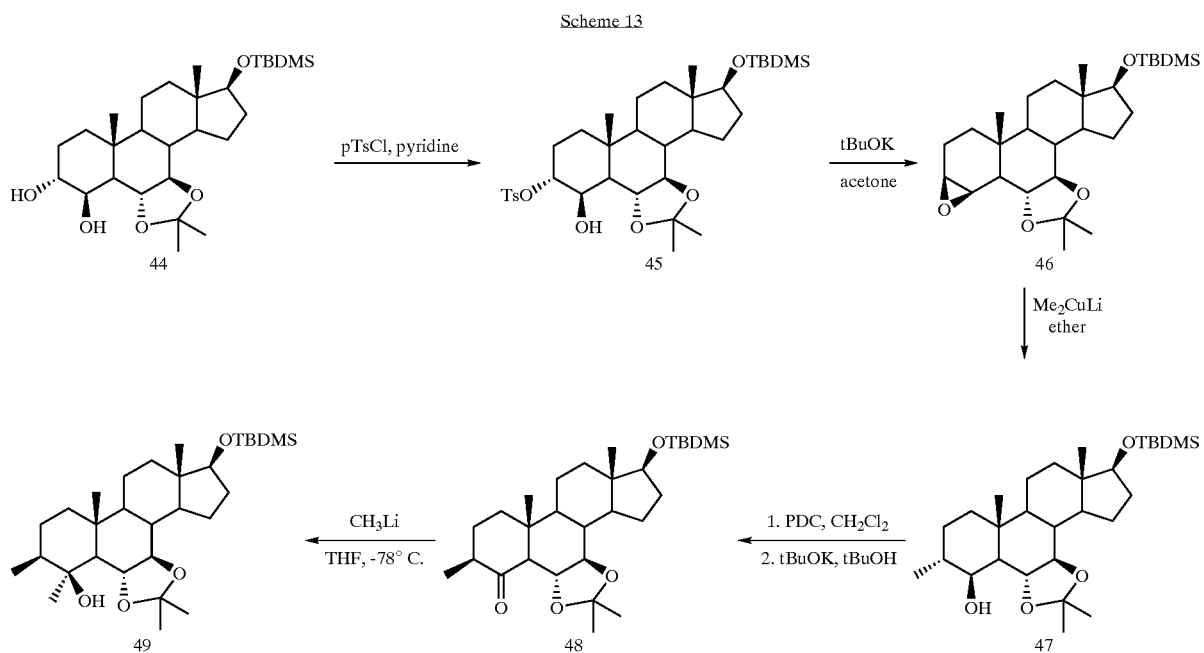

Alternatively, compounds of Structure 6 may have oxygen or hydrocarbon substitution at C5. Exemplary synthetic methodology to provide oxygen or hydrocarbon substitution at C5 for a compound of Structure 6 is provided below. It should be recognized that the same or analogous synthetic methodology can be applied to provide oxygen or hydrocarbon substitution at C5 for any compound of Structures 5–12 where C5 oxygen or hydrocarbon substitution is desired.

Epoxidation of compound 10 followed by ring opening can be used to generate a hydroxy and subsequently an alkoxy substitution at C5 of the carbon skeleton. For example, epoxidation of the double bond in compound 10 can yield the corresponding epoxide derivative 50 which may be readily converted to the tertiary hydroxyl compound 24 (Scheme 14 below). Subsequent reduction of compound 24 using NaBH$_4$ in THF and methylation using MeI in the presence of tBuOK in THF can give the diacetoxy compound 51 (Scheme 15 below). Alkyl substitution at C5 may be achieved using an appropriate alkyl copper lithium reagent. For example, treatment of compound 10 with (CH$_3$)$_2$CuLi in ether may produce the C5 methyl derivative 52 (Scheme 16).

Scheme 14

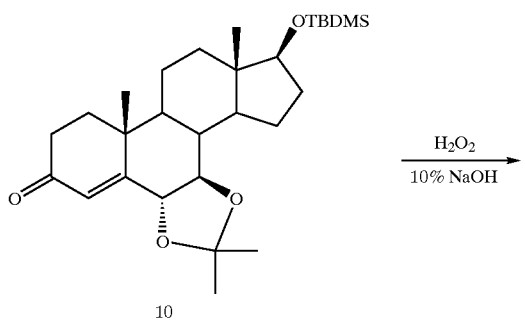

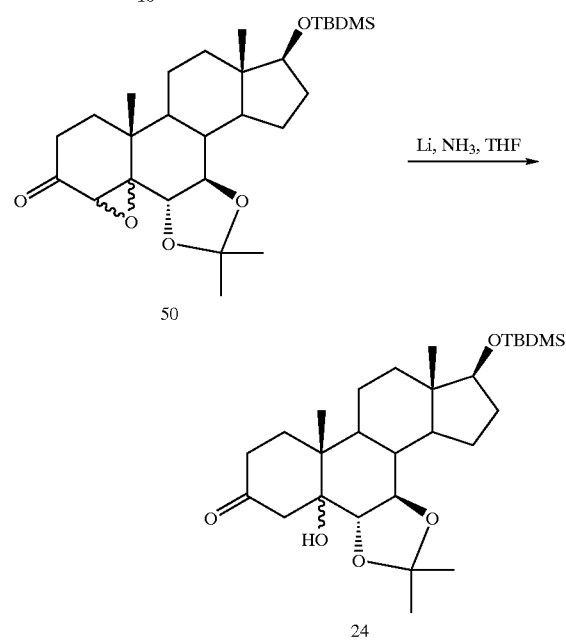

Scheme 15

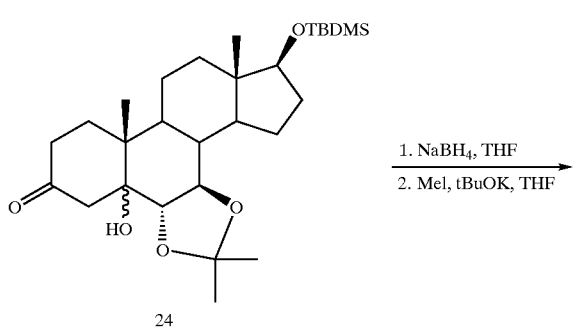

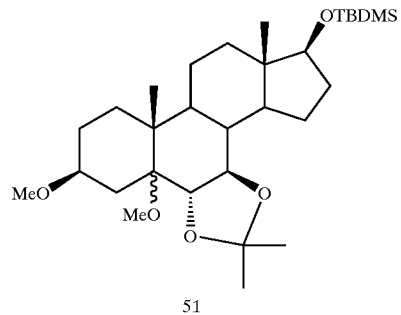

Scheme 16

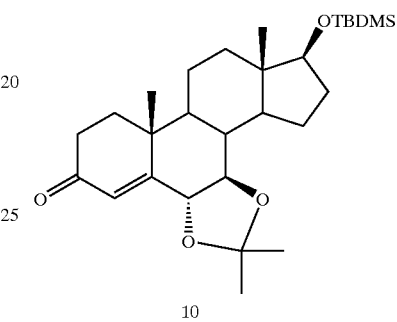

Compounds of Structure 6 may have oxygen and/or hydrocarbon substitution at C9. Exemplary synthetic methodology to provide oxygen and/or hydrocarbon substitution at C9 for a compound of Structure 6 is provided below. It should be recognized that the same or analogous synthetic methodology can be applied to provide oxygen and/or hydrocarbon substitution at C9 for any compound of Structures 5–12 where C9 oxygen and/or hydrocarbon substitution is desired.

Hydroxylation at the C9 position may be achieved by reaction of a $\Delta^{9,11}$ olefinic compound with m-chloroperbenzoic acid followed by reduction with LiAlH$_4$, as outlined in Scheme 17. For example, using this procedure, compound 53 (prepared from the dehydration of compound 60; e.g., NaH, CS$_2$, MeI, heat) may be used as the starting material to produce compound 54 which, upon reduction of the epoxide can produce the C9 hydroxyl-containing derivative 55. Subsequent reaction of the tertiary alcohol in compound 55 with dimethyl sulfate in aqueous sodium hydroxide may be used to give the corresponding alkoxy derivative, compound 56.

Scheme 17

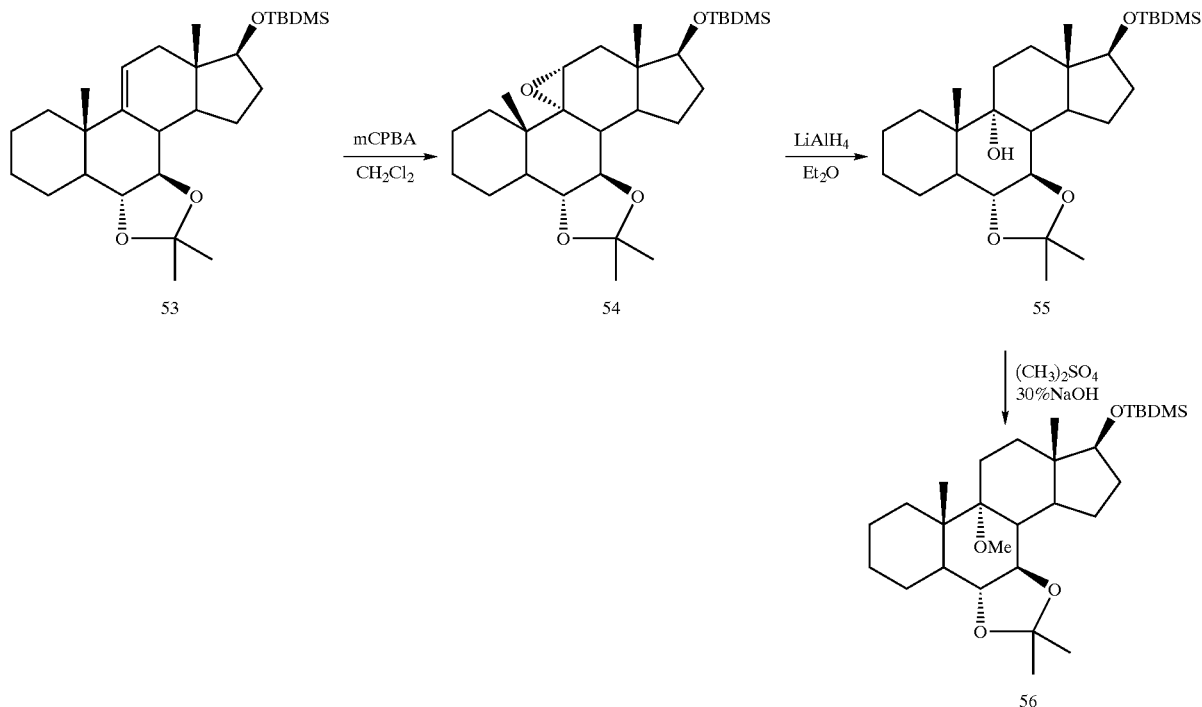

Alternatively, compounds of Structure 6 may have hydrocarbon substitution at C9. Exemplary synthetic methodology to provide hydrocarbon substitution at C9 for a compound of Structure 6 is provided below. It should be recognized that the same or analogous synthetic methodology can be applied to provide hydrocarbon substitution at C9 for any compound of Structures 5–12 where C9 hydrocarbon substitution is desired.

Cyclopropanation of compound 53 using $CH_2I_2$ and Zn—Cu followed by catalytic hydrogenation may provide the corresponding C9-alkyl substituted compound 57 (Scheme 18).

Scheme 18

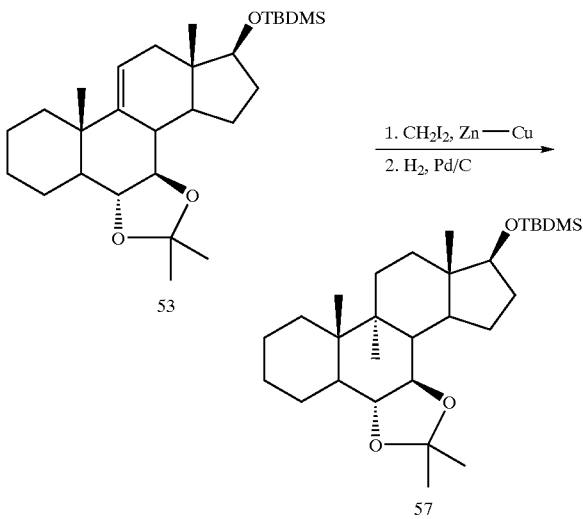

Alternatively, compounds of Structure 6 may have halide substitution at C9. Exemplary synthetic methodology to provide halide substitution at C9 for a compound of Structure 6 is provided below. It should be recognized that the same or analogous synthetic methodology can be applied to provide halide substitution at C9 for any compound of Structures 5–12 where C9 halide substitution is desired.

Introduction of a halogen atom at C9 can be achieved in a number of ways including reaction of a C9 tertiary alcohol (see, e.g., compound 55 in Scheme 17) with thionyl chloride. Thus, reaction of compound 55 with $SOCl_2$ in $CH_2Cl_2$, may be used to provide the chloro derivative 59 as shown in Scheme 19.

Scheme 19

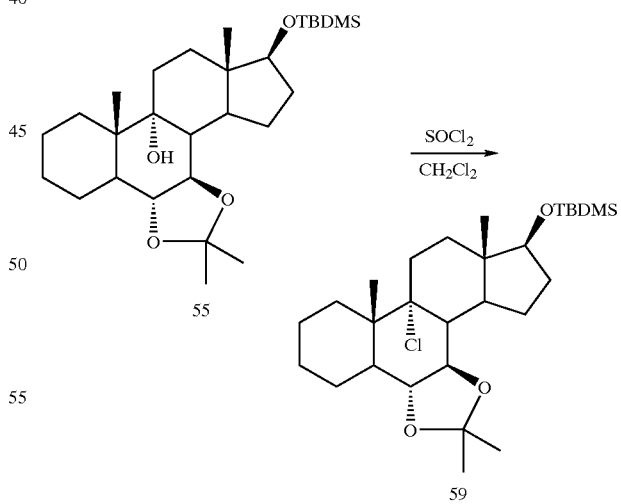

Compounds of Structure 6 preferably have a methyl substituent at C10. However, the C10 position may be derivatized so as to have many functional groups other than methyl. Exemplary synthetic methodology to provide oxygen and/or hydrocarbon substitution at C10 for a compound of Structure 6 is provided below. It should be recognized that the same or analogous synthetic methodology can be applied to provide oxygen and/or hydrocarbon substitution at C10 for any compound of Structures 5–12 where C10 oxygen and/or hydrocarbon substitution is desired.

The derivatization of the C10 position may be achieved via the route shown in Scheme 20. A 10β-hydroxy steroid 60 (prepared, for example, as outlined in Scheme 22 below) may be derivatized using nitrosyl chloride (NOCl) in pyridine to yield a nitrite derivative such as 61. Irradiation of the nitrite 61 then can lead to a mixture of the oximes 62 and 63. Compound 63 is reduced to the corresponding imine 64 by treatment with aqueous TiCl$_3$ in dioxane and acetic acid. The hemiacetal acetate 65 may be produced upon treatment of 64 with NaNO$_2$ in aqueous acetic acid. This can also lead to deprotection of the 6,7-hydroxyl groups. The acetonide can be reintroduced by reaction of the crude product with 2,2-dimethoxypropane and camphor sulfonic acid. Alkaline hydrolysis (NaOH, MeOH) to give the hydroxy aldehyde 66 is followed by protection of the secondary alcohol at C11 as the benzyl ether using BnBr, NaH in DMF to afford compound 67.

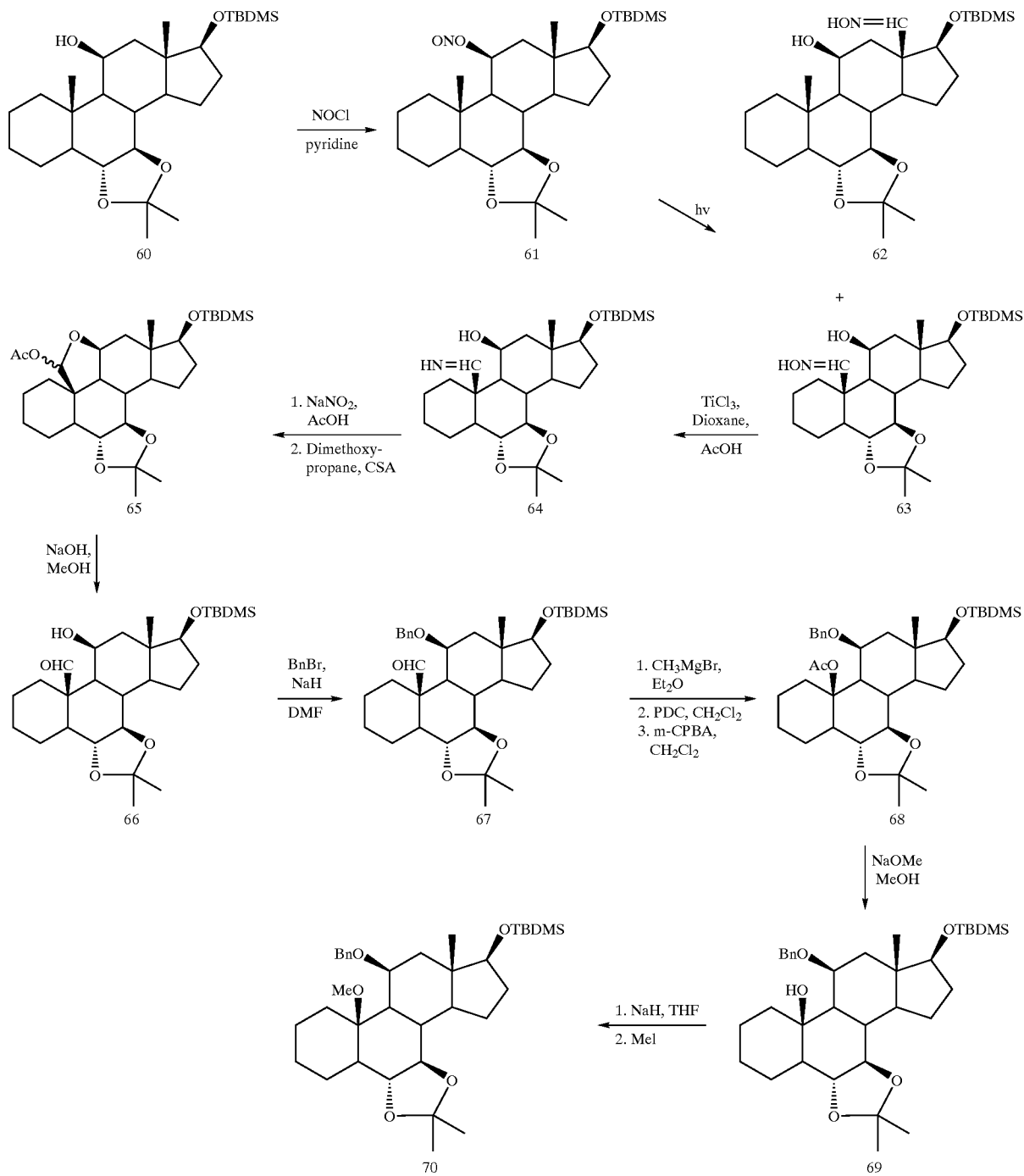

Scheme 20

A Grignard reaction of compound 67 with CH$_3$MgBr followed by PDC oxidation in CH$_2$Cl$_2$ then by a Bayer-Williger oxidation with m-chloroperbenzoic acid in methylene chloride can give the C10 acetoxy derivative 68. Removal of the acetate group may be accomplished with base, for example, sodium methoxide in methanol, to give the C10-β alcohol 69. This C10 hydroxyl group may then be further derivatized to the alkoxide analogue 70, using, for example, sodium hydride in THF followed by treatment with an alkylating agent such as methyl iodide. Alternatively, conversion of the C10 hydroxyl group in compound 69 to the corresponding chloride derivative 71 is achieved using a chlorinating agent, e.g., thionyl chloride, as shown in Scheme 21.

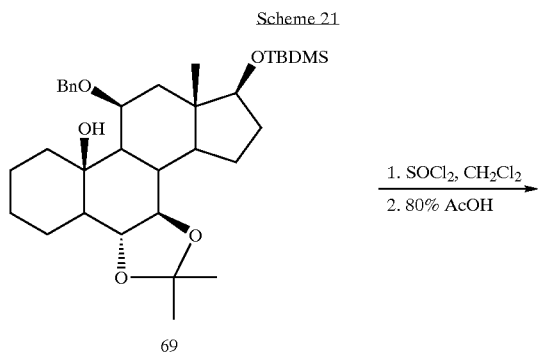

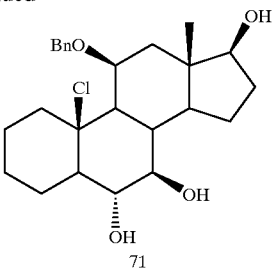

Compounds of Structure 6 may have oxygen and/or hydrocarbon substitution at C11. Exemplary synthetic methodology to provide oxygen and/or hydrocarbon substitution at C11 for a compound of Structure 6 is provided below. It should be recognized that the same or analogous synthetic methodology can be applied to provide oxygen and/or hydrocarbon substitution at C11 for any compound of Structures 5–12 where C11 oxygen and/or hydrocarbon substitution is desired.

The preparation of compounds of Structure 6 containing an oxygen function at the C11 position may be achieved according to the pathway shown in Scheme 22 from the commercially available starting material 72 and related compounds.

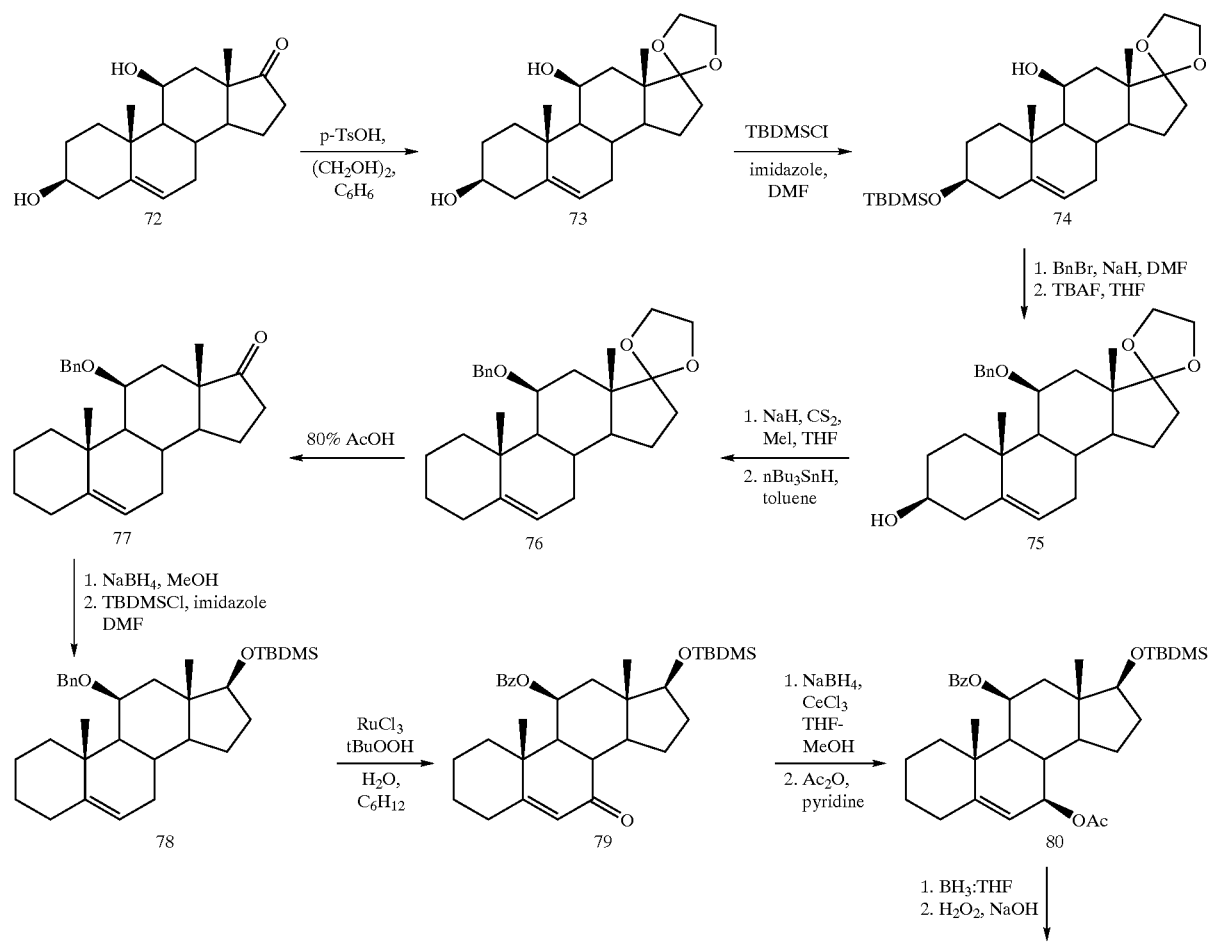

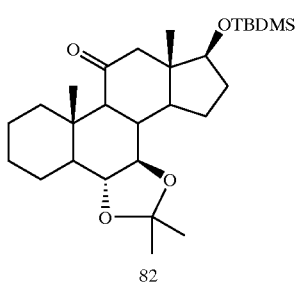 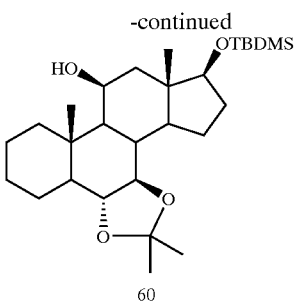 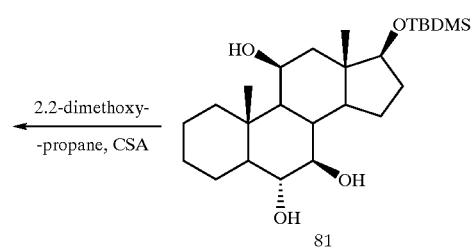

If starting with a steroid having a hydroxyl group in the A-ring, as in compound 75 (prepared from the commercially available compound 72 (Scheme 22)), removal of the C3 hydroxyl may be achieved using a two step procedure involving preparation of the methyl xanthate using NaH, $CS_2$ and $CH_3I$ in THF followed by $nBu_3SnH$ reduction and deprotection (80% AcOH) to yield compound 77. After reduction and protection of the C17 ketone using $NABH_4$ in methanol followed by TBDMSCl and imidazole in DMF, oxidation of the C7 position can be achieved using a number of oxidizing conditions such as $CrO_3$ and 3,5-dimethylpyrazole in $CH_2Cl_2$ or $RuCl_3$ and tBuOOH in $H_2O$ and cyclohexane. Subsequent reduction ($NaBH_4$, $CeCl_3$, THF-MeOH) of the C7 ketone and acetylation can provide the C7 acetoxy derivative 80. Hydroboration of compound 80 provides a product with the 6α,7β,11β-hydroxylation pattern as in triol 81. Protection of the 6α,7β hydroxyls in compound 81 using 2,2-dimethoxypropane in the presence of camphor sulfonic acid (CSA) followed by oxidation using PDC in $CH_2Cl_2$ gives compound 82 which contains the C11 ketone.

Compounds of Structure 6 may alternatively or additionally have hydrocarbon substitution at C11. Exemplary synthetic methodology to provide hydrocarbon substitution at C11 for a compound of Structure 6 is provided below. It should be recognized that the same or analogous synthetic methodology can be applied to provide hydrocarbon substitution at C11 for any compound of Structures 5–12 where C11 hydrocarbon substitution is desired.

Conversion of the compound 82 C11-ketosteroid to a quaternary alkyl center may be accomplished as shown in Scheme 23 below.

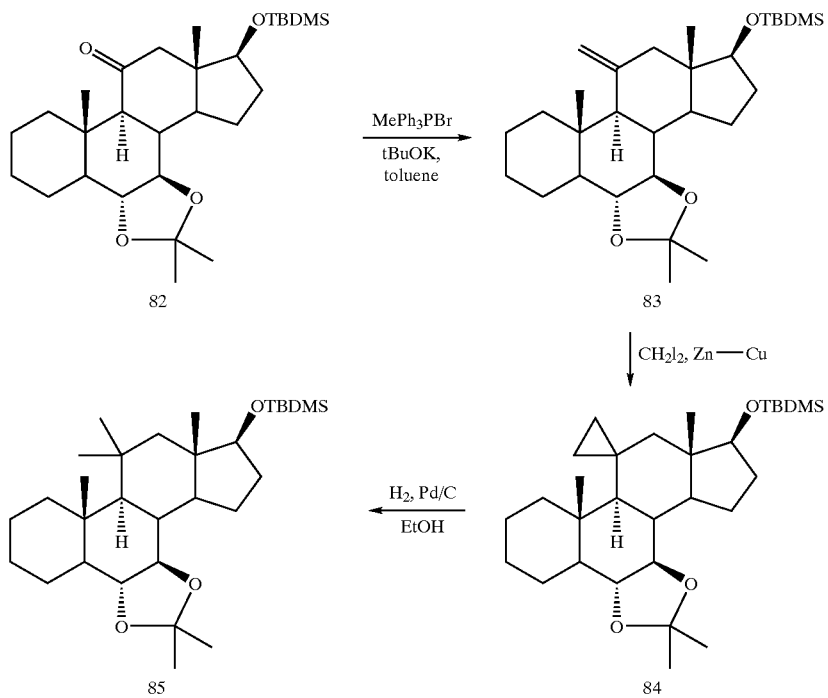

Thus, the C11-ketosteroid 82 in toluene may be added to a solution of methyl triphenylphosphonium bromide and tBuOK to afford compounds with a $\Delta^{11}$ carbon-carbon double bond such as 83. Subsequent treatment of the compound 83 with $CH_2I_2$, Zn—Cu may give the cyclopropyl derivative 84. Hydrogenation of the cyclopropane ring ($H_2$, Pd/C in ethanol) may give the dialkyl derivative 85. Other Wittig reagents may be employed to make analogous alkyl-substituted steroids.

Monoalkylation of the C11 position may be achieved by application of Wittig chemistry on compounds with a C11 ketone, as described above, followed directly by catalytic hydrogenation (as illustrated in Scheme 24). For example, catalytic hydrogenation ($H_2$, Pd/C in ethanol) on compound 83 affords the C11 methylated steroid 86.

Thus, halogenation of the C11 position may be achieved according to the route shown in Scheme 25. For example, treatment of compound 60 with a halogenating agent, e.g., thionyl chloride in $CH_2Cl_2$, gives the corresponding 11β-chloro derivative 87. In general, hydroxyl functionality may serve as a precursor to halide functionality.

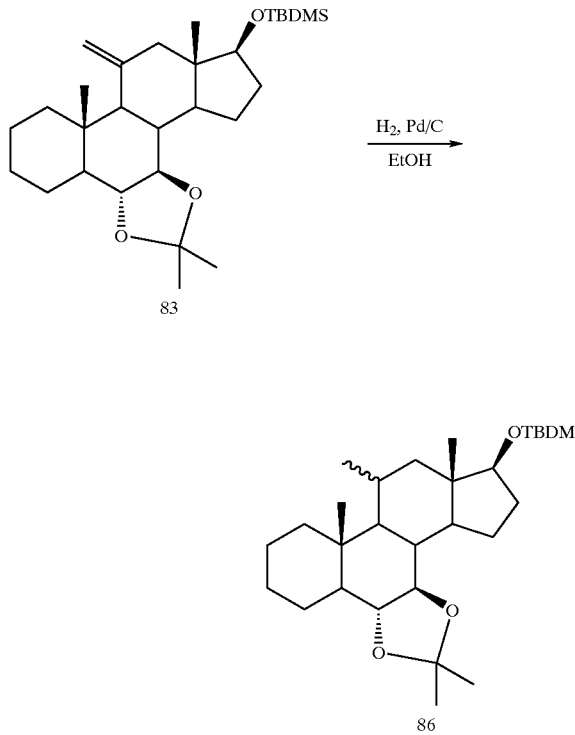

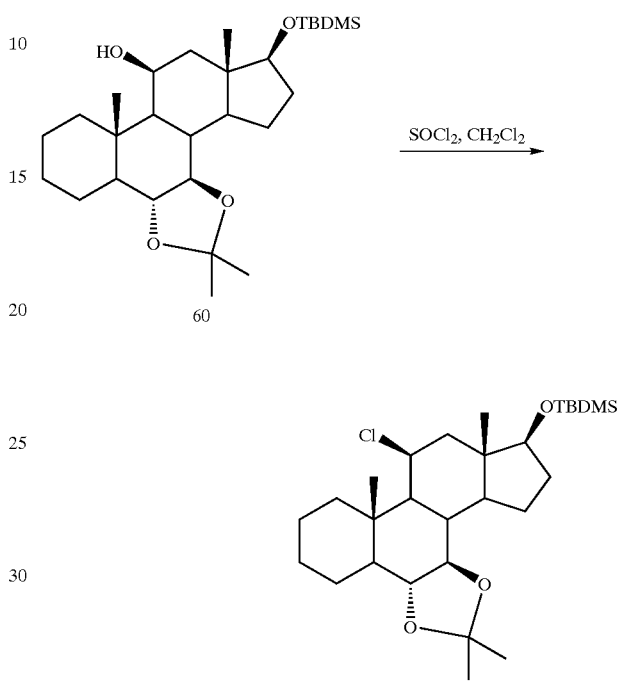

Compounds of Structure 6 may have halide substitution at C11. Exemplary synthetic methodology to provide halide substitution at C11 for a compound of Structure 6 is provided below. It should be recognized that the same or analogous synthetic methodology can be applied to provide halide substitution at C11 for any compound of Structures 5–12 where C11 halide substitution is desired.

Compounds of Structure 6 may have oxygen and/or hydrocarbon substitution at C12. Exemplary synthetic methodology to provide oxygen and/or hydrocarbon substitution at C12 for a compound of Structure 6 is provided below. It should be recognized that the same or analogous synthetic methodology can be applied to provide oxygen and/or hydrocarbon substitution at C12 for any compound of Structures 5–12 where C12 oxygen and/or hydrocarbon substitution is desired.

Placement of an oxygen function at the C12 position may be achieved as illustrated in Scheme 26.

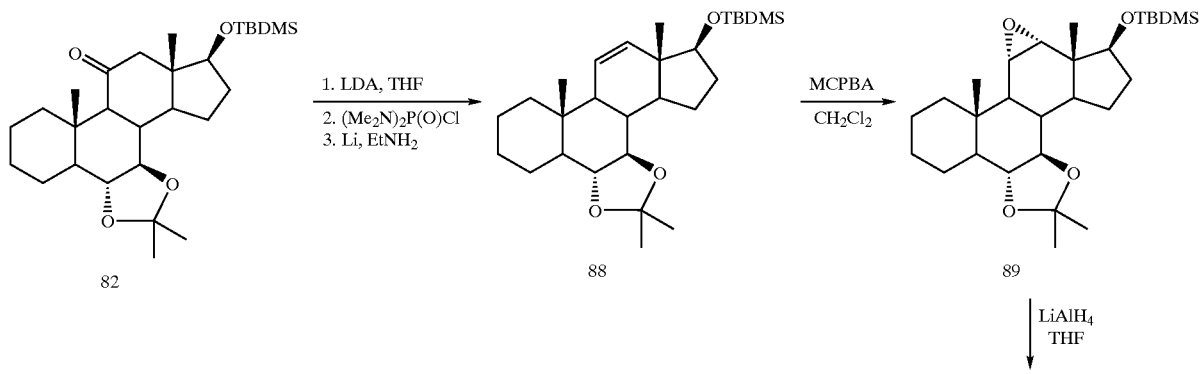

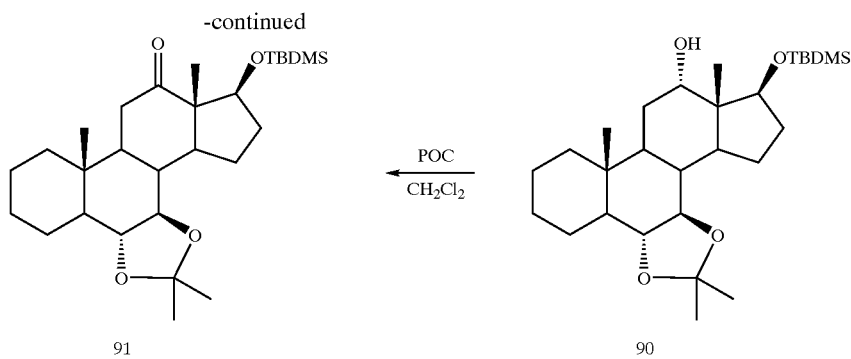

Thus, a C11 ketosteroid, such as compound 82, may be reacted with LDA in THF followed by trapping of the enolate anion with $(Me_2N)_2P(O)Cl$ followed by reduction of the enolphosphate using Li and $EtNH_2$ to provide a compound, such as 88, with a $\Delta^{11,12}$ carbon-carbon double bond. Epoxidation may be achieved using an epoxidizing agent, e.g., mCPBA in $CH_2Cl_2$, to give the corresponding 11α,12α-epoxide derivative 89. Subsequent $LiAlH_4$ reduction of the epoxide can form the 12α-hydroxy derivative (90) which can be oxidized using the appropriate oxidizing agent, for example, pyridinium dichromate (PDC) in methylene chloride to give the desired C12 ketosteroid 91.

Compounds of Structure 6 may have hydrocarbon substitution at C12. Exemplary synthetic methodology to provide hydrocarbon substitution at C12 for a compound of Structure 6 is provided below. It should be recognized that the same or analogous synthetic methodology can be applied to provide hydrocarbon substitution at C12 for any compound of Structures 5–12 where C12 hydrocarbon substitution is desired.

Alkyl groups, such as methyl, may be introduced into the C12 position as shown in Scheme 27 below. The C11 ketosteroid 82, (prepared, for example, according to Scheme 22), and a strong base, e.g., lithium diisopropylamide in THF, are combined and treated with an alkylating agent, e.g., methyl iodide, to afford the C12 methylated product 92. At this stage, the C11 ketone can be removed using a number of methods including those described in connection with Scheme 26 to give the monomethylated product 93. Further treatment with strong base and an alkylating agent, e.g., lithium diisopropylamide and methyl iodide, gives the C12 dimethylated product 94. Again, this compound may be subjected to reducing conditions to remove the C11 ketone group thus giving the C12 dimethyl derivative 95.

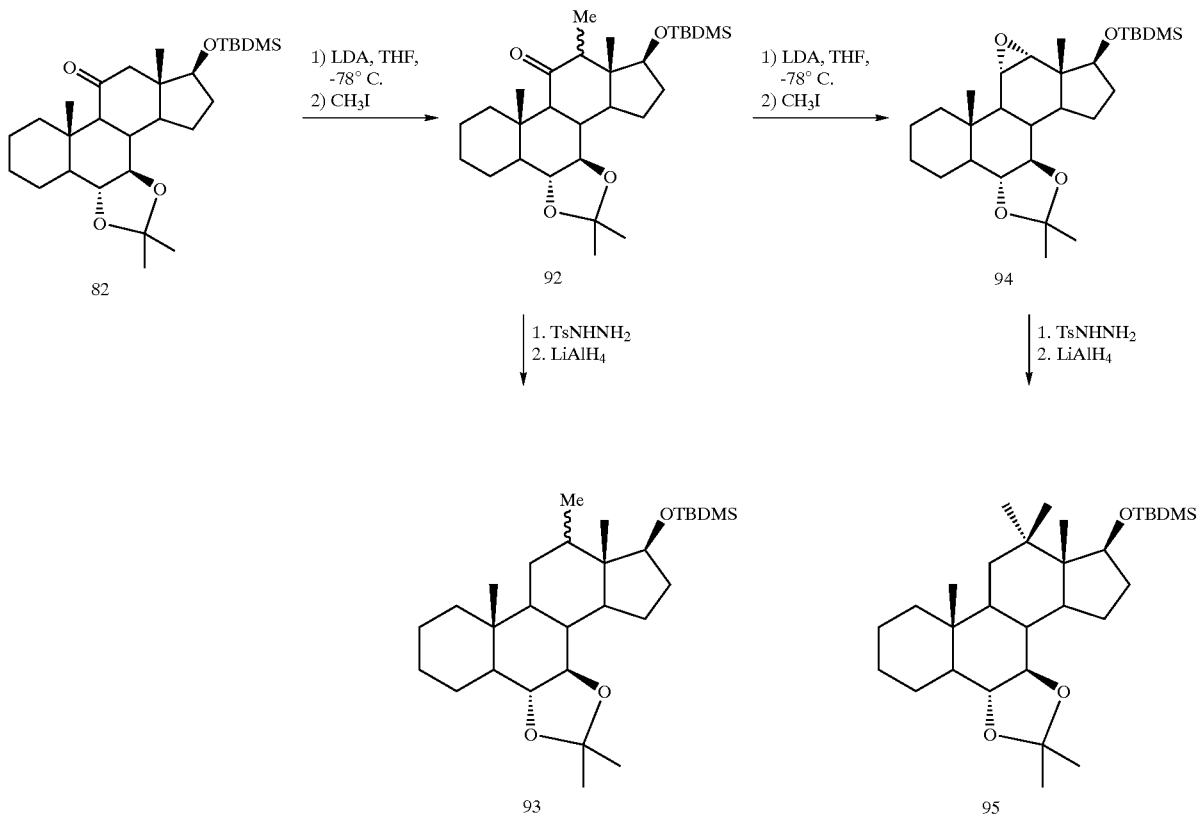

Scheme 27

Compounds of Structure 6 may have oxygen and hydrocarbon substitution at C12. Exemplary synthetic methodology to provide oxygen and hydrocarbon substitution at C12 for a compound of Structure 6 is provided below. It should be recognized that the same or analogous synthetic methodology can be applied to provide oxygen and hydrocarbon substitution at C12 for any compound of Structures 5–12 where C12 oxygen plus hydrocarbon substitution is desired.

Scheme 28 shows the preparation of a tertiary alcohol at the C12 position from the corresponding C12 ketone. In Scheme 28, the C12 ketone 91 is treated with a alkyl lithium reagent, e.g., methyl lithium in diethyl ether, to give the desired tertiary alcohol 96.

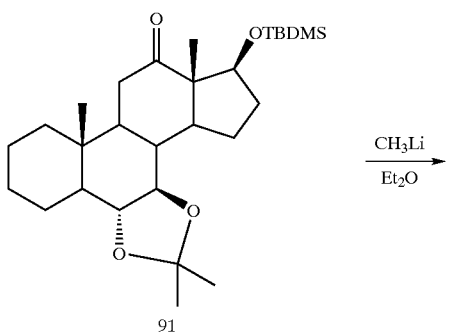

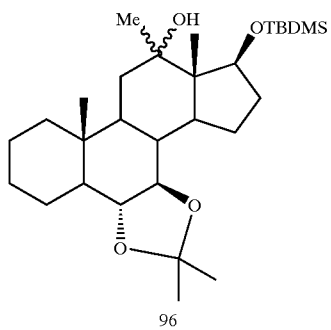

Compounds of Structure 6 may have carbon, oxygen or halogen, to name a few atoms, bonded to C13. Exemplary synthetic methodology to provide such substitution at C13 for a compound of Structure 6 is provided below. It should be recognized that the same or analogous synthetic methodology can be applied to provide the same or analogous substitution at C13 for any compound of Structures 5–12 where such C13 substitution is desired.

Substituents at the C13 position may be introduced according to the pathway shown in Scheme 29 below. In a fashion similar to that previously described in Scheme 20, the C13 position can be substituted with a hydrocarbyloxy moiety, e.g., a methoxy moiety. Thus, the oxime derivative 62, (prepared, for example, as described in Scheme 20), is reduced to the corresponding imine 97 by treatment with aqueous TiCl$_3$ in dioxane and acetic acid. The hemiacetal acetate 98 may be produced upon treatment of compound 97 with NaNO$_2$ in aqueous acetic acid. Alkaline hydrolysis (NaOH, MeOH) to give the hydroxy aldehyde 99 is followed by protection of the secondary alcohol at C11 as the benzyl ether using BnBr, NaH in DMF to afford compound 100.

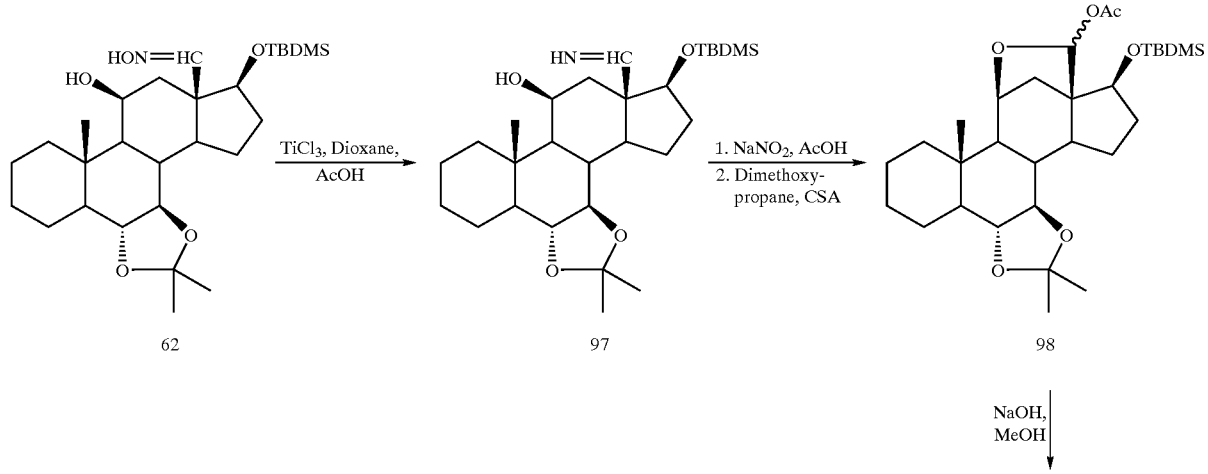

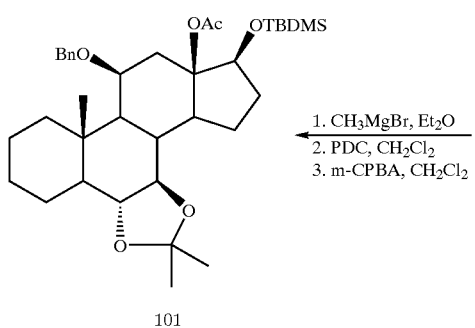

101

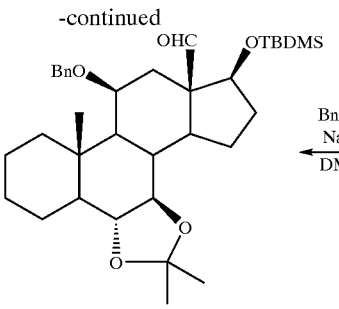

100

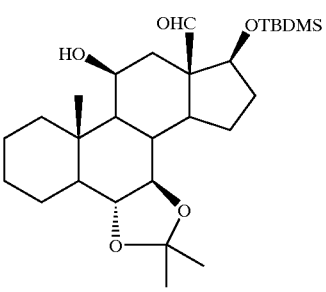

99

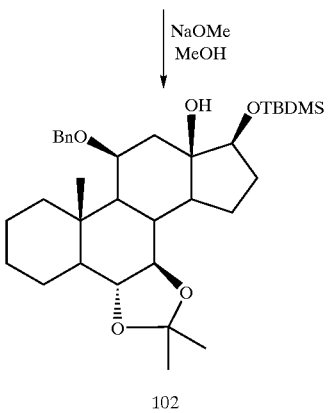

102

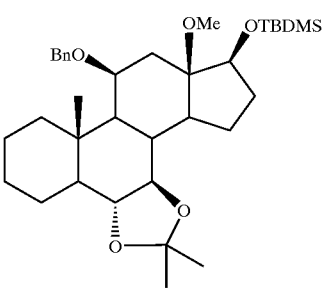

103

A Grignard reaction on compound 100 may be used to introduce additional functionality at C13. For example, treatment of compound 100 with methyl magnesium bromide, followed by oxidation of the resulting C13 secondary alcohol gives the methyl ketone substituent at C13. This may be oxidized, e.g., using Bayer-Williger oxidation with m-chloroperbenzoic acid in methylene chloride, to give the C13 acetoxy derivative 101. This ester may be hydrolyzed by treatment with sodium methoxide in methanol to produce the tertiary alcohol 102. Subsequent reaction of the alcohol with sodium hydride in THF followed by its quenching with methyl iodide may be used to produce the C13 mrethoxysteroid 103. Other alkylating agents could be used to prepare other hydrocarbyloxy derivatives. The C13 hydroxyl moiety may then be converted to a halide, for example a chloride, by the reaction of alcohol 102 with thionyl chloride, thus affording the C13 chlorosteroid 104, as shown in Scheme 30 below.

Scheme 30

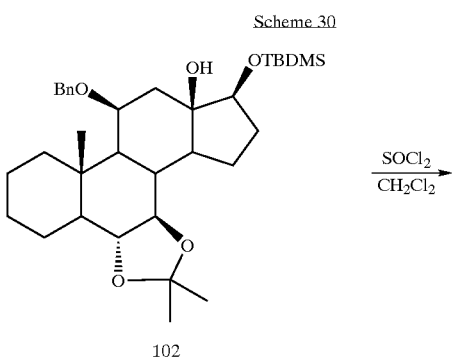

102

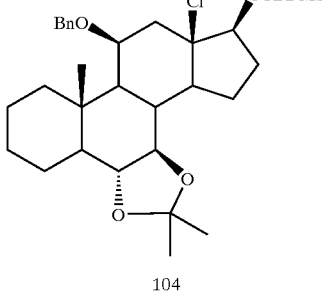

104

Compounds of Structure 6 may have hydrocarbon substitution at C14. Exemplary synthetic methodology to provide hydrocarbon substitution at C14 for a compound of Structure 6 is provided below. It should be recognized that the same or analogous synthetic methodology can be applied to provide hydrocarbon substitution at C14 for any compound of Structures 5–12 where C14 hydrocarbon substitution is desired.

For example, introduction of an alkyl group at C14 of the steroid carbon skeleton could be accomplished by alkylation at the C14 position. One approach to achieve such an alkylation is shown in Scheme 31 below. Initially, preparation of the enone 107 can be accomplished by deprotection (TBAF, THF) of compound 105 followed by oxidation of the secondary alcohol using PDC in $CH_2Cl_2$ to give the C17 ketone derivative 106. Conversion of the ketone 106 to the enone 107 may be achieved using isopropenyl acetate and pTsOH to produce the intermediate enol acetate followed by production of the enone using reagents set forth in Scheme 31. This is followed by conversion of the enone 107 to the silyl enol ether 108 by reacting enone 107 with lithium diethylamide in THF followed by reaction of the resultant anion with triisopropylsilyl triflate (TIPSOTf). The cyclopropane derivative 109 is then prepared from silyl ether 108 using $CH_2I_2$ and Zn—Cu. Deprotection of the silyl enol ether and cleavage of the cyclopropane ring is achieved using TBAF in THF followed by tBuOK in DMSO and aqueous work-up procedures.

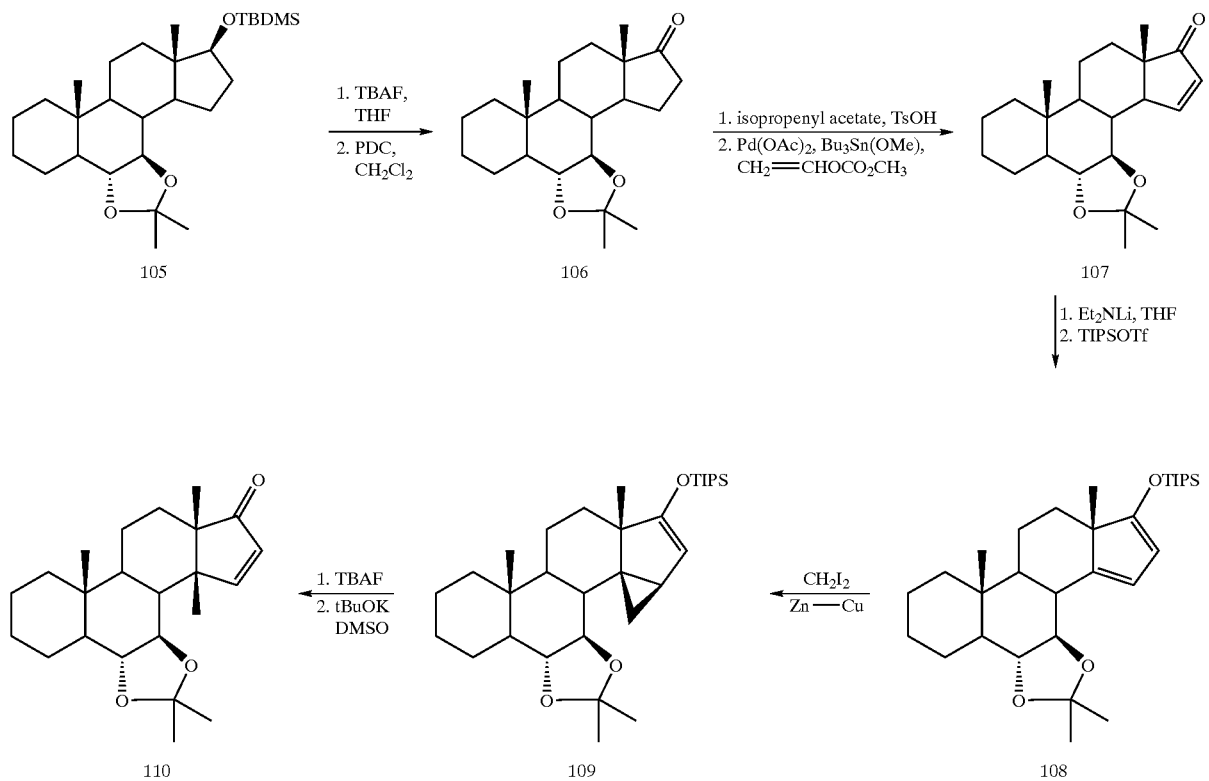

Compounds of Structure 6 may have oxygen and/or hydrocarbon substitution at C15. Exemplary synthetic methodology to provide oxygen and/or hydrocarbon substitution at C15 for a compound of Structure 6 is provided below. It should be recognized that the same or analogous synthetic methodology can be applied to provide oxygen and/or hydrocarbon substitution at C15 for any compound of Structures 5–12 where C15 oxygen and/or hydrocarbon substitution is desired.

For example, introduction of an oxygen functionality at C15 of the steroid carbon skeleton could be accomplished by Michael addition type chemistry using any of a number of alkoxide anions. As outlined in Scheme 32 below, the 4-methoxybenzyloxy compound 111 (a representative C15-hydrocarbyloxy steroid derivative of the invention, where the 4-methoxybenzyloxy group (MPMO) serves as an hydroxyl protecting group) could be produced by reacting the enone 107 with 4-methoxybenzyl alcohol and base (e.g., powdered KOH). The 4-methoxybenzyl protecting group may be removed under oxidizing conditions, e.g., by 2,3-dichloro-5,6-dicyano-1,4-benzoquinone (DDQ) oxidation, to yield the C15 hydroxyl group (compound 112). When this is followed by oxidation of the secondary alcohol (using, for example, PDC in $CH_2Cl_2$), the corresponding C15 ketone (compound 113) may be produced.

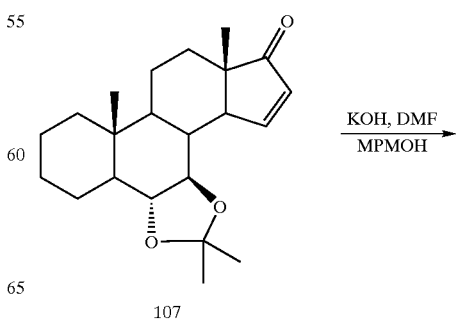

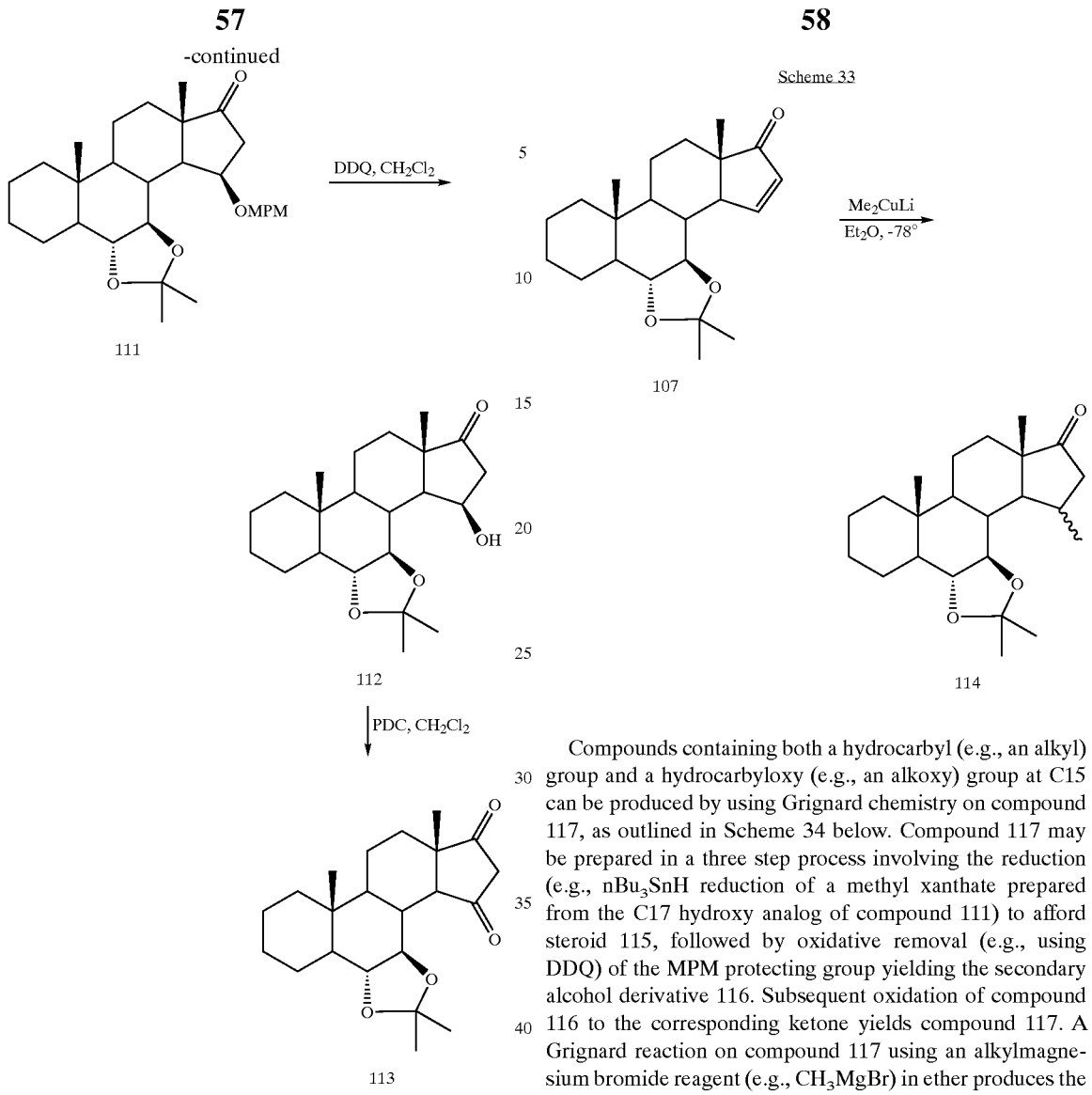

Compounds containing an alkyl group at C15 may also be produced by a Michael type conjugate addition. For example, reaction of compound 107 with an organolithium cuprate (e.g., Me₂CuLi) in Et₂O may be used to produce the methyl derivative 114 as shown in Scheme 33.

Compounds containing both a hydrocarbyl (e.g., an alkyl) group and a hydrocarbyloxy (e.g., an alkoxy) group at C15 can be produced by using Grignard chemistry on compound 117, as outlined in Scheme 34 below. Compound 117 may be prepared in a three step process involving the reduction (e.g., nBu₃SnH reduction of a methyl xanthate prepared from the C17 hydroxy analog of compound 111) to afford steroid 115, followed by oxidative removal (e.g., using DDQ) of the MPM protecting group yielding the secondary alcohol derivative 116. Subsequent oxidation of compound 116 to the corresponding ketone yields compound 117. A Grignard reaction on compound 117 using an alkylmagnesium bromide reagent (e.g., CH₃MgBr) in ether produces the tertiary alcohol 118. Methylation of the tertiary alcohol in 118 with an alkylating agent (e.g., CH₃I (note that an acylating agent can be used in place of an alkylating agent, in Scheme 34 and in every Scheme herein having an alkylating agent)) in the presence of base (e.g., K₂CO₃) yields the tertiary methoxy compound 119.

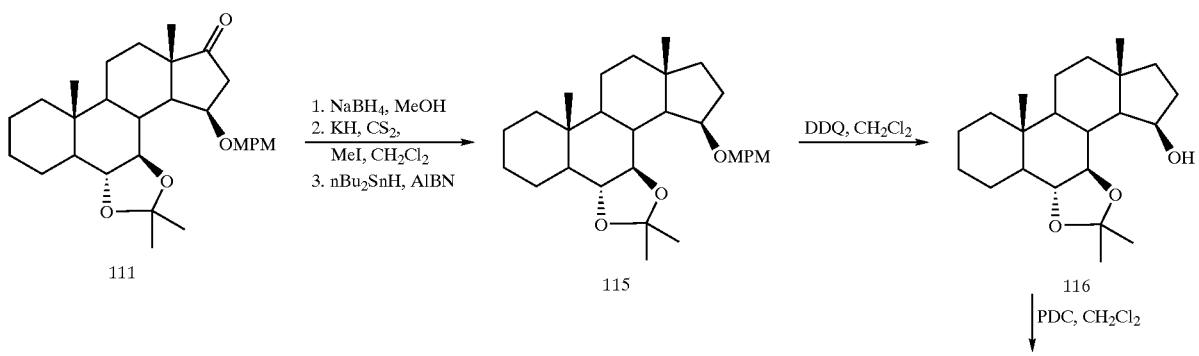

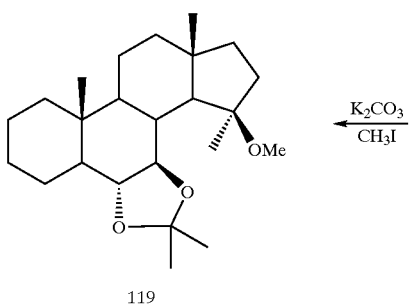
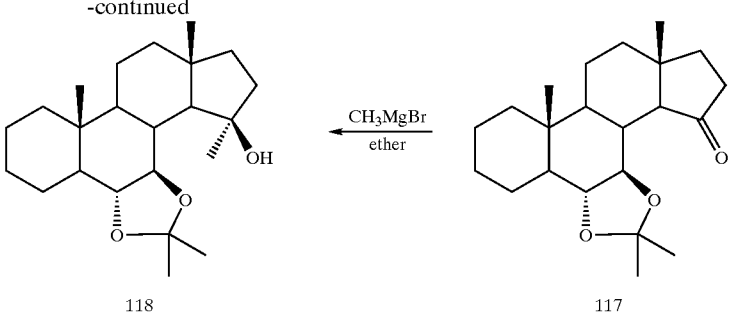

Compounds of Structure 6 may have oxygen and/or hydrocarbon substitution at C16. Exemplary synthetic methodology to provide oxygen and/or hydrocarbon substitution at C16 for a compound of Structure 6 is provided below. It should be recognized that the same or analogous synthetic methodology can be applied to provide oxygen and/or hydrocarbon substitution at C16 for any compound of Structures 5–12 where C16 oxygen and/or hydrocarbon substitution is desired.

Introduction of a tertiary hydroxyl group at C16 of the steroid carbon skeleton may be accomplished using Grignard chemistry on compound 121 as shown in Scheme 35 below. The ketone 121 may be produced via hydroboration of the olefin (using, for example, $Sia_2BH$ in THF then aqueous NaOH, $H_2O_2$) of compound 308 (prepared from compound 106 as outlined in Scheme 35) to afford alcohol 120. The desired C16 ketone functionality may then generated by oxidizing the secondary alcohol at C16, using, for example, PDC in $CH_2Cl_2$, to yield compound 121. Reaction of the ketone 121 with a Grignard reagent, e.g., $CH_3MgBr$ in ether, may be used to produce the corresponding tertiary alcohol derivative, in this example, compound 122. The corresponding alkoxy derivative 123 could then be produced directly from compound 122 using the appropriate base and alkyl halide.

Scheme 35

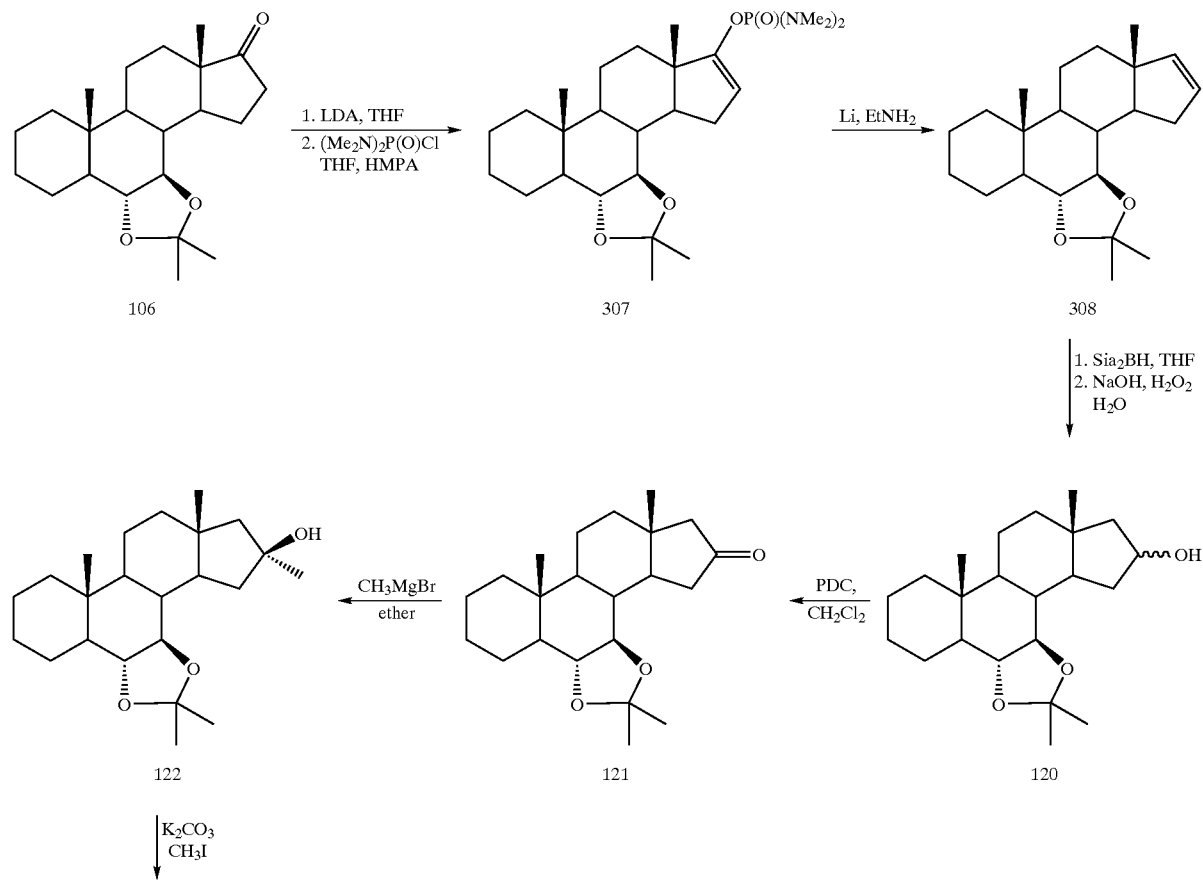

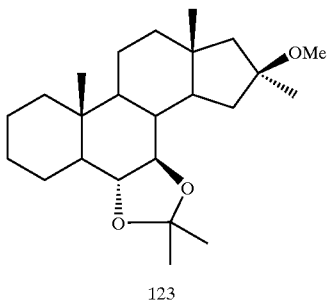

123

Alkoxy groups at C16 may be produced directly from the corresponding C16 hydroxyl compound. For example, compound 124 may be produced by reacting compound 120 with an reagent, e.g., $CH_3I$, and a base, e.g., $K_2CO_3$ (Scheme 36).

Scheme 36

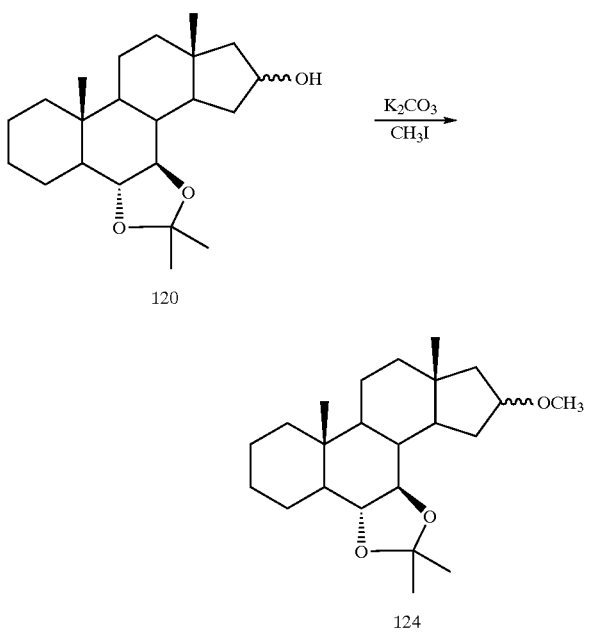

120

124

C16 alkyl groups may be introduced by the direct alkylation of compounds that contain a C17 carbonyl. For example, reaction of compound 106 with $CH_3I$ and LDA (other strong bases and alkylating agents could be used) in THF yields the C16 methyl compound 125 (Scheme 37).

Scheme 37

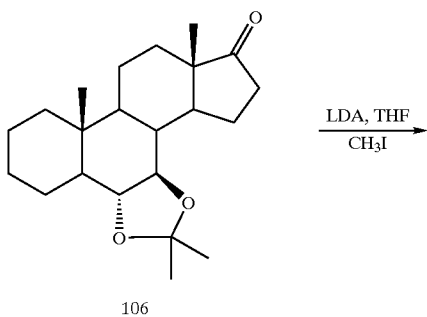

106

-continued

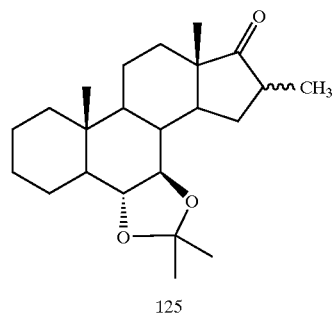

125

Compounds of Structure 6 have oxygen and/or hydrocarbon substitution at C17, including tertiary alcohol and hydroxyl functionality. Exemplary synthetic methodology to provide tertiary alcohol and hydroxyl substitution at C17 for a compound of Structure 6 is provided below. It should be recognized that the same or analogous synthetic methodology can be applied to provide tertiary alcohol and hydroxyl substitution at C17 for any compound of Structures 5–12 where C17 tertiary alcohol or hydroxyl substitution is desired.

Thus, Grignard chemistry similar to that described in Scheme 34 may be used to add a tertiary alcohol functionality to the C17 position. For example, as outlined in Scheme 38 below, compound 106 may be reacted with $CH_3MgBr$ in ether to yield the tertiary alcohol derivative 126. Methylation of the resultant tertiary alcohol gives the corresponding C17 methoxy compound 127. Of course, other alkylating agents could be used to provide a wide range of hydrocarbyloxy compounds.

Scheme 38

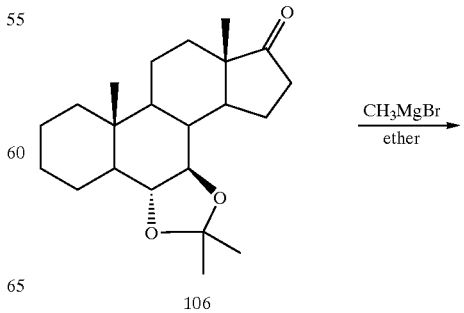

106

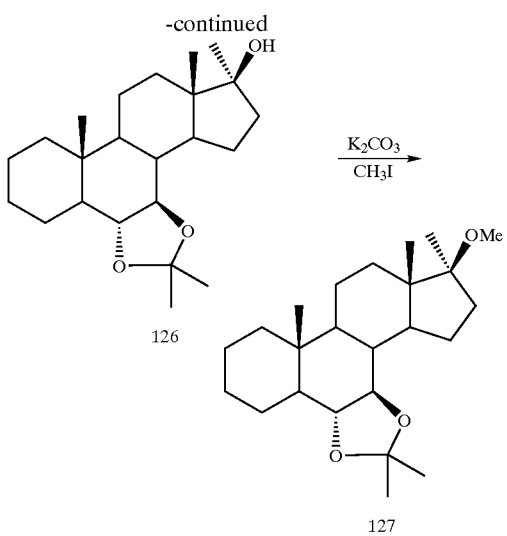

In an aspect of the present invention, C5 stereodefined steroids having hydroxylation at C6 and C7, a 5α hydrogen and no oxygen atom bonded to C3 is provided. In one embodiment, the stereodefined steroid has the Structure 7, including individual enantiomeric or geometric isomers thereof and further including a solvate or pharmaceutically acceptable salt thereof. Structure 7 is defined as follows:

A compound of the formula

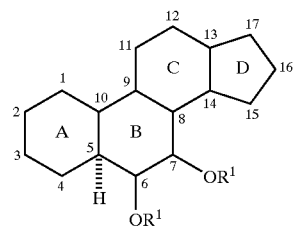

including pharmaceutically acceptable salts and solvates thereof, wherein:

- each of C1, C2, C4, C11, C12, C15, C16 and C17 is independently substituted with
  (a) one of: $=O$, $=C(R^4)(R^4)$, $—C(R^4)(R^4)(C(R^4)-(R^4))_n—$ and $—(O(C(R^4)(R^4))_nO)—$ wherein n ranges from 1 to about 6; or
  (b) two of the following, which are independently selected: $—X$, $—R^4$ and $—OR^1$;
- each of C8, C9, C10, C13 and C14 is independently substituted with one of $—X$, $—R^4$ or $—OR^1$;
- C3 is substituted with one of $=C(R^4)(R^4)$ and $—C(R^4)(R^4)(C(R^4)(R^4))_n—$ wherein n ranges from 1 to about 6, or two of $—X$, and $—R^4$;
- the A, B, C and D rings may independently be fully saturated, partially saturated or fully unsaturated;
- $R^1$ is H or a protecting group such that $—OR^1$ is a protected hydroxyl group, where vicinal $—OR^1$ groups may together form a cyclic structure which protects vicinal hydroxyl groups, and where geminal $—OR^1$ groups may together form a cyclic structure which protects a carbonyl group, with the proviso that either or both of $—OR^1$ at C6 and C7 represent a carbonyl or protected carbonyl group;
- $R^4$ at each occurrence is independently selected from H and $C_{1-30}$ organic moiety that may optionally contain at least one heteroatom selected from the group consisting of boron, halogen, nitrogen, oxygen, silicon and sulfur; where two geminal $R^4$ groups may together form a ring with the carbon atom to which they are both bonded; and
- X represents fluoride, chloride, bromide and iodide.

In a preferred embodiment of compounds of Structure 7, C3 is not bonded to an oxygen atom. In another preferred embodiment, when C3 is substituted with two hydrogen atoms then C17 is not substituted with either $—CH(CH_3)(CH_2)_3CH(CH_3)_2$ or $—CH(CH_3)(CH_2)2C(=O)OCH_3$.

Compounds of Structure 7 have hydroxylation at C6 and C7 and a 5α hydrogen. A synthetic sequence for the preparation of compounds having these structural features has been set forth above, in Scheme 2, which shows the preparation of compound 11. While compound 11 has an oxygen atom bonded to C3, and is thus not a representative compound of Structure 7, compound 11 can be converted to a compound of Structure 7. Thus, as shown in Scheme 39 below, compound 11 may be reduced to compound 128, where lithium in liquid ammonia/t-butanol may be used to afford the desired reduction. Hydrogenation of compound 128 can provide compound 105, having a $—CH_2—$ group at C3 as also shown in Scheme 39.

Scheme 39

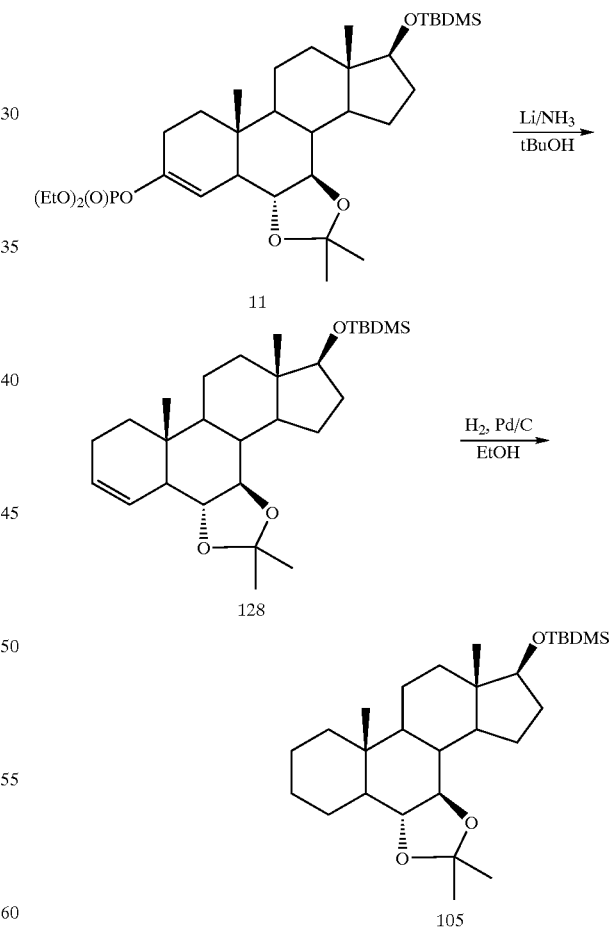

As illustrated in Scheme 40, compound 128 may alternatively be converted to additional compounds of Structure 7. Thus, the C17 protected hydroxyl group of compound 128 may be deprotected to yield compound 129, and then the C17 hydroxyl group of compound 129 may be oxidized to a C17 carbonyl group as in compound 106.

Scheme 40

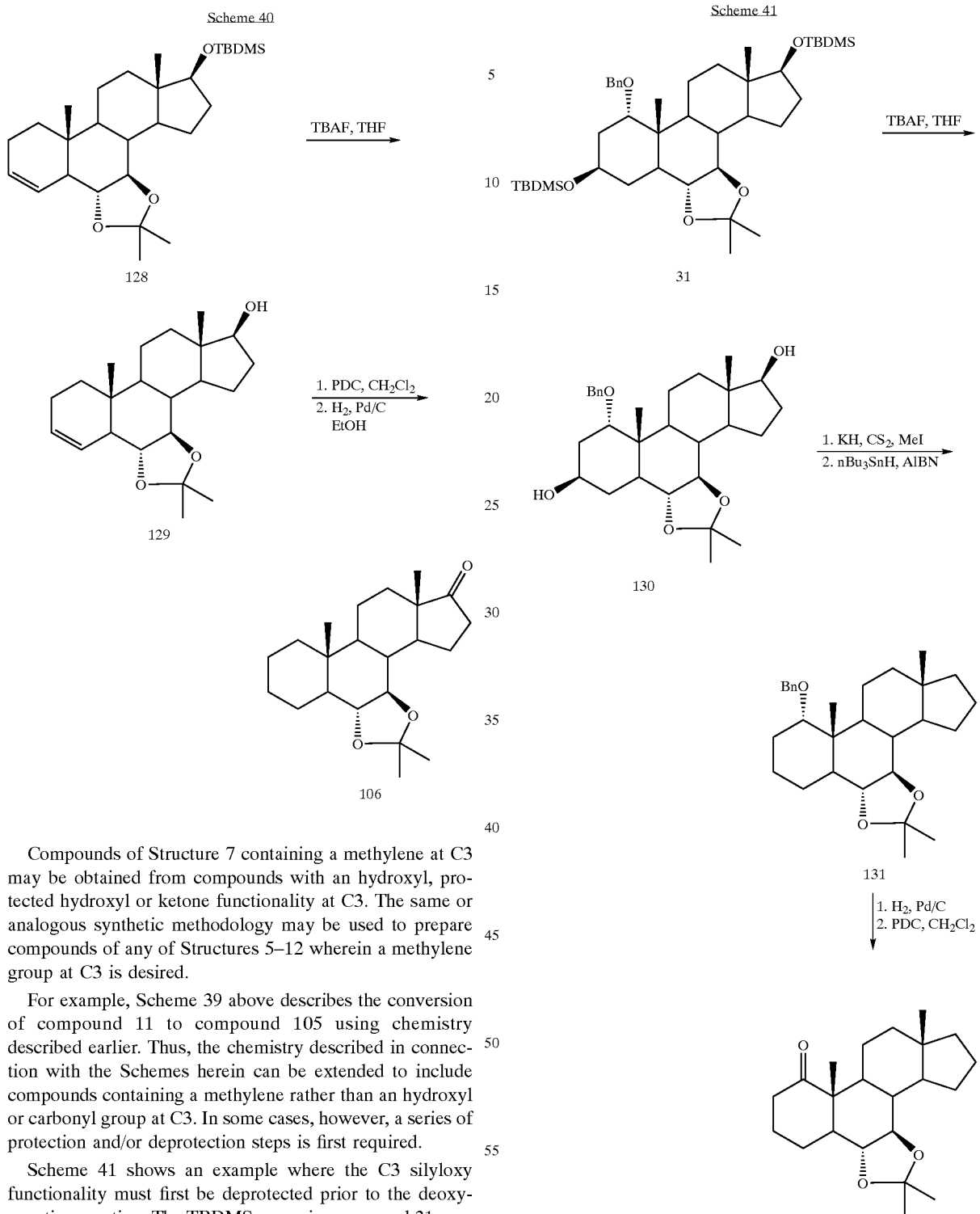

Compounds of Structure 7 containing a methylene at C3 may be obtained from compounds with an hydroxyl, protected hydroxyl or ketone functionality at C3. The same or analogous synthetic methodology may be used to prepare compounds of any of Structures 5–12 wherein a methylene group at C3 is desired.

For example, Scheme 39 above describes the conversion of compound 11 to compound 105 using chemistry described earlier. Thus, the chemistry described in connection with the Schemes herein can be extended to include compounds containing a methylene rather than an hydroxyl or carbonyl group at C3. In some cases, however, a series of protection and/or deprotection steps is first required.

Scheme 41 shows an example where the C3 silyloxy functionality must first be deprotected prior to the deoxygenation reaction. The TBDMS group in compound 31 may be removed using TBAF in THF. Preparation of the methyl xanthate derivative of compound 130 using KH, $CS_2$ and MeI is followed by $nBu_3SnH$ reduction gives the compound (131) containing a methylene group at C3 and a protected hydroxyl group at C1. Oxidation to the C1 ketone is then achieved by removal of the C1 protecting group followed by using a suitable oxidizing agent, e.g., PDC in $CH_2Cl_2$, to give compound 132.

Compounds of Structures 5–12, including Structure 7, having C3 alkyl functionality may be obtained by Wittig chemistry (prepared from the C3 ketone as described in connection with Scheme 11). A number of Wittig reagents can be used for this purpose giving rise to substituents with various chain lengths and branching.

In an aspect of the present invention, demethylated steroids are provided which have oxygen and/or hydrocarbon substitution at C6 and C7, however do not have methyl groups at both of C10 and C13. In one embodiment, the demethylated steroid has the Structure 8, including individual enantiomeric or geometric isomers thereof, and further including a solvate or pharmaceutically acceptable salt thereof. Structure 8 is defined as follows:

A compound of the formula

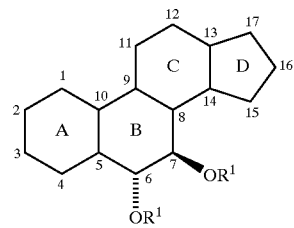

including pharmaceutically acceptable salts and solvates thereof, wherein:

each of C1, C2, C3, C4, C11, C12, C15, C16 and C17 is independently substituted with
(a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6; or
(b) two of the following, which are independently selected: —X, —R$^4$ and —OR$^1$;

each of C5, C8, C9, C10, C13 and C14 is independently substituted with one of —X, —R$^4$ or —OR$^1$;

with the provisos that (a) C10 and C13 are not simultaneously substituted with methyl, and (b) when C10 is substituted with methyl, then C14 is not substituted with a methyl;

the A, B, C and D rings may independently be fully saturated, partially saturated or fully unsaturated;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represent a carbonyl or protected carbonyl group;

R$^4$ at each occurrence is independently selected from H and C$_{1-30}$ organic moiety that may optionally contain at least one heteroatom selected from the group consisting of boron, halogen, nitrogen, oxygen, silicon and sulfur; where two geminal R$^4$ groups may together form a ring with the carbon atom to which they are both bonded; and X represents fluoride, chloride, bromide and iodide.

In a preferred embodiment, compounds of Structure 8 do not have aromatic A rings.

A number of examples of compounds containing substituents other than methyl at C10 or C13 are described herein in connection with Schemes 20, 29 and 30. The substituents include carbonyl, hydroxymethylene, methoxy, ketal, lactone carbonyl, aldehyde, hydroxy, etc. Not described in connection with Schemes 20, 29 and 30 are compounds containing no substitution (i.e., merely hydrogen substitution) at C10 and/or C13. Below are examples discussing synthetic approaches to producing 19-nor-6α,7β-dioxygenated steroids.

The synthesis of many of the various compounds of the present invention has been detailed in connection with compounds 1 and 247, both commercially available starting materials. However, the preparation of analogous compounds, e.g., compound 141, that differs only in the lack of a C10 methyl substituent, can be achieved according to Scheme 42 shown below.

In Scheme 42, the starting material is the commercially available 19-nor-testosterone (133) (Steraloids Inc., Wilton, N.H., or Aldrich Chemical Company, Milwaukee, Wis.). Reduction of compound 133 using NaBH$_4$ in ethanol may give compound 134 which contains the 3β-hydroxyl group. After protection of the 3β-hydroxyl group using TBDMSCl and imidazole in DMF, allylic oxidation on the resultant diprotected compound (135) may be used to afford the enone derivative 136. Reduction and acetylation, as described in previous Sections (Scheme 1), followed by hydroboration using BH$_3$-THF and oxidative work up (H$_2$O$_2$, 30% NaOH), gives compound 138 which contains the 6α,7β,17β-hydroxylation pattern. Protection of the 6α,7β-hydroxyls using 2,2-dimethoxypropane and camphor sulfonic acid can be followed by oxidation of the C17 hydroxyl group using PDC in CH$_2$Cl$_2$ to afford compound 140 containing the C17 ketone functionality. Reaction of compound 140 with the Wittig reagent prepared from ethyltriphenylphosphonium bromide and tBuOK in toluene gives the ethylidene derivative which can be deprotected in 80% acetic acid to yield the trihydroxy compound 141 which is identical to compound 333 except for the lack of a C10 methyl substituent.

Scheme 42

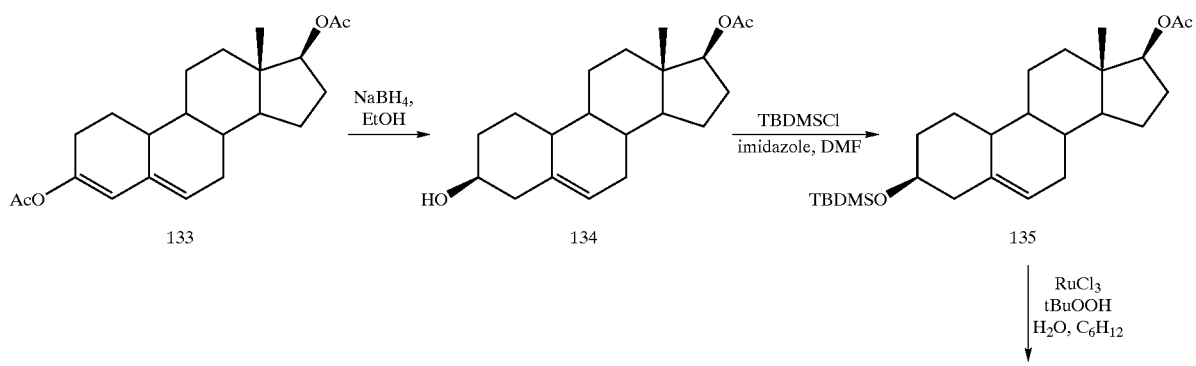

-continued

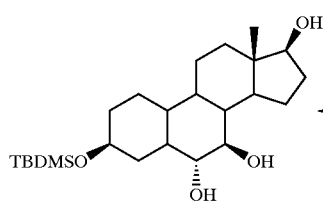 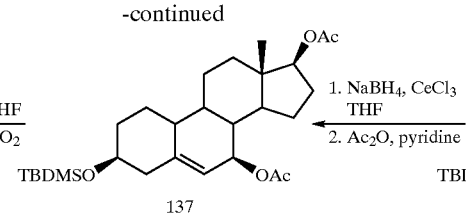 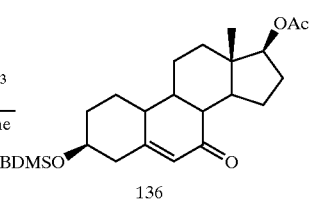

138                                      137                                     136

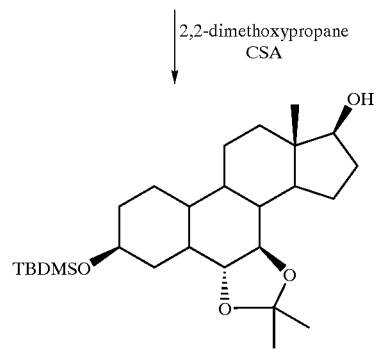    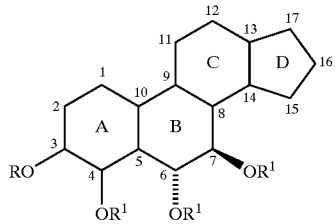    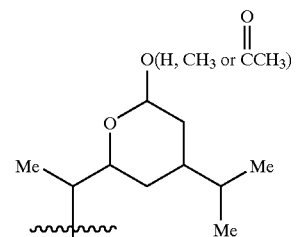

139                 140                 141

In an aspect of the present invention, polyoxygenated steroids having oxygen and/or hydrocarbon substitution at each of C3, C4, C6 and C7, where the oxygen and/or hydrocarbon substitution at C6 has the alpha stereochemistry and the oxygen and/or hydrocarbon substitution at C7 has the beta stereochemistry, are provided. In one embodiment, the polyoxygenated steroid has the Structure 9, including individual enantiomeric or geometric isomers thereof, and further including a solvate or pharmaceutically acceptable salt thereof. Structure 9 is defined as follows:

A compound of the formula

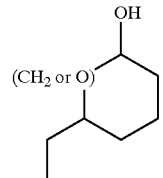

including pharmaceutically acceptable salts and solvates thereof, wherein:

each of C1, C2, C11, C12, C15, C16 and C17 is independently substituted with
  (a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6; or
  (b) two of the following, which are independently selected: —X, —R$^4$ and —OR$^1$;

with the proviso that C17 is not substituted with any of the following:

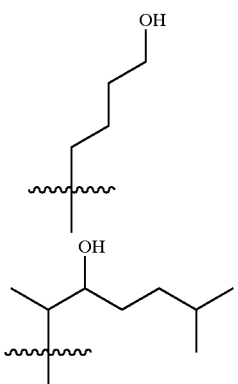

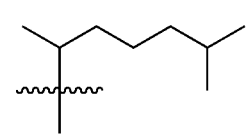

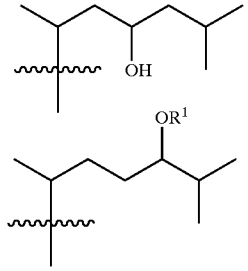

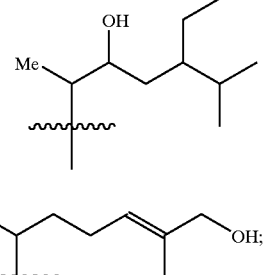

each of C5, C9, C10, C13 and C14 is independently substituted with one of —X, —R⁴ or —OR¹;

C8 is substituted with —X or —R⁴ and is preferably not bonded directly to oxygen;

the A, B, C and D rings may independently be fully saturated, partially saturated or fully unsaturated;

R¹ is H or a protecting group such that —OR¹ is a protected hydroxyl group, where vicinal —OR¹ groups may together form a cyclic structure which protects vicinal hydroxyl groups, and where geminal —OR¹ groups may together form a cyclic structure which protects a carbonyl group;

R⁴ at each occurrence is independently selected from H and $C_{1-30}$ organic moiety that may optionally contain at least one heteroatom selected from the group consisting of boron, halogen, nitrogen, oxygen, silicon and sulfur; where two geminal R⁴ groups may together form a ring with the carbon atom to which they are both bonded; and X represents fluoride, chloride, bromide and iodide.

Compounds having the oxygen and/or hydrocarbon substitution shown in Structure 9 may be prepared from compound 142, which was prepared as described below in Scheme 52. Thus, as shown in Scheme 43, compound 142 may be epoxidized with any number of epoxidization conditions, e.g., using m-chloroperbenzoic acid (m-CPBA) in dichloromethane, to provide the epoxide compound 143. Ring opening of the epoxide group using a mild organic acid (e.g., anhydrous acetic acid, which is preferred) provides compound 144, which is a representative compound of Structure 9.

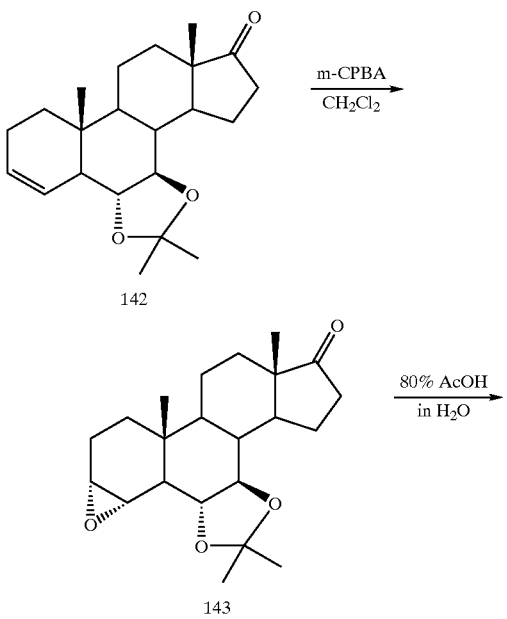

Scheme 43

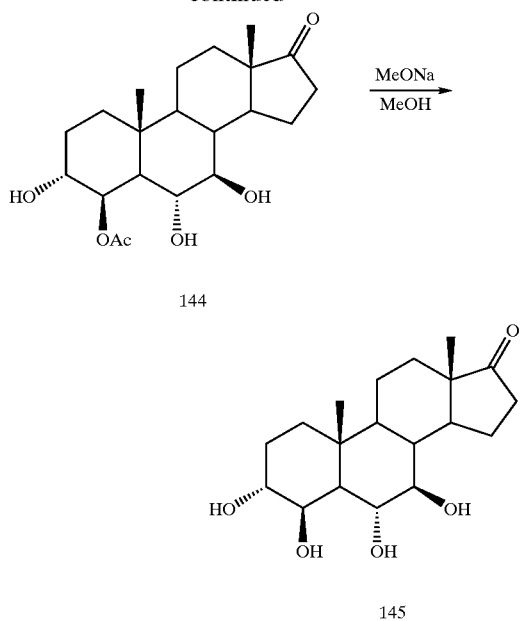

From compound 144, many other compounds of Structure 9 may be prepared. For example, as illustrated in Scheme 43, compound 144 may be deacetylated to provide the tetrahydroxy ketone compound 145. The ketone group at C17 may be subject to Wittig chemistry as discussed above, to provide entry into a large class of tetrahydroxy olefin compounds of Structure 9.

Structure 9, which has a 3,4,6,7-tetraoxygenation pattern, may additionally contain further oxygen-containing substituents. For example, compounds of Structure 9 may have an oxygen atom at C11. Synthetic methodology to introduce a C11 oxygen atom, which may be employed to prepare compounds of Structures 5–12 including Structure 9, may be achieved by chemistry shown in Scheme 44, or by chemistry analogous to that shown in Scheme 44.

For example, rather than using a commercially available starting material with a C11 hydroxyl functionality or $\Delta^{9,11}$ carbon-carbon double bond, the formation of the m-bischloroiodosobenzylformyl ester followed by its photolysis generates the desired unsaturation at the $\Delta^{9,11}$ position (compound 149). Thus, the C6 and C7 hydroxyls in compound 146 (prepared according to Scheme 61) may be protected using 2,2-dimethoxypropane and camphor sulfonic acid to give compound 147. Subsequent reaction of 147 with m-bischloroiodosobenzylformyl chloride in pyridine followed by photolysis in $CCl_4$ gives compound 149. Protection of the A-ring hydroxyl groups followed by hydroboration/oxidation yields the C11 hydroxy derivative 151. Complete deprotection using 80% acetic acid gives the hexol 152.

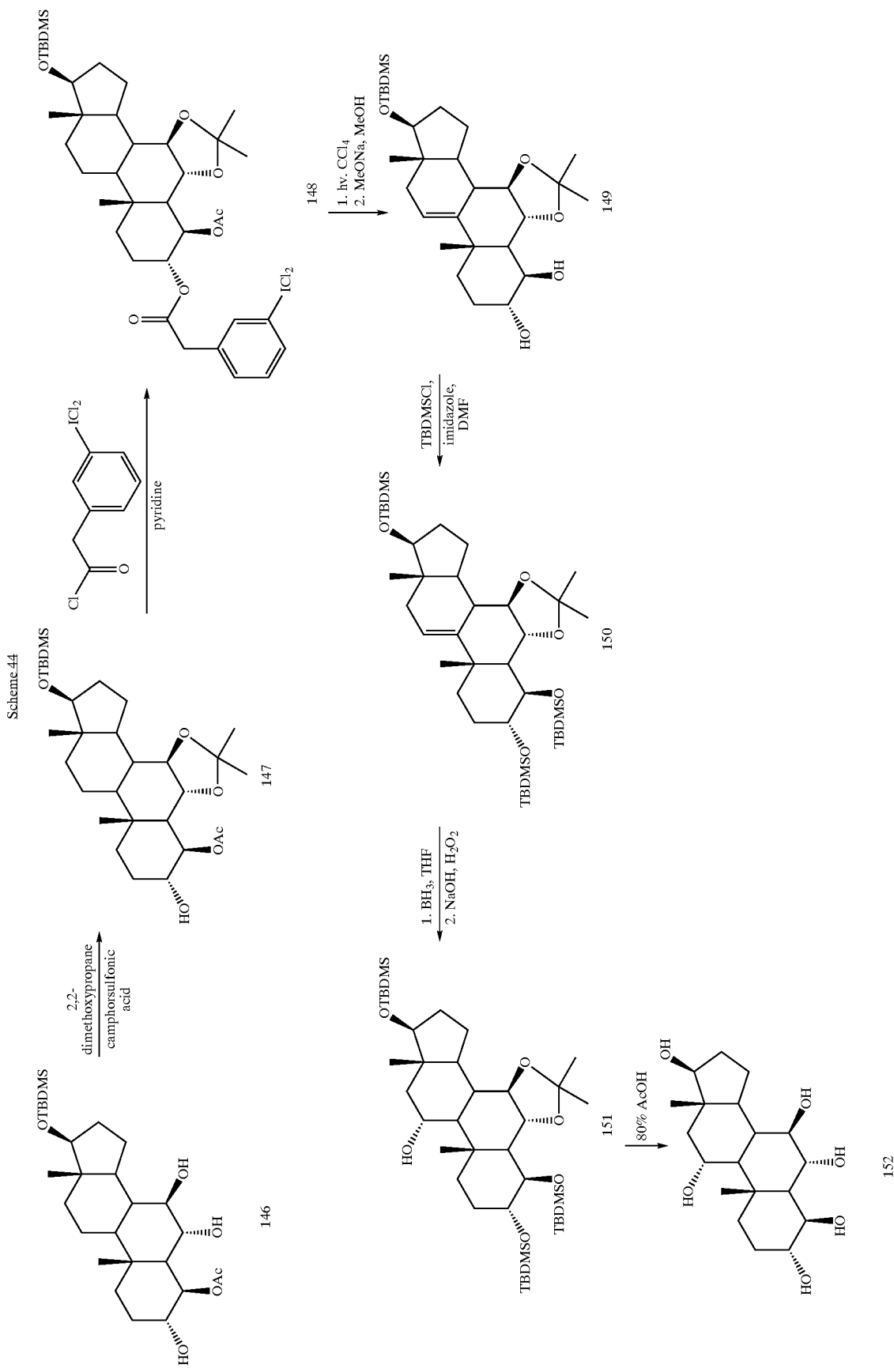

In an aspect of the present invention, steroid ketones having a pyran or δ-lactone ring in the C17 sidechain are provided. In one embodiment, the steroid ketone has the Structure 10, including individual enantiomeric or geometric isomers thereof, and further including a solvate or pharmaceutically acceptable salt thereof. Structure 10 is defined as follows:

A compound of the formula

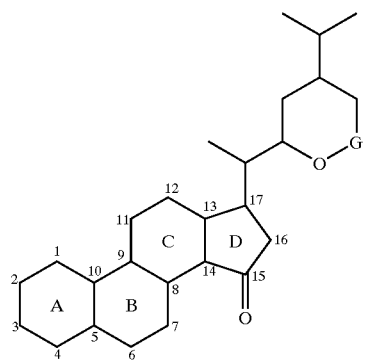

including pharmaceutically acceptable salts and solvates thereof, wherein:

each of C1, C2, C3, C4, C11, C12, C15 and C16 is independently substituted with
(a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6; or
(b) two of the following, which are independently selected: —X, —R$^4$ and —OR$^1$;

with the proviso that C3 and C4 are not simultaneously substituted with hydroxyl or protected hydroxyl, and are preferably not simultaneously substituted with oxygen atoms;

each of C5, C8, C9, C10, C13 and C14 is independently substituted with one of —X, —R$^4$ or —OR$^1$;

G is —C(=O)—, —CH(OR$^1$)—, —C(R$^4$)(OR$^1$)— or —C(OR$^1$)(OR$^1$)—;

the A, B, C and D rings may independently be fully saturated, partially saturated or fully unsaturated;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and X represents fluoride, chloride, bromide and iodide.

Convenient access to the C17 sidechain in compounds of Structure 10 begins with L-carvone, as shown in Scheme 45.

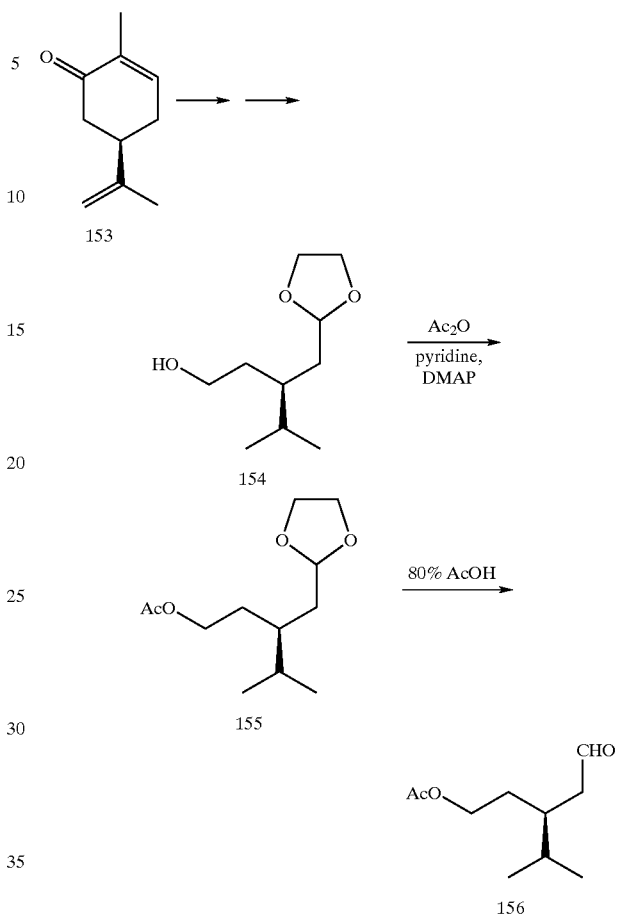

L-Carvone (153) may be converted to compound 154 according to literature procedures. See, e.g., *Tetrahedron Letters* 25(41):4685–4688 (1984). The primary alcohol in compound 154 is then protected by, e.g., conversion to an acetate ester. Removal of the ketal protecting group in compound 155 using acidic conditions provides aldehyde 156.

The compound 156 can provide access to the C17 sidechain in compounds of Structure 10 as shown in Scheme 46 below. Thus, compound 145 as prepared in Scheme 43, may be treated with the ylid prepared from ethyltriphenylphosphonium bromide and base to afford compound 157 (used as starting material in Scheme 46). Thereafter, the four hydroxyl groups may be converted to protected hydroxyl groups, for example benzyloxy groups, as shown in compound 158. Compound 158 is then coupled with the aldehyde 156 (Scheme 45) in the presence of a Lewis acid, to provide compound 159. Deprotection of the C29 acetoxy group may then be accomplished with base to provide diol compound 160, which may then be oxidized to the δ-lactone compound 161. Allylic oxidation of compound 161 may introduce a carbonyl moiety at C15 with concurrent oxidation of the benzyl groups (Bn) to benzoate (Bz) groups, to form compound 162.

Reduction of the conjugated Δ$^{16}$ carbon-carbon double bond in the D-ring of compound 162 gives compound 163. Removal of the benzoate groups in 163 may be achieved using basic conditions (for example NaOMe in MeOH) with concurrent epimerization at C14 to yield product 164 which contains an epimeric mixture of the compounds containing the cis C/D ring junction and the trans C/D ring junction. Finally, protection of the C15 ketone followed by reduction of the δ-lactone to the lactol and deprotection (80% acetic acid) may be accomplished to give 22,29-epoxy-3,4,6,7,29-pentahydroxy-14β-stigmastan-15-one (compound 165) and it's C14 epimer 22,29-epoxy-3,4,6,7,29-pentahydroxy-14α-stigmastan-15-one.

Scheme 46

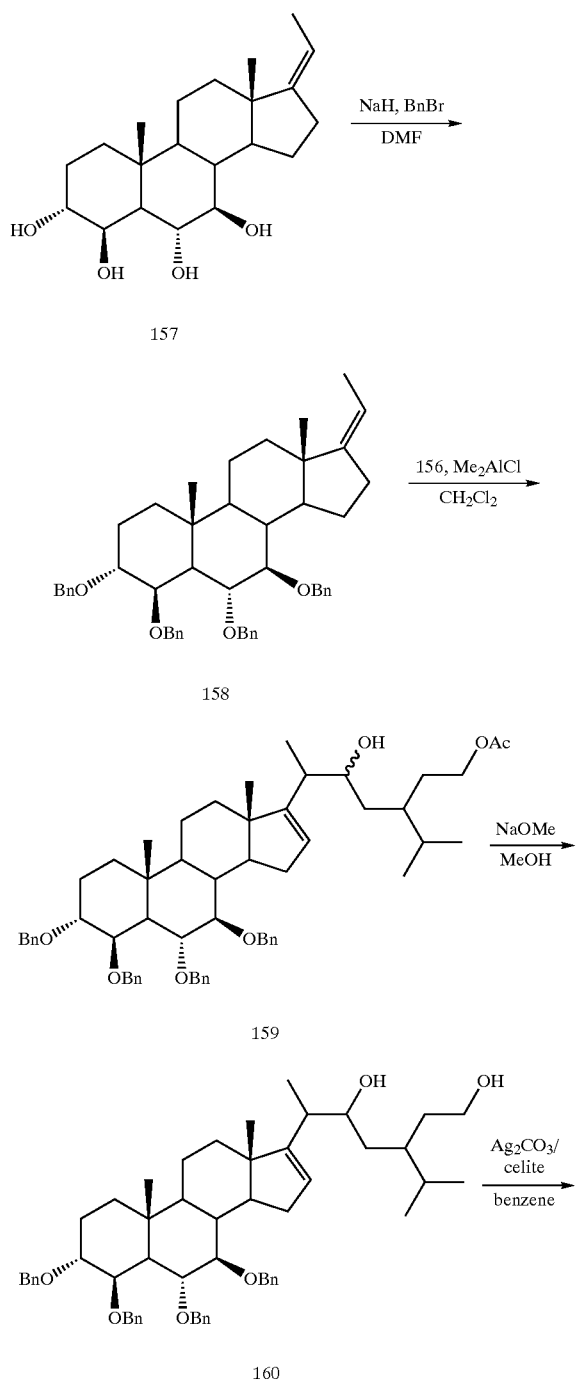

-continued

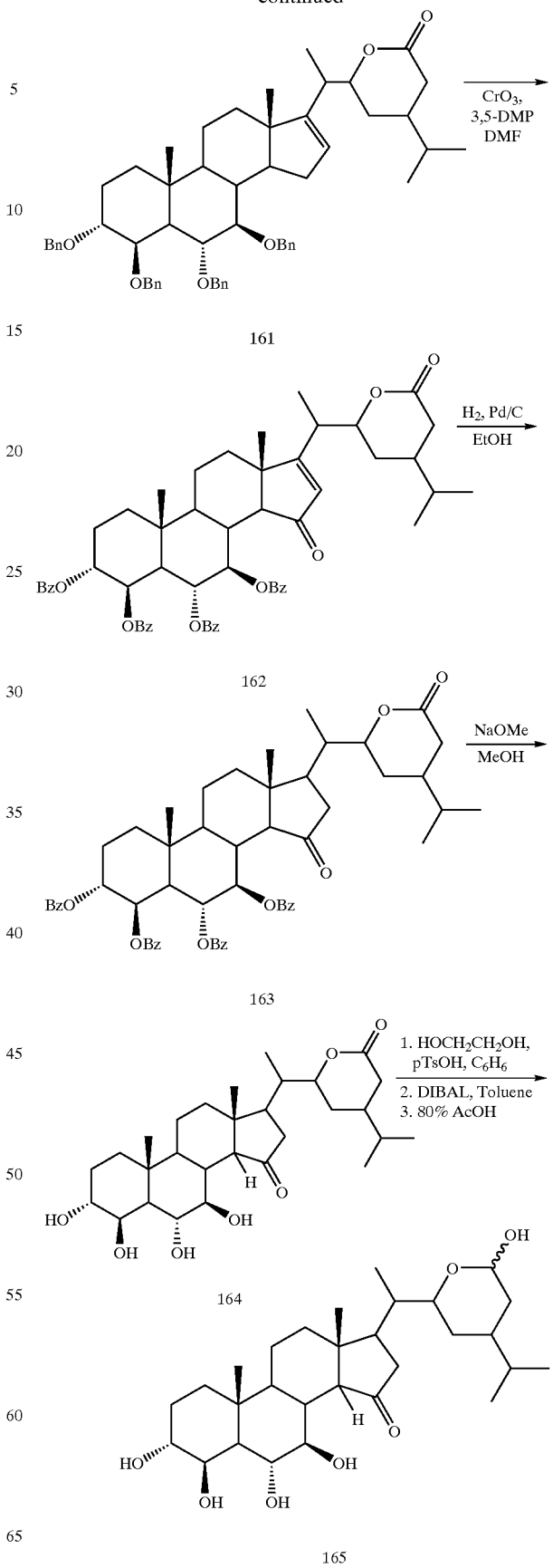

Compounds of Structure 10 may have a C15 ketone and C22,29 epoxy functionality. In fact, compounds containing a variety of functionality in the A–D rings in addition to a C15 ketone and a sidechain hemiacetal may be produced using a combination of methodology described herein.

For example, as illustrated in Scheme 47, compound 176, which contains a methylene at C3, a carbonyl at C15 and a sidechain hemiacetal, may be produced by using methodology described herein. The C15 ketone and the sidechain hemiacetal may then be incorporated using methodology described in detail above (in connection with Schemes 45 and 46).

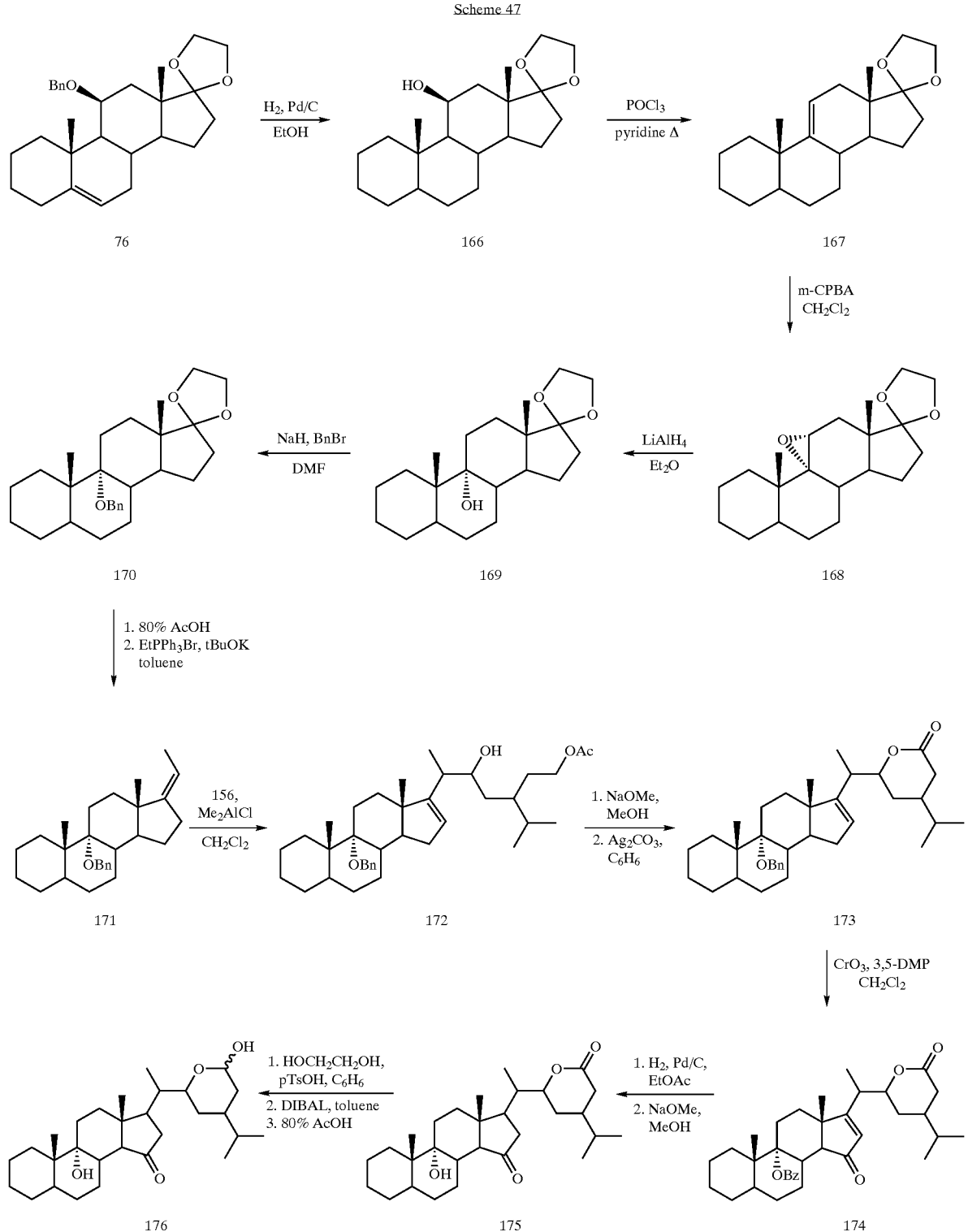

Scheme 47

As shown in Scheme 47, compound 76 can be deprotected using $H_2$, Pd/C in ethanol to give a compound containing the C11 hydroxyl functionality which, upon heating in $POCl_3$ and pyridine, may produce compound 167 containing the $\Delta^{9,11}$ double bond and its $\Delta^{11,12}$ isomer. Epoxidation (of 167) using mCPBA followed by $LiAlH_4$ reduction may be used to afford compound 169 which contains the C9 hydroxyl functional group. Protection of this hydroxyl group followed by removal of the ketal protecting group and Wittig chemistry may be done to yield the olefinic product 171. Conversion of compound 171 to lactol 176 may be accomplished using standard methods described herein.

A second example involves the preparation of derivative 186, a compound that contains the C15 ketone and the sidechain hemiacetal as well as a C1 hydroxyl functionality. Compound 186 may be produced in a multi-step procedure from the commercially available starting material 177 as shown in Scheme 48. The first step involves protection of compound 178 using e.g., ethylene glycol, pTsOH in benzene. Subsequent Michael addition using, e.g., benzyl alcohol and potassium hydroxide gives the C1 benzyloxy derivative 179. LS-Selectride® reduction of the ketone 179 followed by protection of the resultant alcohol as the benzyloxy derivative may be used to give compound 180. The conversion of compound 180 to lactol 186 may then be achieved using methods described in Scheme 47 and described in detail in other previous examples.

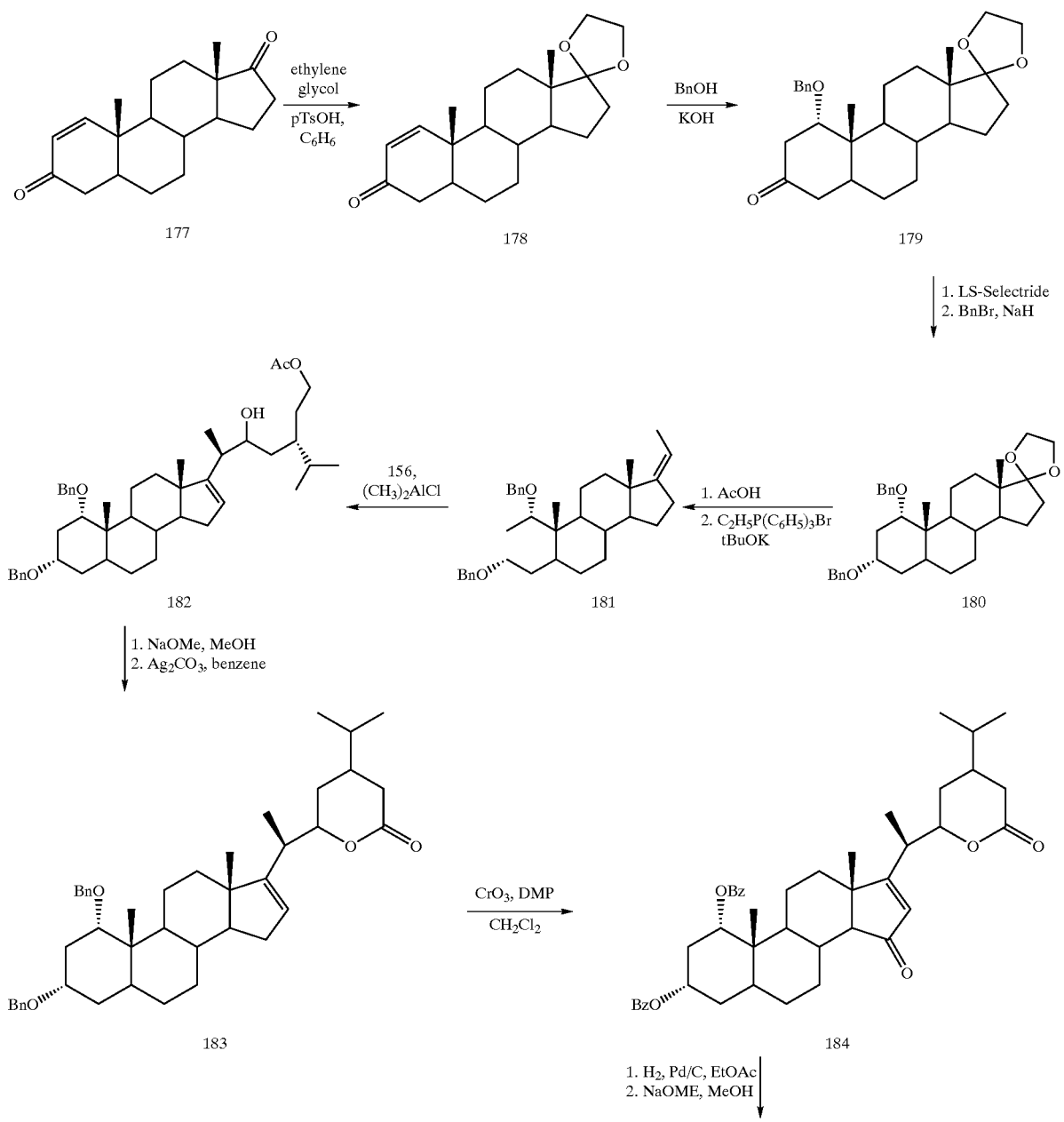

Schem 48

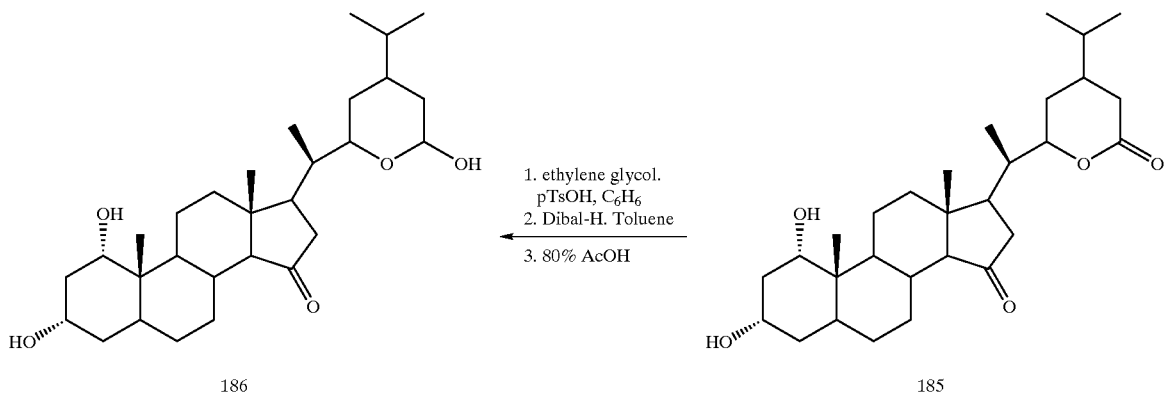

Thus, the methodology described herein may be used to produce compounds with functionality at carbons in the steroidal ring structure as well as both the C15 ketone functionality and sidechain hemiacetal.

In a related aspect of the present invention, steroids having oxygenation at C6 and C7, with a pyran-or δ-lactone-containing sidechain at C17 are provided. In one embodiment, the steroid has the Structure 11, including individual enantiomeric or geometric isomers thereof, and further including a solvate or pharmaceutically acceptable salt thereof. Structure 11 is defined as follows:

A compound of the formula

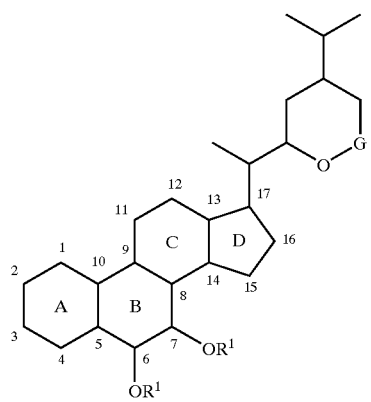

including pharmaceutically acceptable salts and solvates thereof, wherein:

each of C1, C2, C3, C4, C11, C12, C15 and C16 is independently substituted with (a) one of: =O, =C($R^4$)($R^4$), —C($R^4$)($R^4$)(C($R^4$)-($R^4$))$_n$— and —(O(C($R^4$)($R^4$))$_n$O)— wherein n ranges from 1 to about 6; or (b) two of the following, which are independently selected: —X, —$R^4$ and —$OR^1$;

with the proviso that C3 and C4 are not simultaneously substituted with hydroxyl or protected hydroxyl, and are preferably not simultaneously substituted with oxygen atoms;

each of C5, C8, C9, C10, C13 and C14 is independently substituted with one of —X, —$R^4$ or —$OR^1$;

G is —C(=O)—, —CH($OR^1$)—, —C($R^4$)($OR^4$)— or —C($OR^1$)(OR)—;

the A, B, C and D rings may independently be fully saturated, partially saturated or fully unsaturated;

$R^1$ is H or a protecting group: such that —$OR^1$ is a protected hydroxyl group, where vicinal —$OR^1$ groups may together form a cyclic structure which protects vicinal hydroxyl groups, and where geminal —$OR^1$ groups may together form a cyclic structure which protects a carbonyl group, with the proviso that either or both of —$OR^1$ at C6 and C7 represents a carbonyl or protected carbonyl group;

$R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and X represents fluoride, chloride, bromide and iodide.

The preparation of compounds of Structure 11 may be achieved using methodology set forth many places herein. For example, compounds 196 (Scheme 49) and 207 (Scheme 50) may be synthesized from compounds 30 and 55 in multi-step processes. Methods used to convert the C17 silyloxy group in compound 30 to the olefin 190 are analogous to those described in detail in previous examples, as are the methods used to convert compound 190 to compound 196. The same holds true for the conversions of compounds 55 to 200 and 200 to 207, respectively.

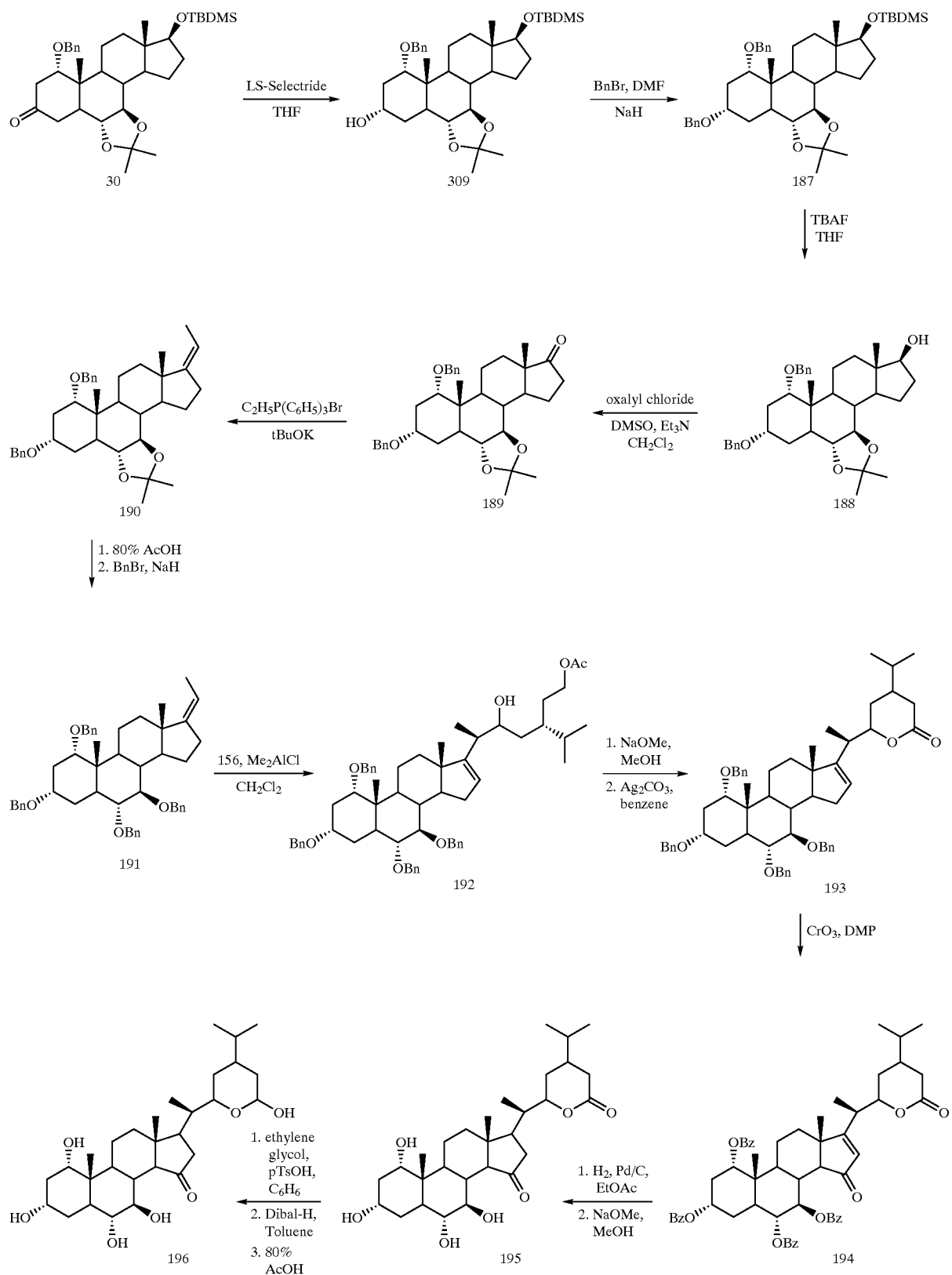

Scheme 50

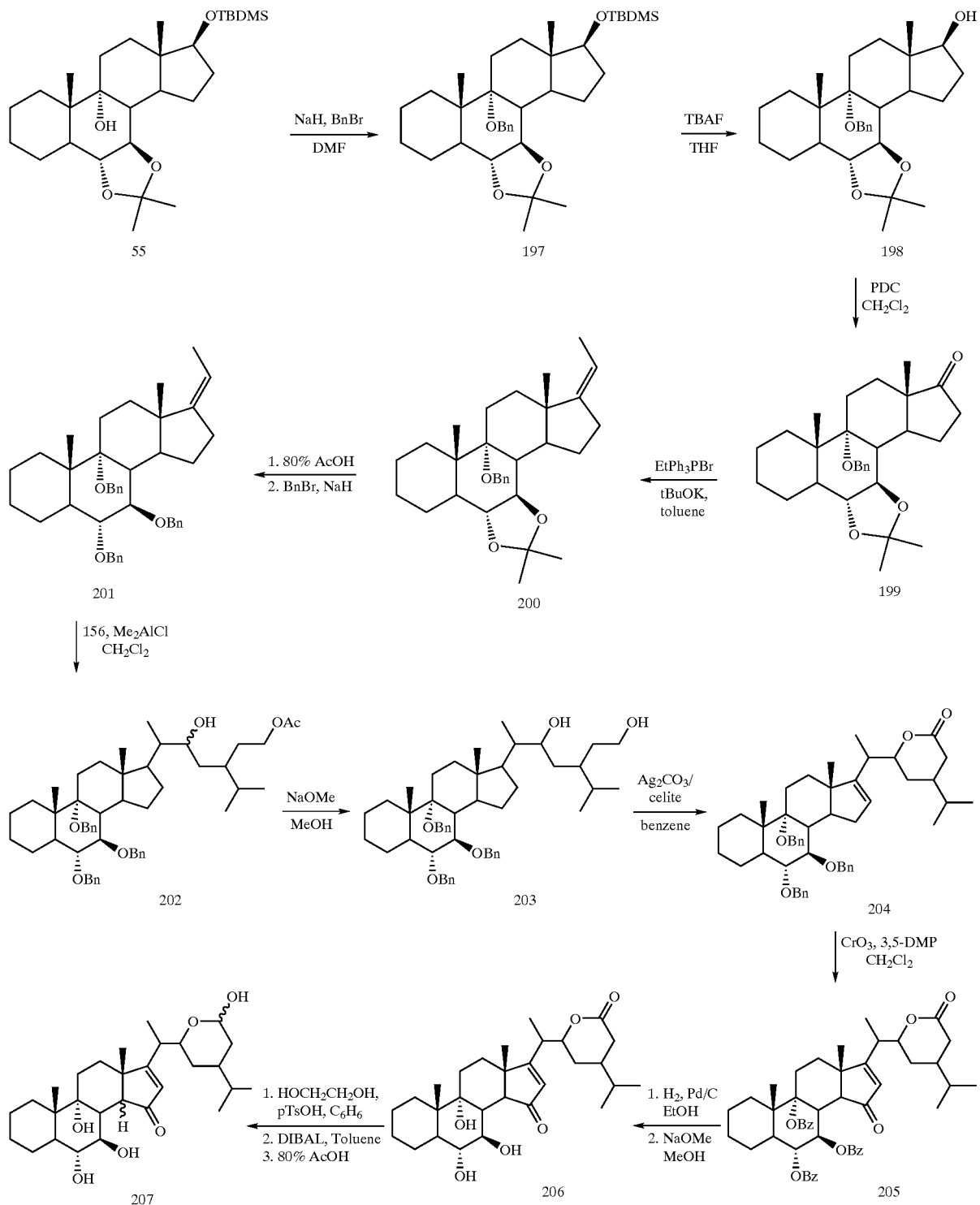

The chemistry described in Schemes 49 and 50 above are just two examples of how the methods discussed herein may be applied to produce compounds containing a 6,7-dioxygenation pattern and the hemiacetal or δ-lactone sidechain. Thus, the methodology described previously may be used to produce compounds with functionality at C2, C4, C8, etc.

In an aspect of the present invention, steroid epoxides are provided. In one embodiment, the steroid epoxide has the Structure 12, including individual enantiomeric or geometric isomers thereof, and further including a solvate or pharmaceutically acceptable salt thereof. Structure 12 is defined as follows:

A compound of the formula

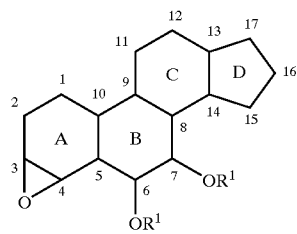

including pharmaceutically acceptable salts and solvates thereof, wherein:
 each of C1, C2, C11, C12, C15, C16 and C17 is independently substituted with
  (a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6; or
  (b) two of the following, which are independently selected: —X, —R$^4$ and —OR$^1$;
 each of C5, C8, C9, C10, C13 and C14 is independently substituted with one of —X, —R$^4$ or —OR$^1$;
 the A, B, C and D rings may independently be fully saturated, partially saturated or fully unsaturated;
 R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and X represents fluoride, chloride, bromide and iodide.

Preferably, in compounds of Structure 12, C7 does not have carbonyl substitution when C5 has hydroxy or —OR$^1$ substitution.

As with the previous examples, introduction of functional groups at various positions within the steroid ring structure of compounds containing a 3,4-epoxide group of Structure 12 may be achieved using methods described herein. For example, as shown in Scheme 51, an oxygen atom may be placed at C9 and/or C11, via epoxidation of Δ$^{9,11}$ double bond.

Thus, LS-selectride reduction followed by remote oxidation using reagents described earlier on a compound such as compound 10 may provide an olefinic compound 208 (Scheme 51). Transformations to the Δ$^{9,11}$ olefin can be achieved using standard methodology and concurrent reaction of both the Δ$^{3,4}$ and Δ$^{9,11}$ double bonds provide the desired epoxides at C3–C4 and C9–C11. Oxidation of the C3 hydroxyl moiety with PDC in CH$_2$Cl$_2$ then may be used to give the desired unsaturated A-ring (and optionally ring-opening the epoxide rings will provide a 3,6,7,9-polyhydroxylated steroid 215).

Scheme 51

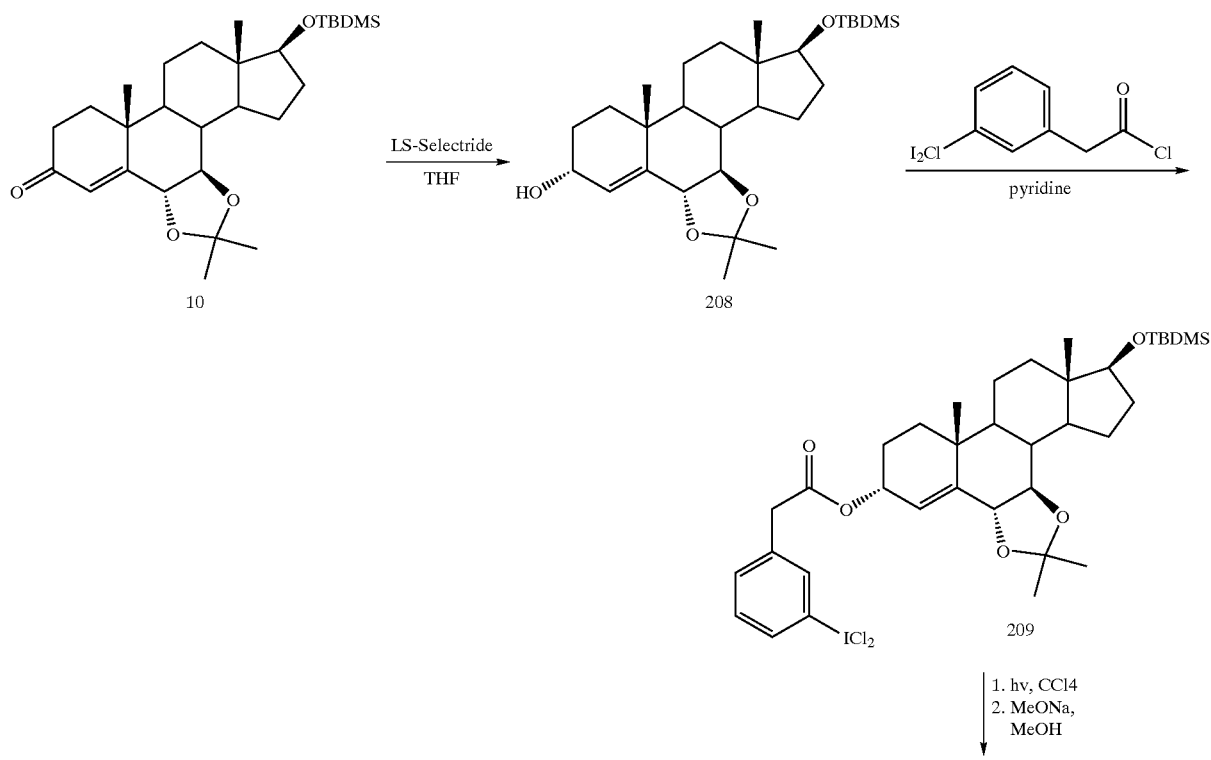

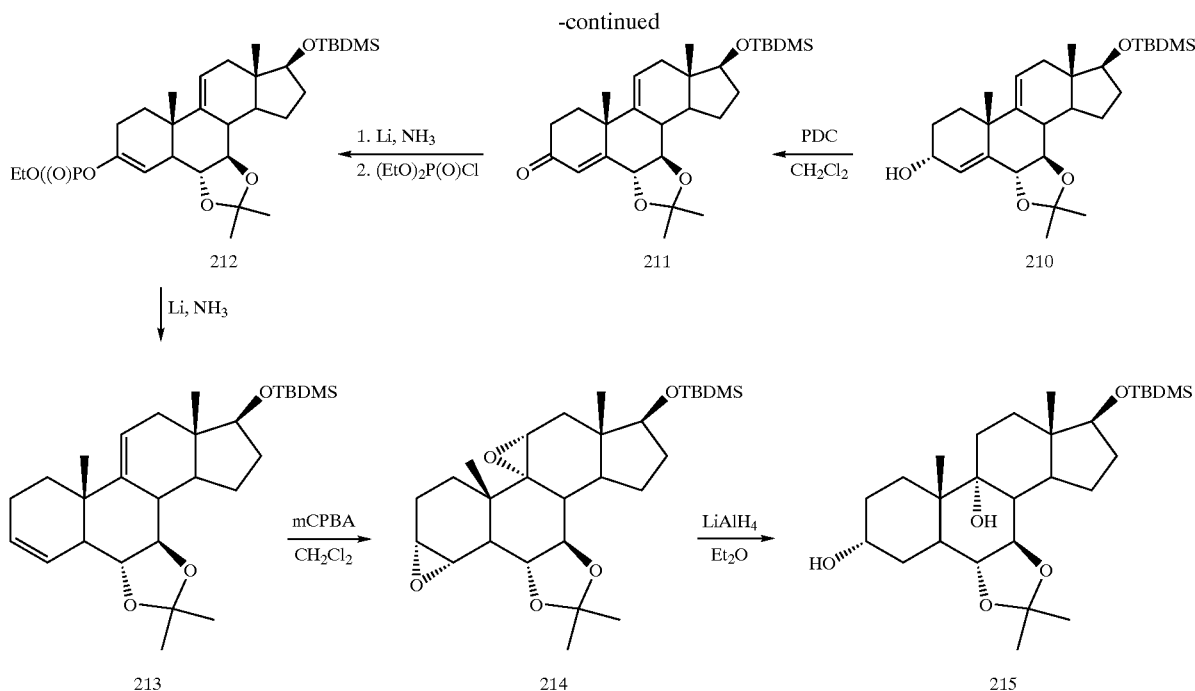

The introduction of an alkyl group in the C16 position may also be achieved using similar chemistry described above. In the following example (Scheme 52), a methyl group is incorporated into this position from the condensation of the D-ring enolate with methyl iodide. This methodology is analogous to that described in connection with Scheme 37. As shown in Scheme 52, the alkylated epoxide 218 may be subjected to epoxide-ring-opening conditions to afford a 3,4,6,7-tetrahydroxy steroid 220.

Scheme 52

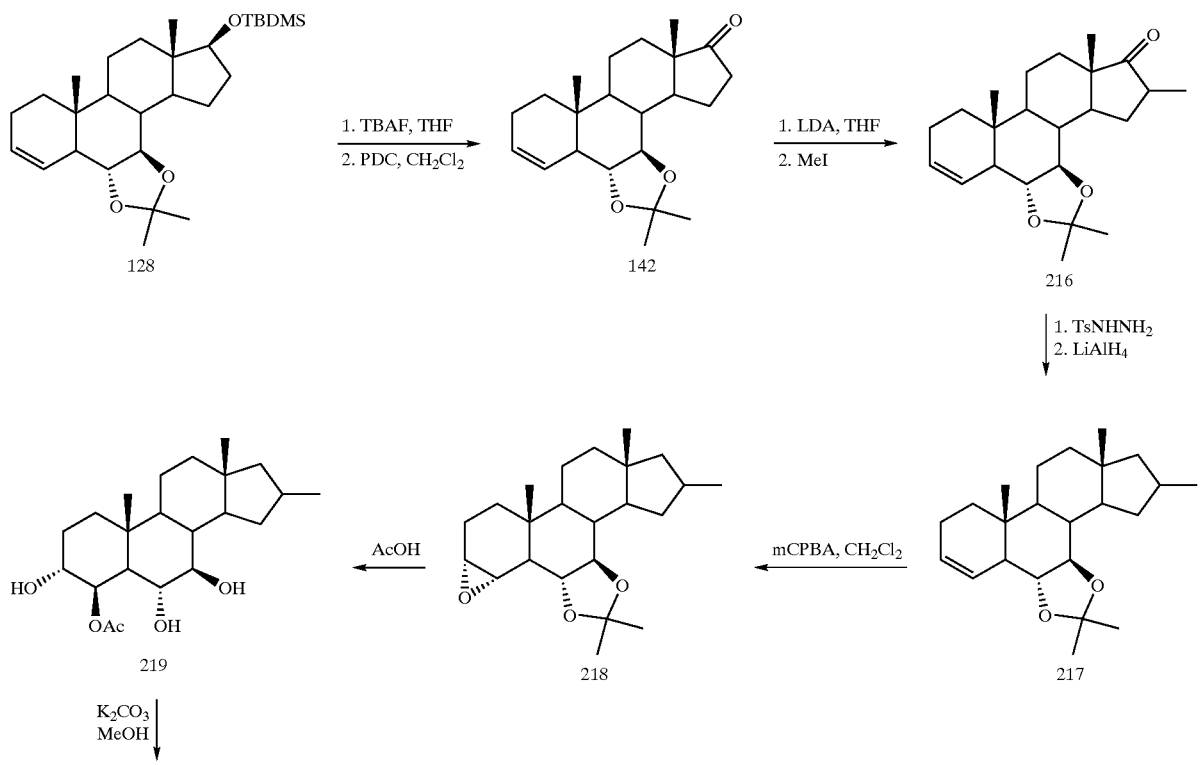

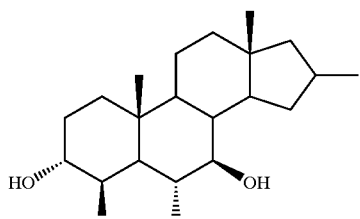

220

Compounds having 6α,7β-hydroxylation pattern have been discussed in detailed previous sections. Alternatively, compounds containing other stereochemistries at C6 and C7 may also be produced as discussed in the following section. For example, selective tosylation of compound 221 (prepared according to Scheme 73) using pTsCl in pyridine followed by treatment with potassium carbonate may yield the epoxide containing compound 223. Subsequent ring opening using aqueous acid may yield compounds with the 6β,7α stereochemistry as shown in Scheme 53.

Scheme 53

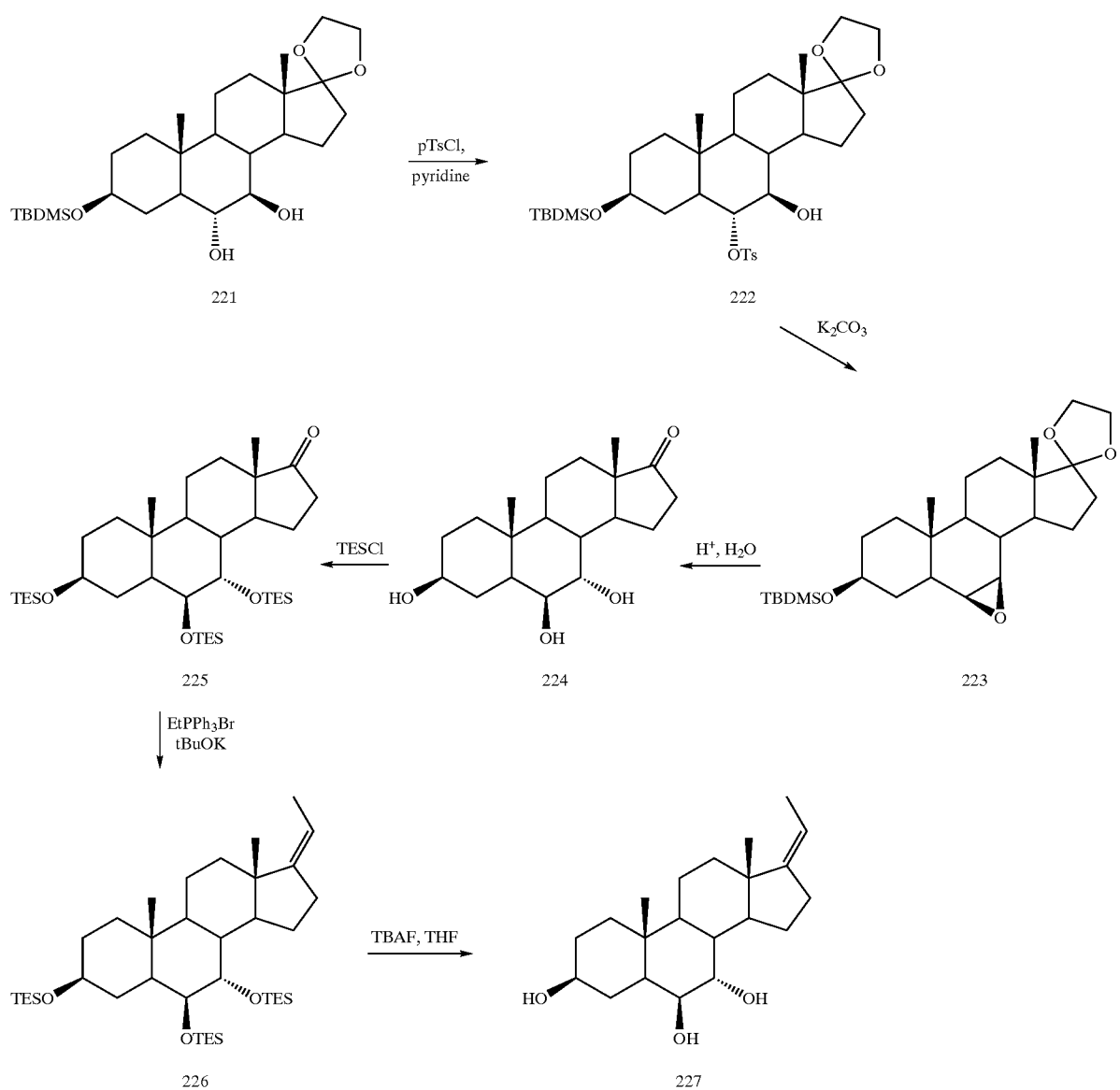

Compounds with the 6α,7α stereochemistry can be prepared from commercially available starting materials as shown in Scheme 54. Thus, cholesteryl acetate may be oxidized using RuCl$_3$ and tBuOOH in CH$_2$Cl$_2$ to afford the enone containing compound 229. Exchange of the protecting group at C3 to the tBDMS derivative is followed by lithium ammonia reduction and trapping of the enolate anion with (MeO)$_2$PCl giving the enol phosphate 231. A second lithium-ammonia reduction gives the Δ$^{6,7}$ double bond which may be oxidized with OsO$_4$ to afford compound 233 containing the 3β,6α,7α-trihydroxylation pattern.

Scheme 54

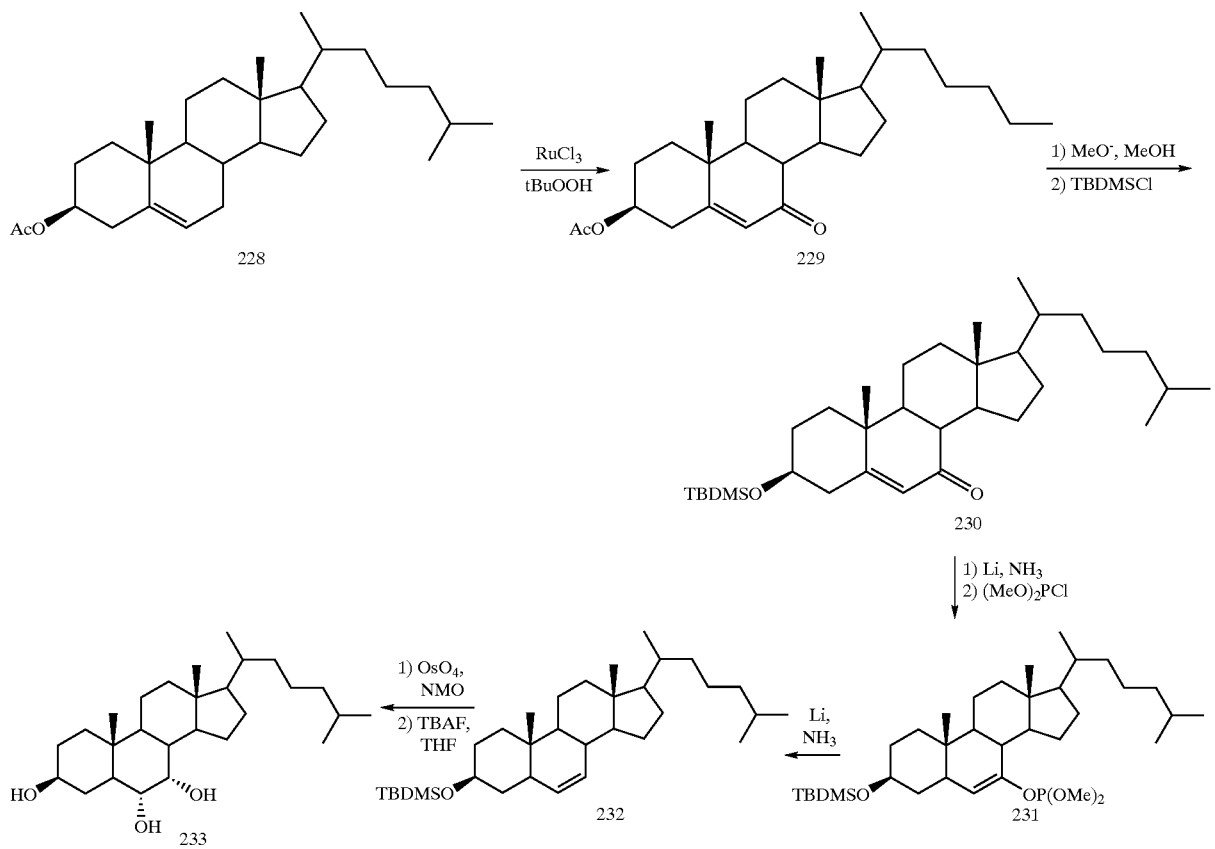

More generally, compounds of the present invention may be characterized by the following formula:

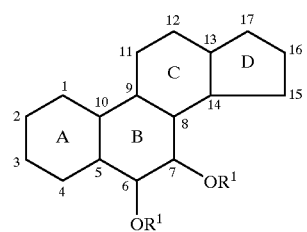

including pharmaceutically acceptable salts and solvates thereof, wherein:

each of C1, C2, C3, C4, C11, C12, C15 and C16 is independently substituted according to any of (a) and (b):

(a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6;

(b) two of: —X, —R$^4$ and —OR$^1$, each independently selected;

each of C5, C6, C7, C8, C9, C10, C13 and C14 is independently substituted with one of —X, —R$^4$ or —OR$^1$;

C17 is substituted according to any of (c), (d), (e), (f), (g), (h) and (i):

(c) =C(R$^2$)(R$^3$) except when C14 is substituted with methyl;

(d) —R$^5$ and —OR$^6$ so long as the A and B rings are not aromatic, and when C10 is substituted with methyl then C5 is not bonded directly to oxygen, where R$^5$ and R$^6$ may together form a direct bond so C17 is a carbonyl group, or may together with C17 form a cyclic 3–6 membered ether or 4–6 membered lactone; otherwise R$^5$ is R$^4$ or —OR$^6$ and R$^6$ is R$^1$ or R$^4$;

(e) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6, as long as one of the following conditions i), ii), iii) or iv) apply:

i) C5 is substituted with a hydrogen in the alpha configuation, and C3 is not bonded to oxygen, and when C3 is substituted with two hydrogen atoms then C17 is not substituted with either —CH(CH$_3$)(CH$_2$)$_3$CH(CH$_3$)$_2$ or —CH(CH$_3$)(CH$_2$)2C(=O)OCH$_3$;

ii) C10 and C13 are not simultaneously substituted with methyl, and when C10 is substituted with methyl, then C14 is not substituted with a methyl, and the A ring is never aromatic;

iii) if C3 and C4 are bonded to oxygen atoms, and the C6 —$OR^1$ substituent has the alpha configuration, and the C7-$OR^1$ substituent has the beta configuration, then C17 is not substituted with any of the following:

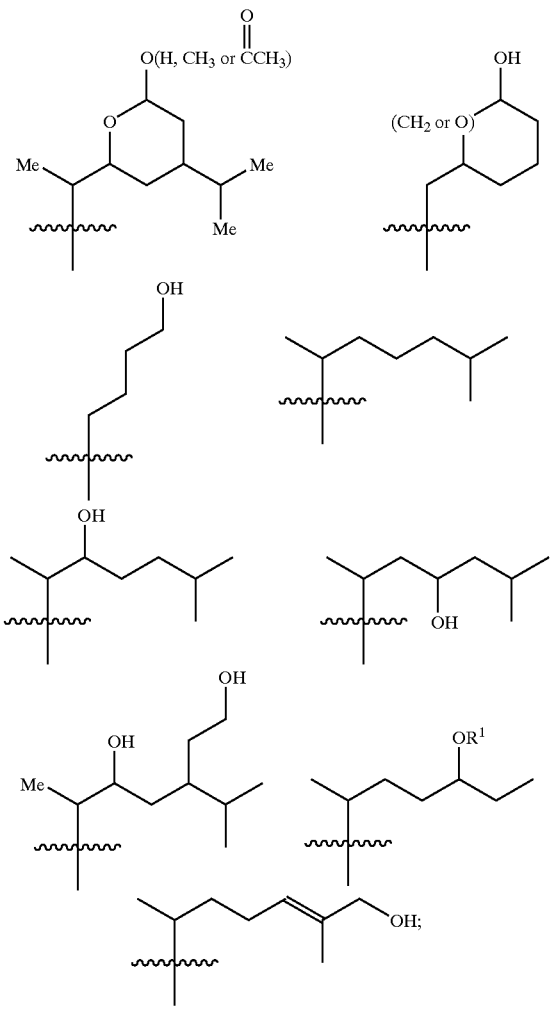

iv) C3 and C4 are each bonded to the same oxygen atom so as to form an oxirane ring, with the proviso that C7 does not have carbonyl substitution when C5 has hydroxyl or —$OR^1$ substitution;

(f) two of the following substituents, which are independently selected: —X, —$R^4$ and —$OR^1$, as long as one of the above conditions i), ii), iii) or iv) apply;

(g) a cyclic structure of the formula

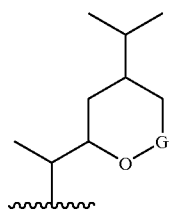

wherein G is —C(=O)—, —CH($OR^1$)—, —C($R^4$)($OR^1$)— or —C($OR^1$)($OR^1$)—, as long as C3 and C4 are not simultaneously substituted with hydroxyl or protected hydroxyl;

(h) two hydrogen atoms, as long as C3 is not substituted with a carbonyl group;

(i) one hydrogen atom and one group selected from $C_1$–$C_{30}$ hydrocarbyl groups and $C_1$–$C_{30}$ halogen substituted hydrocarbyl groups, excluding —CH($CH_3$)($CH_2$)$_3$CH($CH_3$)$_2$;

the A, B, C and D rings may independently be fully saturated, partially saturated or fully unsaturated;

$R^1$ is H or a protecting group such that —$OR^1$ is a protected hydroxyl group, where vicinal —$OR^1$ groups may together form a cyclic structure which protects vicinal hydroxyl groups, and where geminal —$OR^1$ groups may together form a cyclic structure which protects a carbonyl group, with the proviso that either or both of —$OR^1$ at C6 and C7 represents a carbonyl or protected carbonyl group;

$R^2$, $R^3$ and $R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^1$ groups may together form a ring with the carbon atom to which they are both bonded; and X represents fluoride, chloride, bromide and iodide.

In a preferred embodiment, the compounds of the invention have one of the structure set forth below, and mixtures thereof:

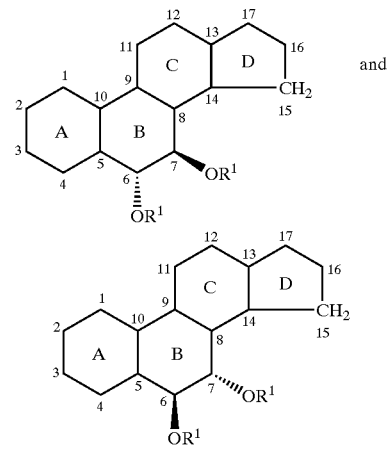

including pharmaceutically acceptable salts and solvates thereof, wherein:

each of C1, C2, C3, C4, C11, C12 and C16 is independently substituted according to (a) or (b):

(a) one of: =O, =C($R^4$)($R^4$), —C($R^4$)($R^4$)(C($R^4$)-($R^4$))$_n$— and —(O(C($R^4$)($R^4$))$_n$O)— wherein n ranges from 1 to about 6, (b) two of: —X, —$R^4$ and —$OR^1$, each independently selected;

C5 is substituted with a hydrogen atom;

each of C5, C6, C7, C8, C9, C10, C13 and C14 is independently substituted with one of —X, —$R^4$ or —$OR^1$, although C5 is preferably substituted with hydrogen; and C17 is substituted according to (c), (d), (e) or (f):

(c) two substituents selected from hydrogen, halogen, $C_1$–$C_{30}$ saturated hydrocarbyl excluding —CH($CH_3$)($CH_2$)$_3$CH($CH_3$)$_2$, halogen substituted $C_1$–$C_{30}$ saturated hydrocarbyl, $C_1$–$C_{30}$ unsaturated hydrocarbyl, and halogen substituted $C_1-C_{30}$ unsaturated hydrocarbyl;

(d) one substituent selected from $=C(R^4)(R^4)$ with the proviso that C14 is not substituted with methyl;

(e) at least one oxygen atom-containing substituent selected from $=O$, $—(O(C(R^4)(R^4))_nO)—$ wherein n ranges from 1 to about 6, $—OH$, and $—OR^1$;

(f) at least one nitrogen atom-containing substituent selected from $—N(R^4)(R^4)$ wherein the two $R^4$ groups may together with the nitrogen atom form one or more rings, so that the nitrogen atom-containing substituent includes nitrogen atom-containing heterocyclic groups; wherein the A, B, C and D rings may independently be fully saturated, partially saturated or fully unsaturated, however fully saturated rings are preferred;

$R^1$ is H or a protecting group such that $—OR^1$ is a protected hydroxyl group, where $—OR^1$ groups bonded to adjacent carbon atoms may together form a cyclic structure which protects both hydroxyl groups;

$R^4$ at each occurrence is independently selected from H and $R^5$;

$R^5$ is a $C_{1-30}$ organic moiety that may optionally contain at least one heteroatom selected from the group consisting of boron, halogen, nitrogen, oxygen, silicon and sulfur; where two geminal $R^5$ groups may together form a ring with the carbon atom to which they are both bonded; and X represents fluoride, chloride, bromide or iodide.

The compounds of general and preferred structures as disclosed herein may be prepared by synthetic methodology as set forth in the Schemes 1–54, the references cited herein and the Examples provided herein, as well as knowledge of the skilled artisan. The following are preferred synthetic procedures useful in preparing compounds of the present invention.

In one aspect, the invention provides a process for introducing an exocyclic olefin group to the C17 position of a 6,7-dioxygenated steroid. The process includes the step of providing a compound of Formula (10) (such a compounds may be commercially available or may be prepared by techniques disclosed herein), and then reacting the compound of Formula (10) with a Wittig reagent of Formula (11) in the presence of a base, to provide an olefin compound of Formula (12)

Each of the compounds of Formulas (10) and (12) include pharmaceutically acceptable salts and solvates thereof. In Formula (10), (11) and (12):

each of C1, C2, C3, C4, C11, C12, C15 and C16 is independently substituted according to any of (a) and (b):

(a) one of: $=O$, $=C(R^4)(R^4)$, $—C(R^4)(R^4)(C(R^4)-(R^4))_n—$ and $—(O(C(R^4)(R^4))_nO)—$ wherein n ranges from 1 to about 6;

(b) two of: $—X$, $—R^4$ and $—OR^1$, each independently selected;

each of C5, C6, C7, C8, C9, C10, C13 and C14 is independently substituted with one of $—X$, $—R^4$ or $—OR^1$;

$R^1$ is H or a protecting group such that $—OR^1$ is a protected hydroxyl group, where vicinal $—OR^1$ groups may together form a cyclic structure which protects vicinal hydroxyl groups, and where geminal $—OR^1$ groups may together form a cyclic structure which protects a carbonyl group, with the proviso that either or both of $—OR^1$ at C6 and C7 represents a carbonyl or protected carbonyl group;

Ra, Rb and $R^4$ at each occurrence is independently selected from H and $C_{1-30}$ organic moiety that may optionally contain at least one heteroatom selected from the group consisting of boron, halogen, nitrogen, oxygen, silicon and sulfur, where two geminal $R^4$ groups may together form a ring with the carbon atom to which they are both bonded; and X represents fluoride, chloride, bromide and iodide, which is independently selected at each occurrence.

In preferred embodiments of the process, the base is selected from sodium t-butoxide, potassium t-butoxide and sodium hydride and the like. The base is preferably in admixture with an aprotic solvent. Suitable aprotic solvents include toluene, tetrahydrofuran, methylene chloride, dimethylformamide, dimethylsulfoxide, benzene and diethyl ether. In another preferred embodiment, Ra and Rb are independently selected from hydrogen and $C_1-C_7$ alkyl, and X is selected from chloride, bromide and iodide.

In another aspect, the invention provides a process for introducing 6α,7β-dioxygenation into a steroid. The process includes the steps of providing a steroid of Formula (13) having a carbonyl group at C7 and a double bond between C5 and C6. Steroids of Formula (13) may be prepared by, for example, synthetic methodology disclosed herein. In a subsequent step, the carbonyl group is reduced to a hydroxyl group, followed by a hydroboration of the double bond to provide a hydroxyl group at C6, wherein the C6 hydroxyl group has the α-configuration and the C7 hydroxyl group has the β-configuration,

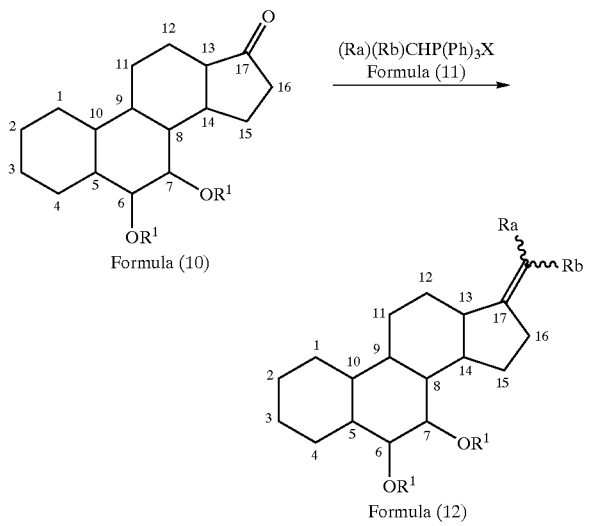

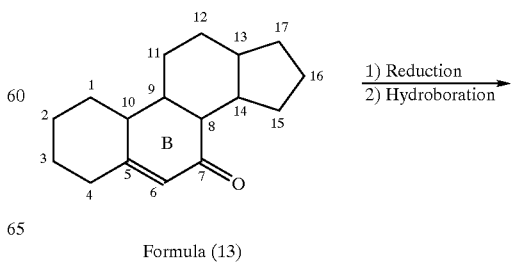

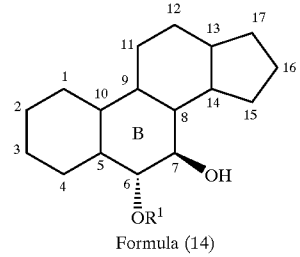

Formula (14)

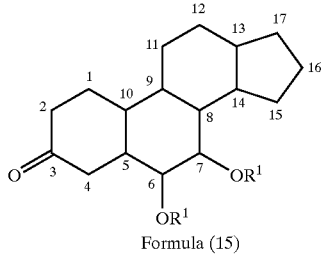

Formula (15) →Reduction

The compounds of Formulas (13) and (14) include pharmaceutically acceptable salts and solvates thereof. In Formula (13) and (14):

each of C1, C2, C3, C4, C11, C12, C15, C16 and C17 is independently substituted according to any of (a) and (b):
(a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6;
(b) two of: —X, —R$^4$ and —OR$^1$, each independently selected;

each of C8, C9, C10, C13 and C14 is independently substituted with one of —X, —R$^4$ or —OR$^1$;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and X represents fluoride, chloride, bromide and iodide.

In preferred embodiments of the process, the reduction is accomplished with sodium borohydride in combination with cerium(III) chloride heptahydrate. In another preferred embodiment of the process, the hydroboration is conducted with a hydroboration reagent selected from BH$_3$ and 9-BBN, and preferably in the presence of an aprotic solvent. Suitable aprotic solvents include tetrahydrofuran, methylene chloride, diethyl ether, dimethyl sulfide and carbon disulfide. The hydroboration is preferably immediately followed by treatment with a peroxide, such as hydrogen peroxide or t-butylperoxide, and a base, such as sodium hydroxide and potassium hydroxide.

Another aspect of the invention provides a process for a stereocontrolled introduction of a hydroxyl group at C3 of a steroid nucleus. The process includes the step of providing a steroid compound of Formula (15) having a carbonyl group at C3. Steroid compounds of Formula (15) may be prepared by, for example, synthetic methods disclosed herein. This is followed by reducing the carbonyl group to a hydroxyl group with a reducing agent so as to provide at least one compound of Formulas (16) and (17)

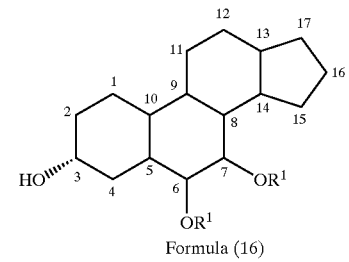

Formula (16)

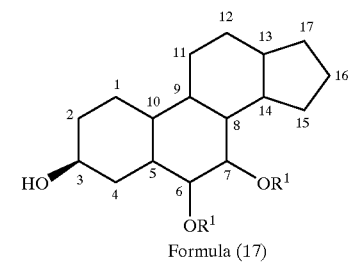

Formula (17)

Each of the compounds of Formulas (15), (16) and (17) include pharmaceutically acceptable salts and solvates thereof. In the compounds of Formulas (15), (16) and (17):

each of C1, C2, C4, C11, C12, C15, C16 and C17 is independently substituted according to any of (a) and (b):
(a) one of: =O, =C(R$^4$)(R$^4$), —C(R$^4$)(R$^4$)(C(R$^4$)-(R$^4$))$_n$— and —(O(C(R$^4$)(R$^4$))$_n$O)— wherein n ranges from 1 to about 6;
(b) two of: —X, —R$^4$ and —OR$^1$, each independently selected;

each of C5, C6, C7, C8, C9, C10, C13 and C14 is independently substituted with one of —X, —R$^4$ or —OR$^1$;

R$^1$ is H or a protecting group such that —OR$^1$ is a protected hydroxyl group, where vicinal —OR$^1$ groups may together form a cyclic structure which protects vicinal hydroxyl groups, and where geminal —OR$^1$ groups may together form a cyclic structure which protects a carbonyl group, with the proviso that either or both of —OR$^1$ at C6 and C7 represents a carbonyl or protected carbonyl group;

R$^4$ at each occurrence is independently selected from H and C$_{1-30}$ organic moiety that may optionally contain at least one heteroatom selected from the group consisting of boron, halogen, nitrogen, oxygen, silicon and sulfur, where two geminal R$^4$ groups may together form a ring with the carbon atom to which they are both bonded; and X represents fluoride, chloride, bromide and iodide.

In a preferred embodiment of this process, the reducing agent is selected from lithium trisiamylborohydride, lithium tri-sec-butylborohydride and potassium tri-secbutylborohydride, and will predominantly provide the hydroxyl compound of Formula (16) (relative to the hydroxyl compound of Formula (17)). In another preferred embodiment, the reducing agent is selected from sodium borohydride and lithium aluminum hydride, and will predominantly provide the hydroxyl compound of Formula (17). In general, the inventive process will achieve a reduction of compounds of Formula (15) such that the product mixture contains a ratio of Formula (16) to Formula (17) compounds of other than 1:1.

As used herein, the term organic moiety of an indicated carbon number range refers to a stable arrangement of atoms composed of at least one and not more than about the maximum carbon number set forth in the range, typically not more than about 30 carbon atoms, and any number of non-carbon atoms.

The $C_{1-30}$ organic moiety may be a saturated or unsaturated hydrocarbyl radical. A saturated hydrocarbyl radical is defined according to the present invention as any radical composed exclusively of carbon and hydrogen, where single bonds are exclusively used to join carbon atoms together. Thus, any stable arrangement of carbon and hydrogen atoms, having at least one carbon atom, is included within the scope of a saturated hydrocarbon radical according to the invention. Some specific terminology that may be used to refer to specific carbon atom arrangements will be discussed below.

The carbon atoms may form an alkyl group, i.e., an acyclic chain of carbon atoms which may be branched or unbranched (linear). Methyl, ethyl, n-propyl, iso-propyl, n-butyl, iso-butyl, sec-butyl and t-butyl are alkyl groups having 1 to 4 carbon atoms (commonly referred to as lower alkyl groups), and are exemplary of alkyl groups of the invention. The carbon atoms may form a cycloalkyl group, i.e., a cyclic arrangement of carbon atoms, where cyclopropyl, cyclobutyl, cyclopentyl are cycloalkyl groups of the invention having 3–5 carbon atoms. Additional groups within the scope of "cycloalkyl" as defined herein are polycycloalkyl groups, defined below.

A polycycloalkyl group is an arrangement of carbon atoms wherein at least one carbon atom is a part of at least two separately identifiable rings. The polycycloalkyl group may contain bridging between two carbon atoms, where bicyclo[1.1.0]butyl, bicyclo[3.2.1]octyl, bicyclo[5,2.0] nonyl, tricycl[2.2.1.0$^1$]heptyl, norbornyl and pinanyl are representative examples. The polycycloalkyl group may contain one or more fused ring systems, where decalinyl (radical from decalin) and perhydroanthracenyl are representative examples. The polycycloalkyl group may contain a spiro union, in which a single atom is the only common member of two rings. Spiro[3.4]octyl, spiro[3.3]heptyl and spiro[4.5]decyl are representative examples.

In addition, the saturated hydrocarbyl radical can be composed of any combination of two or more of the above, i.e., any combination of alkyl and cycloalkyl groups. Thus, the $R^4$ or $R^5$ groups may be an alkyl group (e.g., methyl) with a cycloalkyl (e.g., cyclohexyl) substituent, so that $R^4$ or $R^5$ is a cyclohexylmethyl group. As another example, $R^4$ or $R^5$ may be a cycloalkyl group (e.g., cyclooctyl) having two alkyl substituents (e.g., a methyl and ethyl substituent), so that $R^4$ or $R^5$ is a methylethylcyclooctyl group. As a final example, $R^4$ or $R^5$ may be a cycloalkyl group with an alkyl substituent, where the alkyl substituent is substituted with a polycycloalkly substituent.

As indicated above, $R^4$ or $R^5$ may be an unsaturated hydrocarbyl radical. Such an $R^4$ or $R^5$ group is defined as having a carbon arrangement as set forth above for saturated hydrocarbyl radicals, with the additional feature that at least one bond between any two carbon atoms is other than a single bond. An alkyl group with a single double bond is referred to as an alkenyl group, while an alkyl group having more than one double bond is referred to as an alkapolyenyl group, where alkadienyl (2 double bonds) and alkatrienyl (3 double bonds) are exemplary. An alkyl group with a single triple bond is referred to as an alkynyl group, while an alkyl group having more than one triple bond is referred to as a alkapolyynyl group, where alkydiynyl (2 triple bonds) and alkatriynyl (3 triple bonds) are exemplary.

Likewise, the cycloalkyl group may have one or more double or triple bonds, and be included within the scope of an unsaturated hydrocarbyl radical according to the invention. Cycloalkenyl and cycloalkynyl are general names given to groups having a single carbon-based ring with a single double and triple bond in the ring, respectively. Cycloalkadienyl groups are cycloalkyl groups with two double bonds containedin the ring structure. The double bond may be exocyclic to the ring, e.g., a carbon atom of the ring may have a $=CH_2$ group (i.e., a methylidene group) or higher homologue bonded to it.

A ring may be unsaturated to the extent of being aromatic, and still be included within the scope of an unsaturated hydrocarbyl radical. Thus, an aryl group, for example, phenyl and naphthyl, are included within the scope of such hydrocarbyl groups. As any combination of the above is also included within the scope of an unsaturated hydrocarbyl radical, aralkyl ($R^4$ or $R^5$ is an alkyl group with at least one aryl substituent, e.g., benzyl) and alkylaryl ($R^4$ or $R^5$ is an aryl ring with at least one alkyl substituent, e.g., tolyl) groups are included within the scope of $R^4$ or $R^5$. $C_6$ aryls are a preferred component of organic moieties of the invention.

$R^4$ or $R^5$ includes organic moieties that contain a heteroatom. Heteroatoms according to the invention are any atom other than carbon and hydrogen. A preferred class of heteroatoms are naturally occurring atoms (other than carbon and hydrogen). Another preferred class are non-metallic (other than carbon and hydrogen). Another preferred class consists of boron, nitrogen, oxygen, silicon, phosphorous, sulfur, selenium and halogen (i.e., fluorine, chlorine, bromine and iodine, with fluorine and chlorine being preferred). Another preferred class consists of nitrogen, oxygen, sulfur and halogen. Another preferred class consists of nitrogen, oxygen and sulfur. Oxygen is a preferred heteroatom. Nitrogen is a preferred heteroatom.

For example, $R^4$ or $R^5$ may be a hydrocarbyl radical as defined above, with at least one substituent containing at least one heteroatom. In this paragraph, $R^4$ will be used to refer to both $R^4$ and $R^5$. In other words, $R^4$ may be a hydrocarbyl radical as defined above, wherein at least one hydrogen atom is replaced with a heteroatom. For example, if the heteroatom is oxygen, the substituent may be a carbonyl group, i.e., two hydrogens on a single carbon atom are replaced by an oxygen, to form either a ketone or aldehyde group. Alternatively, one hydrogen may be replaced by an oxygen atom, in the form of an hydroxy, alkoxy, aryloxy, aralkyloxy, alkylaryloxy (where alkoxy, aryloxy, aralkyloxy, alkylaryloxy may be collectively referred to as hydrocarbyloxy), heteroaryloxy, —OC(O)$R^4$, ketal, acetal, hemiketal, hemiacetal, epoxy and —OSO$_3$M. The heteroatom may be a halogen. The heteroatom may be a nitrogen, where the nitrogen forms part of an amino (—NH$_2$, —NHR$^4$, —N(R$^4$)$_2$), alkylamido, arylamido, arylalkylamido, alkylarylamido, nitro, —N(R$^4$)SO$_3$M or aminocarbonylamide group. The heteroatom may be a sulfur, where the sulfur forms part of a thiol, thiocarbonyl, —SO$_3$M, sulfonyl, sulfonamide or sulfonhydrazide group. The heteroatom may be part of a carbon-containing substituent such as formyl, cyano, —C(O)OR$^4$, —C(O)OM, —C(O)R$^4$, —C(O)N(R$^4$)$_2$, carbamate, carbhydrazide and carbohydroxamic acid.

In the above exemplary heteroatom-containing substituents, M represents proton or a metal ion. Preferred metal ions, in combination with a counterion, form physiologically tolerated salts. A preferred metal from which a metal ion may be formed include an alkali metal [for example, lithium (Li), sodium (Na), potassium (K), rubidium (Rb) and cesium (Cs)] an alkaline earth metal (for example, magnesium (Mg), calcium (Ca) and strontium (Sr)], or manganese (Mn), iron (Fe), zinc (Zn) or silver (Ag). An alkali metal or an alkaline earth metal are preferred M groups. Sodium, potassium, magnesium and calcium are preferred M groups. Sodium and potassium are preferred M groups.

Another class of organic moieties according to the invention are hydrocarbyl radicals as defined above, wherein at least one carbon is substituted for at least one heteroatom. Examples of such organic moieties are heterocycloalkyl (a cycloalkyl group having at least one carbon replaced with at least one heteroatom), heterocycloalkenyl, heteroaryl, heteroaryloxy, heteroaralkyl, heteroaralkenyl, etc. Collectively, this class of organic moieties may be referred to as heterohydrocarbyls. Another example of such organic moieties have a heteroatom bridging (a) the radical to which the organic moiety is bonded and (b) the remainder of the organic moiety. Examples include alkoxy, aryloxy, arylalkyloxy and alkylaryloxy radicals, which may collectively be referred to herein as hydrocarbyloxy radicals or moieties. Thus, —OR$^4$ is an exemplary R$^4$ group of the invention. Another example is —NHR$^4$.

Examples of heterocycloalkylene are pyrrolidinylene, piperidinylene, tetrahydrofuranylene, di and tetrahydropyranylene. Examples of heterocycloalkyl are radicals derived from pyrrolidine, imidazolidine, oxazolidine, pyrazolidine, piperidine, piperazine and morpholine. Examples of heterocycloalkenyl substituents are radicals derived by removal of a hydrogen from 2- and 3-pyrroline, oxazoline, 2- and 4-imidazoline and 2- and 3-pyrazoline.

While the organic moiety may have up to about 30 carbon atoms, preferred organic moieties of the invention have fewer than 30 carbon atoms, for example, up to about 25 carbon atoms, more preferably up to about 20 carbon atoms. The organic moiety may have up to about 15 carbon atoms, or up to about 12 or 10 carbon atoms. A preferred category of organic moieties has up to about 8 or 6 carbon atoms.

The following are exemplary R$^4$ and R$^5$ organic moieties where R$^4$ or R$^5$ is joined to the steroid nucleus through a carbon atom: alkyl, alkenyl, alkynyl, cycloalkyl, cycloalkenyl, aryl, heterocyclyl, alkylcarbonyl, alkenylcarbonyl, alkynylcarbonyl, cycloalkylcarbonyl, cycloalkenylcarbonyl, arylcarbonyl, heterocyclylcarbonyl, alkyloxycarbonyl, alkenyloxycarbonyl, alkynyloxycarbonyl, cycloalkyloxycarbonyl, cycloalkenyloxycarbonyl, aryloxycarbonyl, heterocyclyloxycarbonyl, carboxylic acid, cyano and formyl.

The following are exemplary R$^4$ and R$^5$ organic moieties where R$^4$ or R$^5$ is joined to the steroid nucleus through an oxygen atom: hydroxy, oxo, alkoxy, alkenyloxy, alkynyloxy, cycloalkoxy, cycloalkenyloxy, aryloxy, alkylcarbonyloxy, alkenylcarbonyloxy, alkynylcarbonyloxy, cycloaikylcarbonyloxy, cycloalkenylcarbonyloxy, arylcarbonyloxy and heterocyclyloxy.

R$^4$ and R$^5$ organic moieties may contain a nitrogen atom through which the R$^4$ or R$^5$ organic moiety is joined to the steroid nucleus. Examples are nitro and organic moieties of the formula —NL$^2$L$^3$ wherein L$^2$ and L$^3$ are independently hydrogen, alkyl, alkenyl, alkynyl, cycloalkyl, cycloalkenyl, aryl, formyl, heterocyclyl, alkylcarbonyl, alkenylcarbonyl, alkynylcarbonyl, cycloalkylcarbonyl, cycloalkenylcarbonyl, arylcarbonyl and heterocyclylcarbonyl, such that L$^2$ and L$^3$ together may be alkylene or alkenylene to thereby form a 3- to 8-membered saturated or unsaturated ring in combination with the nitrogen atom to which they are attached.

The following are exemplary R$^4$ and R$^5$ organic moieties where the R$^4$ or R$^5$ moiety is joined to the steroid nucleus through a sulfur atom: alkylsulfide, alkenylsulfide, alkynylsulfide, cycloalkylsulfide, cycloalkenylsulfide, arylsulfide, heterocyclylsulfide, alkylcarbonylsulfide, alkenylcarbonylsulfide, alkynylcarbonylsulfide, cycloalkylcarbonylsulfide, cycloalkenylcarbonylsulfide, arylcarbonylsulfide, heterocyclylcarbonylsulfide, and groups of the formulas: —S(O)$_n$H, —S(O)$_n$L$^4$, —S(O)$_m$OH, —S(O)$_m$OL$^4$, —OS(O)$_m$OL$^4$, and —O(S)$_m$OH, wherein L$^4$ is selected from alkyl, alkenyl, alkynyl, cycloalkyl, cycloalkenyl, aryl and heterocyclyl.

In the above R$^4$ and R$^5$ organic moieties, the alkyl, alkenyl, alkynyl, cycloalkyl, cycloalkenyl and aryl groups (collectively referred to as the R$^4$ or R$^5$ hydrocarbyl groups) may be fully or partially halogenated, and/or substituted with up to five L$^5$ groups. The heterocyclyl, heterocyclyloxy, heterocyclylcarbonyl, heterocyclyloxycarbonyl, heterocyclylcarbonyloxy groups (collectively referred to as the R$^4$ heterocyclyl groups) may likewise be fully or partially halogenated and/or substituted with up to five L$^5$ groups.

L$^5$ groups contain a carbon, oxygen, nitrogen or sulfur atom through which they are joined to a carbon atom of the R$^4$ or R$^5$ hydrocarbyl groups or a carbon or nitrogen atom of the R$^4$ or R$^5$ heterocyclyl groups.

The following are exemplary L$^5$ groups wherein a carbon atom of L$^5$ is joined to the R$^4$ hydrocarbyl or heterocyclyl group: alkyl, alkenyl, alkynyl, cycloalkyl, cycloalkenyl, aryl, alkylcarbonyl, alkenylcarbonyl, alkynylcarbonyl, cycloalkylcarbonyl, cycloalkenylcarbonyl, arylcarbonyl, alkyloxycarbonyl, alkenyloxycarbonyl, alkynyloxycarbonyl, cycloalkyloxycarbonyl, cycloalkenyloxycarbonyl and aryloxycarbonyl.

The following are exemplary L$^5$ groups wherein an oxygen atom of L$^5$ is joined to the R$^4$ hydrocarbyl or heterocyclyl group: hydroxy, oxo, alkoxy, alkenyloxy, alkynyloxy, cycloalkoxy, cycloalkenyloxy, aryloxy, alkylcarbonyloxy, alkenylcarbonyloxy, alkynylcarbonyloxy, cycloalkylcarbonyloxy, cycloalkenylcarbonyloxy and arylcarbonyloxy.

The L$^5$ group may contain a nitrogen atom through which the L$^5$ group is joined to the R$^4$ or R$^5$ hydrocarbyl or heterocyclyl group. Examples include nitro and nitrogen-containing groups of the formula —NL$^6$L$^7$ wherein L$^6$ and L$^7$ are independently hydrogen, alkyl, alkenyl, alkynyl, cycloalkyl, cycloalkenyl, aryl, formyl, alkylcarbonyl, alkenylcarbonyl, alkynylcarbonyl, cycloalkylcarbonyl, cycloalkenylcarbonyl and arylcarbonyl such that L$^6$ and L$^7$ together may be alkylene or alkenylene to thereby form a 3- to 8-membered saturated or unsaturated ring in combination with the nitrogen atom to which they are attached.

The following are exemplary L$^5$ groups wherein a sulfur atom of L$^5$ is joined to the R$^4$ or R$^5$ hydrocarbyl or heterocyclyl group: alkylsulfide, alkenylsulfide, alkynylsulfide, cycloalkylsulfide, cycloalkenylsulfide, arylsulfide, alkylcarbonylsulfide, alkenylcarbonylsulfide, alkynylcarbonylsulfide, cycloalkylcarbonylsulfide, cycloalkenylcarbonylsulfide, arylcarbonylsulfide, and groups of the formulas: —S(O)$_n$L$^8$, —S(O)$_m$OH, —S(O)$_m$OL$^8$, —OS(O)$_m$OL$^8$, and —O(S)$_m$OH, wherein L$^8$ is selected from alkyl, alkenyl, alkynyl, cycloalkyl, cycloalkenyl, aryl and heterocyclyl.

In the exemplary R$^4$ and R$^5$ organic moieties, the alkyl, alkenyl, alkynyl, cycloalkyl, cycloalkenyl and aryl groups which form part of L$^5$ (collectively referred to as the L$^5$ hydrocarbyl groups) may be fully or partially halogenated, and/or substituted with up to three L$^9$ groups. The heterocyclyl, heterocyclyloxy, heterocyclylcarbonyl, heterocyclyloxycarbonyl, heterocyclylcarbonyloxy groups (collectively referred to as the L$^5$ heterocyclyl groups) may likewise be fully or partially halogenated, and/or substituted with up to three L$^9$ groups.

L$^9$ groups contain a carbon, oxygen, nitrogen or sulfur atom through which they are joined to the L$^5$ hydrocarbyl group or the L$^5$ heterocyclyl group.

The following are exemplary L$^9$ groups wherein a carbon atom of L$^9$ is joined to the L$^5$ hydrocarbyl or heterocyclyl group: alkyl, alkenyl, alkynyl, cycloalkyl, cycloalkenyl, aryl, heterocyclyl, alkylcarbonyl, alkenylcarbonyl, alkynylcarbonyl, cycloalkylcarbonyl, cycloalkenylcarbonyl, arylcarbonyl, heterocyclylcarbonyl, alkyloxycarbonyl, alkenyloxycarbonyl, alkynyloxycarbonyl, cycloalkyloxycarbonyl, cycloalkenyloxycarbonyl, aryloxycarbonyl and heterocyclyloxycarbonyl.

The following are exemplary L$^9$ groups wherein an oxygen atom of L$^9$ is joined to the L$^5$ hydrocarbyl or heterocyclyl group: hydroxy, oxo, alkoxy, alkenyloxy, alkynyloxy, cycloalkoxy, cycloalkenyloxy, aryloxy, heterocyclyloxy, alkylcarbonyloxy, alkenylcarbonyloxy, alkynylcarbonyloxy, cycloalkylcarbonyloxy, cycloalkenylcarbonyloxy, arylcarbonyloxy and heterocyclylcarbonyloxy.

The L$^9$ group may contain a nitrogen atom through which the L$^9$ group is joined to the L$^5$ hydrocarbyl or heterocyclyl group. Such nitrogen-containing include nitro and groups having the formula —NL$^{10}$L$^{11}$ wherein L$^{10}$ and L$^{11}$ are independently hydrogen, alkyl, alkenyl, alkynyl, cycloalkyl, cycloalkenyl, aryl, heterocyclyl, formyl, alkylcarbonyl, alkenylcarbonyl, alkynylcarbonyl, cycloalkylcarbonyl, cycloalkenylcarbonyl, arylcarbonyl and heterocyclylcarbonyl such that L$^{10}$ and L$^{11}$ together may be alkylene or alkenylene to thereby form a 3- to 8-membered saturated or unsaturated ring in combination with the nitrogen atom to which they are attached.

The following are exemplary L$^9$ groups wherein an sulfur atom of L$^9$ is joined to the L$^5$ hydrocarbyl or heterocyclyl group: alkylsulfide, alkenylsulfide, alkynylsulfide, cycloalkylsulfide, cycloalkenylsulfide, arylsulfide, heterocyclylsulfide alkylcarbonylsulfide, alkenylcarbonylsulfide, alkynylcarbonylsulfide, cycloalkylcarbonylsulfide, cycloalkenylcarbonylsulfide, arylcarbonylsulfide, heterocyclylcarbonylsulfide and groups of the formulas: —S(O)$_n$L$^{12}$, —S(O)$_m$OH, —S(O)$_m$OL$^{12}$, —OS(O)$_m$OL$^{12}$, and —O(S)$_m$OH, wherein L$^{12}$ is selected from alkyl, alkenyl, alkynyl, cycloalkyl, cycloalkenyl, aryl and heterocyclyl.

In the exemplary R$^4$ and R$^5$ organic moieties, the alkyl, alkenyl, alkynyl, cycloalkyl, cycloalkenyl and aryl groups which form part of L$^9$ (collectively referred to as the L$^9$ hydrocarbyl groups) may be fully or partially halogenated, and/or substituted with up to three L$^{13}$ groups. The heterocyclyl, heterocyclyloxy, heterocyclylcarbonyl, heterocyclyloxycarbonyl, heterocyclylcarbonyloxy groups (collectively referred to as the L$^9$ heterocyclyl groups) may likewise be fully or partially halogenated, and/or substituted with up to three L$^{13}$ groups.

An L$^{13}$ group contains a carbon, oxygen, nitrogen or sulfur atom through which the L$^{13}$ group is joined to the L$^9$ hydrocarbyl group or L$^9$ heterocyclyl group.

The following are exemplary L$^{13}$ groups wherein a carbon atom of L$^{13}$ is joined to the L$^9$ hydrocarbyl or heterocyclyl group: alkyl, alkenyl, alkynyl, cycloalkyl, cycloalkenyl, aryl, heterocyclyl, alkylcarbonyl, alkenylcarbonyl, alkynylcarbonyl, cycloalkylcarbonyl, cycloalkenylcarbonyl, arylcarbonyl, heterocyclylcarbonyl, alkyloxycarbonyl, alkenyloxycarbonyl, alkynyloxycarbonyl, cycloalkyloxycarbonyl, cycloalkenyloxycarbonyl, aryloxycarbonyl and heterocyclyloxycarbonyl.

The following are exemplary L$^{13}$ groups wherein an oxygen atom of L$^{13}$ is joined to the L$^9$ hydrocarbyl or heterocyclyl group: hydroxy, oxo, alkoxy, alkenyloxy, alkynyloxy, cycloalkoxy, cycloalkenyloxy, aryloxy, heterocyclyloxy, alkylcarbonyloxy, alkenylcarbonyloxy, alkynylcarbonyloxy, cycloalkylcarbonyloxy, cycloalkenylcarbonyloxy, arylcarbonyloxy and heterocyclylcarbonyloxy.

The L$^{13}$ group may contain a nitrogen atom through which the L$^{13}$ group is joined to the L$^9$ hydrocarbyl or heterocyclyl group. Such nitrogen-containing L$^{13}$ groups include nitro and groups of the formula —NL$^{14}$L$^{15}$ wherein L$^{14}$ and L$^{15}$ are independently hydrogen, alkyl, alkenyl, alkynyl, cycloalkyl, cycloalkenyl, aryl, heterocyclyl, formyl, alkylcarbonyl, alkenylcarbonyl, alkynylcarbonyl, cycloalkylcarbonyl, cycloalkenylcarbonyl, arylcarbonyl and heterocyclylcarbonyl such that L$^{15}$ and L$^{15}$ together may be alkylene or alkenylene to thereby form a 3- to 8-membered saturated or unsaturated ring in combination with the nitrogen atom to which they are attached.

The following are exemplary L$^{13}$ groups wherein an sulfur atom of L$^{13}$ is joined to the L$^9$ hydrocarbyl or heterocyclyl group: alkylsulfide, alkenylsulfide, alkynylsulfide, cycloalkylsulfide, cycloalkenylsulfide, arylsulfide, heterocyclylsulfide, alkylcarbonylsulfide, alkenylcarbonyisulfide, alkynylcarbonylsulfide, cycloalkylcarbonylsulfide, cycloalkenylcarbonylsulfide, arylcarbonylsulfide, heterocyclylcarbonylsulfide and groups of the formulas: —S(O)$_n$L$^{14}$, —S(O)$_m$OH, —S(O)$_m$OL$^{14}$, —OS(O)$_m$OL$^{14}$, and —O(S)$_m$OH, wherein L$^{14}$ is selected from alkyl, alkenyl, alkynyl, cycloalkyl, cycloalkenyl, aryl and heterocyclyl.

In the groups set forth above, m is independently 1 or 2, and n is independently 0, 1 or 2.

Certain of the R$^4$ and R$^5$ substituents may contain asymmetric carbon atoms. Compounds containing such substituents may therefore exist in enantiomeric and diastereomeric forms and in racemic mixtures thereof. All are within the scope of the present invention. A racemate or racemic mixture does not imply a 50:50 mixture of stereoisomers.

In accordance with the description of exemplary R$^4$ or R$^5$ organic moieties, the following terms have the designated meanings, unless explicitly stated otherwise:

Alkyl, alkenyl and alkynyl refer to straight or branched chain hydrocarbons having 1 to 30 carbon atoms (at least two carbon atoms for an alkynyl group) and no unsaturation, at least one double bond or at least one triple bond, respectively. Preferred carbon number ranges are 1 to 20 and 1 to 10.

Cycloalkyl and cycloalkenyl refer to cyclic hydrocarbon groups of 3 to 8 carbon atoms, where a cycloalkyl group is saturated, and a cycloalkenyl group has at least one double bond within the cyclic structure. Suitable cycloalkyl groups include cyclopropyl, cyclobutyl, cyclopentyl, cyclohexyl, cycloheptyl and cyclooctyl.

Aryl refers to refers to aromatic groups which have at least one ring having a conjugated pi electron system and includes carbocyclic aryl, heterocyclic aryl and biaryl groups.

Carbocyclic aryl refers to aromatic groups wherein the ring atoms of the aromatic ring are carbon atoms. Carbocyclic aryl groups include phenyl, naphthyl and indenyl groups.

Heterocyclic aryl refers to a mono- or bicyclic ring system of about 5 to about 12 carbon atoms, where each monocyclic ring may possess from 0 to about 4 heteroatoms, and each bicyclic ring may possess about 0 to about 5 heteroatoms selected from N, O, and S provided said heteroatoms are not vicinal oxygen and/or sulfur atoms. Examples of such mono- and bicyclic ring systems include, without limitation, benzofuran, benzothiophene, indole, benzopyrazole, coumarin, isoquinoline, pyrrole, thiophene, furan, thiazole, imidazole, pyrazole, triazole, quinoline, pyrimidine, pyridine, pyridone, pyrazine, pyridazine, isothiazole, isoxazole and tetrazole.

Biaryl refers to phenyl substituted by carbocyclic aryl or heterocyclic aryl as defined herein, ortho, meta or para to the point of attachment of the phenyl ring.

Heterocyclyl refers to a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached to the steroid nucleus through any heteroatom or carbon atom of the heterocyclic ring which results in the creation of a stable structure. Examples of such heterocyclic groups include piperidinyl, piperazinyl, 2-oxopiperazinyl, 2-oxopiperidinyl, 2-oxopyrrolodinyl, 2-oxcazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

Heterocyclyloxy and heterocyclylcarbonyl refer to heterocyclyl groups bonded through an oxygen atom or a carbonyl group, respectively, to one of the to one or more of the steroid nucleus, $R^4$ hydrocarbyl group, $L^5$ hydrocarbyl group or $L^9$ hydrocarbyl group.

Heterocyclyloxycarbonyl refers to a heterocyclyloxy group bonded through a carbonyl group to one or more of the steroid nucleus, R4 hydrocarbyl group, $L^5$ hydrocarbyl group or $L^9$ hydrocarbyl group.

Heterocyclylcarbonyloxy refers to a heterocyclylcarbonyl group bonded through an oxygen atom to one or more of the steroid nucleus, R4 hydrocarbyl group, $L^5$ hydrocarbyl group or $L^9$ hydrocarbyl group.

Alkylcarbonyl, alkenylcarbonyl, alkynylcarbonyl, cycloalkylcarbonyl, cycloalkenylcarbonyl and arylcarbonyl refer to moieties wherein a carbonyl group (C=O) provides the carbon atom through which the moiety is joined to one of the steroid nucleus, R4 hydrocarbyl group, $L^5$ hydrocarbyl group or $L^9$ hydrocarbyl group, and an alkyl, alkenyl, alkynyl, cycloalkyl, cycloalkenyl or aryl group, respectively, is also joined to the carbonyl group.

Alkyloxycarbonyl, alkenyloxycarbonyl, alkynyloxycarbonyl, cycloalkyloxycarbonyl, cycloalkenyloxycarbonyl and aryloxycarbonyl refer to moieties wherein a carbonyl group (C=O) provides the carbon atom through which the moiety is joined to one of the steroid nucleus, R4 hydrocarbyl group, $L^5$ hydrocarbyl group or $L^9$ hydrocarbyl group, and an alkoxy, alkenyloxy, alkynyloxy, cycloalkoxy, cycloalkenyloxy or aryloxy group, respectively, is also joined to the carbonyl group.

Alkoxy, alkenyloxy, alkynyloxy, cycloalkoxy, cycloalkenyloxy and aryloxy refer to groups wherein oxygen is bonded to an alkyl, alkenyl, alkynyl, cycloalkyl, cycloalkenyl or aryl group, respectively, and that oxygen is also bonded to one of the steroid nucleus, R4 hydrocarbyl group, $L^5$ hydrocarbyl group or $L^9$ hydrocarbyl group.

Alkylcarbonyloxy, alkenylcarbonyloxy, alkynylcarbonyloxy, cycloalkylcarbonyloxy, cycloalkenylcarbonyloxy and arylcarbonyloxy refer to groups wherein oxygen is bonded to an alkylcarbonyl, alkenylcarbonyl, alkynylcarbonyl, cycloalkylcarbonyl, cycloalkenylcarbonyl and arylcarbonyl group, respectively, and that oxygen is also bonded to one of the steroid nucleus, R4 hydrocarbyl group, $L^5$ hydrocarbyl group or $L^9$ hydrocarbyl group.

Alkylsulfide, alkenylsulfide, alkynylsulfide, cycloalkylsulfide, cycloalkenylsulfide and arylsulfide refer to groups wherein sulfur is bonded to an alkyl, alkenyl, alkynyl, cycloalkyl, cycloalkenyl or aryl group, respectively, and that sulfur atom is also bonded to one of the steroid nucleus, R4 hydrocarbyl group, $L^5$ hydrocarbyl group or $L^9$ hydrocarbyl group.

Alkylcarbonylsulfide, alkenylcarbonylsulfide, alkynylcarbonylsulfide, cycloalkylcarbonylsulfide, cycloalkenylcarbonylsulfide and arylcarbonylsulfide refer to groups wherein a sulfur atom is bonded to a alkylcarbonyl, alkenylcarbonyl, alkynylcarbonyl, cycloalkylcarbonyl, cycloalkenylcarbonyl or arylcarbonyl group, respectively, and that sulfur atom is also bonded to one of the steroid nucleus, R4 hydrocarbyl group, $L^5$ hydrocarbyl group or $L^9$ hydrocarbyl group.

Alkylene refers to a straight chain bridge of 1 to 5 carbon atoms, which may be substituted with 1 to 3 lower alkyl groups or fully or partially halogenated lower alkyl groups.

Alkenylene refers to a straight chain bridge of 2 to 5 carbon atoms having one or two double bonds, which may be substituted with 1 to 3 lower alkyl groups or fully or partially halogenated lower alkyl groups.

Alkynylene refers to a straight chain bridge of 2 to 5 carbon atoms having one or two triple bonds, which may be substituted with 1 to 3 lower alkyl group or fully or partially halogenated lower alkyl groups.

A lower alkyl group refers to C1–C5 alkyl groups, e.g., methyl, ethyl, n-propyl, iso-propyl, n-butyl, t-butyl, sec-butyl, iso-butyl, n-pentyl, iso-pentyl, etc.

Halogen refers to fluorine, chlorine, bromine and iodine, and a halogenated group refers to a carbon atom having at least one halogen bonded thereto.

Formyl refers to —C(=O)H; hydroxyl refers to —OH; and oxo refers to an oxygen atom which forms part of a carbonyl group.

A pharmaceutically acceptable salt includes acid addition salts and base addition salts.

Acid addition salts refer to those salts formed from steroid compounds of the invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts include those salts derived from steroids of the invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

In another embodiment, the present invention provides compositions which include a 6,7-dioxygenated steroid compound as described above in admixture or otherwise in association with one or more inert carriers, as well as optional ingredients if desired. A pharmaceutical composition comprising a compound in combination with a pharmaceutically acceptable carrier or diluent, the compound having the formula

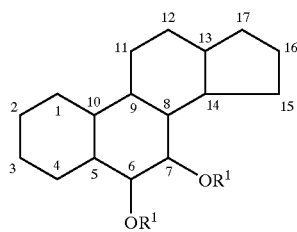

including pharmaceutically acceptable salts and solvates thereof, wherein:
  each of C5, C6, C7, C8, C9, C10, C13 and C14 is independently substituted with —X, —$R^4$ and —$OR^1$;
  each of C1, C2, C3, C4, C11, C12, C15, C16 and C17 is independently substituted with a substituent selected from (a) or (b), wherein
    (a) represents one of: =O, =C($R^4$)($R^4$), C($R^4$)($R^4$)(C($R^4$)($R^4$))$_n$— and —(O(C($R^4$)($R^4$))$_n$O)—, wherein n ranges from 1 to about 6; and
    (b) represents two of: —X, —$R^4$ and —$OR^1$, which are independently selected at each occurrence;
  the A, B, C and D rings may independently be fully saturated, partially saturated or fully unsaturated;
  $R^1$ is H or a protecting group such that —$OR^1$ is a protected hydroxyl group, where the C6 and C7-$OR^1$ groups may together form a cyclic structure which protects both hydroxyl groups;
  $R^4$ at each occurrence is independently selected from H and $R^5$;
  $R^5$ is a $C_{1-30}$ organic moiety that may optionally contain at least one heteroatom selected from the group consisting of boron, halogen, nitrogen, oxygen, silicon and sulfur; where two geminal $R^4$ groups may together form a ring with the carbon atom to which they are both bonded; and
  X represents fluoride, chloride, bromide or iodide;
  with the proviso that C15 is not bonded to an oxygen atom.

In preferred compositions: C17 is substituted with a hydrocarbyl group; such as a $C_1$-$C_7$ alkyl group; or such as an olefinic group of the formula =C($R^4$)($R^4$), where preferably $R^4$ is hydrogen or $C_1$-$C_{10}$ alkyl; in a preferred embodiment the C17 hydrocarbyl group excludes —CH(CH$_3$)(CH$_2$)$_3$CH(CH$_3$)$_2$. In other preferred compositions, C17 is substituted with two atoms independently selected from hydrogen and halogen atoms; or C17 is substituted with at least one oxygen atom; or C17 is substituted with a hydroxyl or protected hydroxyl group; or C17 is substituted with a carbonyl or protected carbonyl group; or C17 is substituted with an alkoxy group. In preferred compositions, the substituent at C17 excludes

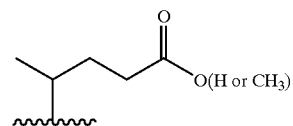

In other preferred composition, C15 is substituted with two hydrogen atoms; and/or C4 is substituted with hydrogen and one of —X, —$R^5$ or —$OR^1$; and/or C5 is substituted with hydrogen; and/or C4 is bonded to at least one hydrogen such that when C4 is bonded to two hydrogen atoms then C3 is not bonded to either oxygen or to two hydrogen atoms. In other preferred composition, C4 is bonded to two hydrogen atoms only when C3 is not bonded to either oxygen or to two hydrogen atoms. In another preferred composition, C4 is bonded to methyl only when C4 is not bonded to two methyls or formyl. In other preferred compositions, the compounds have a hydrogen at C5 in the alpha configuration. In another preferred composition, the compounds have an —$OR^1$ group at C6 with the alpha configuration. In another preferred composition, the compounds have an —$OR^1$ group at C7 with the beta configuration. In another preferred composition, the compounds have an —$OR^1$ substituent at C6 with the alpha configuration and an —$OR^1$ substituent at C7 with the beta configuration. In other preferred compositions, the compounds have at least one of C3 and C4 bonded to an oxygen atom, and in a preferred embodiment, both C3 and C4 are bonded to an oxygen atom. In another preferred composition, C10 of the compound is substituted with a methyl group; and/or C13 of the compound is substituted with a methyl group; or both C10 and C13 of the compounds are substituted with methyl groups. In a preferred composition, both C6 and C7 are bonded to hydrogen atoms. In another preferred composition, at least one of C1, C2, C3, C4, C5, C8, C9, C10, C11, C12, C13, C14, C15, C16 and C17 is substituted exclusively with hydrogen atoms, and more preferably C1 and C2 are substituted exclusively with hydrogen atoms; and/or C11 and C12 are substituted exclusively with hydrogen atoms; and/or C15 and C16 are substituted exclusively with hydrogen atoms. In a preferred composition, the compounds have a saturated A ring; and/or a saturated B ring; and/or a saturated C ring; and/or a saturated D ring. Compositions with compounds having a saturated A ring are preferred, and compositions with compounds having fully saturated A,B,C and D rings are more preferred. In another preferred composition, the A ring of the compound does not contain a bicyclic structure. In yet another preferred composition, C3 and C4 of the compound are not both substituted solely with hydrogen atoms. These compositions may be used for the treatment of asthma, allergy, inflammation including arthritis, and thrombosis. These compositions may also be formed into a medicament, which may used in the treatment of, for example, asthma, allergy, inflammation including arthritis, and thrombosis.

These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 80 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers.

Thus, the present invention provides a pharmaceutical or veterinary composition (hereinafter, simply referred to as a pharmaceutical composition) containing a 6,7-dioxygenated steroid compound as described above, in admixture with a pharmaceutically acceptable carrier. The invention further provides a pharmaceutical composition containing an effective amount of a 6,7-dioxygenated steroid compound as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of steroid in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes an active 6,7-dioxygenated steroid compounds as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active steroid compound. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the active steroid component(s) and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of asthma, allergy, inflammation (including arthritis) or thrombosis.

The pharmaceutical compositions may be prepared by methodology well known in the pharmaceutical art. Various steroid compounds are, and have been widely used as active ingredients in pharmaceutical composition intended for therapeutic use, and accordingly one of ordinary skill in the art is familiar with preparing such compositions. The steroid compounds of the present invention may be formulated into pharmaceutical compositions in a like manner.

A composition intended to be administered by injection can be prepared by combining the 6,7-dioxygenated steroid with water so as to form a solution. A surfactant may be added to facilitate the formation of a homogeneous solution or suspension. Surfactants are compounds that non-covalently interact with the steroid so as to facilitate dissolution or homogeneous suspension of the steroid in the aqueous delivery system.

The compounds and compositions described above have utility in treating allergy and asthma, arthritis and/or thrombosis. The compounds and composition described above may also be used to treat a condition associated with an elevated level of NFκB, wherein a subject in need thereof is administered an amount of the compound (or composition containing the compound) effective to lower the NFκB activity. As used herein, "treating allergy and asthma, arthritis and/or thrombosis" refers to both therapy for allergy and asthma, arthritis and thrombosis, and for the prevention of the development of the allergic response, bronchoconstriction, inflammation and the formation of blood clots that cause thrombosis and associated diseases. As also used herein, NF-kB activity refers to any increase or decrease in the transcriptional activity of genes that is attributable to, directly or indirectly, the binding of any members of the NF-kB family of proteins to all DNA sequences recognized by this family of proteins.

An effective amount of a compound or composition of the present invention is used to treat allergy, asthma, arthritis or thrombosis in a warm-blooded animal, such as a human. Methods of administering effective amounts of anti-allergy, anti-asthma, anti-arthritis and anti-thrombotic agents are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices. Generally, oral or intravenous administration is preferred for the treatment of arthritis and thrombosis, while oral or inhalation/intranasal are preferred for asthma and allergy. The dosage amount and frequency are selected to create an effective level of the agent without harmful effects. It will generally range from a dosage of about 0.1 to 100 mg/kg/day, and typically from about 0.1 to 10 mg/Kg/day where administered orally or intravenously, for anti-allergy, anti-asthma, anti-arthritis or anti-thrombotic effects. Also, the dosage range will be typically from about 0.01 to 1 mg/Kg/day where administered intranasally or by inhalation for anti-asthma and anti-allergy effects.

Administration of compounds or compositions of the present invention may be carried out in combination with the administration of other agents. For example, it may be desired to administer a bronchodilator or a glucocorticoid agent for effects on asthma, a glucocorticoid for effects on arthritis, or an anti-histamine for effects on allergy. Non-steroid compounds may be co-administered with the steroids of the present invention, and/or non-steroid compounds may used in combination with the steroid compounds of the invention to provide a therapy for one or more of asthma, allergies, arthritis and thrombosis.

The following examples are offered by way of illustration and not by way of limitation.

Unless otherwise stated, flash chromatography and column chromatography may be accomplished using Merck silica gel 60 (230–400 mesh). Flash chromatography may be carried out according to the procedure set forth in: "Purification of Laboratory Chemicals", 3rd. edition, Butterworth-Heinemann Ltd., Oxford (1988), Eds. D. D. Perrin and W. L. F. Armarego, page 23. Column chromatography refers to the process whereby the flow rate of eluent through a packing material is determined by gravity. In all cases flash chromatography and radial chromatography may be used interchangeably. Radial chromatography is performed using silica gel on a Chromatotron Model #7924T (Harrison Research, Palo Alto, Calif.).

A typical work-up procedure for a reaction mixture involves dilution of the reaction mixture with an organic solvent (ethyl acetate or diethyl ether) and washing of the organic mixture with saturated sodium bicarbonate followed by saturated sodium chloride. The organic layer is then dried over MgSO$_4$, the mixture is filtered and the filtrate evaporated to dryness in vacuo to yield the crude product which may or may not require further purification.

A typical work-up procedure for a Wittig reaction involves first quenching by the dropwise addition of water. The mixture is then diluted with ethyl acetate and washed with saturated sodium bicarbonate and then sodium chloride. The organic layer is dried over magnesium sulphate, filtered and evaporated to dryness.

A typical work-up procedure for a hydroboration reaction involves pouring the reaction mixture into saturated sodium chloride solution (200 ml) followed by extraction of the aqueous slurry with methylene chloride and then washing the combined organic layers with aqueous 25% sodium thiosulphate solution. The organic layer is then dried over magnesium sulphate, filtered and evaporated to dryness.

Reactions may typically be monitored with thin layer chromatography (TLC) using Silica gel 60 F$_{254}$ plates (EM Science, Gibbstown, N.J.) and an appropriate solvent system. Thin layer chromatography may be carried out according to the procedure set forth in: "Purification of Laboratory Chemicals", 3rd. edition, Butterworth-Heinemann Ltd., Oxford (1988), Eds. D. D. Perrin and W. L. F. Armarego, page 30. After elution is complete, the TLC plate is dried, lightly sprayed with a 10% solution of H$_2$SO$_4$ in ethanol and then heated until the spots corresponding to the compounds appear. Unless otherwise stated, filtrations are carried out using a Whatman (type 1) filter paper.

EXAMPLES

SECTION 1

Synthesis of 3,4,6,7-Polyhydroxylated Steroids

Steroids with the same or closely related ring-structure hydroxylation pattern as compound 237 (shown by the structure below) can be synthesized starting from a number of steroid precursors including 4-androsten-3,17-dione (1) and others with C3 oxygen functionalities and Δ$^5$ carbon-carbon double bonds such as dehydroisoandrosterone (247).

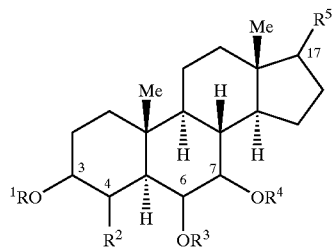

237 (3β,4α,6α,7β,17β) where R$^1$=R$^3$=R$^4$=H, and R$^2$=R$^5$=OH

For example, after protection of the ketone functionalities of androsten-3,17-dione (1) (Example 1, Scheme 55) with any one of a number of appropriate carbonyl protecting groups and concomitant migration of the carbon-carbon double bond, allylic oxidation introduces a C7 oxygen. A number of oxidizing agents and experimental conditions can be used for this oxidation step including but not limited to chromium trioxide/3,5-dimethylpyrazole complex, pyridinium chlorochromate (PCC), pyridinium dichromate (PDC), and tBuOOH with RuCl$_3$. Reduction of the resultant ketone with an appropriate reducing agent gives the hydroxyl functionality at C7. Several metal hydride reducing agents can be used for this task including sodium borohydride and lithium aluminum hydride. Generally, reduction of the C7 carbonyl produces the βOH configuration by hydride attack from the least hindered face of the steroid.

Introduction of the C6 oxygen can be achieved, after protection of the C7 hydroxyl with an appropriate protecting group, by methods such as hydroboration/oxidation or epoxidation followed by ring opening. The Δ$^5$ carbon-carbon double bond can be epoxidized with any of a number of peracids including m-chloroperbenzoic acid, trifluoroperacetic acid or 3,5-dinitroperoxybenzoic acid. Generally, the epoxide introduced has the α-configuration arising from attack on the least hindered face of the steroid ring structure. Subsequent ring opening of the epoxide can be accomplished under acidic conditions such as 80% aqueous acetic acid at 60° C. This produces an allylic alcohol at the C6 position with the α-configuration. Alternatively, hydroboration of the Δ$^5$ double bond with an appropriate borane complex followed by oxidation using reagents such as basic hydrogen peroxide will also introduce an hydroxyl group in the α-configuration at C6.

Hydroxyl groups can be introduced at the C3 and C4 positions starting from the A-ring 4-ene-3-one functionalization pattern. Reduction of the α,β-unsaturated ketone can be accomplished using lithium dissolved in liquid ammonia. The resultant enolate can be trapped with an electrophile such as trimethylsilylchloride or diethylchlorophosphate. Hydroboration-oxidation of the silyl enol ether results in the introduction of an oxygen at C4. This method generates the 3β,4α hydroxylation pattern. Alternatively, a second reduction using lithium in liquid ammonia on the enol phosphate produces the Δ$^3$ carbon-carbon double bond. Epoxidation of the Δ$^3$ double bond with a peracid such as m-chloroperbenzoic acid produces the α-epoxide. Ring opening of this epoxide could be achieved using a number of acidic or basic conditions. For example, treatment of the 3α,4α-epoxy functionality with glacial acetic acid in compound 238 (Example 3, Scheme 61) produces the 3α-hydroxy, 4β-acetoxy pattern. Removal of the acetate group using any of a number of reagents including potassium carbonate (or sodium methoxide) in methanol gives the 3α,4β-hydroxylation pattern.

Example 1

The Steroid 3β,4α,6α,7β,17β-Pentahydroxy-5α-androstane (237) can be Synthesized According to the Reaction Sequence Illustrated by Scheme 55

Scheme 55

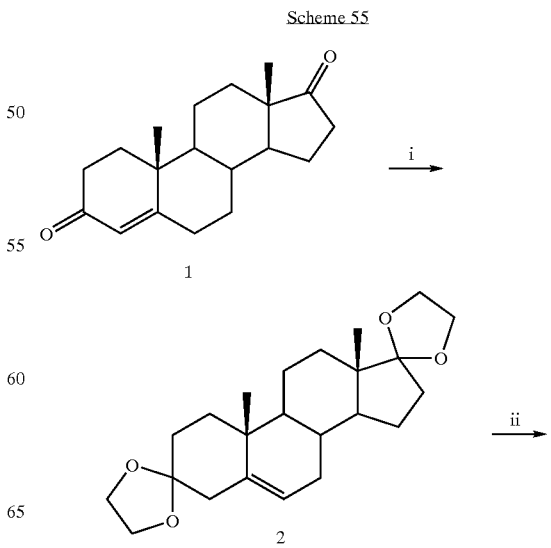

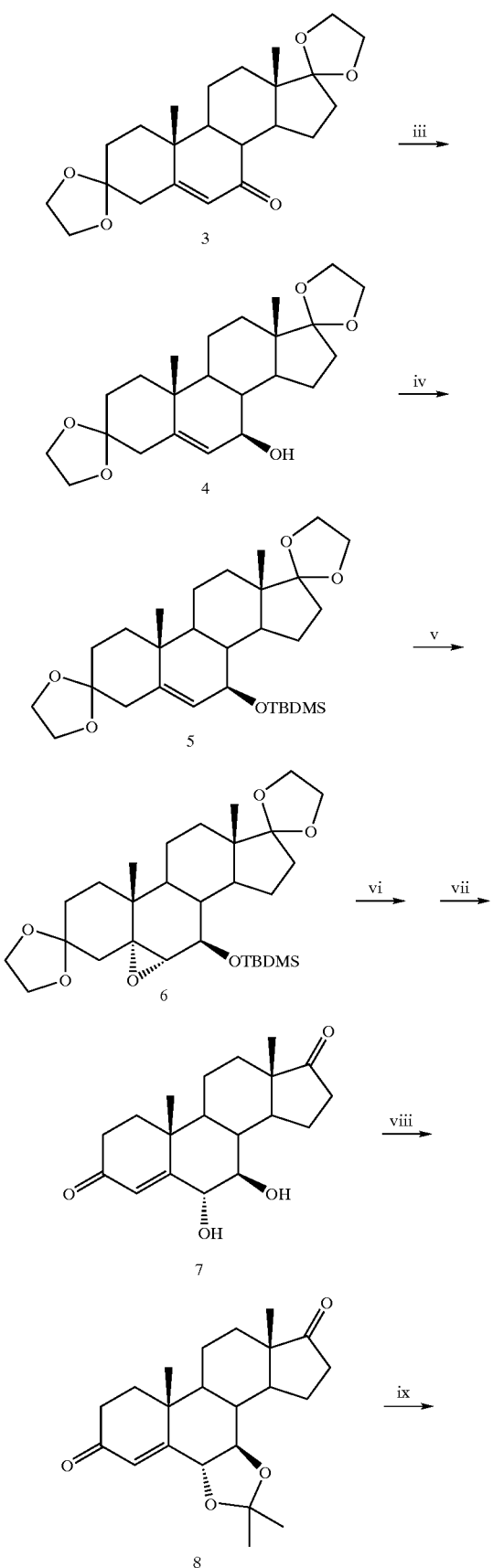
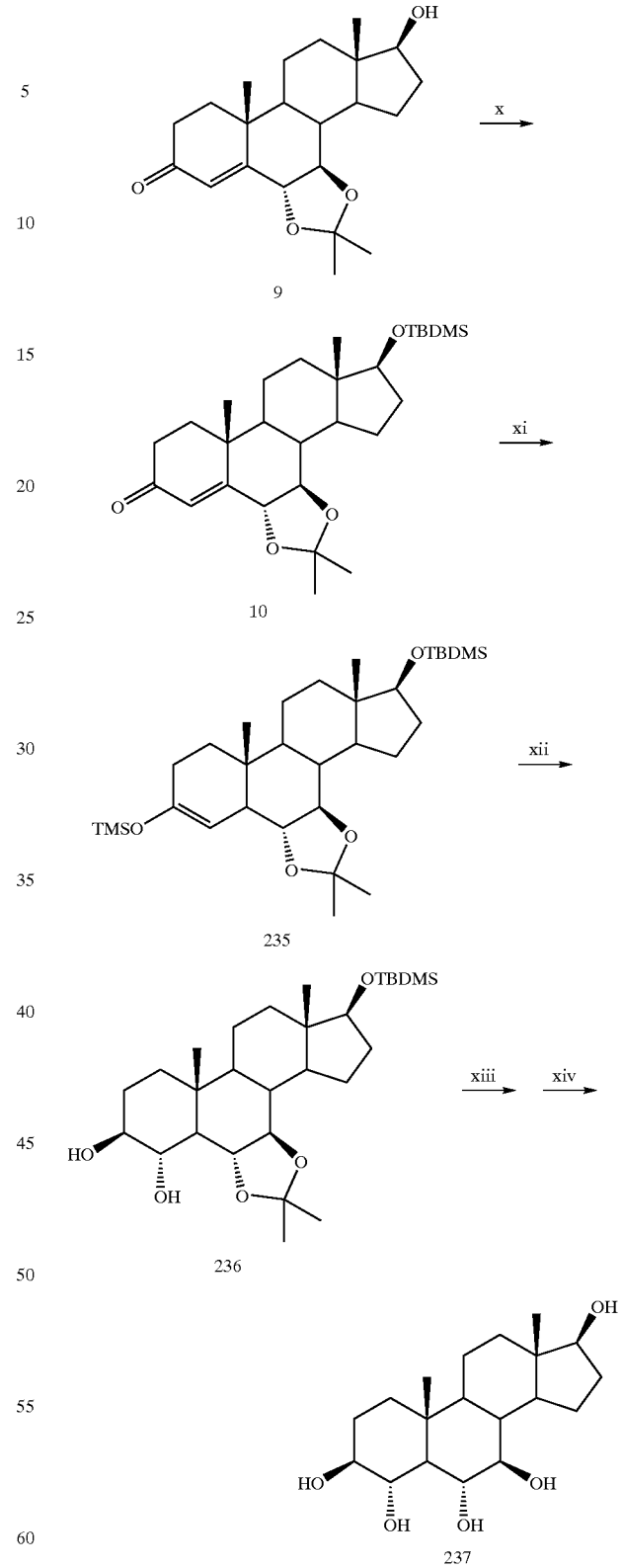
Key: (i) p-TsOH, (CH₂OH)₂, benzene (ii) CrO₃, 3,5-dimethylpyrazole, CH₂Cl₂ (iii) NaBH₄, CeCl₃, THF-MeOH (iv) TBDMSCl, imidazole, DMF (v) m-CPBA, CH₂Cl₂ (vi) 80% AcOH (vii) TBAF, THF (viii) 2,2-dimethoxypropane, CSA, DMF (ix) NaBH₄, MeOH (x) TBDMSCl, imidazole, DMF (xi) 1.Li/NH₃-THF, 2. TMSCl, Et₃N (xii) 1. BH₃-THF complex, 2. 30% NaOH, 30% H₂O₂, THF (xiii) TBAF, THF (xiv) p-TsOH, H2O, THF.

Commercially available 4-androsten-3,17-dione (1) (20.0 g, 62.8 mmol) is stirred with ethylene glycol (10 mL) and a catalytic amount of p-toluenesulfonic acid (1.0 g, 5.2 mmol) in benzene (500 mL) at reflux under nitrogen for 26 hours (Scheme 56). The water generated by the reaction is removed during this time using a Dean-Stark apparatus. The mixture is then cooled to room temperature and Et$_2$O is added. The mixture is washed with sodium bicarbonate, then water and dried over magnesium sulfate. Filtration and concentration gives a pale yellow solid that is washed with methanol to give the diketal 2 as a white powder (14.6 g, 39.0 mmol, 62%). A monoketal byproduct (5.13 g, 15.0 mmol) is recovered from the filtrate and recycled. The overall yield, accounting for the byproduct, is 86% of diketal 2.

Allylic oxidation at the C7 position of the diketal 2, using a chromium trioxide-3,5-dimethylpyrazole complex in dichloromethane, affords compound 3 (Scheme 56). Chromium trioxide (46.7 g, 467 mmol) and dry dichloromethane (450 mL) are added to a flask under nitrogen, and then cooled to −20° C. using a dry-ice/CaCl$_2$ solution. 3,5-Dimethylpyrazole (44.9 g, 467 mmol) is added and the mixture is stirred at −20 to −30° C. for 1.5 hours. This is followed by the addition of diketal 2 (7.00 g, 18.7 mmol) and continued stirring for 7 hours at −20° C. The reaction is quenched with water and filtered. The filtrate is washed with water, the volume reduced to 200 mL and then dried over MgSO$_4$. Filtration and concentration gives a dark brown oil that is purified using silica gel column chromatography (CH$_2$Cl$_2$/EtOAc) to give the enone 3 in 68% yield (4.95 g, 12.8 mmol).

Reduction of enone 3 to the allylic alcohol 4 (Scheme 56) is carried out using sodium borohydride and cerium(III) chloride heptahydrate in THF and methanol. Freshly distilled THF (200 mL) and methanol (50 mL) are added to a flask containing the enone 3 (15.3 g, 39.4 mmol) and CeCl$_3$.7H$_2$O (16.0 g, 42.9 mmol) under nitrogen. NaBH$_4$ (3.20 g, 84.6 mmol) is added in portions, and stirring is continued for 1 hour at room temperature. Dichloromethane is added, the mixture is washed with NaOH (0.6 N) then water and the organic layer is dried over MgSO$_4$. Filtration and concentration yields compound 4 as a white solid (14.1 g, 36.1 mmol, 92 %).

Scheme 56

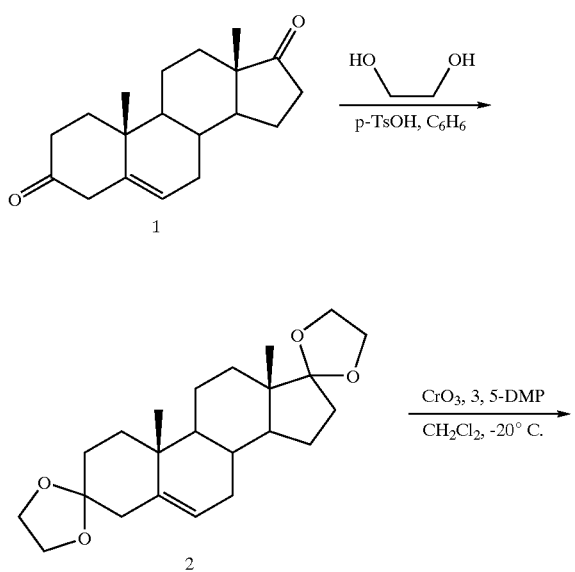

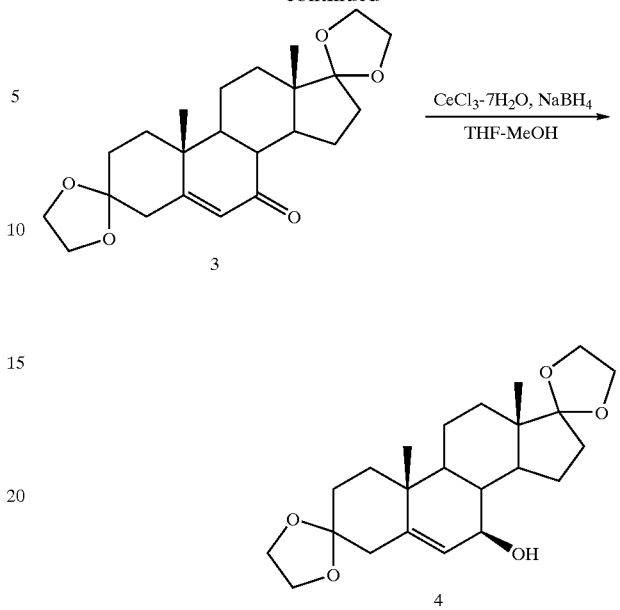

The C-7 hydroxyl moiety of alcohol 4 is then protected as a silyl ether (Scheme 57). Compound 4 (14.1 g, 36.1 mmol) is dissolved in dry DMF (50 mL) then imidazole (5.9 g, 86.7 mmol) and TBDMSCl (6.7 g, 44.5 mmol) are added, and the mixture is stirred under nitrogen for 5 hours. Dichloromethane is added, the mixture is washed with water, and the organic layer is dried over MgSO$_4$. Filtration and concentration gives a light yellow solid that is recrystallized from methanol to give compound 5 as a white solid in 61% yield (11.2 g, 22.2 mmol).

The subsequent epoxidation of compound 5 (Scheme 57) is carried out using meta-chloroperbenzoic acid (m-CPBA). Compound 5 (0.72 g, 1.4 mmol) is dissolved in dry dichloromethane (5 mL), m-CPBA (0.50 g, 2.9 mmol) is added and the mixture is stirred vigorously for 20 minutes. Saturated sodium bicarbonate is added and the aqueous slurry is extracted with dichloromethane. The combined organic extracts are washed sequentially with sodium carbonate solution, water, 10% sodium thiosulfate, then again with water. Drying (MgSO$_4$), filtration and concentration gives a white solid that is purified using flash chromatography to yield compound 6 in 77% yield (0.57 g, 1.1 mmol).

Compound 6 is treated with acid to deprotect the C3 and C17 ketones and to open the epoxide moiety to yield the 6-hydroxy-7-silyloxy compound 310 (Scheme 57). Aqueous acetic acid (80%, 1 mL) is added to a flask containing compound 6. The mixture is heated at 65° C. for 5 hours, cooled and poured onto dichloromethane. The mixture is washed with sodium bicarbonate and dried over MgSO$_4$. After filtration and concentration, the resultant crude product 310 is used in the next step without further purification.

Compound 310 (2.30 mg, 5.32 mmol) in THF (10 mL) is treated with tetrabutylammonium fluoride (TBAF) (8 mL, 1M solution in THF) at room temperature under nitrogen for ten minutes in order to remove the silyl protecting group (Scheme 57). The reaction mixture is concentrated and then purified by flash chromatography (3:1 CH$_2$Cl$_2$/EtOAc) to give compound 7 (1.37 mg, 4.31 mmol) in 81% yield.

Scheme 57

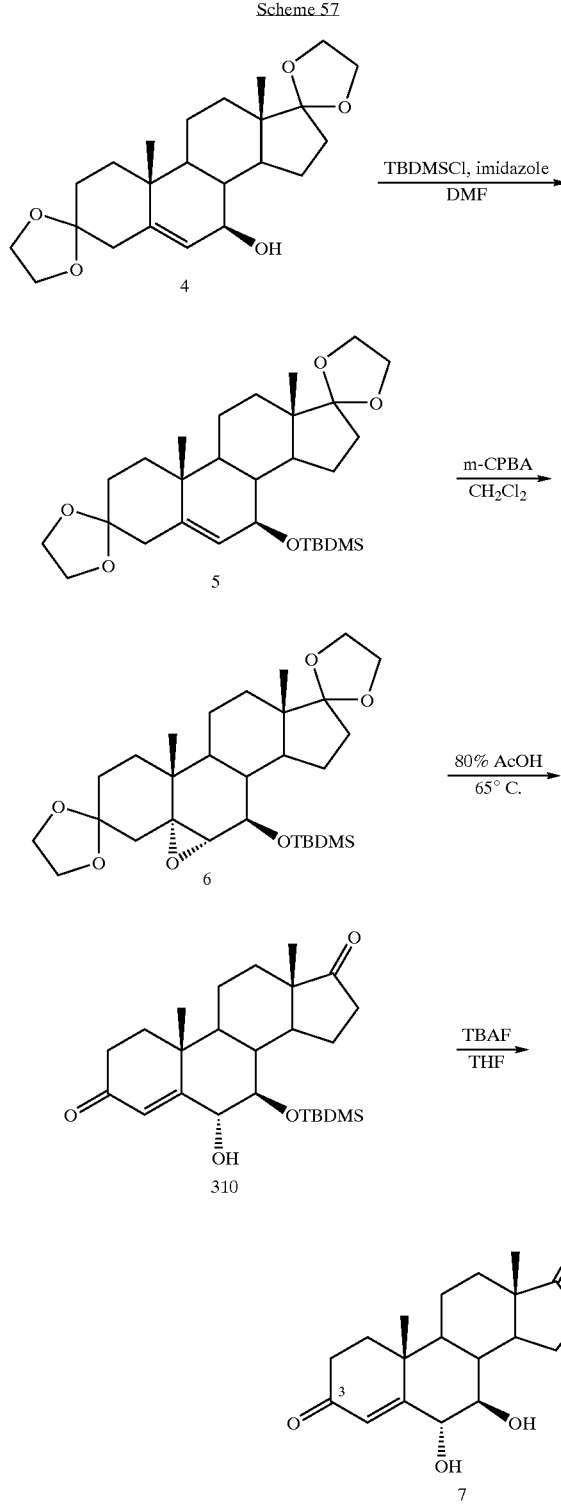

Protection of the 6,7-diol of compound 7 is accomplished by treatment with 2,2-dimethoxypropane and a catalytic amount of (1S)-(+)-10-camphorsulfonic acid (CSA) to produce acetonide 8 (Scheme 58). Compound 7 (1 g, 3.14 mmol) and a catalytic amount of CSA are dissolved in dry DMF (2 mL) and 2,2-dimethoxypropane (10 mL). The mixture is heated at 100° C. for 0.5 hours. Dichloromethane is added and the mixture is washed with water. The organic layer is dried over MgSO$_4$, filtered and concentrated to yield compound 8 (1.10 g, 3.07 mmol, 98%) which is used directly in the next reaction without further purification.

Chemoselective reduction of the C-17 carbonyl moiety (Scheme 58), followed by protection of the resultant alcohol as a silyl ether is necessary. Compound 8 (83 mg, 0.23 mmol) is dissolved in methanol (250 mL) under nitrogen and NaBH$_4$ (15 mg) is added in portions over a period of 1.5 hours. After an additional 30 minutes, the reaction is quenched with acetic acid, then neutralized with NaHCO$_3$. The methanol is evaporated, and the residue taken up in dichloromethane. The mixture is washed with water and dried over MgSO$_4$. Flash chromatography (2:1 CH$_2$Cl$_2$/EtOAc) gives compound 9 (72 mg, 0.20 mmol, 87%) as the major product.

Protection of the C17 hydroxyl group as a silyl ether to produce compound 10 is followed by reduction of the a,o-unsaturated ketone in the A-ring using lithium in liquid ammonia-THF, with trapping of the enolate by trimethylsilyl chloride (Scheme 58). A solution of compound 10 (75.2 mg, 0.158 mmol) in t-BuOH (0.020 mL) and THF (1.5 mL) is transferred to a flask containing lithium metal in dry, distilled ammonia (11.4 mg in 10 mL) at −78° C. After 20 minutes at −78° C., isoprene (0.5 mL) is added to destroy the excess lithium. The mixture is then warmed to room temperature and the solvent is evaporated in vacuo. The residue is dissolved in THF (5 mL), cooled to −78° C. and Et$_3$N (1.1 mL, 0.30 mmol) and TMSCl (0.80 mL, 0.30 mmol) are added. The cooling bath is removed and the mixture is stirred for 15 minutes. Saturated NaHCO$_3$ is added and this aqueous layer is extracted with Et$_2$O and dichloromethane. The combined organic layers are washed twice with brine, dried over MgSO$_4$ and concentrated. The crude product is purified by radial chromatography to give compound 235 in 67% yield (58.5 mg, 0.10 mmol).

The C4 hydroxyl is introduced by hydroboration-oxidation of the silyl enol ether 235 (Scheme 58). Compound 235 (58.5 mg, 0.106 mmol) is dissolved in dry THF (15 mL) and cooled in an ice-bath. Borane (1.0M THF complex: 0.32 mL, 0.32 mmol) is added and the mixture is warmed to room temperature and stirred for 45 minutes. More BH$_3$-THF complex (0.16 mL) is added and stirring is continued for 2 hours. The mixture is then cooled in an ice-bath and 15% NaOH (0.5 mL) and 30% H$_2$O$_2$ (0.5 mL) are added. Vigorous stirring is continued for 2 hours. The aqueous layer is then extracted with dichloromethane, then Et$_2$O, and the combined organic extracts are washed with 10% aqueous Na$_2$S$_2$O$_3$, then brine and dried over MgSO$_4$. The crude product is purified using radial chromatography to yield compound 236 (34.0 mg, 0.0688 mmol, 65%) and the corresponding 3β-silyl ether (11.8 mg, 0.0208 mmol, 20%).

Two step deprotection of compound 236 using TBAF in THF then aqueous acidic-THF, gives 3β,4α,6α,7β,17β-pentahydroxy-5α-androstane (237).

Scheme 58

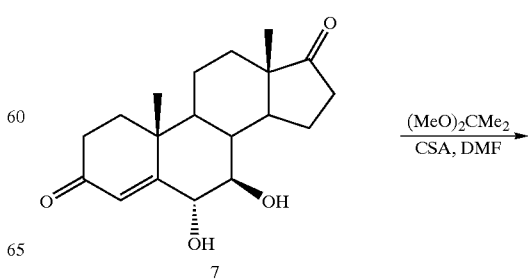

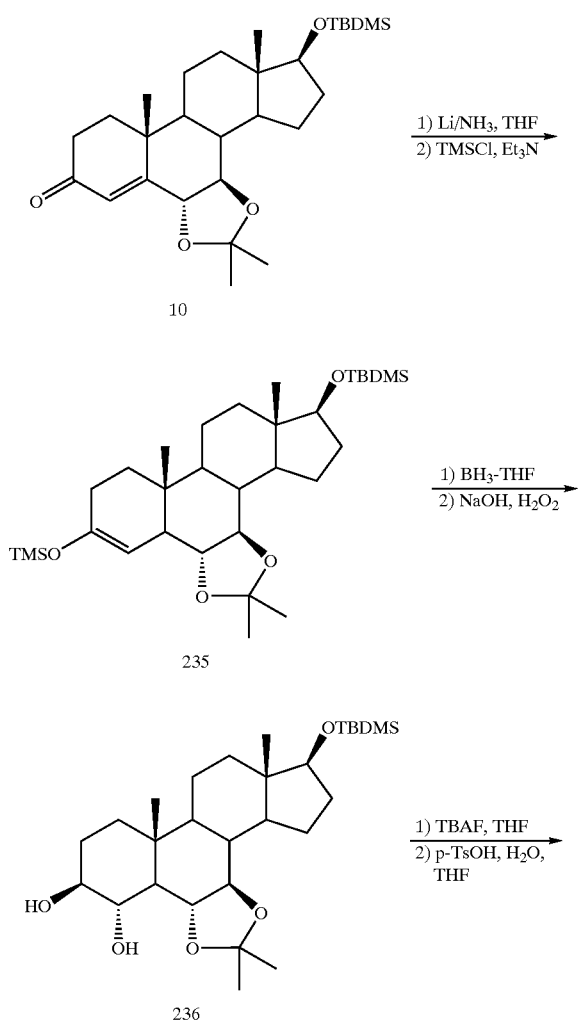
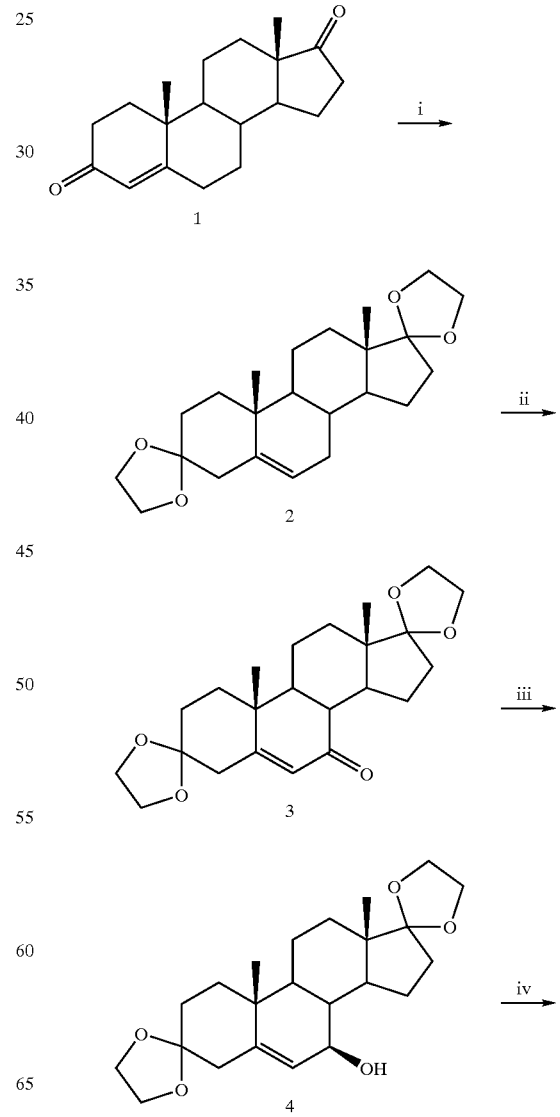
Example 2
The Steroid 3α,4α-Epoxy-6α,7β,17β-Trihydroxy-5α-androstane (239) can be Synthesized According to the Reaction Sequence Shown in Scheme 59

127
-continued
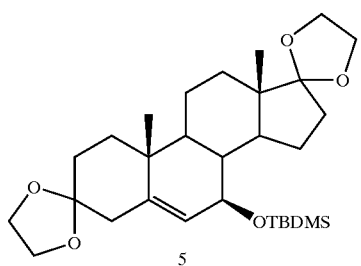
5
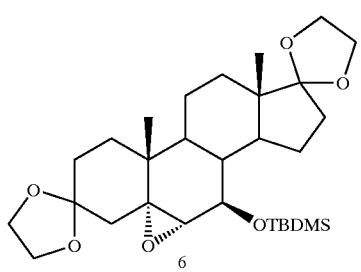
6
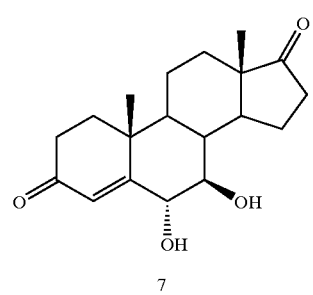
7
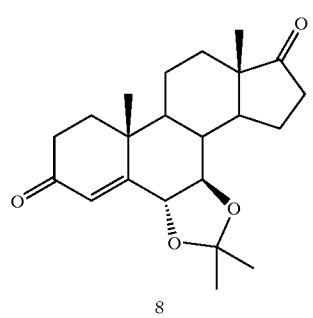
8
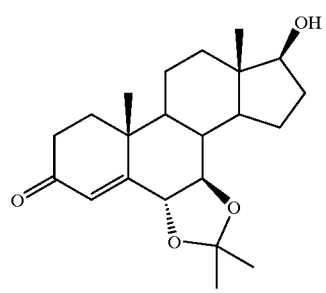
9
128
-continued
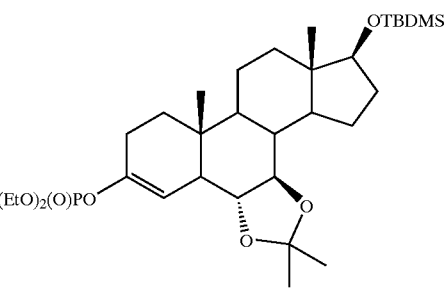
10
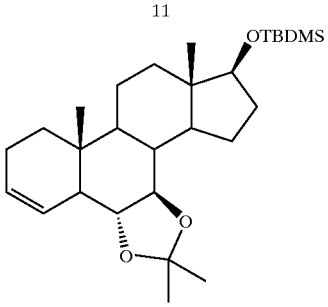
11
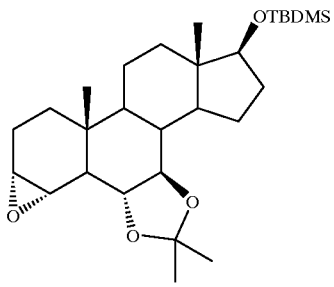
128
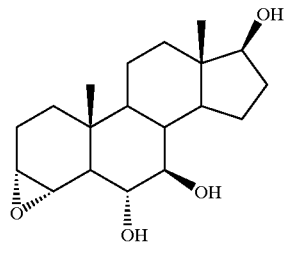
238
239
Key; (i) p-TsOH, (CH$_2$OH)$_2$, benzene (ii) CrO$_3$, 3,5-dimethylpyrazole, CH$_2$Cl$_2$ (iii) NaBH$_4$, CeCl$_3$, THF-MeOH (iv) TBDMSCl, imidazole, DMF (v) m-CPBA, CH$_2$Cl$_2$ (vi) 80% AcOH (vii) TBAF, THF (viii) 2,2-dimethoxypropane, CSA, DMF (ix) NaBH$_4$, MeOH (x) TBDMSCl, imidazole, DMF (xi) 1. Li/NH$_3$-THF, 2. Cl(O)P(OEt)$_2$ (xii) Li/NH$_3$, t-BuOH (xiii) m-CPBA, CH$_2$Cl$_2$ (xiv) TBAF, THF (xv) p-TsOH, THF, H$_2$O.

3α,4α-Epoxy-6α,7β,17β-trihydroxy-5α-androstane (239) can be produced from intermediate 10 in the synthesis of 3β,4α,6α,7β,17β-pentahydroxy-5α-androstane (258) (Scheme 60). A solution of compound 10 (111 mg, 0.234 mmol) in THF (4 mL) is transferred to a flask containing lithium metal in liquid ammonia (6.4 mg in 10 mL) at −78° C. under argon. After 30 minutes at −78° C., isoprene (0.5 mL) is added to destroy the excess lithium. The mixture is warmed to room temperature and the solvent is evaporated in vacuo. The residue is dissolved in THF (5 mL) and cooled to −78° C., then ClP(O)(OEt)$_2$ (0.044 mL, 0.30 mmol) is added and the mixture is stirred for 1 hour. Water and dichloromethane are added, the mixture acidified, and the aqueous layer extracted with dichloromethane and Et$_2$O. The combined organic layers are washed with water and dried over MgSO$_4$. The crude product is purified by radial chromatography to give compound 11 (85.1 mg, 0.139 mmol) in 59% yield.

Reduction of compound 11 with lithium in liquid ammonia in the presence of t-butyl alcohol produces the olefin 128. A solution of compound 11 (85.1 mg, 0.139 mmol) and t-BuOH (0.05 mL) in THF (6 mL) is transferred to a flask containing lithium metal (16 mg) in liquid ammonia at −30° C. under argon. After 30 minutes, the ammonia is allowed to evaporate, then water is added. After acidification with aqueous HCl, the mixture is extracted with Et$_2$O, then EtOAc and the combined organic layers are washed with water and dried over MgSO$_4$. The crude product is purified by radial chromatography to give compound 128 (50.3 mg, 0.109 mmol) in 78% yield.

Epoxidation of 128 with meta-chloroperbenzoic acid (m-CPBA) in dichloromethane gives the epoxide 238. Compound 128 (50.3 mg, 0.109 mmol) is dissolved in dry dichloromethane (1.5 mL) and m-CPBA (43.0 mg) is added. The mixture is stirred at room temperature for 1.5 hours and then transferred to a separatory funnel and washed with 10% Na$_2$S$_2$O$_3$, saturated NaHCO$_3$ and water and dried over MgSO$_4$. Filtration and evaporation of the filtrate gives compound 238 in 78% yield (52.0 mg, 0.109 mmol) which is used in the next step without further purification.

Two step deprotection of compound 238 with TBAF in refluxing THF and then acidic aqueous THF gives compound 239.

Scheme 60

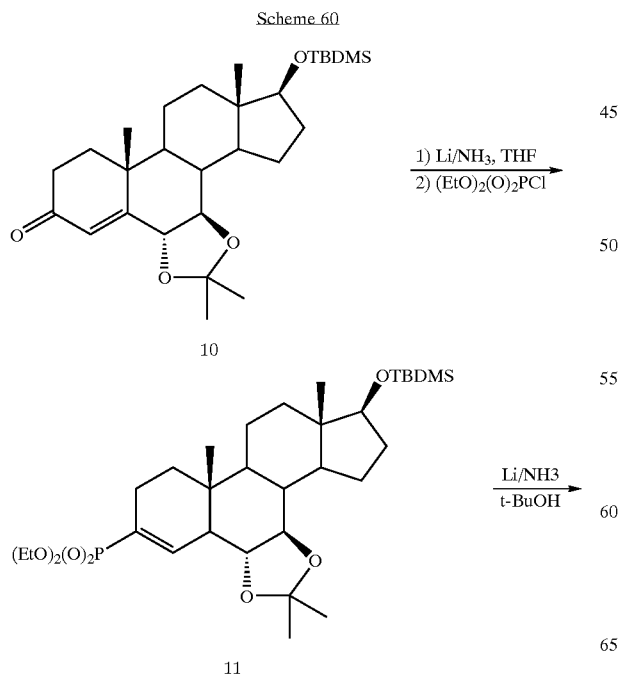

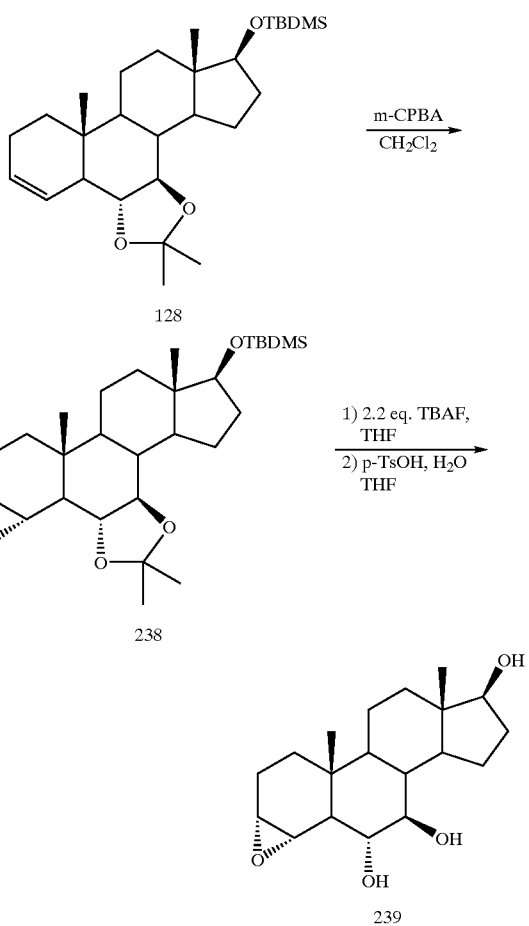

Example 3

The Steroid 3α,4β,6α,7β,17β-Pentahydroxy-5α-androstane (241) can be Synthesized According to the Following Reaction Sequence (Scheme 61)

Scheme 61

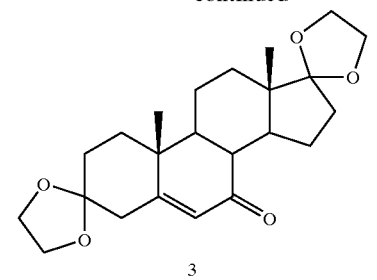
3
iii →
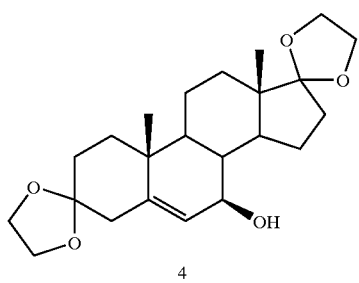
4
iv →
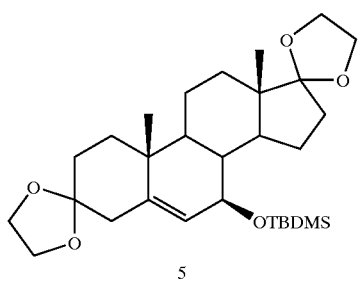
5
v →
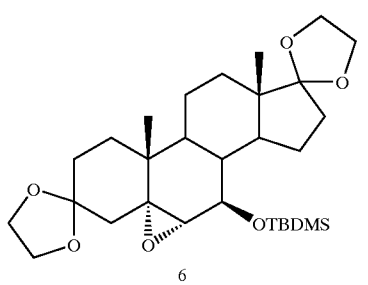
6
vi → vii →
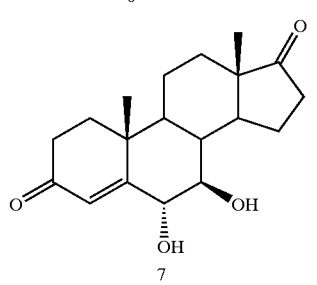
7
viii →
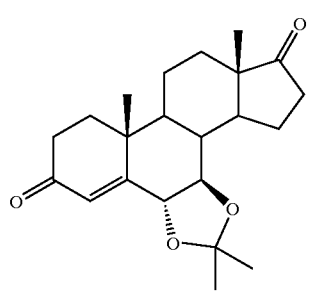
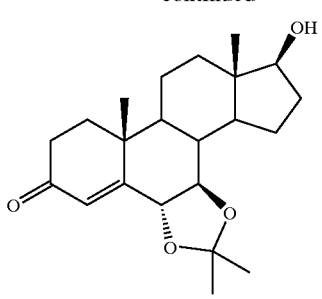
9
x →
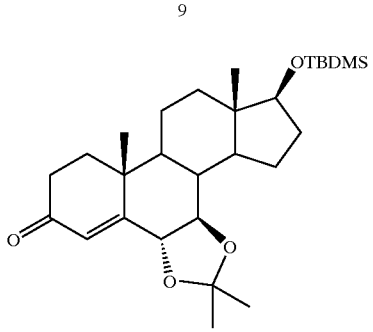
10
xi →
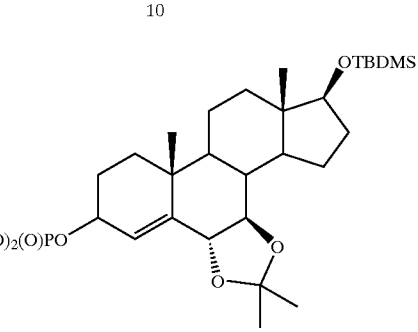
11
xii →
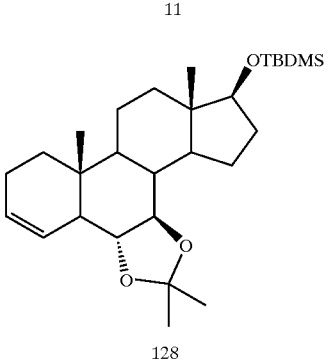
128
xiii →
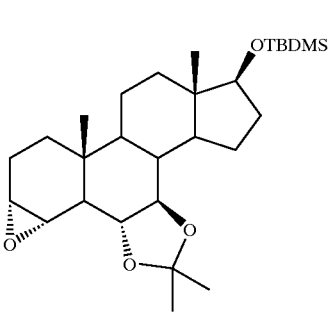
238
xiv →

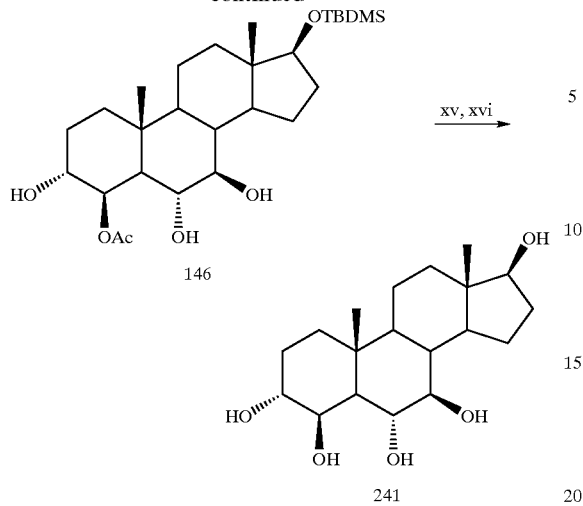

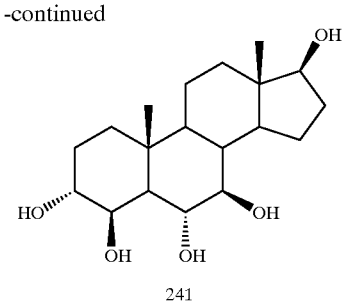

Key: (i) p-TsOH, (CH₂OH)₂, benzene (ii) CrO₃, 3,5-dimethylpyrazole, CH₂Cl₂ (iii) NaBH₄, CeCl₃, THF-MeOH (iv) TBDMSCl, imidazole, DMF (v) m-CPBA, CH₂Cl₂ (vi) 80% AcOH (vii) TBAF, THF, (viii) 2,2-dimethoxypropane, CSA, DMF (ix) NaBH₄, MeOH (x) TBDMSCl, imidazole, DMF (xi) 1. Li/NH₃-THF, 2. Cl(O)P(OEt)₂ (xii) Li/NH₃-THF, t-BuOH (xiii) m-CPBA, CH₂Cl₂ (xiv) AcOH, 60° C. (xv) K₂CO₃, MeOH, reflux (xvi) TBAF, THF, reflux.

The synthesis of 3α,4β,6α,7β,17β-pentahydroxy-5α-androstane (241) is carried out to the intermediate 238 using the same conditions as in the synthesis of 3α,4α-epoxy-6α,7β,17β-trihydroxy-5α-androstane (239). The subsequent epoxide ring opening with concurrent removal of the acetonide functionality (Scheme 62) is achieved by heating with glacial acetic acid to yield compound 146, which contains an acetoxy functionality at C4. To a flask containing compound 238 (18.5 mg, 0.038 mmol) is added acetic acid (0.30 mL). The mixture is stirred with heating at 60° C. for 24 hours, then at room temperature for 2 days. The acetic acid is removed in vacuo to give compound 146 in 93% yield (18 mg, 0.036 mmol).

Deprotection of the C4 hydroxyl using K₂CO₃ in refluxing methanol, and deprotection of the C17 hydroxyl using TBAF yields the pentahydroxy compound 241.

Example 4
3β,4α,6α,7β,17β-Pentahydroxy-5α-androstane 6,7-Acetonide (246)

The steroid 3β,4α,6α,7β,17β-pentahydroxy-5α-androstane 6,7-acetonide (246) can be synthesized according to the reaction sequence illustrated by Scheme 63.

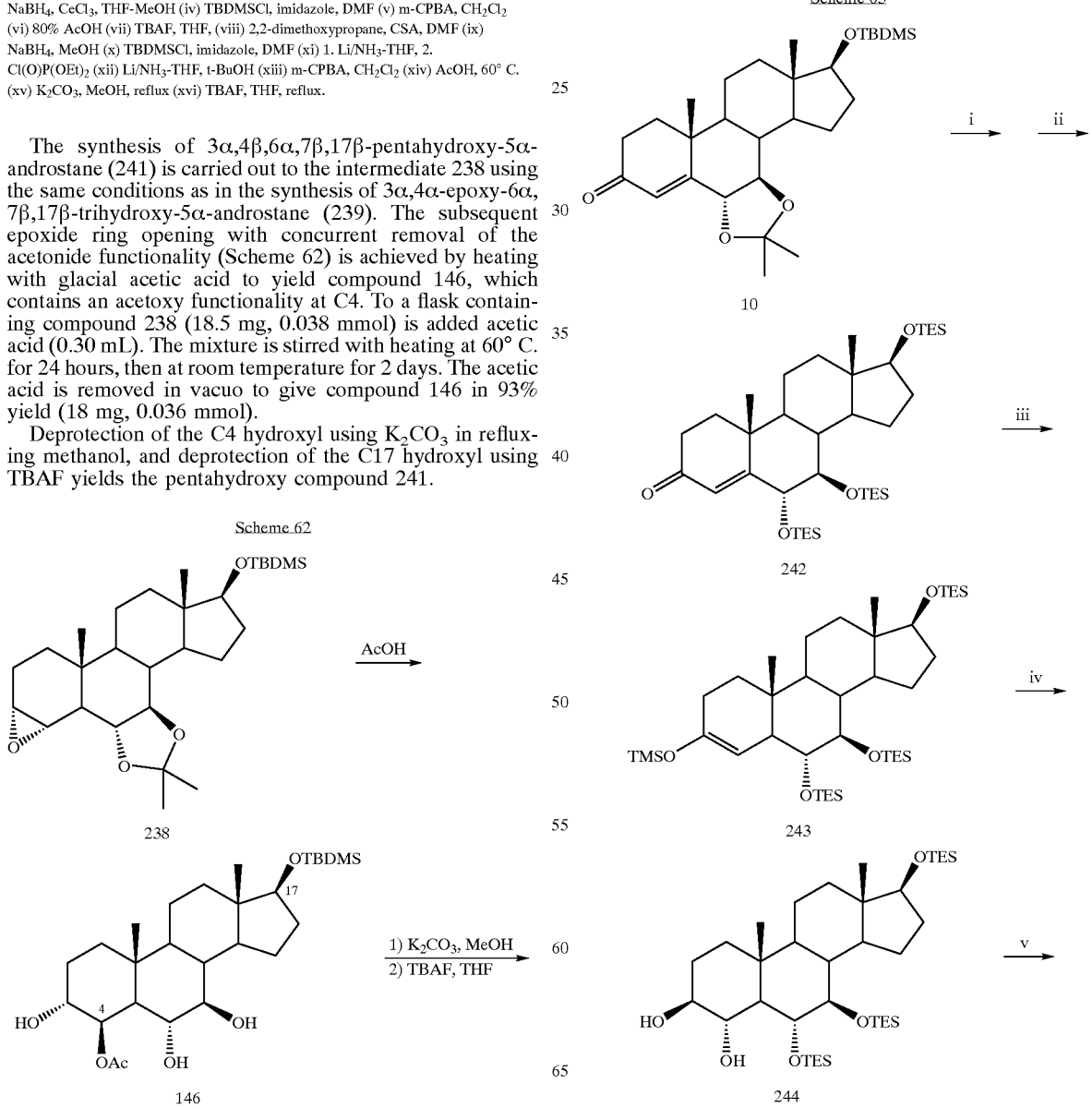

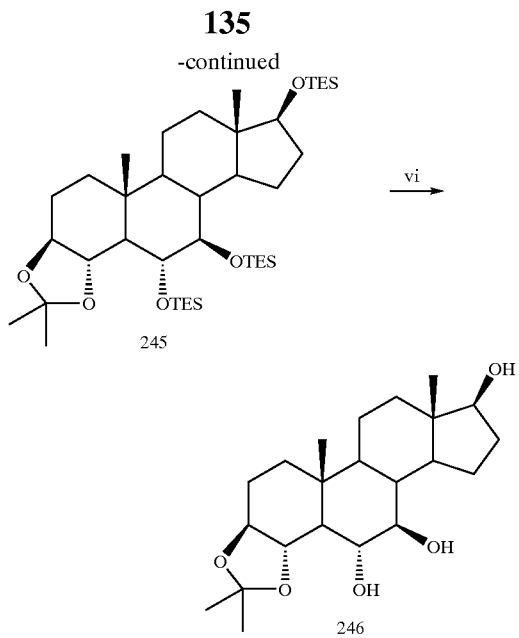

245

246

Key: (i) 80% AcOH (ii) TESCl, imidazole, DMF (iii) 1. Li/NH$_3$-THF, 2. TMSCl, Et$_3$N (iv) 1. BH$_3$-THF, 2. 30% NaOH, 30% H$_2$O$_2$ (v) 2,2-dimethoxypropane, CSA, DMF (vi) TBAF, THF.

Compound 10 is prepared as described in Section 1, Example 1. Deprotection of the 6,7 and 17 hydroxyl moieties is achieved with 80% acetic acid solution and, after appropriate work-up, reprotection of these groups as the silyl ether derivative is accomplished to afford 242. Compound 10 is dissolved in 80% acetic acid and the mixture is concentrated in vacuo after stirring for 8 hours at room temperature. The residue is placed in dry DMF containing imidazole and TBDMSCl and stirred for 20 hours at room temperature under a nitrogen atmosphere. Ether is added and the mixture washed with 5% HCl aqueous solution, saturated NaHCO$_3$ solution and saturated NaCl solution. The organic mixture is dried over MgSO$_4$, filtered and evaporated. Purification of this residue by chromatography over silica gel gives compound 242.

Reduction of the α,β-unsaturated ketone in the A-ring is achieved using lithium in liquid ammonia-THF, with trapping of the enolate by trimethylsilyl chloride. A solution of compound 242 in a 1:4 mixture of t-BuOH and THF is transferred to a flask containing lithium metal in dry, distilled ammonia at −78° C. After 20 minutes at −78° C., isoprene is added to destroy the excess lithium. The mixture is then warmed to room temperature and the solvent is evaporated in vacuo. The residue is dissolved in THF, cooled to −78° C. and Et$_3$N and TMSCl are added. The cooling bath is removed and the mixture is stirred for 15 minutes. Saturated NaHCO$_3$ is added and this aqueous layer is extracted with Et$_2$O and dichloromethane. The combined organic layers are washed twice with brine, dried over MgSO$_4$ and concentrated. The crude product is purified by radial chromatography to give compound 243.

The C4 hydroxyl is introduced by hydroboration-oxidation of the silyl enol ether 243. Compound 243 is dissolved in dry THF and cooled in an ice-bath. Borane (1.0 M THF complex) is added and the mixture is warmed to room temperature and stirred for 45 minutes. More BH$_3$-THF complex is added and stirring is continued for 2 hours. The mixture is then cooled in an ice-bath and 30% NaOH and 30% H$_2$O$_2$ are added. Vigorous stirring is continued for 12 hours. The aqueous layer is then extracted with dichloromethane, then Et$_2$O, and the combined organic extracts are washed with 10% aqueous Na$_2$S$_2$O$_3$, then brine and dried over MgSO$_4$. The crude product is purified using radial chromatography to yield compound 244.

Protection of the 3,4-diol of compound 244 is accomplished by treatment with 2,2-dimethoxypropane and a catalytic amount of (1S)-(+)-10-camphorsulfonic acid (CSA) to produce acetonide 245. Compound 244 and a catalytic amount of CSA are dissolved in dry DMF and 2,2-dimethoxypropane. The mixture is heated at 100° C. for 0.5 hours. Dichloromethane is added and the mixture is washed with saturated NaHCO$_3$ solution. The organic layer is dried over MgSO$_4$, filtered and concentrated to yield compound 245 which is used directly in the next reaction without further purification.

Compound 245 is then converted to the triol 246 with TBAF. Thus, the trisilyl ether 245 is dissolved in THF and treated with tetrabutylammonium fluoride (TBAF) (1 M solution in THF) at room temperature under nitrogen for 5 hours. The reaction mixture is poured into CH$_2$Cl$_2$ and washed with brine, dried (MgSO$_4$) and concentrated in vacuo. The residue is then purified by flash chromatography (3:1 CH$_2$Cl$_2$/EtOAc) to give compound 246.

SECTION 2

The Synthesis of 22,29-Epoxy-15-one Steroids

Steroids that are related to 22,29-epoxy-3,4,6,7,29-pentahydroxy-14β-stigmastan-15-one (165) by the presence of a C15 ketone and a cyclic hemiacetal functionality in the steroid side chain (i.e., a C22 hydroxyl functionality condensing with a C29 aldehyde functionality to form a tetrahydropyran ring and a C29 hydroxyl group) can be synthesized by a number of methods. The key steps include the introduction of the C15 oxygen, the synthesis of the appropriate side chain (described in Section 3), and the coupling of the side chain. A number of commercially available steroids containing either a ketone or an acetyl moiety at C17 (e.g., pregnenolone (C17 acetyl), 4-androsten-3,17-dione (C17 ketone), dehydroisoandrosterone (C17 ketone) can be used as starting materials.

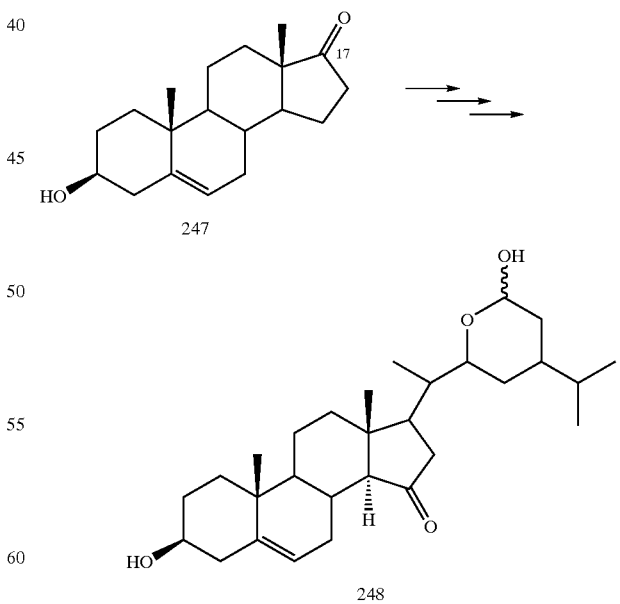

247

248

In one method (Example 5, Scheme 64), the C17 ketone is treated with the Wittig reagent prepared by the reaction of ethyltriphenylphosphonium bromide and potassium t-butoxide in THF in order to introduce a (Z)-17(20)

ethylidene moiety. Reaction of the Wittig product with an aldehyde-containing compound such as 5-acetoxy-3-(1'-methylethyl)-pentanal (156, Section 3, Example 8, Scheme 71) in the presence of a Lewis acid gives products that contain the required C22 oxygen, present as an hydroxyl functionality, and the C29 oxygen protected as the acetate. The latter ene reaction gives both stereoisomers at C22, the ratios of which are dependent on reaction conditions and choice of the aldehyde starting material. Therefore, the four possible diastereomers arising from the configurations at C22 and C24 can be synthesized by utilizing either the 3R or 3S isomer of compound 156.

The ene reaction described above results in a $\Delta^{16}$ carbon-carbon double bond which can be utilized to introduce a C15 oxygen via allylic oxidation. For example, after protection of the C22 hydroxyl group of the ene product with an appropriate protecting group such as t-butyldimethylsilyl, allylic oxidation, using a reagent such as chromium trioxide/ 3,5-dimethylpyrazole complex, introduces a ketone functionality at the C15 position. Reduction of the $\Delta^{16}$ double-bond produces a steroidal compound that has the identical D-ring functionality as 22,29-epoxy-3,4,6,7,29-pentahydroxy-14β-stigmastan-15-one (165).

Removal of the C29 protecting group, typically an acetate moiety, followed by oxidation of the resultant primary alcohol produces the required aldehyde at C29. Removal of the C22 protecting group, generally a t-butyldimethylsilyl group, results in the formation of the side chain hemiacetal moiety found in compound 165.

The second strategy for the attachment of the required hemiacetal side chain and C15 ketone functionality involves introduction of the C15 oxygen before side chain coupling (Example 6, Scheme 67). In this method the first step involves conversion of the C17 ketone functionality of a steroidal intermediate to the enol acetate by treatment with isopropenyl acetate and p-toluenesulfonic acid. Conversion of the enol acetate to the α,β-unsaturated ketone is accomplished by treatment with palladium acetate and tributyltin methoxide.

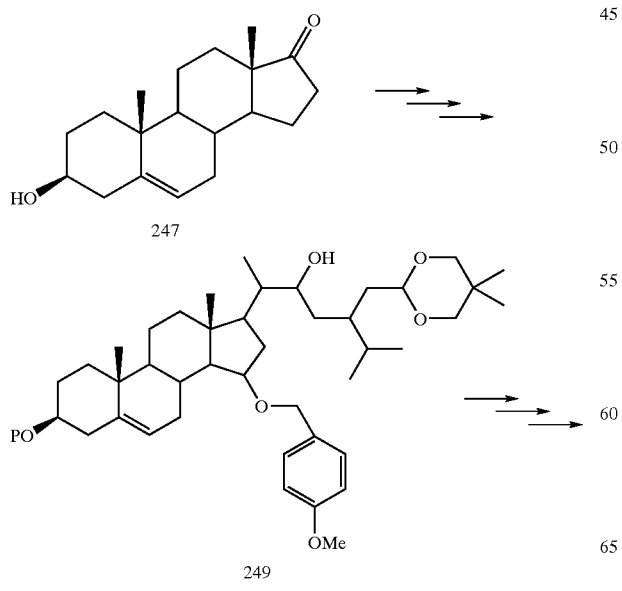

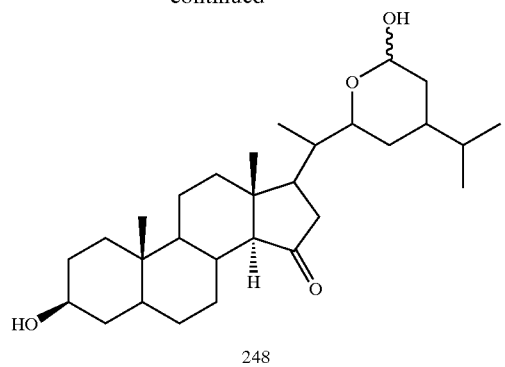

248

Introduction of the C15 oxygen is then accomplished using a Michael-type addition to the enone by an alkoxide derived from p-methoxybenzyl alcohol in the presence of potassium hydroxide. This functionality can later be selectively deprotected and the resultant alcohol oxidized to the C15 ketone.

Elaboration of the C17 ketone functionality to an acetyl group is a process that begins with the attack of an acetylide anion. A reagent such as commercially available lithium acetylide-ethylene diamine complex can be used for this task. Dehydration of the product yields the compound with a conjugated $\Delta^{16}$ carbon-carbon double bond. Hydration of the acetylene moiety using reagents such as mercury-impregnated Dowex resin in methanol, THF and water produces an acetyl group at C17 ($\Delta^{16}$, C20 ketone). The $\Delta^{16}$ carbon-carbon double-bond is reduced using sodium dithionite and bicarbonate under phase transfer conditions.

The methyl ketone is then converted to an epoxide by treatment with a sulphur ylid prepared from trimethylsulphonium iodide and n-butyllithium in THF. The epoxide is then opened stereoselectively using a Lewis acid such as magnesium bromide etherate to give the C22 aldehyde. An alkyl anion generated via a lithium-halide exchange reaction from an appropriate halogen, such as the iodide 284 (Example 9, Scheme 72), is then used to attack the steroidal aldehyde to generate the same side chain, in a protected form, as found in compound 165. Deprotection of the C29 aldehyde produces the desired side chain.

The details of these two strategies are presented in Examples 5 and 6, which follow.

Example 5

22,29-Epoxy-3,29-dihydroxy-14β-stigmastan-15-one (260)

As an example of the first method described in the introduction to section 2, the steroid 22,29-epoxy-3,29-dihydroxy-14β-stigmastan-15-one (260) can be synthesized according to the following reaction sequence outlined in Scheme 64.

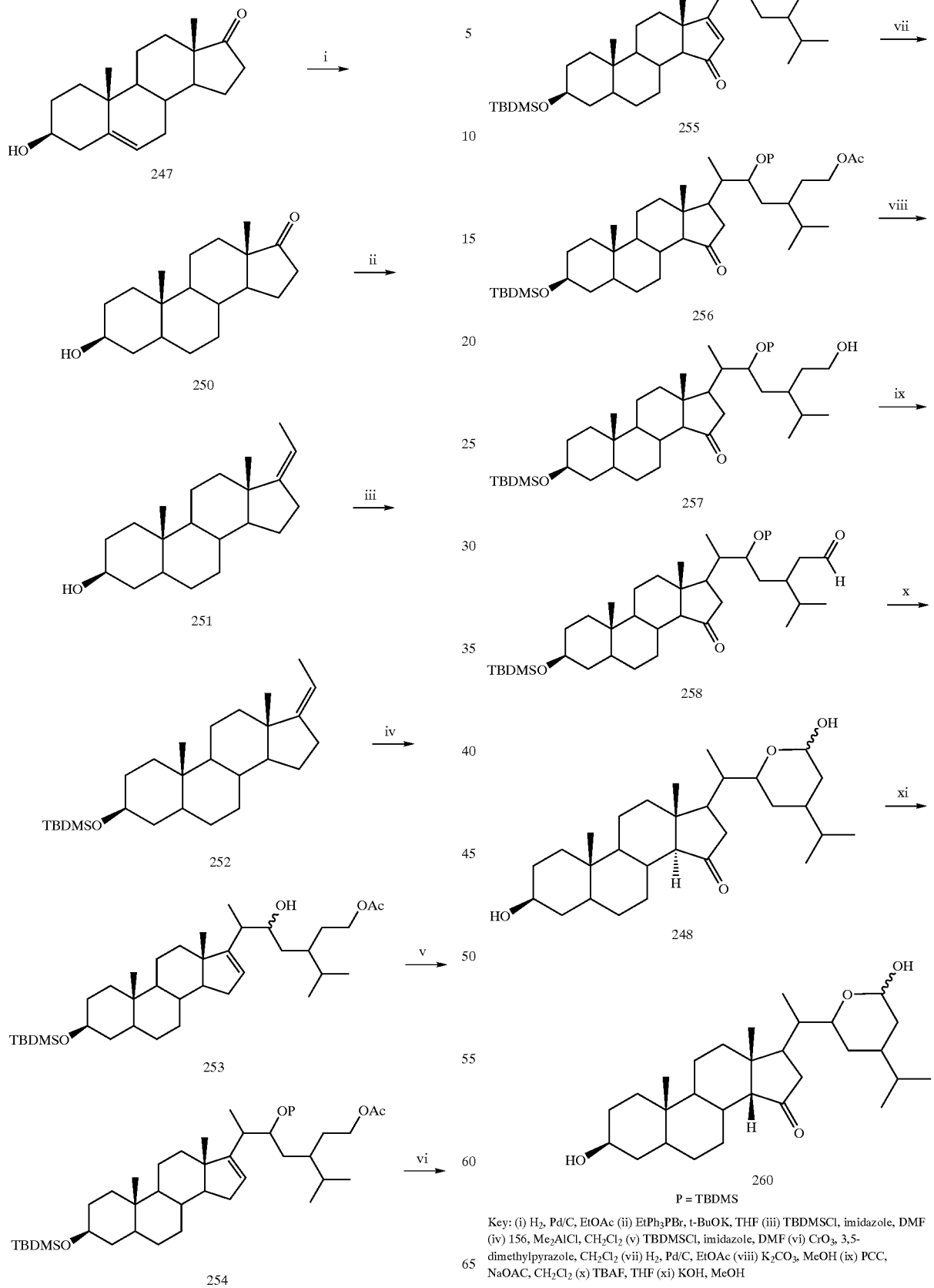
Scheme 64
Key: (i) H₂, Pd/C, EtOAc (ii) EtPh₃PBr, t-BuOK, THF (iii) TBDMSCl, imidazole, DMF (iv) 156, Me₂AlCl, CH₂Cl₂ (v) TBDMSCl, imidazole, DMF (vi) CrO₃, 3,5-dimethylpyrazole, CH₂Cl₂ (vii) H₂, Pd/C, EtOAc (viii) K₂CO₃, MeOH (ix) PCC, NaOAC, CH₂Cl₂ (x) TBAF, THF (xi) KOH, MeOH
P = TBDMS The synthesis of 22,29-epoxy-3,29-dihydroxy-14β-stigmastan-15-one (260) can be accomplished in ten steps from dehydroisoandrosterone (247). Catalytic hydrogenation of the $\Delta^5$ carbon-carbon double bond in compound 247 yields compound 250, which contains a trans-fused A/B ring-system. Compound 247 is dissolved in EtOAc and 10% Pd/C is added. The mixture is stirred under $H_2$ at room temperature overnight. Filtration through celite and concentration yields compound 250, which can be used directly in the next reaction.

A Wittig reaction on compound 250 using the phosphorous ylid prepared from ethyltriphenylphosphonium bromide and potassium t-butoxide in THF gives compound 251. Ethyltriphenylphosphonium bromide is stirred as a suspension in THF. Potassium t-butoxide is added under a stream of nitrogen and the mixture stirred at room temperature for 1 hour. Compound 250 is added to the anion thus formed as a solution in THF. The mixture is refluxed for 2 hours under nitrogen then cooled to room temperature and quenched by the dropwise addition of water. Saturated ammonium chloride is added and this aqueous layer is extracted with EtOAc and the combined organic phases washed with water and brine and dried over $MgSO_4$. Filtration and concentration gives the crude product 251 which is purified using silica flash chromatography with a step-gradient of hexanes and EtOAc.

Protection of the 3β-hydroxyl is accomplished using t-butyldimethylsilyl chloride and imidazole in DMF to yield 252. Compound 251 is dissolved in DMF and imidazole is added. After addition of TBDMSCl, the mixture is stirred overnight at room temperature. Dichloromethane is then added and the mixture is washed with water and the organic phase dried over $MgSO_4$. Filtration and concentration yields the crude product 252 which can be used without further purification.

Compound 252 is then coupled with the aldehyde 156 in the presence of an appropriate Lewis acid to yield compound 253. The aldehyde 156 is dissolved in dichloromethane and $Me_2AlCl$ (1.0M in hexane) is added at −78° C. After 5 minutes a solution of compound 252 in dichloromethane is added. The mixture is then warmed to room temperature over 16 hours. It is then cooled to −78° C. and quenched with a methanol/water mixture. The layers are separated and the aqueous phase is extracted with $Et_2O$. The combined organic layers are then washed sequentially with 1N HCl, saturated aqueous $NaHCO_3$ and brine and then dried over $MgSO$,. After filtration and evaporation to dryness, the C22 isomers are separated using silica flash chromatography to yield compounds 253a and 253b.

Compound 253a (or 253b) is then dissolved in dry DMF and imidazole is added. TBDMSCl is then added and the mixture is stirred at room temperature for 14 hours and then at 60° C. for 3 hours. The mixture is diluted with $Et_2O$, washed with water and then dried over $MgSO_4$. After filtration and evaporation, the crude product is purified using silica flash chromatography with EtOAc and hexane mixtures as the eluent to give compound 254.

Allylic oxidation at C15 of compound 254 with $CrO_3$ and 3,5-dimethylpyrazole in dichloromethane gives compound 255. $CrO_3$ and dichloromethane are added to a flask and cooled to −20° C., and are allowed to stir at this temperature for 15 minutes. 3,5-Dimethylpyrazole is added and then the reaction stirred for an additional 1.5 hours. Compound 254 in dichloromethane is added and the mixture is kept at −20° C. for 5 days. The mixture is then warmed to room temperature and filtered through silica gel, washing with EtOAc.

Evaporation of the solvent gives the crude product which is purified using flash chromatography (EtOAc/hexane) to yield pure compound 255.

Reduction of the $\Delta^{16}$ carbon-carbon double bond in compound 255 can then be achieved using hydrogen and palladium on carbon in EtOAc. Compound 255 is dissolved in EtOAc and a catalytic amount of 10% Pd/C is added. The mixture is stirred under a hydrogen atmosphere overnight, then filtered through Celite and concentrated to yield, after purification, compound 256.

Removal of the acetate protecting group in the side chain of compound 256 can then be carried out using potassium carbonate in methanol (or NaOMe in MeOH) to give compound 257. Compound 256 is dissolved in methanol and $K_2CO_3$ is added. The mixture is refluxed for 3 hours, cooled to room temperature and poured onto dichloromethane. Aqueous (10%) $NaHCO_3$ is added and the layers are separated. The aqueous layer is extracted with dichloromethane and the combined organic extracts are washed with water and dried over $MgSO_4$. Filtration, evaporation and purification yields compound 257.

Oxidation of the resultant primary alcohol 257 to the aldehyde 258 can be achieved using PCC. Compound 257 and NaOAc are stirred in dichloromethane and PCC is added. The mixture is stirred at room temperature for 3 hours and then filtered through Celite. The filtrate is concentrated and the residue purified using flash chromatography to give compound 258.

Deprotection of both hydroxyl moieties in compound 258 can be achieved in one step using tetrabutylammonium fluoride. Compound 258 is dissolved in THF and tetrabutylammonium fluoride in THF is added. The mixture is stirred overnight at room temperature and then concentrated in vacuo and purified to give 22,29-epoxy-3,29-dihydroxy-14α-stigmastan-15-one (248).

Epimerization of compound 248 at the C14 position using KOH in MeOH yields 22,29-epoxy-3,29-dihydroxy-14β-stigmastan-15-one (260). Compound 248 is dissolved in MeOH and a solution of KOH in MeOH (25 mg/ml) is added. The mixture is refluxed for 15 minutes then cooled to room temperature. Water is added and the aqueous slurry is extracted with chloroform and then dried over $MgSO_4$. Filtration and concentration gives the crude product that contains an epimeric mixture of compounds 248 and 260. Separation of 248 and 260 is achieved using column chromatography.

An alternative route to compound 260 (Scheme 65) involves preparation of the δ-lactone in the sidechain and subsequent Dibal-H reduction to yield the compound containing the C29 hemiacetal functionality. For example, the 3β-hydroxyl in compound 251 is protected as the benzyloxy functionality followed by the standard ene reaction described in example 5. Deprotection of the C29 acetoxy group is then accomplished using sodium methoxide in methanol. The resultant diol 263 is then oxidized to the δ-lactone using silver carbonate on celite in refluxing benzene. Compound 263 is dissolved in benzene and silver carbonate embedded on celite is added and the mixture refluxed for 12 hours. The reaction mixture is then filtered, evaporated and the residue purified by flash chromatography to yield lactone 264. Allylic oxidation of compound 264 using chromium trioxide and 3,5-dimethylpyrazole in dichloromethane introduces a carbonyl moiety at C15 (compound 265). Reduction of the conjugated $\Delta^{16}$ carbon-carbon double bond using hydrogen and palladium on carbon in EtOAc followed by removal of the benzoate groups using NaOMe in 1:1 CHCl₃/MeOH, yields product 266. Finally, protection of the C15 ketone as the ethylene ketal followed by selective reduction of the δ-lactone to the lactol is then accomplished using DIBAL at −78° C. and deprotection using 80% aqueous acetic acid to give compound 260.

p-methoxybenzyl alcohol in KOH, is used instead of the analogous benzyloxy alkoxide used by Cantral et al. Scheme 66 below shows an example of this chemistry on the enone in compound 270, which is produced in three steps from transdehydroandrosterone (247) using procedures described by Takahashi et al., *Tetrahedron*, 41(24): 5747–5754, 1985.

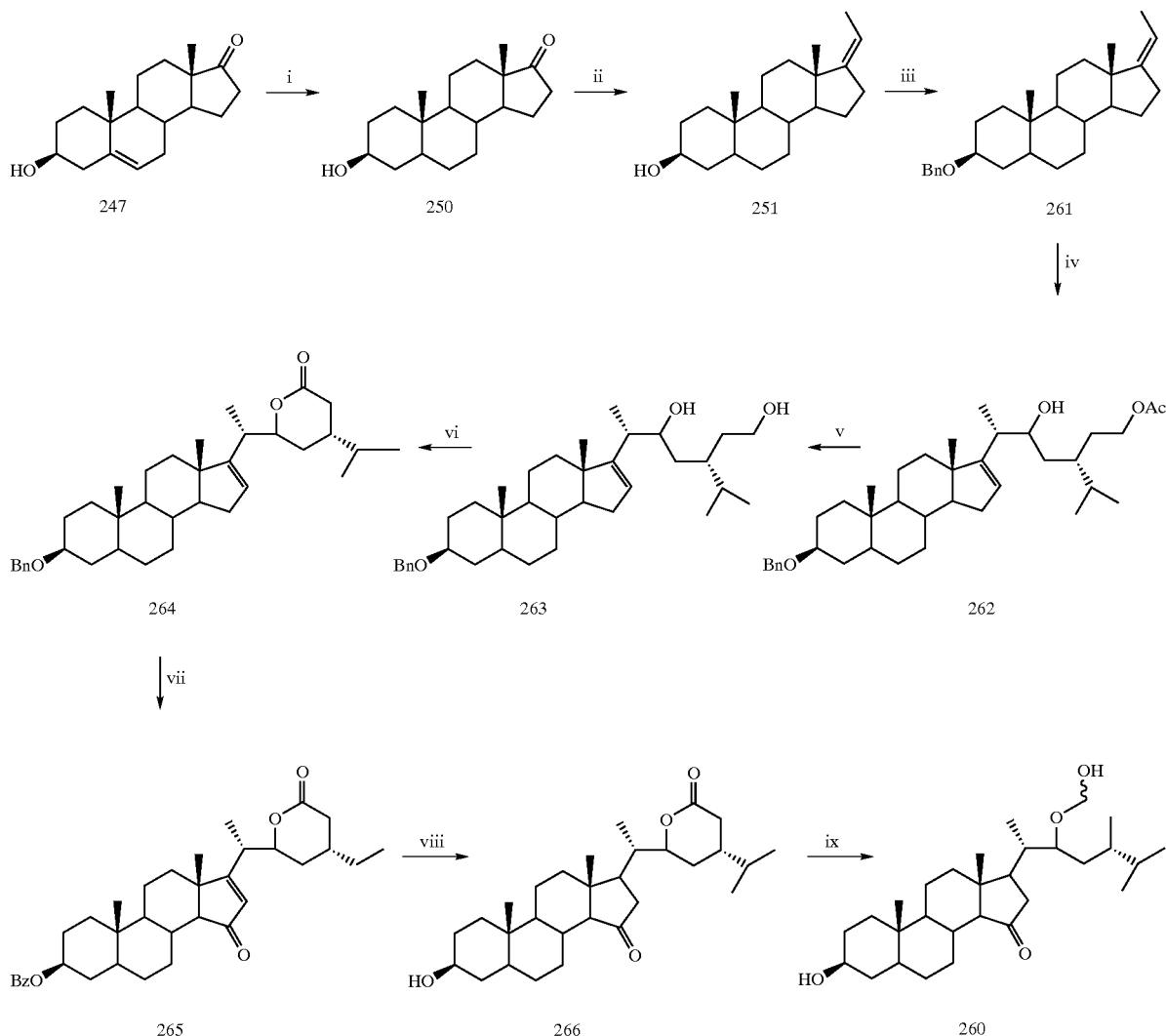

Scheme 65

Key: (i) H₂, Pd/C, 1:1 EtOAc/EtOH (ii) EtPh₃PBr, t-BuOK, toluene (iii) BnBr, NaH, DMF (iv) 156, (CH₃)₂AlCl, CH₂Cl₂ (v) MeONa, MeOH (vi) Ag₂CO₃/celite, benzene (vii) CrO₃, 3,5-dimethylpyrazole, CH₂Cl₂ (viii) 1. H₂, Pd/C, EtOAc 2. NaOMe, MeOH (ix) 1. HOCH₂CH₂OH, pTsOH, benzene, 2. DIBAL, CH₂Cl₂., −78° C., 3. 80% AcOH.

Example 6

As stated at the beginning of this section, a second method for the introduction of the C15 oxygen involves using a Michael addition as described by Cantral et al., *J. Org. Chem.*, 29:64, 1963. Selective removal of the protecting group followed by oxidation of the resultant secondary alcohol to a ketone at C15 is required. It has been shown by Horita et al., *Tetrahedron*, 42(11):3021–3028, 1986 that p-methoxybenzyl protecting groups can be removed in the presence of many other protecting groups, including benzyl functionalities, using 2,3-dichloro-5,6-dicyanobenzoquinone (DDQ). Therefore, the alkoxide produced from Scheme 66

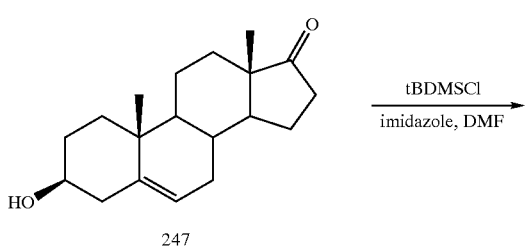

-continued

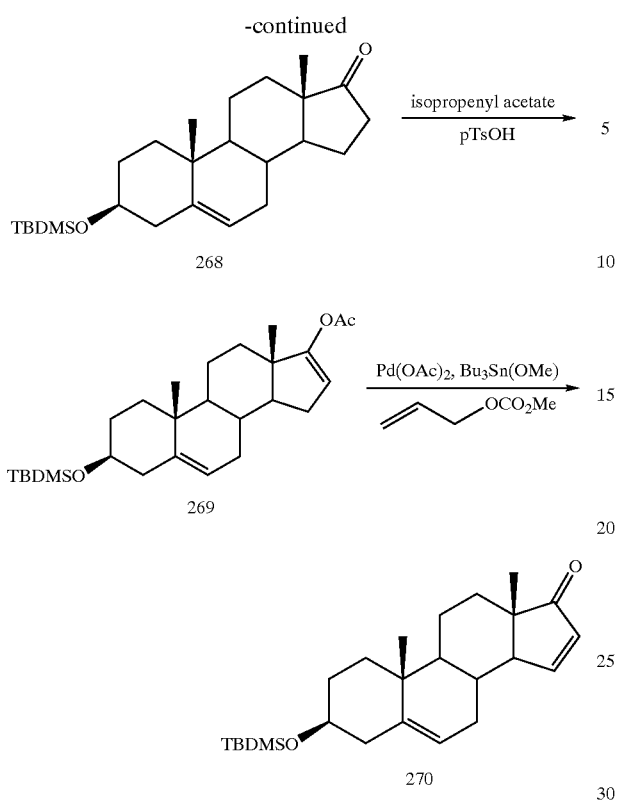

The reaction procedures for the Michael Addition illustrated in Scheme 67 are as follows. Compound 270 is dissolved in p-methoxybenzyl alcohol and powdered KOH is added. The mixture is stirred under nitrogen at room temperature for 4 hours. The mixture is diluted with Et$_2$O and washed with water. The organic layer is dried over MgSO$_4$, filtered and concentrated. The crude residue is purified using flash chromatography with a step gradient (EtOAc/hexane) elution to yield compound 271.

Scheme 67

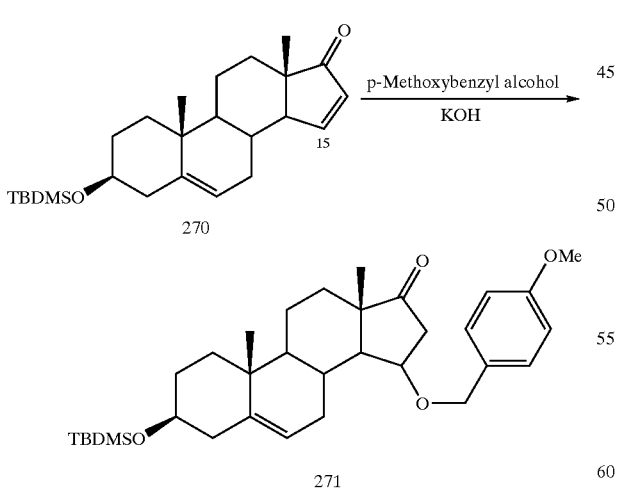

Attachment of the sidechain can be accomplished on compounds containing a C17 ketone functionality using a Wittig/ene procedure as illustrated earlier (Example 5), or by using a procedure involving a compound containing a methyl ketone at C17, such as ketone 275. The conversion of compounds with C17 ketone functionalities to methyl ketone derivatives is accomplished in a four step process using procedures described in the literature. An example of this methodology is illustrated in Scheme 68.

Scheme 68

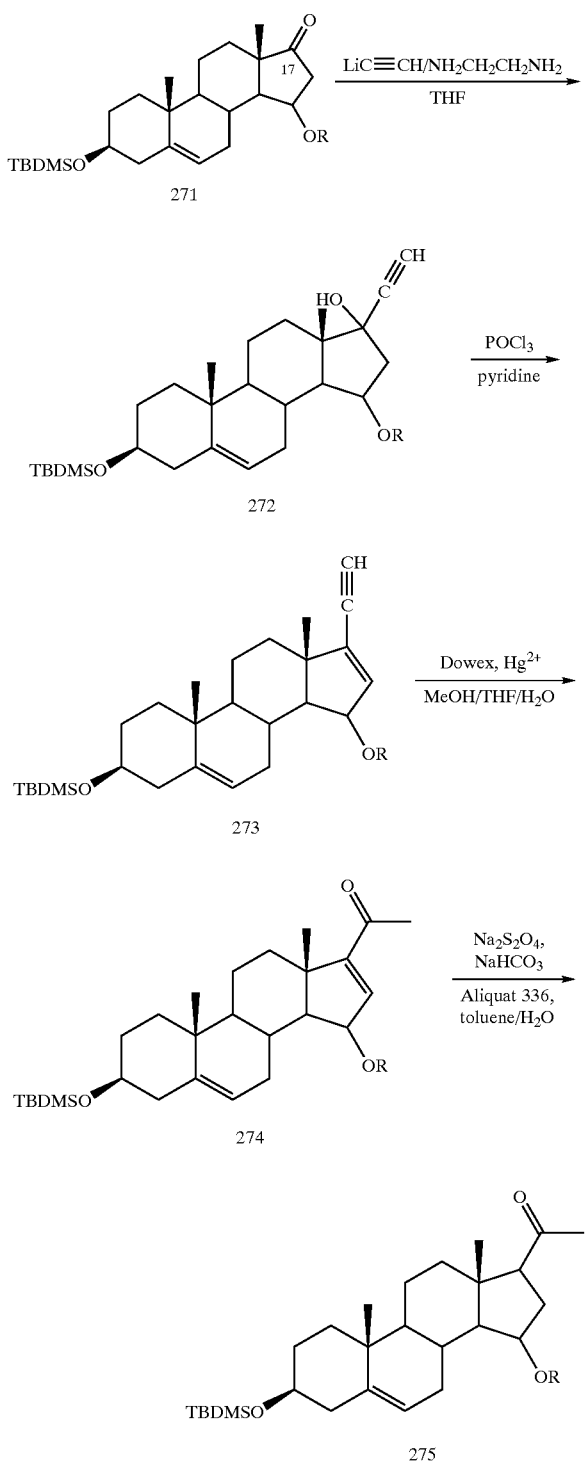

R = p-methoxybenzyl

The first step in the above process involves conversion of compound 271 to the acetylenic alcohol compound 272 using lithium acetylide-ethylenediamine complex. The acetylide complex is suspended in THF, and after cooling to −20° C., a solution of compound 271 in THF is added. The mixture is stirred at room temperature for 6 hours, cooled to 0° C. and then quenched with water. The mixture is extracted with dichloromethane then the combined organic extracts are washed with brine and water and then dried over $MgSO_4$. After filtration and concentration the residue is purified using silica flash chromatography (1:6 EtOAc/hexane) to yield compound 272.

Dehydration of compound 272 yields the conjugated carbon-carbon double bond in the D-ring of compound 273. Compound 272 is dissolved in dry pyridine and phosphorus oxychloride is added. The mixture is stirred for 30 minutes at room temperature and then poured onto ice-water. The aqueous slurry is extracted with dichloromethane and the combined organic extracts are washed with aqueous $NaHCO_3$ and water and dried over $MgSO_4$. After filtration and concentration the crude product is purified using silica flash chromatography (1:6 EtOAc/hexane) to yield compound 273.

Mercury (2+) impregnated Dowex-50W resin, in a solvent mixture of methanol, THF and water is then used to produce the conjugated methyl ketone 274 from compound 273. Compound 273 is dissolved in methanol/THF (2:1) and two drops of water are added. $Hg^{2+}$/Dowex resin is added and the mixture is stirred at 60° C. overnight. Filtration and concentration yields a crude residue which is purified by silica flash chromatography (1:2 EtOAc/hexane) to give methyl ketone 274.

The $\Delta^{16}$ carbon-carbon double bond in compound 274 is reduced using sodium dithionite. Compound 274 in toluene is added to a mixture of sodium dithionite and sodium bicarbonate in water. The phase transfer catalyst Aliquat® 336 is added and the mixture is refluxed for 3 hours. The mixture is extracted with dichloromethane and the organic phase is dried over $MgSO_4$. Filtration and concentration of the filtrate in vacuo gives a crude residue, containing compound 275.

Selective deprotection of the C15 hydroxyl in 275 can be accomplished, at this stage or after coupling of the appropriate sidechain, according to the procedures described by Horita et al. (*Tetrahedron*, 1986, 42(11), 3021–3028) which involve oxidation of the p-methoxybenzyl ether with 2,3-dichloro-5,6-dicyanobenzoquinone (DDQ) in dichloromethane and water. Oxidation of the resultant C15 hydroxyl group to the ketone functionality can be accomplished using a number of methods including PCC in dichloromethane.

Example 7

As described in the introduction to this section, the hemiacetal sidechain functionality in compounds such as 165 can be introduced using Grignard 25 methodology. This first involves a two step conversion from the methyl ketone functionality at C17 to a C22 aldehyde containing compound. The methodology for such a conversion, illustrated in Scheme 69, has previously been described by a number of groups including Koreeda et al., *Tetrahedron Letters*, No. 19, 1641–1644, 1978.

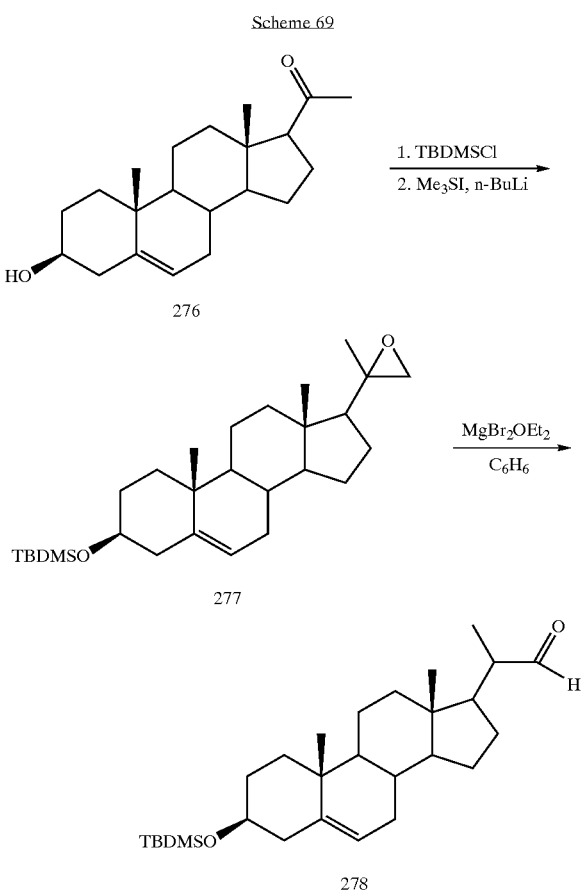

Scheme 69

The coupling (Scheme 70) of the desired sidechain to the steroidal aldehyde 278 is achieved by nucleophilic attack of a carbanion. Compound 28 is prepared in situ by treatment of the iodide 284 with t-BuLi in $Et_2O$ at −78° C. (see Section 3, Example 9, Scheme 72) and the solution of the aldehyde 278 in $Et_2O$ is then added. The mixture is stirred for 1.5 hours at −78° C. then warmed to room temperature and EtOAc is added. The organic layer is washed sequentially with water, 1N HCl, and water, then dried over $MgSO_4$. After filtration and concentration, the crude product is purified using silica flash chromatography to yield compound 281. Deprotection of the sidechain, using standard procedures such as 80% aqueous acetic acid at 60° C., gives the desired sidechain hemiacetal.

Scheme 70

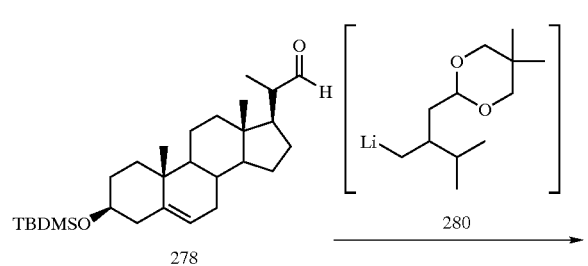

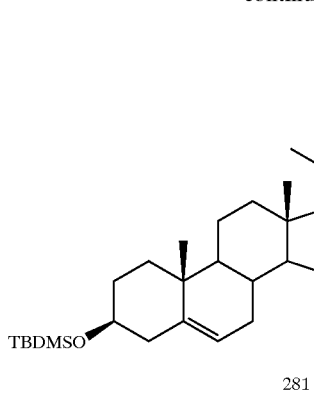

281

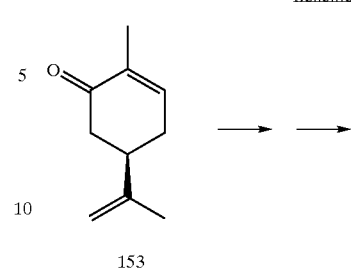

Scheme 71

SECTION 3

The Synthesis of Various Side Chain Carbon Skeletons for Coupling to Steroid Nuclei The synthesis of compound 165, and analogues outlined are convergent (i.e., a highly functionalized side chain is coupled with a functionalized steroid nucleus). The two methods employed to couple the side chain carbon skeleton to the steroid ring structure were described in Section 2. Below is a description of the production of the side chain carbon skeletons to be used in the coupling reactions.

The first method involves the synthesis of 5-acetoxy-3-(1'-methylethyl)-pentanal (156) and related aldehydes from the primary alcohol 154 (produced from L-carvone, which is available from, e.g., Aldrich Chemical Co., Milwaukee, Wis.). This sequence gives rise to compound 156 with the S-configuration. The compound with the R-configuration is synthesized from D-carvone. It is also noteworthy that any appropriate alcohol protecting group can be used in place of the acetate ester to generate an aldehyde compound suitable for coupling to the steroid via an ene-type reaction on compound 252 and related steroids.

The second method (Scheme 72) involves the synthesis of compound 284 and related alkyl halides from the carboxylic acid compound 282. This sequence also generates a product (280) with the S-configuration. Again, the enantiomer of compound 280 is synthesized from D-carvone. As above, any appropriate aldehyde protecting group can be used in place of the ketal functionality in 280, for the steps in the production of the carbanion used in the coupling reaction (generated from a lithium/halide exchange reaction on the corresponding alkyl halide).

Example 8

5-Acetoxy-3-(1'-methylethyl)-pentanal (156)

The intermediate 5-acetoxy-3-(1'-methylethyl)-pentanal (156), used in the Wittig reaction described in previous sections, can be synthesized according to the reaction sequence shown in Scheme 71.

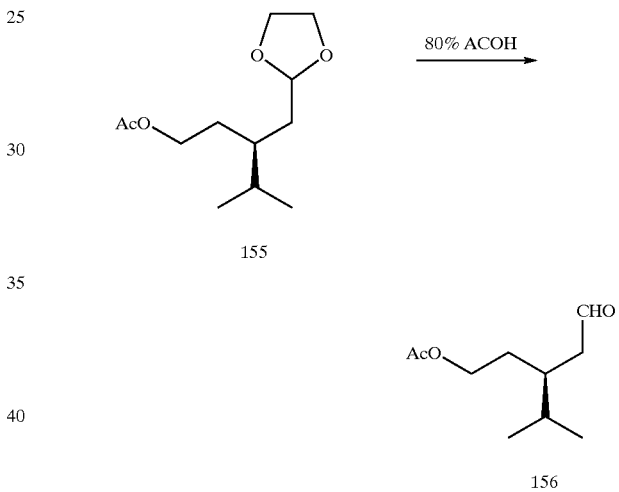

Conversion of L-carvone (153) to compound 154 is accomplished following literature procedures (*Tetrahedron Letters*, 1984, 25(41), 4685–4688). Protection of the primary alcohol in compound 154 is accomplished by conversion to an acetate ester. Compound 154 (207 mg, 1.10 mmol) is dissolved in pyridine (2 mL) and DMAP (10 mg) and acetic anhydride (2 mL) are added. The mixture is stirred at room temperature overnight and then diluted with Et$_2$O. The mixture is washed with 10% aqueous NaHCO$_3$ then water and dried over MgSO$_4$. Purification of the crude product is achieved using silica flash chromatography (1:4 EtOAc/hexane) to give compound 155 (249 mg, 1.08 mmol) in 98% yield.

Removal of the ketal protecting group in ketal 155 using 80% acetic acid gives the desired aldehyde 156. Compound 155 (150 mg, 0.652 mmol) is suspended in 80% AcOH (5 mL) and the mixture is heated at 70° C. for 2 hours. The solvent is removed in vacuo and the residue is taken up in Et$_2$O (50 mL). The mixture is then washed with aqueous NaHCO$_3$ and brine and then dried over MgSO$_4$. Filtration and evaporation of the filtrate gives pure compound 156 (110 mg, 0.591 mmol) in 91% yield.

Example 9

The intermediate 280, used in the coupling reaction described in previous sections, can be synthesized according to the reaction sequence summarized in Scheme 72.

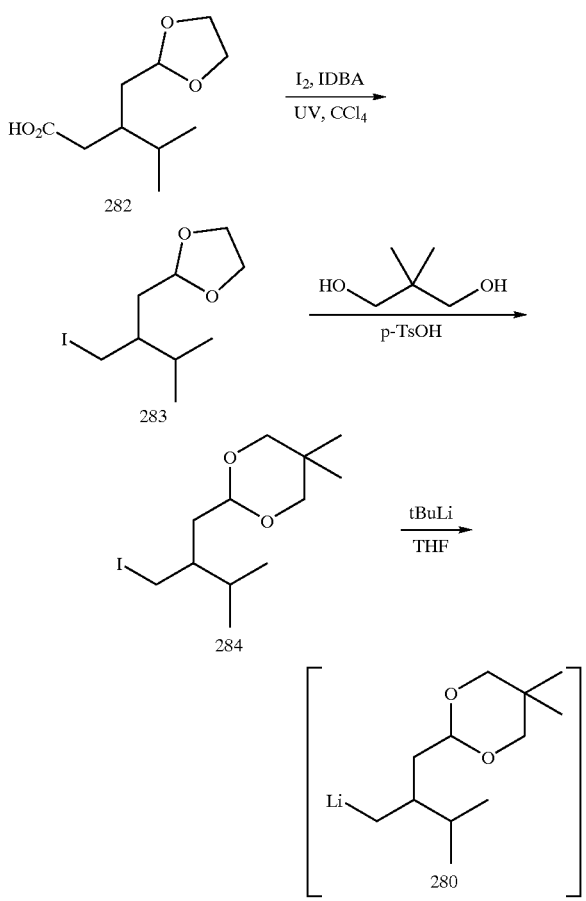

Compound 282 is first synthesized using standard literature procedures (*Tetrahedron Letters*, 25(41), 4685–4688, 1984) and then converted to 280 in a three step procedure. Compound 282 (1.04 g, 5.12 mmol) is dissolved in dry $CCl_4$ (120 mL), and $I_2$ (2.57 g) and iodobenzenediacetate (IDBA) (3.28 g) are added. The mixture is refluxed while irradiating with a 100 Watt bulb for 10 minutes. After cooling to room temperature, 5% aqueous $Na_2S_2O_3$ solution (300 mL) is added until the solution is colorless then the layers are separated. The organic phase is washed with water and dried over $MgSO_4$. Purification gives pure compound 283 (657 mg, 2.30 mmol, 45% yield).

Exchange of the aldehyde protecting groups is achieved to produce compound 284 from compound 283 using 2,2-dimethyl-1,3-propanediol and p-toluenesulphonic acid as a catalyst. Compound 283 (42 mg, 0.18 mmol) is dissolved in benzene (5 mL) and 2,2-dimethyl-1,3-propanediol (300 mg) and p-toluenesulphonic acid (3 mg) are added. The mixture is heated at reflux overnight then cooled and evaporated to dryness in vacuo. The residue is purified using silica flash chromatography (19:1 $CH_2Cl_2$/Hexanes) to yield compound 284 (40 mg, 0.14 mmol, 80%).

Finally, a lithium iodine exchange reaction on 284 using t-butyllithium in THF gives the desired product 280. t-BuLi (1.7 M solution in pentane, 0.25 mL) is added to a solution of compound 284 (52.1 mg, 0.160 mmol) in dry $Et_2O$ (2.0 mL) at −78° C. The solution is stirred at −78° C. until no starting material remains by GC analysis. This solution is used directly in the coupling reaction with the aldehyde 278 (Example 7, Scheme 70).

SECTION 4

The Synthesis of 3,4,6,7-Polyhydroxy-22,29-epoxy-15-one Steroids

The synthesis of polyhydroxylated steroids containing one or both of the C15 ketone and the side chain hemiacetal found in 22,29-epoxy-3,4,6,7,29-pentahydroxy-14β-stigmastan-15-one (165) can be accomplished using a combination of the methods described in the first two sections. One can either begin with the functionalization of the A and B rings, then the functionalization of the D-ring and coupling of the side chain or the converse. In the compounds containing a C15 ketone and/or a C29 hemiacetal, the A/B ring can contain 2, 3 or 4 hydroxyl groups at carbons 3, 4, 6 and/or,7 in any combination and in any combination of configurations.

The following describes synthetic routes to the compounds 22,29-epoxy-3,6,7,29-tetrahydroxy-14β-stigmastan-15-one (304) and 22,29-epoxy-3,4,6,7,29-pentahydroxy-14β-stigmastan-15-one (165) and the corresponding H14α epimers. These are examples of compounds containing the C15 ketone and the side chain C29 hemiacetal that are derived from synthetic transformations described in the first two sections and the same methodology can be applied in the production of compounds containing other hydroxylation patterns at carbons 3, 4, 6 and 7 in the A/B ring system.

Also included below is the synthetic route to 22.29-epoxy-3,6,7,29-tetrahydroxystigmastanol (306), a compound that contains a polyhydroxylated A/B ring system and a hemiacetal side chain but lacks the C15 ketone functionality found in compound 165.

Example 10

22,29-Epoxy-3,6,7,29-tetrahydroxy-14β-stigmastan-15-one (304)

The steroid 22,29-epoxy-3,6,7,29-tetrahydroxy-14β-stigmastan-15-one (304) can be synthesized according to Scheme 73.

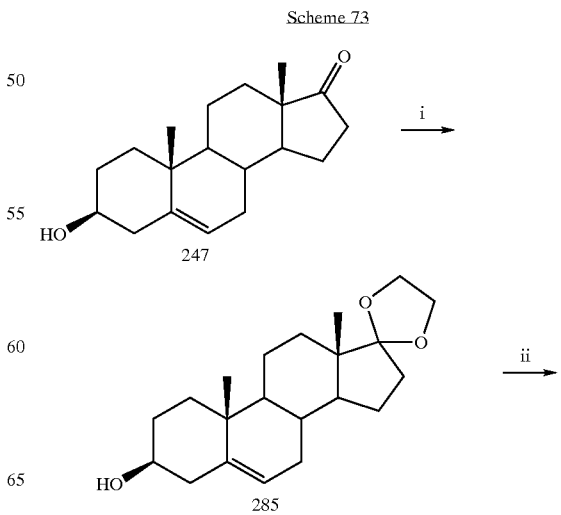

153
-continued
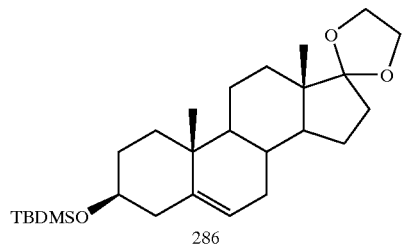
286
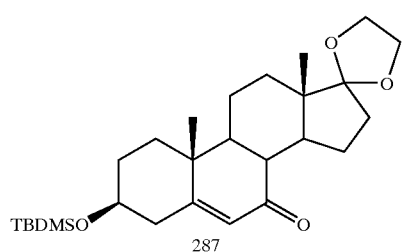
287
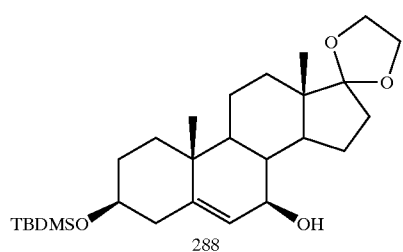
288
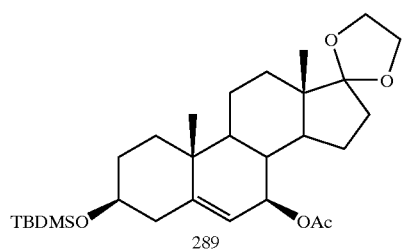
289
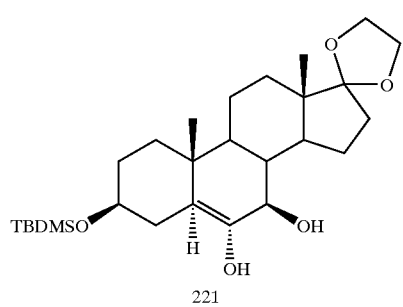
221
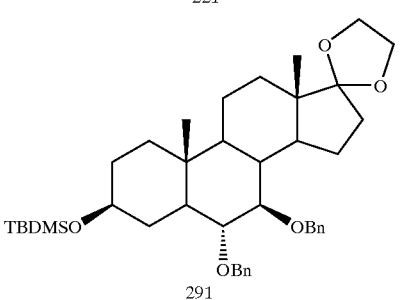
291
154
-continued
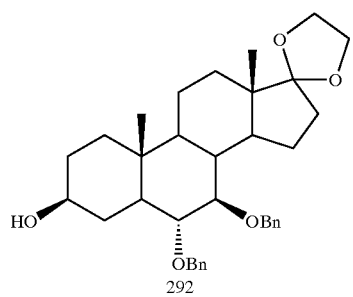
292
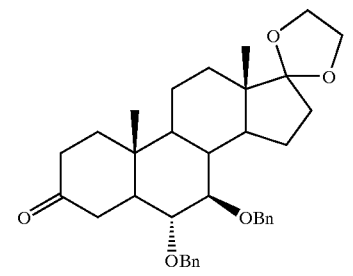
293
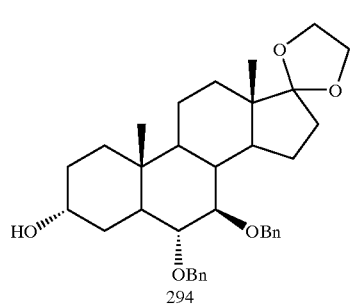
294
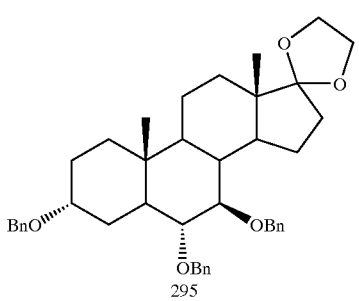
295
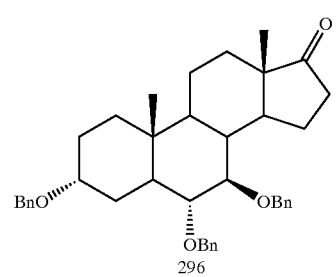
296
Key: (i) p-TsOH, (CH$_2$OH)$_2$, Benzene (ii) TBDMSCl, imidazole, DMF (iii) CrO$_3$, 3, 5-dimethylpyrazole, CH$_2$Cl$_2$ (iv) NaBH$_4$, CeCl$_3$, THF-MeOH (v) Acetic Anhydride, pyridine (vi) BH$_3$:THF complex, then H$_2$O$_2$, ⁻OH (vii) NaH, DMF, Benzyl bromide (viii) TBAF, THF (ix) PDC, CH$_2$Cl$_2$ (x) LS-Selectride®, THF (xi) NaH, DMF, Benzyl bromide (xii) AcOH, H$_2$O, acetone.

155
-continued
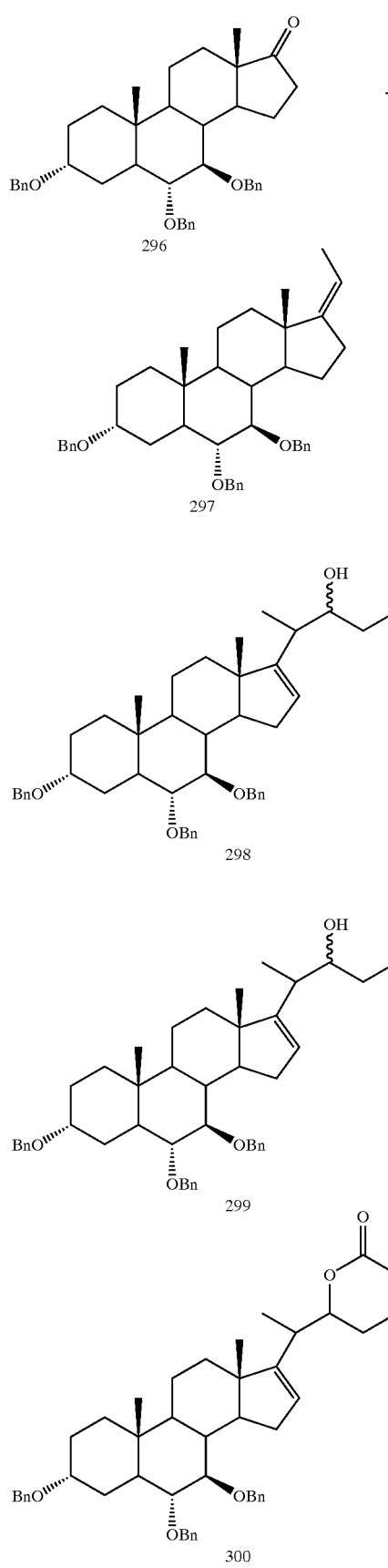
156
-continued
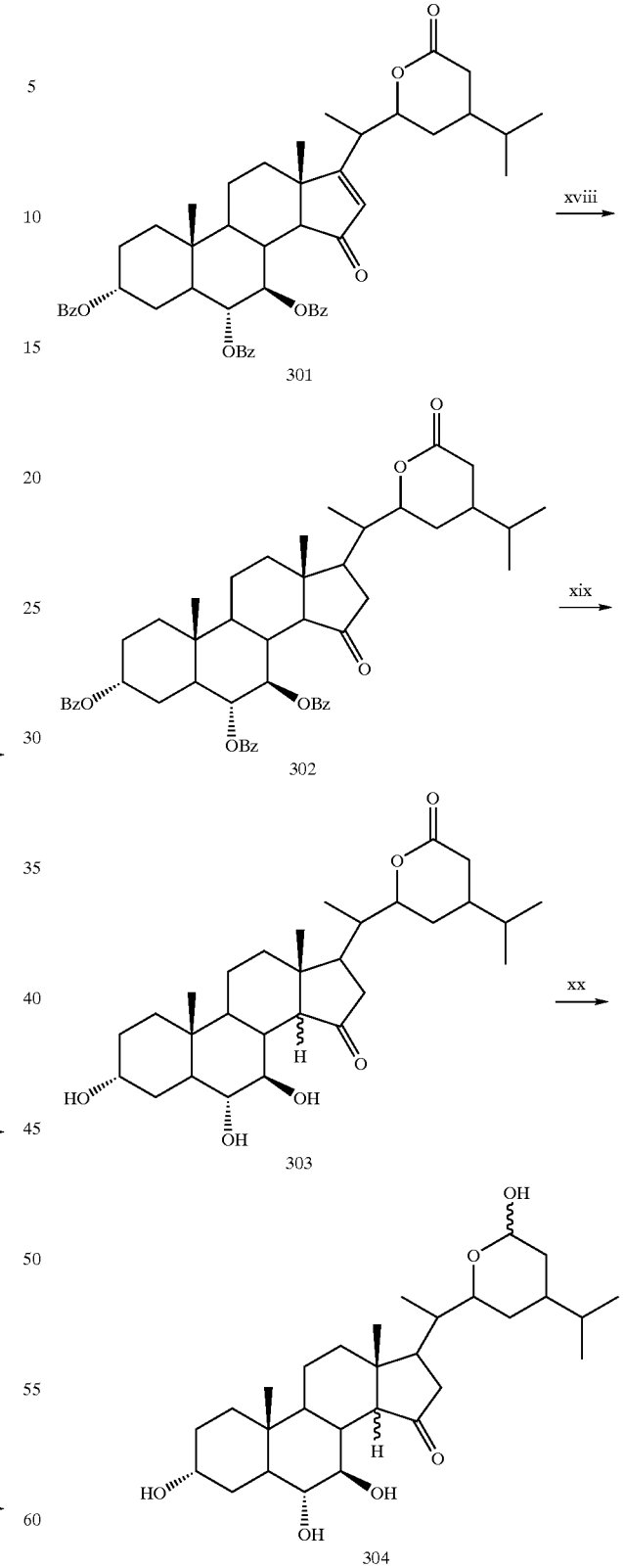
(xiii) EtPh$_3$PBr, t-BuOK, THF (xiv) 156, (CH$_3$)$_2$AlCl, CH$_2$Cl$_2$ (xv) MeONa, MeOH (xvi) Ag$_2$CO$_3$/celite, benzene (xvii) CrO$_3$, 3,5-dimethylpyrazole, DMF (xviii) H$_2$, Pd/C, EtOAc/EtOH (xix) KOH, MeOH (xx) 1. (CH$_2$OH)$_2$, pTsOH, benzene, 2. DIBAL, Toluene, 3. 80% AcOH.

The steroid 22,29-epoxy-3,6,7,29-tetrahydroxy-14β-stigmastan-15-one (304) can be synthesized starting from the commercially available steroid dehydroisoandrosterone (247). The C17 ketone of compound 247 is first protected as the ketal by treatment with ethylene glycol and a catalytic amount of p-toluenesulfonic acid in refluxing benzene. Protection of the 3β hydroxyl as a silyl ether is then achieved using t-butyldimethylsilyl chloride and imidazole in DMF to give compound 286. Allylic oxidation of compound 286 using chromium trioxide and 3,5-dimethylpyrazole introduces a carbonyl moiety at the C7 position (compound 287). Chemoselective 1,2-reduction of this ketone using sodium borohydride and cerium chloride yields the allylic alcohol 288 in a THF-methanol solvent system.

Introduction of the C6 alcohol can be accomplished using the sequence described in Example 1, or by hydroboration using a borane-THF complex followed by oxidative hydrolysis with basic hydrogen peroxide. In the second method, the allylic alcohol in compound 288 is first protected as the acetate using acetic anhydride and pyridine and the product 289 is dissolved in dry THF and at 0° C. a solution of 1.0 M borane in THF is added. The mixture is stirred at 0° C. for 30 minutes and then at room temperature for 2.5 hours. A 3N NaOH solution is then added dropwise followed by 30% aqueous $H_2O_2$. The mixture is stirred at room temperature for 16 hours and then poured into saturated sodium chloride solution. The aqueous slurry is extracted with chloroform and the combined organic layers are dried over $MgSO_4$. Filtration and evaporation of the filtrate gives a crude product which is purified by flash chromatography to yield compound 221.

Protection of the vicinal 6,7-diol 221 is then achieved as the dibenzyloxy derivative using benzyl bromide and sodium hydride in dimethylformamide. Compound 221 is dissolved in dimethylformamide and sodium hydride is added. The mixture is stirred for 1 hour at room temperature then benzyl bromide is added. Stirring is continued for 2.5 hours then the reaction is quenched by the addition of water and stirring is continued for 30 minutes. The mixture is extracted with diethyl ether and then washed successively with 5% HCl, saturated sodium bicarbonate and saturated sodium chloride. The organic layer is dried over magnesium sulphate, filtered and evaporated to dryness. The resultant crude residue is purified using flash chromatography to yield compound 291.

Deprotection of the C3 alcohol in compound 291 is achieved using TBAF in THF at reflux for 2 hours to yield compound 292. Subsequent oxidation using PDC gives the ketone 293. To affect this transformation the crude product 292 is dissolved in $CH_2Cl_2$ and PDC is added. The mixture is stirred at room temperature for 22 hours. Filtration through a bed of celite followed by purification of the evaporated filtrate using flash chromatography gives the product ketone 293 as a white solid.

Selective reduction of 293 gives the o-hydroxyl group at C3 in 83% yield. To achieve this, a solution of compound 293 in THF is cooled to −78° C. and LS-Selectride® is added slowly and stirring is continued at −78° C. for 1 hour under nitrogen. Methanol is added and the reaction mixture is warmed to room temperature. Standard work-up followed by purification by flash chromatography gave compound 294 in approximately 80% yield. The 3β-epimer is obtained in approximately 10% yield. Protection of the α-hydroxyl group in compound 294 is achieved as the benzyloxy derivative. Thus, compound 294 is dissolved in dimethylformamide and sodium hydride is added. The mixture is stirred for 1 hour at room temperature then benzyl bromide is added. Stirring is continued for 16 hours then the reaction is quenched by the slow addition of water and stirring is continued for 30 minutes. The mixture is extracted with diethyl ether and then washed successively with 5% HCl, saturated sodium bicarbonate and saturated sodium chloride. The organic layer is dried over magnesium sulphate, filtered and evaporated to dryness. The resultant crude residue is purified using flash chromatography to yield compound 295.

Deprotection of the C17 ketal in compound 295 using a mixture of acetic acid, water and acetone (2:1:2) for 14 hours at reflux gives compound 296 in 99% yield after purification. Compound 296 is converted to olefin 297 using the ylid prepared by the treatment of ethyltriphenylphosphonium bromide with potassium t-butoxide in THF. The coupling of the carbon structure of the side chain is achieved using the aldehyde 156 (Scheme 45) and the Lewis acid, dimethylaluminum chloride, in dichloromethane to yield the C22 epimers 298a and 298b after purification. Deprotection of the C29 acetoxy group is then accomplished using sodium methoxide in methanol. The resultant diol 299 is then oxidized to the δ-lactone using silver carbonate on celite in refluxing benzene. Compound 299 is dissolved in benzene and silver carbonate embedded on celite is added and the mixture refluxed for 12 hours. The reaction mixture is then filtered, evaporated and the residue purified by flash chromatography to yield lactone 300. Allylic oxidation of compound 300 using chromium trioxide and 3,5-dimethylpyrazole in dichloromethane introduces a carbonyl moiety at C15 (compound 301). Reduction of the conjugated $\Delta^{16}$ carbon-carbon double bond using hydrogen and palladium on carbon in EtOAc gives compound 302. Removal of the benzoate groups in ester 302 is achieved with concurrent epimerization at C14 to yield the trihydroxy product 303 which contains the cis C/D ring junction in addition to the trihydroxy product containing the trans C/D ring junction which are separable by chromatography. Finally, protection of the C15 ketone as the ethylene ketal (($CH_2OH)_2$, pTsOH, benzene) followed by selective reduction of the δ-lactone to the lactol using DIBAL at −78° C. and deprotection (80% AcOH) can give 22,29-epoxy-3,6,7,29-tetrahydroxy-14β-stigmastan-15-one (304).

As an alternative, compound 221 may be treated to remove all of the protecting group, for example using 80% acetic acid. Thereafter, the hydroxyl groups in the B-ring may be selectively protected. This may be done with 2,2-dimethoxypropane and camphorsulfonic acid. The ketone group at C17 may then be elaborated to an exocyclic double bond using Wittig chemistry, for example, using ethyltriphenylphosphoniium bromide, t-BuOK and THF affords ethylidene substitution at C17. Thereafter, the C3 hydroxyl group may be oxidized to a carbonyl group with, e.g., oxalyl chloride, DMSO, $Et_3N$ in methylene chloride, followed by reduction of the resulting C3 carbonyl with LS-Selectride® (Aldrich Chemical Co., Milwaukee, Wis.) to afford the 3-α hydroxy group. Deprotection of the hydroxyl groups in the B-ring then affords compound 330. This is an alternative route to compound 330 from what is shown in Scheme 79.

Example 11

Compound 306 can be synthesized from compound 300 according to the reaction sequence in Scheme 74.

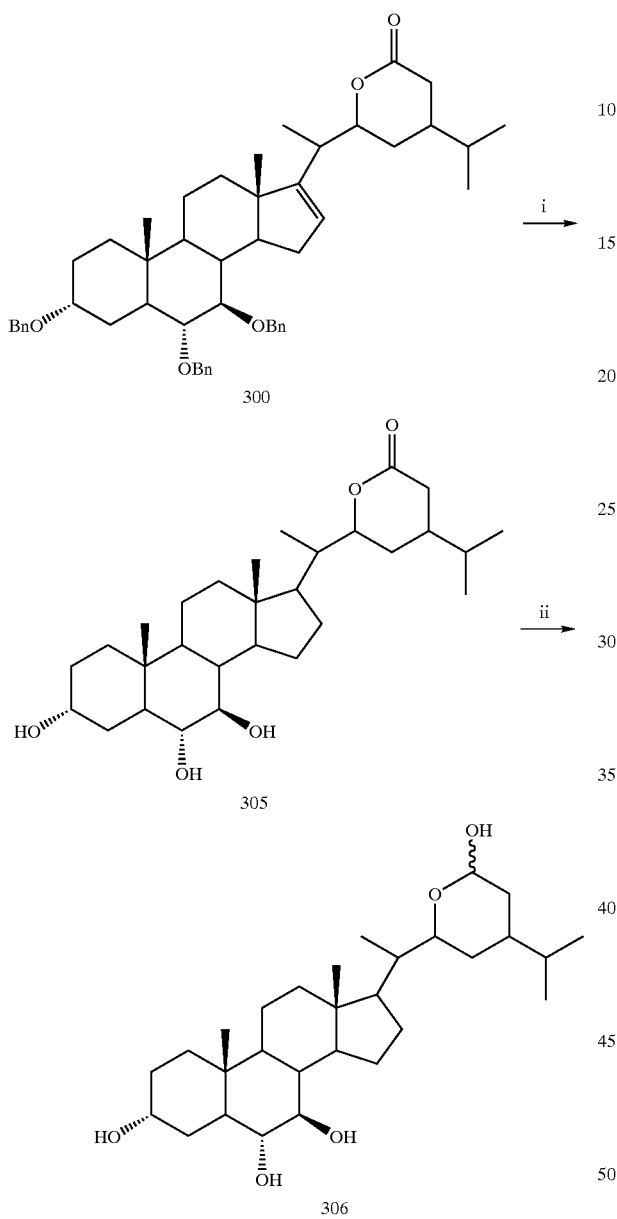

Key: (i) $H_2$, Pd/C, EtOAc/EtOH (ii) DIBAL, Toluene, -78° C.

Compound 306 can be synthesized from compound 300 in a two step process with the first step being the deprotection of the hydroxyl groups using hydrogen and palladium on carbon in EtOAc and EtOH with concurrent reduction of the $\Delta^{16}$ carbon-carbon double bond. The above mixture is stirred at room temperature for 12 days, filtered and purified by flash chromatography to yield 305. Selective reduction of the δ-lactone to the lactol is then accomplished as follows. Compound 305 is dissolved in THF and cooled to -78° C. DIBAL is added and the mixture is stirred at -78° C. for 3 hours. Standard workup and purification using silica flash chromatography gives give 22,29-epoxy-3,6,7,29-tetrahydroxystigmastanol (306).

Example 12

Reaction conditions described in the previous sections can be applied to the synthesis of compound 165 as illustrated in Scheme 75.

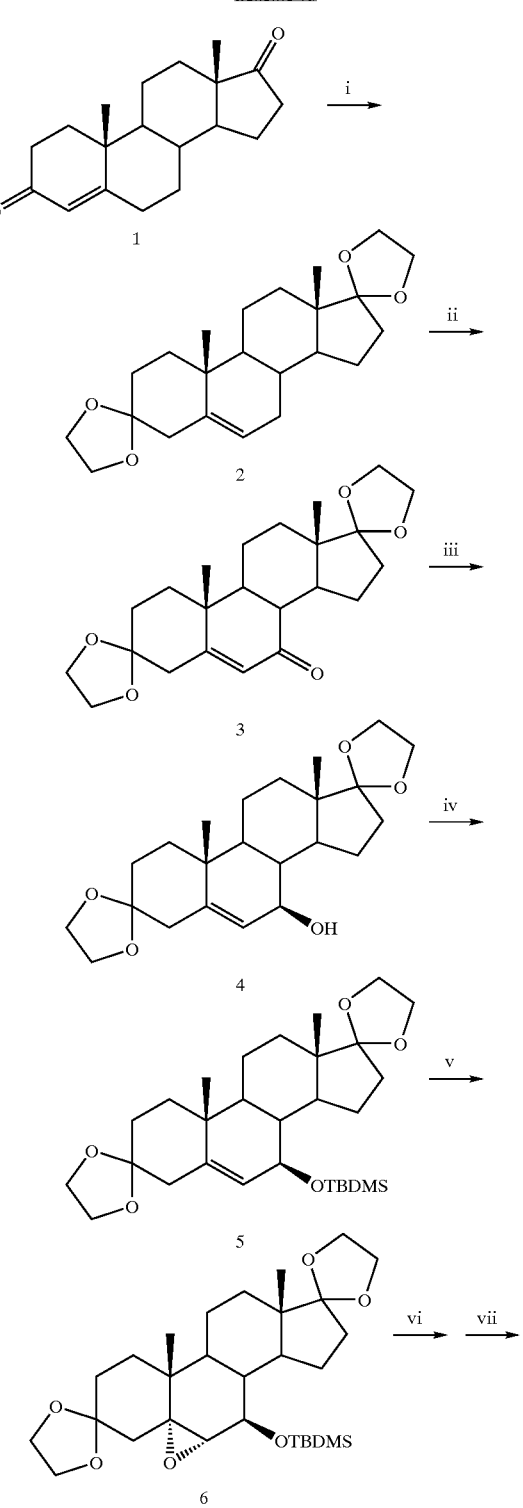

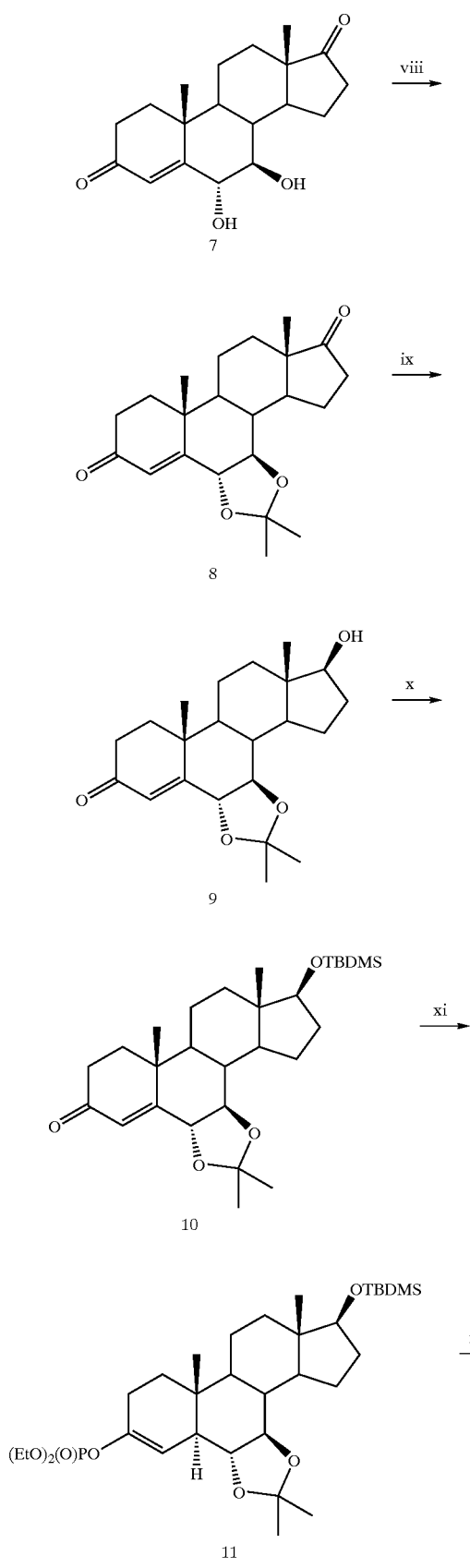
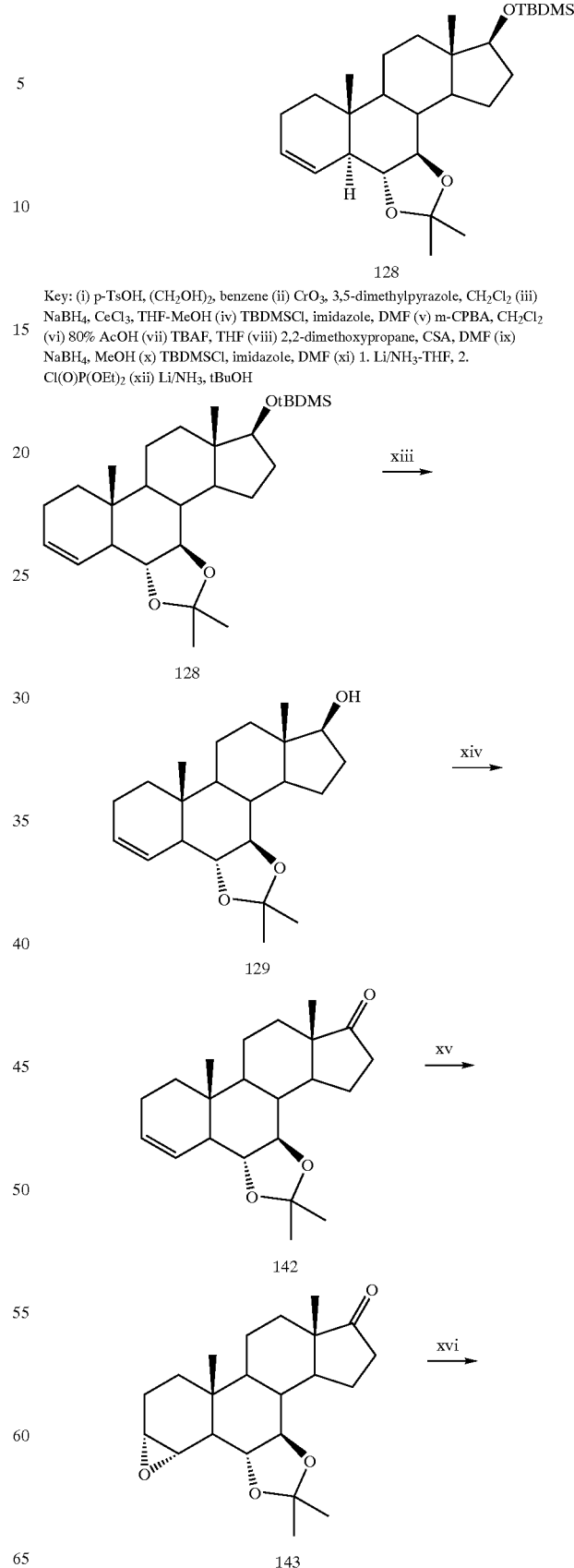
Key: (i) p-TsOH, (CH$_2$OH)$_2$, benzene (ii) CrO$_3$, 3,5-dimethylpyrazole, CH$_2$Cl$_2$ (iii) NaBH$_4$, CeCl$_3$, THF-MeOH (iv) TBDMSCl, imidazole, DMF (v) m-CPBA, CH$_2$Cl$_2$ (vi) 80% AcOH (vii) TBAF, THF (viii) 2,2-dimethoxypropane, CSA, DMF (ix) NaBH$_4$, MeOH (x) TBDMSCl, imidazole, DMF (xi) 1. Li/NH$_3$-THF, 2. Cl(O)P(OEt)$_2$ (xii) Li/NH$_3$, tBuOH Key: (xiii) TBAF, THF (xiv) oxalyl chloride, DMSO, Et₃N (xv) m-CPBA, CH₂Cl₂ (xvi) AcOH (xvii) K₂CO₃, MeOH (xviii) EtPPh₃Br, t-BuOK, THF (xix) BnBr, NaH, DMF (xx) 156, Me₂AlCl, CH₂Cl₂ (xxi) NaOMe, MeOH, THF (xxii) Ag₂CO₃/celite, benzene (xxiii) CrO₃, 3,5-dimethylpyrazole, CH₂Cl₂.

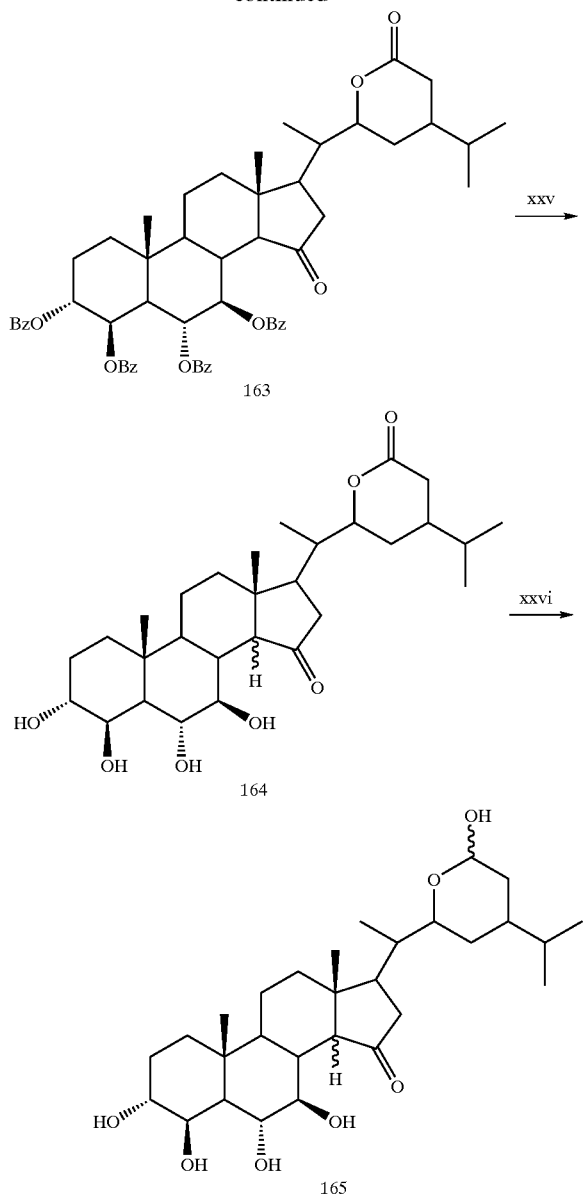

Key: (xxiv) H₂, Pd/C, EtOAc (xxv) KOH, MeOH (xxvi) 1. (CH₂OH)₂, pTsOH, benzene, 2. DIBAL, Toluene, -78° C. 3.80% AcOH The synthesis of 22,29-epoxy-3,4,6,7,29-pentahydroxy-14β-stigmastan-15-one (165) is carried out starting with the commercially available steroid 4-androstene-3,17-dione (1). The synthesis from compound 1 to the intermediate 128 has already been described (Example 3, Scheme 61) for the synthesis of 3α,4β,6α,7β-pentahydroxy-5α-androstanol (241).

Preparing the D-ring of compound 128 for the side chain coupling procedures described in subsequent examples (Example 16, Scheme 79) begins with the removal of the silyl group at C17 of steroid 128. Compound 128 is dissolved in THF and TBAF (1.0 M in THF) is added. The mixture is heated at reflux for 2 hours and then concentrated in vacuo. The residue is purified by flash chromatography to give alcohol 129.

The hydroxyl moiety in alcohol 129 is convert to the ketone using oxalyl chloride in CH₂Cl₂. Compound 129 is dissolved in CH₂Cl₂ and added to a solution of oxalyl chloride in CH₂Cl₂ at -78° C. After stirring at -78° C. for 15 minutes, triethylamine is added and stirring is continued for 5 minutes. Standard work-up and purification gave compound 142 as a white solid.

The conversion of compound 142 to compound 145 is accomplished using the same procedures described in Example 3 (Scheme 61) for the conversion of compound 128 to compound 241. Epoxidation of compound 142 using m-CPBA in dichloromethane to yield epoxide 143 is followed by epoxide opening using acetic acid to give the 3,6,7-trihydroxy-4-acetoxy compound 144 and removal of the acetate group attached to the oxygen on C4 using K₂CO₃ in methanol to yield compound 145.

Synthesis of compound 165 from compound 145 is accomplished using the same types of reactions described in previous sections. Compound 145 is converted to ethylidene 157 using the ylid prepared from ethyltriphenylphosphonium bromide and potassium t-butoxide in THF. The four hydroxyl groups are then protected as benzyl moieties to yield the tetrabenzyloxy compound 158. Coupling of the side chain is achieved using the aldehyde 156 (Scheme 71) and a Lewis acid such as dimethylaluminum chloride in dichloromethane to yield compound 159. Deprotection of the C29 acetoxy group is then accomplished using sodium methoxide in methanol. The resultant diol is then oxidized to the δ-lactone 161 using silver carbonate on celite in benzene. Allylic oxidation of compound 161 using chromium trioxide and 3,5-dimethylpyrazole in dichloromethane introduces a carbonyl moiety at C15 with concurrent oxidation of the benzyl groups to benzoate groups (compound 162). Reduction of the conjugated $\Delta^{16}$ carbon-carbon double bond using hydrogen and palladium on carbon in EtOAc and EtOH gives compound 163. Removal of the benzoate groups in ester 163 is achieved using basic conditions (for example KOH in MeOH) with concurrent epimerization at C14 to yield product 164 which contains an epimeric mixture of the compounds containing the cis C/D ring junction and the trans C/D ring junction. Finally, protection of the C15 ketone as the ethylene ketal ((CH₂OH)₂, pTsOH, benzene) followed by selective reduction of the δ-lactone to the lactol using DIBAL at -78° C. and deprotection (80% AcOH) can give 22,29-epoxy-3,4,6,7,29-pentahydroxy-14β-stigmastan-15-one (165) and it's C14 epimer give 22,29-epoxy-3,4,6,7,29-pentahydroxy-14α-stigmastan-15-one.

SECTION 5

Additional Examples of the Synthesis of Novel Polyhydroxylated Steroids With Biological Activities In addition to the compounds described in previous sections, a number of related compounds with biological activities have been produced. These include, among others, compounds containing the 3α,6α,7β-hydroxylation pattern with varying functionalities at the C17 position, as well as compounds containing the 3β,6α,7β-hydroxylation pattern with varying functionalities at the C17 position. Some of the procedures used for the production of these compounds are described in the following examples.

Example 13

A number of 3,6,7-hydroxylated compounds can be prepared from the intermediate compound 221. As described in Scheme 73, compound 221 may be prepared from the commercially available starting material dehydroisoandrosterone (247). Specifically, compound 247 (20.0 g, 69.3 mmol) is dissolved in benzene (200 ml) in a 500 ml round bottom flask which is then connected to a Dean-Stark apparatus. p-Toluenesulfonic acid monohydrate (0.501 g, 2.64 mmol) is added followed by ethylene glycol (20 ml) and the mixture is refluxed for 4.5 hours. The mixture is cooled to room temperature and diluted with diethyl ether (200 ml). The organic layer is washed with saturated sodium bicarbonate (2×100 ml) then by saturated sodium chloride (2×100 ml). The organic layer is dried with $MgSO_4$, filtered and evaporated to dryness to yield the product 285 (22.8 g, 68.6 mmol, 99%) which is used in the next reaction without further purification. Protection of the 3β-hydroxyl in compound 285 as a silyl ether may then be achieved as follows. Compound 285 (22.5 g, 67.7 mmol) is dissolved in a mixture of dimethylformamide (112.5 ml) and dichloromethane (112.5 ml). Imidazole (11.3 g, 166.0 mmol) is added followed by t-butyldimethylsilyl chloride (15.8 g, 104.8 mmol). The mixture is stirred at room temperature for 6 hours under Argon then diluted with diethyl ether (675 ml). The organic mixture is washed with aqueous 5% HCl (2×135 ml) followed by saturated sodium bicarbonate (2×135 ml) then by saturated sodium chloride (2×135 ml). The organic layer is dried with $MgSO_4$, filtered and evaporated to dryness to yield the crude product 286. The crude product is then recrystallized from ethyl acetate/methanol (3:2) to give compound 286 (25.9 g, 58.0 mmol, 83% over two steps) as white crystals. Allylic oxidation of compound 286 may then introduce a carbonyl moiety at the C7 position (compound 287). Compound 286 (15.0 g, 33.6 mmol) is dissolved in cyclohexane (60 ml) and $H_2O$ (7.3 ml) is added. Ruthenium(III) chloride hydrate (0.0561 g, 0.27 mmol) is added followed by the dropwise addition of t-butylhydroperoxide (37.6 ml). The mixture is stirred at room temperature for 24 hours and then diluted with ethyl acetate (376 ml). The organic mixture is washed with saturated sodium chloride (2×188 ml) then with 25% sodium thiosulphate (2×188 ml). The organic layer is dried with $MgSO_4$, filtered and evaporated to dryness to yield the crude product. The crude product is recrystallized from ethyl acetate to yield compound 287 (8.6 g, 18.7 mmol, 56%). Chemoselective 1,2-reduction of the ketone in compound 287 may yield 288. Thus, compound 287 (14.7 g, 31.9 mmol) is dissolved in tetrahydrofuran (118 ml) and cerium (III) chloride heptahydrate (17.6 g, 47.2 mmol) in methanol (35 ml) is added. The mixture is cooled using an ice-bath and sodium borohydride (2.5 g, 66.1 mmol) is added slowly. The mixture is warmed to room temperature and then stirred for 2.5 hours. Aqueous 5% HCl (44 ml) is then slowly added to the mixture followed by ethyl acetate (588 ml). The reaction is washed with aqueous 5% HCl (120 ml) followed by saturated sodium bicarbonate (120 ml) then by saturated sodium chloride (120 ml). The organic layer is dried with $MgSO_4$, filtered and evaporated to dryness to yield the product 288 (14.8 g) which is used in the next reaction without further purification. Compound 288 (14.8 g) is then dissolved in pyridine (30 ml) and acetic anhydride (15 ml) and a catalytic amount of 4-dimethylaminopyridine (30 mg) is added. The mixture is stirred at room temperature for 16 hours and then diluted with ethyl acetate (300 ml). The organic mixture is washed with saturated sodium bicarbonate (2×60 ml) then by saturated sodium chloride (2×60 ml). The organic layer is dried with $MgSO_4$, filtered and evaporated to dryness to yield the crude product. Recrystallization from methanol gives compound 289 (12.6 g, 25.0 mmol, 78% yield over two steps). Hydroboration of compound 289 affords the 6α,7β-hydroxylation pattern. Thus, compound 289 (8.4 g, 16.6 mmol) is dissolved in dry THF (50 ml) and the mixture is cooled to 0° C. A solution of 1.0 M borane in THF (20 ml) is added and the mixture is stirred at 0° C. for 30 minutes and then at room temperature for 2.5 hours. An aqueous 10N NaOH solution (10 ml) is then added dropwise followed by 30% aqueous $H_2O_2$ (10 ml). The mixture is stirred at room temperature for 18 hours and then poured into saturated sodium chloride solution (200 ml). The aqueous slurry is extracted with methylene chloride (2×250 ml) and the combined organic layers are washed with aqueous 25% sodium thiosulphate solution (2×250 ml) and the organic layer is dried over $MgSO_4$. Filtration and evaporation of the filtrate gives a crude product which is purified by silica gel flash chromatography (3:1 hexane/ethyl acetate) to yield compound 221 (5.9 g, 12.3 mmol, 74%).

Scheme 76 illustrates the synthesis of compounds 326 and 327 from compound 221. Compound 221 (1.2 g, 2.4 mmol) is dissolved in acetic anhydride (3 ml) and pyridine (3 ml) and a catalytic amount of 4-dimethylaminopyridine (40 mg) is added. The mixture is stirred at room temperature for 3 hours then diluted with ethyl acetate (100 ml). The organic mixture is washed with aqueous 5% HCl then saturated sodium bicarbonate (100 ml) and saturated sodium chloride (100 ml). The organic layer is dried with $MgSO_4$, filtered and evaporated to dryness to yield the product 321 (1.3 g) which is used in the next reaction without further purification. Removal of the silyl protecting group using TBAF in THF gives compound 322 which contains the 3β-hydroxyl group. The crude product 321 is dissolved in THF (10 ml) and 1.0 M tetrabutylammonium fluoride (4 ml) is added. The mixture is refluxed for 1 hour, cooled to room temperature then poured into saturated sodium chloride solution (50 ml). The aqueous slurry is extracted with methylene chloride (5×40 ml) and the organic layer is dried over $MgSO_4$. Filtration and evaporation of the filtrate gives a crude product which is purified by silica gel flash chromatography (1:1 hexane/ethyl acetate) to yield compound 322 (0.85 g, 1.9 mmol, 76% yield over two steps). Inversion of the stereochemistry at C3 is then accomplished by oxidation using PDC in $CH_2Cl_2$ to give the ketone 323 followed by L-Selectride® reduction to yield predominantly the 3α-hydroxyl compound 324. Thus, compound 322 (0.84 g, 1.9 mmol) is dissolved in $CH_2Cl_2$ (15 ml) and PDC (1.2 g, 3.2 mmol) is added. The mixture is stirred for 40 hours at room temperature and then diluted with diethyl ether (50 ml). Filtration and evaporation to dryness gives the crude product which is purified by silica gel flash chromatography (9:1 hexanes/ethyl acetate) to yield compound 323 (0.81 g, 1.8 mmol, 95%). Compound 323 (0.34 g, 0.75 mmol) is then dissolved in THF (10 ml) and then cooled to −78° C. L-Selectride (1.0 M in THF, 1.6 ml) is added and the mixture is stirred at −78° C. for 1 hour. The mixture is warmed to room temperature and an aqueous 10N NaOH solution (1 ml) is then added dropwise followed by 30% aqueous $H_2O_2$ (1 ml). The mixture is stirred at room temperature for 1 hour and then poured into ethyl acetate (50 ml). The organic mixture is washed with aqueous 5% HCl (2×25 ml) then saturated sodium bicarbonate (2×25 ml) and saturated sodium chloride (2×25 ml). The organic layer is dried with $MgSO_4$, filtered and evaporated to dryness and purified using silica gel flash chromatography (3:1 hexane/ethyl acetate) to yield compound 324 (0.214 g, 0.48 mmol, 64%).

Removal of the acetate protecting groups may then be accomplished. Compound 324 (0.25 g, 0.56 mmol) is dissolved in methanol (10 ml) and sodium methoxide (250 mg) is added. The mixture is stirred at room temperature for 3 hours and then diluted with ethyl acetate (50 ml). The organic mixture is washed with aqueous 5% HCl (2×25 ml)

then saturated sodium bicarbonate (2×25 ml) and saturated sodium chloride (2×25 ml). The organic layer is dried with $MgSO_4$, filtered and evaporated to dryness and purified using silica gel flash chromatography (ethyl acetate) to yield compound 325 (0.185 g, 0.51 mmol, 91%). Compound 325 (141 mg, 0.385 mmol) is then dissolved in 80% acetic acid (10 ml) and stirred at 70° C. for 14 hours. The mixture is diluted with ethyl acetate (50 ml) and washed with saturated sodium bicarbonate (2×25 ml) and saturated sodium chloride (2×25 ml). The organic layer is dried with $MgSO_4$, filtered and evaporated to dryness and purified using silica gel flash chromatography (ethyl acetate) to yield compound 326 (0.054 g, 0.17 mmol, 44%). Finally, reduction of the ketone 326 (0.023 g, 0.072 mmol) by $NaBH_4$ (0.034 g) in 95% ethanol (1 ml) at room temperature for 2 hours produced the tetrahydroxy compound 327 (0.018 g, 0.056 mmol, 78%).

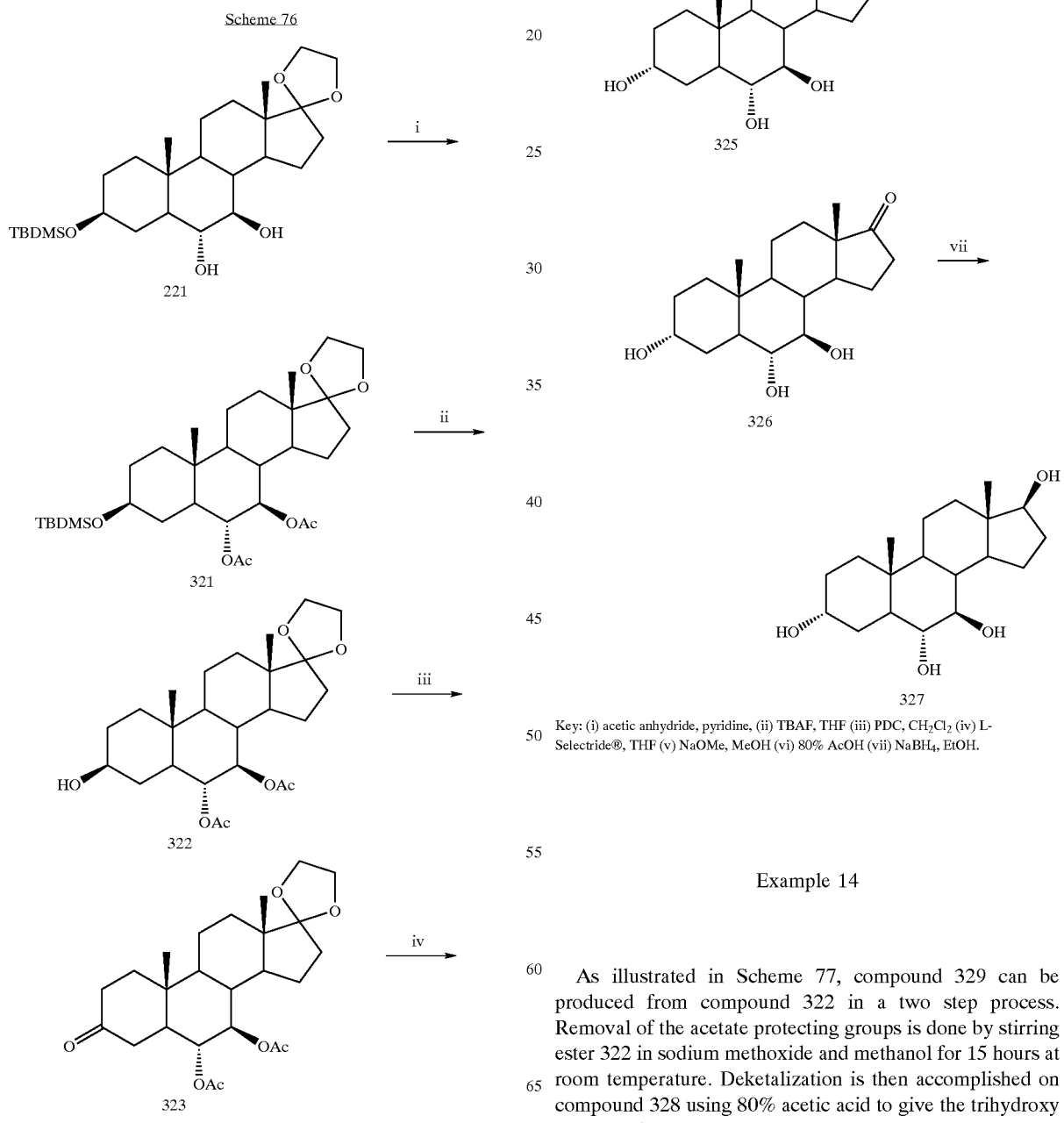

Key: (i) acetic anhydride, pyridine, (ii) TBAF, THF (iii) PDC, $CH_2Cl_2$ (iv) L-Selectride®, THF (v) NaOMe, MeOH (vi) 80% AcOH (vii) $NaBH_4$, EtOH.

Example 14

As illustrated in Scheme 77, compound 329 can be produced from compound 322 in a two step process. Removal of the acetate protecting groups is done by stirring ester 322 in sodium methoxide and methanol for 15 hours at room temperature. Deketalization is then accomplished on compound 328 using 80% acetic acid to give the trihydroxy compound 329.

Scheme 77

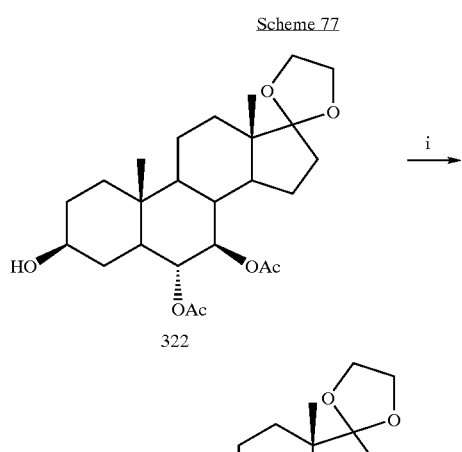

Key: (i) NaOMe, MeOH (ii) 80% AcOH

Example 15

Compound 329 can also be produced directly from compound 221 in a single step using 80% AcOH as shown in Scheme 78. Thus, ketal 221 (1.3 g, 2.7 mmol) is dissolved in 80% aqueous acetic acid (20 ml) and the mixture is stirred for 3 hours at room temperature. Evaporation to dryness provides compound 329 (0.79 g, 2.5 mmol, 93%) which is used in subsequent reactions without further purification.

Scheme 78

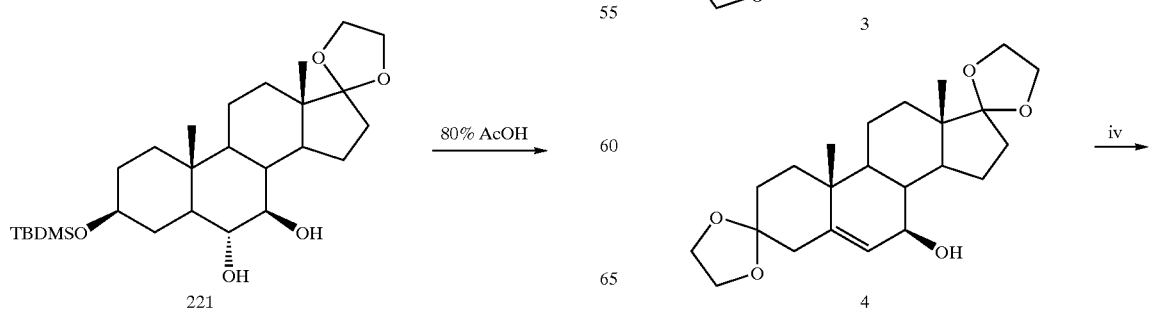

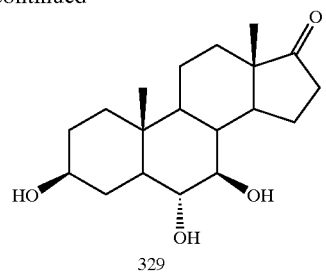

Example 16

The steroid 3α,6α,7β-trihydroxy-17(20)-pregnene (330) can be synthesized according to the reaction sequence shown in Scheme 79.

Scheme 79

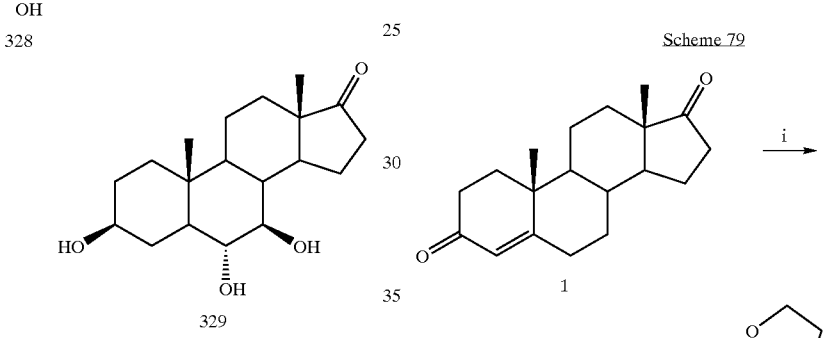

173
-continued
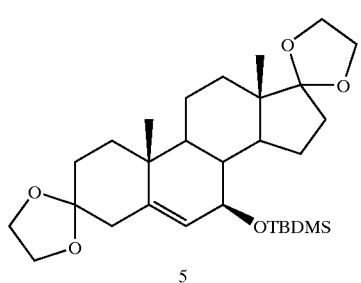
5
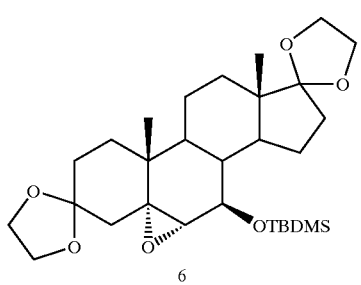
6
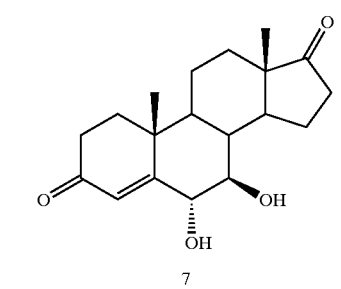
7
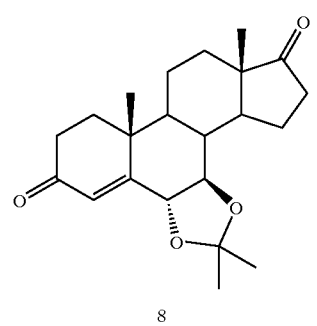
8
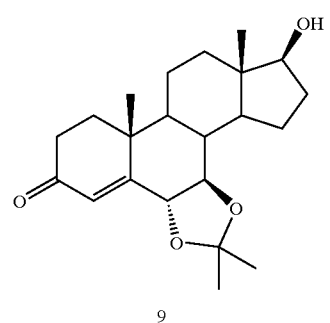
9
174
-continued
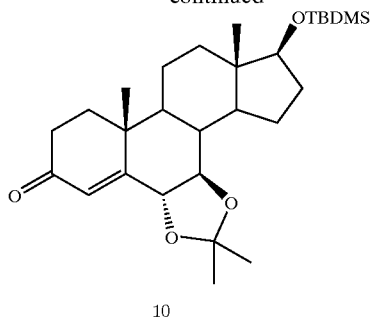
10
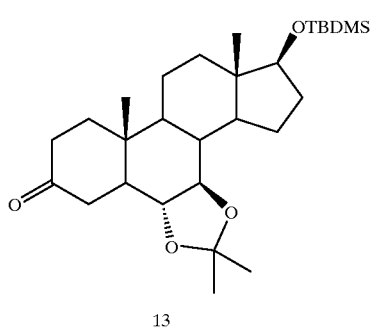
13
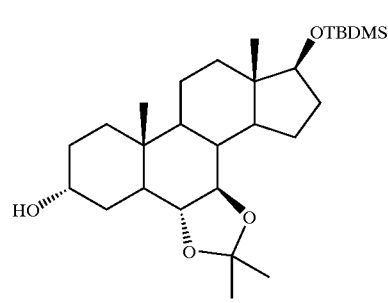
14
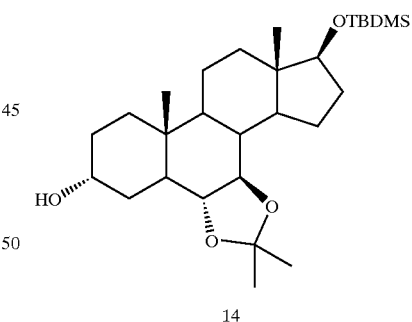
14
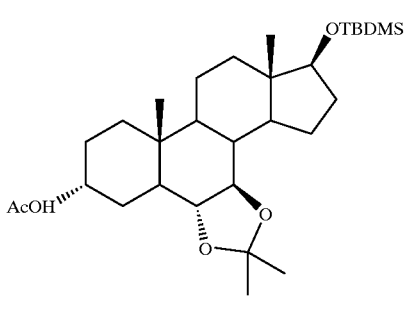
15

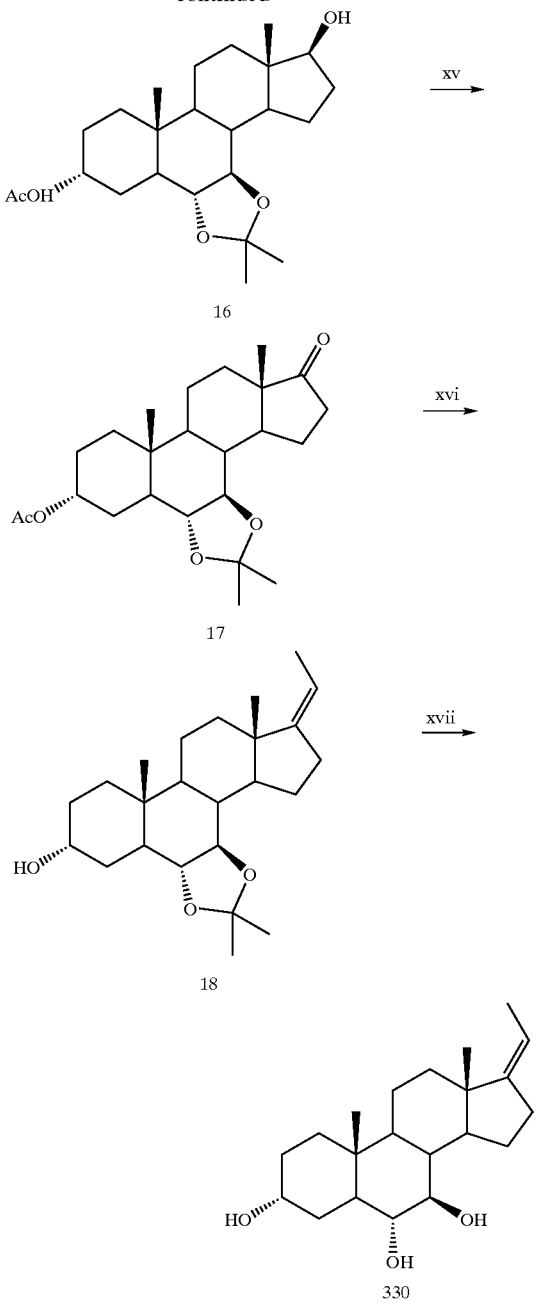

Key: (i) p-TsOH, (CH₂OH)₂, benzene (ii) CrO₃, 3,5-dimethylpyrazole, CH₂Cl₂ (iii) NaBH₄, CeCl₃, THF-MeOH (iv) TBDMSCl, imidazole, DMF (v) m-CPBA, CH₂Cl₂ (vi) 80% AcOH (vii) TBAF, THF (viii) 2,2-dimethyoxypropane, CSA, DMF (ix) NaBH₄, MeOH (x) TBDMSCl, imidazole, DMF (xi) 1. Li/NH₃, Et₂O 2. PDC, CH₂Cl₂ (xii) L-Selectride®, THF. (xiii) acetic anhydride, pyridine (xiv) TBAF, THF (xv) (COCl)₂, Et₃N, DMSO (xvi) EtPh₃PBr, t-BuOK, THF (xvii) 80% acetic acid.

Compound 330 can be produced from compound 10 (as shown in Scheme 79). A solution of compound 10 (0.82 g, 1.73 mmol) in diethyl ether (15 ml) is transferred to a flask containing lithium metal (55 mg) in liquid ammonia (30 ml) at −78° C. under argon. After 30 minutes at −78° C., NH₄Cl (2.0 g) is added and the ammonia is evaporated. Water (10 ml) is added and the layers are separated. The aqueous layer is extracted with CH₂Cl₂ (2×25 ml) and the combined organic layers are washed with water (25 ml) and dried over magnesium sulphate. After filtration and evaporation to dryness, the residue is dissolved in CH₂Cl₂ (15 ml) and PDC (600 mg, 1.59 mmol) is added. The mixture is stirred at room temperature for 18 hours then filtered through a bed of celite. The filtrate is then purified using silica gel flash chromatography (5:1 hexane/ethyl acetate) to give compound 13 (653 mg, 1.40 mmol, 81%).

The ketone 13 is then reduced by the following procedure. Compound 13 (1.2 g, 2.53 mmol) is dissolved in THF (30 ml) then the mixture is cooled to −78° C. and L-Selectride® (1.0M in THF, 3.8 ml) is added. The mixture is stirred at −78° C. for 2.5 hours and then warmed to 0° C. Aqueous 10% NaOH (10 ml) is added followed by 30% H₂O₂ (10 ml). After stirring for 2 hours, water (20 ml) is added and the aqueous slurry is extracted with CH₂Cl₂ (4×100 ml). The combined organic extracts are then washed with 10% Na₂S₂O₃ (2×100 ml) and saturated soldium chloride (2×100 ml). The organic layer is dried over magnesium sulphate, filtered and evaporated to dryness to yield the product 14 which is used in the next step without further purification. The 3α-hydroxyl group is then protected as the acetate using acetic anhydride and pryidine to give acetate 15. Thus, compound 14 is dissolved in pyridine (15 ml) and acetic anhydride (10 ml) and the mixture is stirred for 12 hours. Ethyl acetate and diethyl ether (1:1, 150 ml) are added and the mixture is washed with 5% HCl (2×50 ml) then by saturated sodium bicarbonate (2×50 ml). The organic layer is dried over magnesium sulphate, filtered and evaporated to dryness and the residue is purified by silica gel flash chromotography (10:1 hexane/ethyl acetate) to give compound 15 (0.89 g, 1.73 mmol, 68% over two steps). Removal of the silyl protecting group at C17 of compound 15 (0.85 g, 1.63 mmol) is accomplished by refluxing in THF (30 ml) and TBAF (1.0M in THF, 3.6 ml) for three hours followed by evaporation to dryness. The residue is then dissolved in CH₂Cl₂ (100 ml) and washed with H₂O (3×30 ml). The organic layer is dried over magnesium sulphate, filtered and evaporated to dryness and the residue is purified by silica gel flash chromatography (1:1 hexane/ethyl acetate) to give compound 16 (0.59 g, 1.45 mmol, 89%). Oxidation of the C17 hydroxyl in compound 16 is then accomplished using oxalyl chloride in DMSO. Thus, compound 16 (0.57 g, 1.40 mmol) is dissolved in CH₂Cl₂ (5 ml) and is added to a solution of oxalyl chloride (0.15 ml, 1.68 mmol) and DMSO (0.24 ml, 3.36 mmol) in CH₂Cl₂ (10 ml) at −78° C. After stirring at −78° C. for 15 minutes, triethylamine (0.98 ml) is added and stirring is continued for 5 minutes. The mixture is warmed to room temperature and H₂O (10 ml) is added. The layers are separated and the organic layer is washed with 5% HCl (2×5 ml) then by saturated sodium bicarbonate (2×5 ml). The organic layer is dried over magnesium sulphate, filtered and evaporated to dryness and the residue is purified by silica gel flash chromatography (2:1 hexane/ethyl acetate) to give compound 17 (0.54 g, 1.33 mmol, 95%).

A Wittig reaction on compound 17 using the phosphorous ylid prepared from ethyltriphenylphosphonium bromide and potassium t-butoxide in THF gives compound 18. Potassium t-butoxide (0.59 g, 5.23 mmol) is added under a stream of nitrogen to a suspension of ethyltriphenylphosphonium bromide (1.94 g, 5.23 mmol) in THF (15 ml) and the mixture is stirred at room temperature for 1 hour. Compound 17 (0.53 g, 1.31 mmol) is dissolved in THF (10 ml) and the solution is added to the ylid in THF. The resultant mixture is refluxed for 12 hours under nitrogen then cooled to room temperature. The mixture is filtered through celite and the filtrate is evaporated to dryness. The residue is dissolved in CH₂Cl₂ (100 ml) and washed with saturated NH₄Cl solution (2×30 ml) and H₂O (2×30 ml). The organic layer is dried over magnesium sulphate, filtered and evaporated to dryness and the residue is purified by silica gel flash chromatography (3:1 hexane/ethyl acetate) to give compound 18 (0.33 g, 0.88 mmol, 67%).

Finally, removal of the acetonide group is accomplished. Thus, compound 18 (20 mg, 0.053 mmol) is dissolved in 80% aqueous acetic acid (1.5 ml) and stirred at 60° C. for 1 hour. The mixture is evaporated to dryness to yield compound 330 (17.8 mg, 0.053 mmol, 99%).

Example 17

A number of compounds with important biological activities can be synthesized from compound 329. For example, compound 333, which contains the 3β,6α,7β-hydroxylation pattern and an ethylidene residue at C17, is prepared in three steps from compound 329 (Scheme 80). Thus, compound 329 (1.81 g, 5.6 mmol) is dissolved in 2,2-dimethoxypropane (25 ml) and a catalytic amount of camphor sulfonic acid (CSA) (0.03 g) is added and the mixture is stirred at room temperature for 3 hours. Ethyl acetate (200 ml) is added and the mixture is washed with 5% aqueous HCl (50 ml) then by saturated sodium bicarbonate (2×100 ml) and by saturated sodium chloride (2×100 ml). The organic layer is dried over magnesium sulphate, filtered and evaporated to dryness and the residue is purified by silica gel flash chromatography (1:1 hexane/ethyl acetate) to give compound 331 (1.54 g, 4.3 mmol, 76%). A Wittig reaction on compound 331 using the phosphorous ylid described in previous sections produces compound 332. Thus, potassium t-butoxide (7.15 g, 63.7 mmol) is added under a stream of nitrogen to a stirring solution of ethyltriphenylphosphonium bromide (23.7 g, 63.7 mmol) in toluene (360 ml). The mixture is then stirred for 1 hour at room temperature then compound 331 (7.7 g, 21.2 mmol) in toluene (210 ml) is added. The mixture is stirred at room temperature for 24 hours under nitrogen then quenched by the dropwise addition of water (120 ml). The mixture is diluted with ethyl acetate (900 ml) and washed with saturated sodium bicarbonate (2×200 ml) sodium chloride (2×200 ml). The organic layer is dried over magnesium sulphate, filtered and evaporated to dryness and the residue is purified by silica gel flash chromatography (2:1 hexane/ethyl acetate) to give compound 332 (7.2 g, 19.2 mmol, 90%). Deprotection of the hydroxyl groups in compound 332 is then achieved by stirring 332 in 80% acetic acid. Thus, compounds 332 (7.2 g, 19.2 mmol) is dissolved in 80% acetic acid (115 ml) and the mixture is stirred at room temperature for 3 hours. Evaporation to dryness followed by purification by silica gel flash chromatography (9:1 CH₂Cl₂/MeOH) gives compound 333 (5.81 g, 17.4 mmol, 90%).

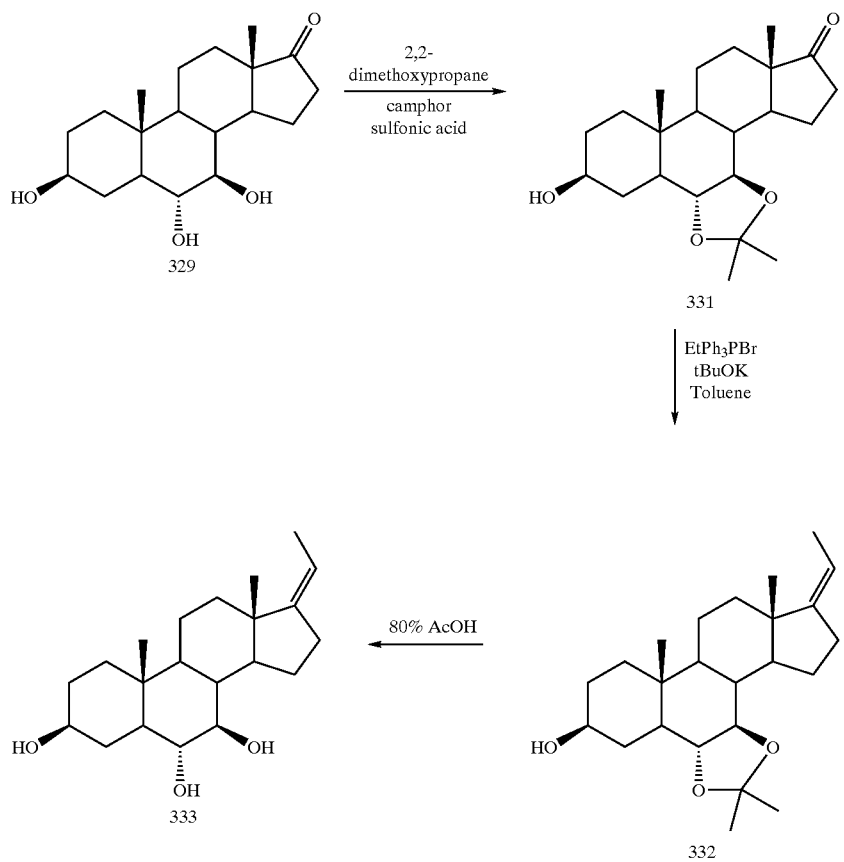

Example 18

Compounds containing a ketone at C3 and a 6,7-hydroxylation pattern can be obtained from compound 332. For example, oxidation of compound 332 using Swern conditions produces compound 334 which can then be deprotected to compound 335 (Scheme 81). Compound 332 (1.01 g, 2.70 mmol) is dissolved in CH$_2$Cl$_2$ (10 ml) and then added to a solution of DMSO (2.5 ml) and 2.0M oxalyl chloride in CH$_2$Cl$_2$ (8.1 ml) at −78° C. After stirring at −78° C. for 15 minutes, triethylamine (4.6 ml) is added and stirring is continued for 15 minutes followed by stirring at room temperature for 30 minutes. The mixture is diluted with ethyl acetate (100 ml) and washed with saturated sodium bicarbonate (2×50 ml) then saturated sodium chloride (2×50 ml). The organic layer is dried over magnesium sulphate, filtered and evaporated to dryness and the residue is purified by silica gel (pretreated with 1% triethylamine in hexanes) flash chromatography (19:1 hexane/ethyl acetate) to give compound 334 (0.77 g, 2.07 mmol, 77%). Deprotection of the hydroxyl groups in compound 334 is achieved, as in previous examples, by stirring the compound 334 (11 mg, 0.030 mmol) in 80% aqueous acetic acid (1.25 ml) at room temperature for 1 hour to give, after evaporation to dryness and purification by silica gel flash chromatography (ethyl acetate), compound 335 (9.8 mg, 0.029 mmol, 97%).

82. Thus, compound 336 (0.028 g, 0.072 mmol) is dissolved in 80% aqueous acetic acid (2 ml) and stirred at room temperature for 1 hour. The mixture is evaporated to dryness and the residue is purified by silica gel flash chromatography (3:2 hexane/ethyl acetate) to give compound 337 (0.024 g, 0.067 mmol, 94%).

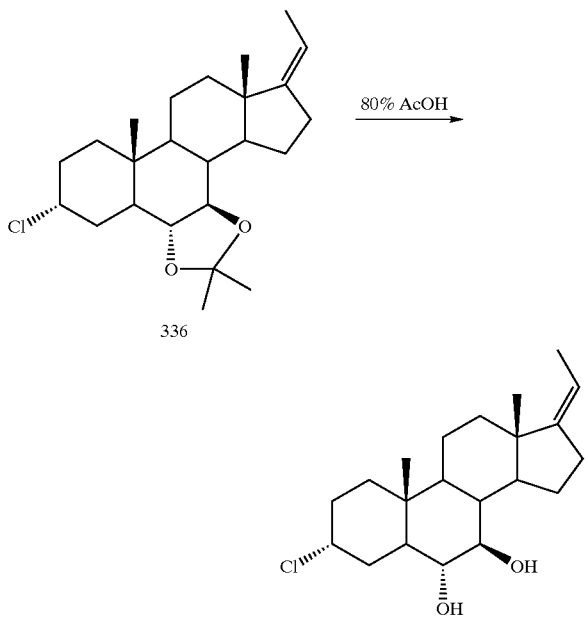

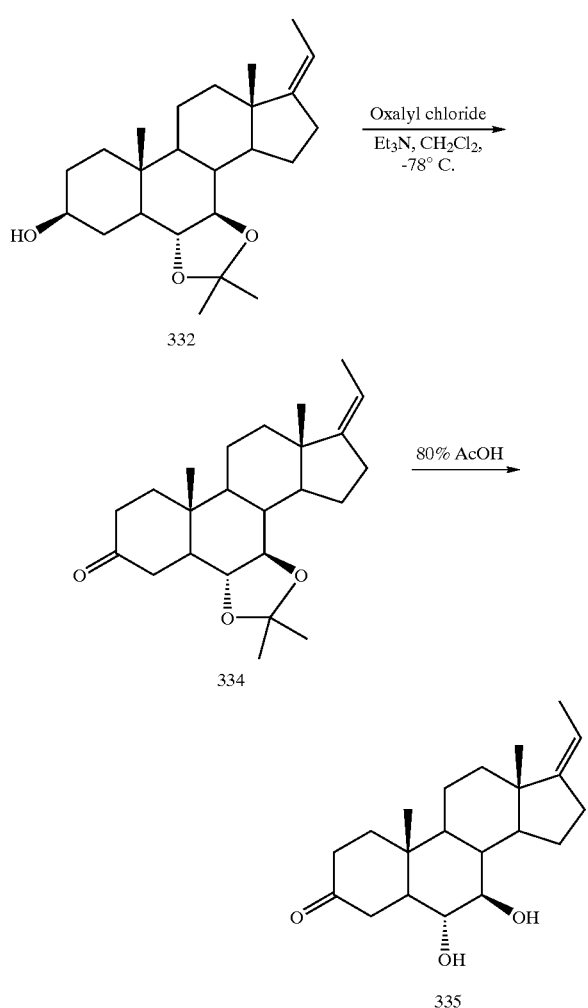

Example 19

A by-product of the Swern oxidation in Scheme 81 is the chloro derivative 336. Compound 336 can be deprotected by treatment with 80% aqueous acetic acid as shown in Scheme Example 20

As described in an earlier section, compound 330 can be prepared by reduction of the C3 carbonyl in compound 334 (e.g., with LS-Selectride®, Aldrich Chemical Co., Milwaukee, Wis.) to afford the 3a hydroxy group followed by deprotection. Thus, compound 334 (0.85 g, 2.3 mmol) is dissolved in THF (25 ml) and cooled to −78° C. LS-Selectride (1.0M in THF, 3.0 ml) is added and the mixture is stirred at −78° C. for 3 hours. Aqueous 10N NaOH (2 ml) and 30% H$_2$O$_2$ (2 ml) are added and the mixture is warmed to 0° C. The mixture is diluted with ethyl acetate (150 ml) and washed with saturated sodium bicarbonate (2×50 ml) then saturated sodium chloride (2×50 ml). The organic layer is dried over magnesium sulphate, filtered and evaporated to dryness and the residue is purified by silica flash chromatography (3:1 hexane/ethyl acetate) to give compound 338 (0.703 g, 1.88 mmol, 80%). Deprotection of the hydroxyl groups in the B-ring then affords compound 330 (Scheme 83). Thus, compound 338 (1.44 g, 3.85 mmol) is dissolved in 80% aqueous acetic acid (25 ml) and stirred at room temperature for 3 hours. The mixture is evaporated to dryness to give compound 330 (1.25 g, 3.74 mmol, 97%). This is an alternative route to compound 330 from what is shown in Scheme 79.

181

Scheme 83

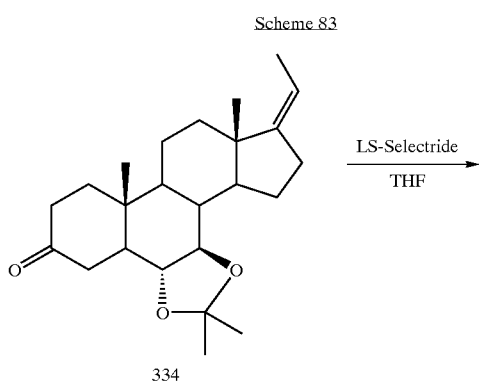

334

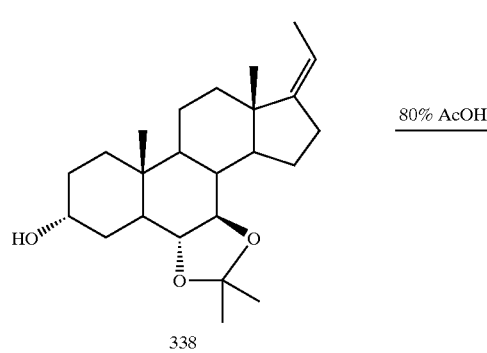

338

330

Example 21

Compounds containing an ethyl residue or another alkyl chain at C17 can be prepared from the corresponding compound containing an exocyclic double at C17. For example, compound 339 is obtained by catalytic hydrogenation of the C17–C20 double bond of compound 338, followed by the deprotection as shown below. Thus, compound 338 (0.15 g, 0.40 mmol) is dissolved 1:1 in acetic acid and ethanol (4 ml) and 10% Pd—C (15 mg) is added. The mixture is stirred under $H_2$ for 16 hours followed by filtration and evaporation to yield the desired product 339 (0.115 g, 0.340 mmol, 85%) (Scheme 84a). The intermediate 17-ethyl-6,7-acetonide 361 is produced if the hydrogenation reaction is carried out in ethyl acetate (Scheme 84b). Thus, compound 338 (0.019 g, 0.050 mmol) is dissolved in ethyl acetate (5 ml) and 10% Pd—C (9 mg) is added. The mixture is stirred under $H_2$ for 14 hours followed by filtration and evaporation to yield the desired product 361 (0.018 g, 0.048 mmol, 96%).

182

Likewise, compound 332 in acetic acid is hydrogenated using $H_2$ and 10% Pd—C to yield the product 340 (Scheme 85).

Scheme 84a

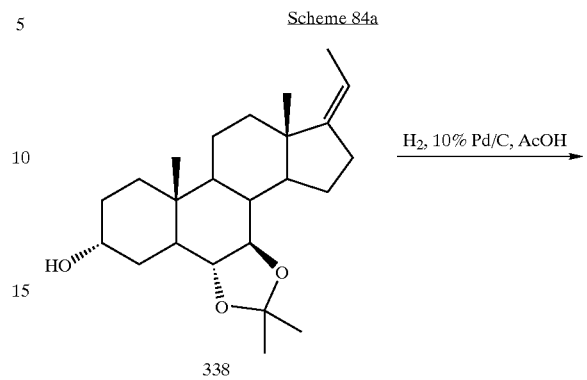

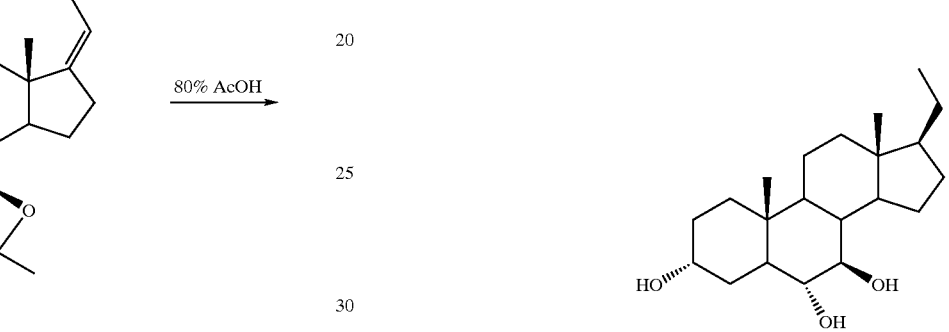

339

Scheme 84b

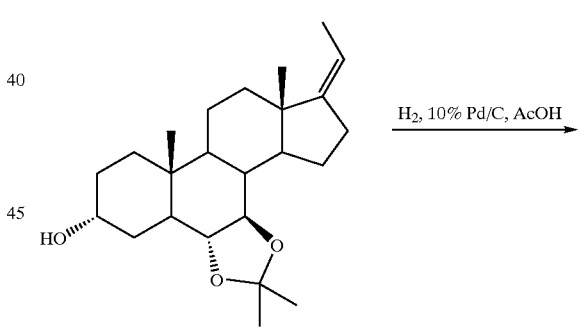

338

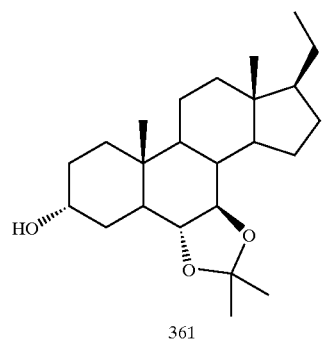

361

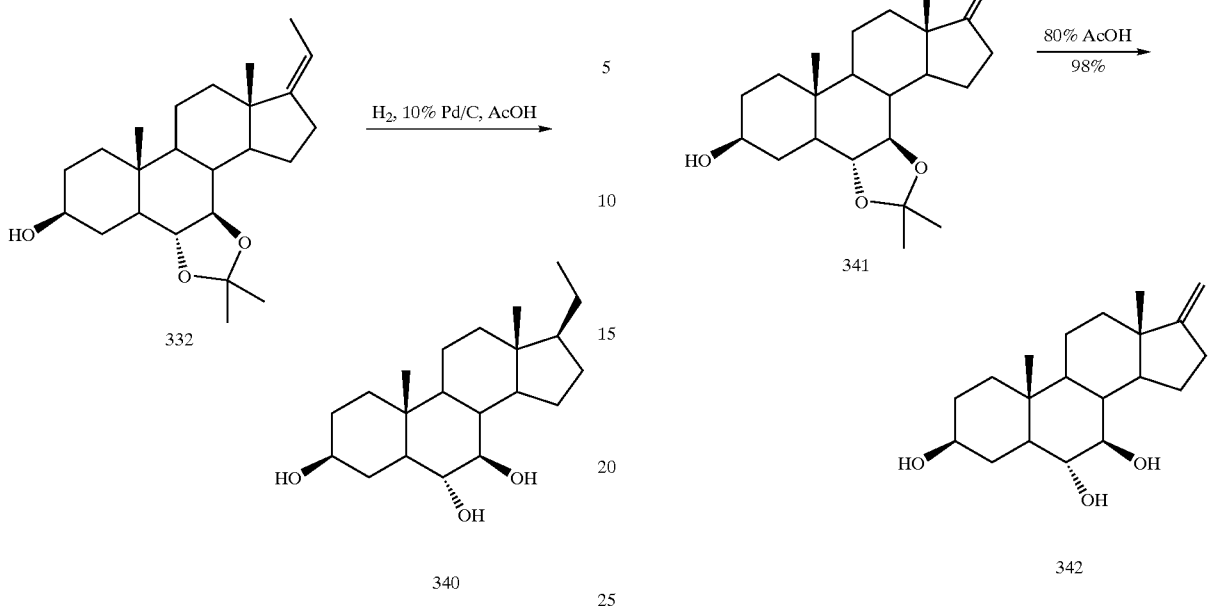

Example 22

Compounds with alternative alkyl groups at C17 can be prepared using different Wittig reagents. For example, compound 342 is easily obtained from a Wittig reaction, similar to the one described previously but using MePh$_3$PBr as the Wittig reagent rather than EtPh$_3$PBr followed by the deprotection of triol 341 as shown below (Scheme 86). Thus, methyltriphenylphosphonium bromide (1.97 g, 5.51 mmol) and tBuOK (0.61 g, 5.4 mmol) are stirred in THF (10 ml) for 1 hour. Ketone 331 (0.411 g, 1.14 mmol) in THF (5 ml) is added to the ylid and the mixture is refluxed for 3 hours. After standard work-up, as described earlier, the crude product is purified using silica gel flash chromatography (3:1 hexane/ethyl acetate) to give compound 341 (0.332 g, 0.920 mmol, 81%). Product 341 (0.204 g, 0.567 mmol) is then treated with 80% acetic acid solution (4 ml) for 1.5 hours at room temperature. The mixture is evaporated in vacuo to give the desired triol 342 (0.173 g, 0.540 mmol, 95%). The corresponding C17 methyl derivative is then prepared by hydrogenation of compound 341 (0.023 g, 0.063 mmol) and 10% Pd—C (15 mg) in ethyl acetate (5 ml) under H$_2$ atmosphere followed by, after filtration and evaporation to dryness, deprotection with 80% acetic acid solution (2.5 ml) to afford compound 343 (0.018 g, 0.056 mmol, 88%) (Scheme 87).

Example 23

Compounds containing a methylene carbon at C3 can be synthesized in a number of different ways. One example involves a modified Barton procedure (Robins et al., *J. Am. Chem. Soc.*, 105:4059–4065, 1983) as shown in Scheme 88. The alcohol 332 (0.10 g, 0.27 mmol) is treated with phenyl chlorothionoformate (0.45 ml, 3.3 mmol) in pyridine (2 ml) and methylene chloride (3 ml) at room temperature for 2 hours. The mixture is evaporated to dryness and the residue is purified by silica gel flash chromatography (30:1 hexane/ethyl acetate) to give the thionester 344 (0.12 g, 0.22 mmol, 84%). The ester 334 (0.091 g, 0.17 mmol) is then treated with nBu$_3$SnH (60 µl, 0.22 mmol) and a catalytic amount of AIBN (4 mg) in toluene (3 ml) at 75° C. for 3 hours under an inert atmosphere. The mixture is evaporated to dryness and compound 345 (0.035 g, 0.1 mmol, 57%) is obtained upon purification using silica gel flash chromatography (30:1 hexane/ethyl acetate). Treatment of compound 345 (0.025 g, 0.069 mmol) with 80% aqueous acetic acid (2 ml) for 1 hour at room temperature followed by evaporation to dryness and purification by silica gel flash chromatography (3:1 hexane/ethyl acetate) gives the diol 346 (0.021 g, 0.066 mmol, 96%).

with saturated sodium bicarbonate (2×15 ml) then by $H_2O$ (2×15 ml). The organic layer is dried over magnesium sulphate, filtered and evaporated to dryness and the residue is purified by silica flash chromatography (4:1 hexane/ethyl acetate) to give compound 348 (0.15 g, 0.31 mmol, 85%). Using a Barton type reaction, compound 348 is treated with NaH, $CS_2$ and MeI in THF to produce the methyl xanthate 349 after work-up and purification. Thus, compound 348 (0.052 g, 0.11 mmol) is dissolved in THF (5 ml) and NaH

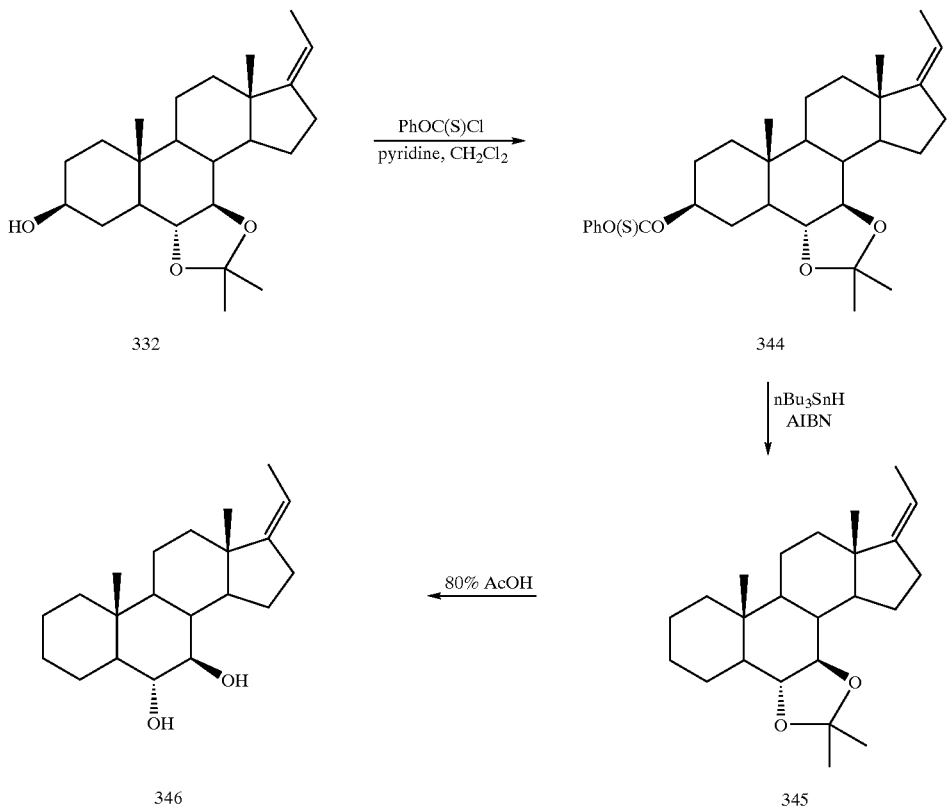

Scheme 88

Example 24

Compounds containing a methylene carbon at C17 can be produced using similar chemistry to that described in Example 23. For example, the alcohol group of compound 331 (0.15 g, 0.42 mmol) is initially protected as a silyl ether by treatment with t-butyldimethylsilyl chloride (0.095 g, 0.63 mmol) and imidazole (0.057 g, 0.84 mmol) in dimethylformamide (4 ml) at room temperature for 4 hours. The mixture is diluted with diethyl ether (75 ml) and washed with saturated sodium bicarbonate (2×25 ml) then $H_2O$ (2×25 ml). The organic layer is dried over magnesium sulphate, filtered and evaporated to dryness and the residue is purified by silica flash chromatography (9:1 hexane/ethyl acetate) to give compound 347 (0.18 g, 0.38 mmol, 90%) (Scheme 89). The ketone function of compound 347 is then reduced with lithium aluminum hydride in diethyl ether to afford the 17β-alcohol 348. Thus, compound 347 (0.18 g, 0.37 mmol) is dissolved in diethyl ether (5 ml), cooled to 0° C. and lithium aluminum hydride (0.018 g, 0.48 mmol) is added. The mixture is stirred at 0° C. for 30 minutes then saturated sodium bicarbonate (1 ml) is added dropwise. The mixture is diluted with diethyl ether (50 ml) and washed (17.4 mg (60% in oil), 0.43 mmol) and imidazole (5 mg, 0.074 mmol) are added. The mixture is stirred at room temperature for 30 minutes then carbon disulfide (0.2 ml) is added and stirring is continued for 2 hours followed by refluxing for 30 minutes. MeI (0.2 ml) is added and refluxing is continued for an addition 30 minutes. $H_2O$ (1 ml) is added dropwise and the mixture is diluted with diethyl ether (100 ml) and washed with 5% HCl (2×30 ml) then saturated sodium bicarbonate (2×30 ml) and then $H_2O$ (2×30 ml). The organic layer is dried over magnesium sulphate filtered and evaporated to dryness and the residue is purified by silica gel flash chromatography (15:1 hexane/ethyl acetate) to give compound 349 (0.054 g, 0.09 mmol, 85%). In the next reaction AIBN is typically used as the radical initiator. Thus, compound 349 (0.05 g, 0.087 mmol) is dissolved in toluene (15 ml) and $nBu_3SnH$ (0.051 g, 0.17 mmol) and a catalytic amount of AIBN (10 mg) are added and the mixture is refluxed for 22 hours under an inert atmosphere. The mixture is cooled to room temperature, evaporated to dryness and purified using silica flash chromatography (40:1 hexane/ethyl acetate) to give compound 350 (0.010 g, 0.022 mmol, 25%). Treatment of compound 350 (0.010 g, 0.022 mmol) with 80% acetic acid (2 ml) for 18 hours at room temperature followed by evaporation to dryness and purification using silica gel flash chromatography (20:1 CHCl₃/MeOH) gives compound 351 (0.0065 g, 0.021 mmol, 96%).

purified by silica gel flash chromatography with 9:1 hexanes-ethyl acetate giving alcohol 352 (0.850 g, 1.91 mmol, 76%). Protection and hydroboration are then accom-

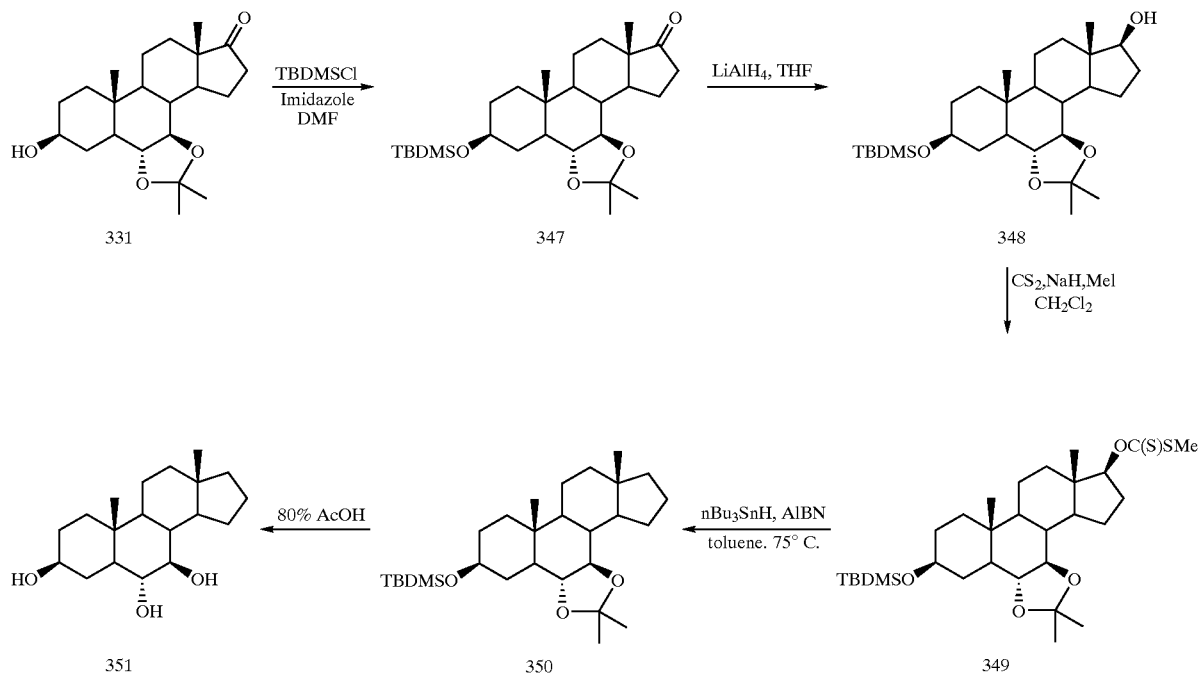

Scheme 89

Example 25

Compounds with higher alkyl chains attached to C17 can be produced sing similar chemistry to that described in previous examples. For example, compound 354 can be produced in 4 steps from commercially available cholesteryl acetate (228), as shown in Scheme 90. Methodology previously described involving C7 oxidation using RuCl₃ and tBuOOH followed by reduction of the C7 ketone using NaBH₄/CeCl₃ affords alcohol 352. Acetylation of compound 352 followed by hydroboration (and subsequent alkaline-peroxide workup) produces the desired compound 354.

Specifically, compound 228.(0.431 g, 1.01 mmol), RuCl₃ (0.020 g, 0.098 mmol), cyclohexane (5 mL), water (0.25 mL) and 70% tBuOOH in water (1.5 mL, 11.0 mmol) are stirred for 24 hours at room temperature. The mixture is diluted with ethyl acetate (125 ml) and washed with an aqueous solution of 10% Na₂SO₃ (2×50 ml) and saturated NaCl (2×50 ml). The organic layer is dried with MgSO₄ and evaporated to dryness. Purification by silica gel flash chromatography with 9:1 hexanes-ethyl acetate affords compound 229 (0.263 g, 0.591 mmol, 59%). The reduction of the C7 ketone proceeds as follows. A mixture of CeCl₃7H₂O (2.00 g, 5.368 mmol) in methanol (5 ml) is added to a solution of ketone 229 (1.11 g, 2.52 mmol) in THF (5 ml) and the mixture is cooled to 0° C. NaBH₄ (0.119 g, 5.14 mmol) is added and the mixture stirred at 0° C. for 1 hour followed by warming to room temperature and continued stirring for 2 hours. The mixture is cautiously quenched with aqueous 5% HCl (10 ml) and diluted with ethyl acetate (250 ml). The emulsion is then washed with aqueous 5% HCl (2×100 ml), saturated aqueous NaHCO₃ (2×100 ml), and saturated aqueous NaCl (2×100 ml). The organic phase is dried with MgSO₄ and evaporated to dryness. The residue is plished. Thus, compound 352 (0.850 g, 1.91 mmol), pyridine (5 ml) and acetic anhydride (5 mL) are stirred at room temperature for 16 hours. The mixture is diluted with ethyl acetate (150 ml) and washed with aqueous 5% HCl (3×50 ml), saturated aqueous NaHCO₃ (2×50 ml), and saturated aqueous NaCl (2×50 ml). The organic phase is dried with MgSO₄ and evaporated to dryness. The residue is purified by silica gel flash chromatography with 19:1 hexanes-ethyl acetate giving product 353 (0.823 g, 1.70 mmol, 99%). The diacetate 353 (0.275 g, 0.5648 mmol) in THF (5 ml) is cooled to 0° C. and BH₃ in THF (1.0 M, 2.5 mL, 2.5 mmol) is added. The mixture is stirred for 3 hours at 0° C., then cautiously quenched with an aqueous 10 N NaOH solution (1 mL) and an aqueous 30% H₂O₂ (1 ml) solution. The resultant mixture is stirred for 16 hours, diluted with ethyl acetate (100 ml) and washed with an aqueous 10% Na₂SO₃ solution (2×50 ml), a saturated aqueous NaHCO₃ solution (2×50 ml) and saturated NaCl solution (2×50 ml). The organic phase is dried over MgSO₄ and evaporated to dryness. Purification by silica gel flash chromatography (3:1 hexanes-ethyl acetate) affords the product 3β-acetoxy-6α, 7β-dihydroxy-5α-cholestane (0.032 g, 0.069 mmol, 13%) which is deprotected by treatment with sodium methoxide (prepared from sodium metal (0.262 g, 11.4 mmol) and methanol (10 ml)) at room temperature for. 1.5 hours. The mixture is diluted with ethyl acetate (30 ml) and then washed with a saturated aqueous NaHCO₃ solution (2×15 ml) and saturated aqueous NaCl solution (2×15 ml). The organic layer is dried with MgSO₄ and evaporated to dryness. The residue is purified by silica gel flash chromatography with 1:1 hexanes-ethyl acetate giving triol 354 (0.029 g, 0.069 mmol, 99%).

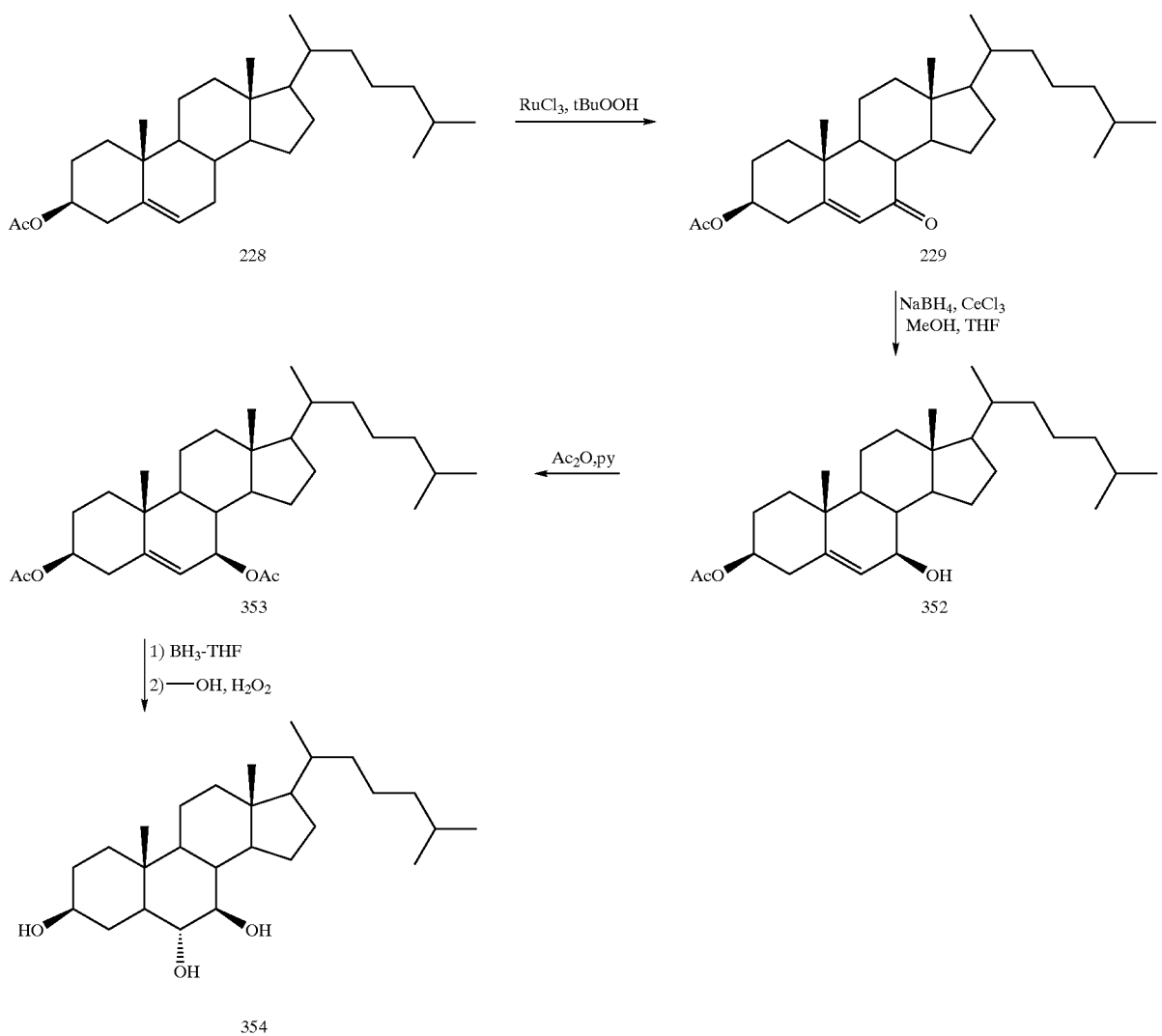

Shceme 90

Example 26

Compounds containing additional functional groups in the A-ring have been prepared and tested for biological activity. For example, compound 360 can be prepared in a multi-step synthesis from compound 335, as illustrated in Scheme 91. Acetylation of compound 335 using acetic anhydride and pyridine and DMAP to give 10 the diacetoxy compound 355. Thus, compound 335 (1.5 g, 4.5 mmol) pyridine (10 ml), acetic anhydride (5 mL) and 4-dimethylaminopyridine (0.028 g, 0.23 mmol) are stirred at room temperature for 12 hours. The mixture is diluted with ethyl acetate (300 ml) and washed with aqueous 5% HCl (3×50 ml), saturated aqueous NaHCO$_3$ (3×50 ml), and H$_2$O (3×50 ml). The organic phase is dried with MgSO$_4$ and evaporated to dryness to yield a crude residue 355 (1.9 g) which is used in the next reaction without further purification. Thus, crude product 355 (0.800 g, 1.9 mmol) is dissolved in AcOH and 10% Pd—C (80 mg) is added. The mixture is then stirred under H$_2$ atmosphere for 16 hours at room temperature. The mixture is filtered and evaporated to dryness to yield a crude residue which is purified by silica gel flash chromatography (5:1 hexane/ethyl acetate) to give compound 356 (0.702 g, 1.67 mmol, 88%). The oxime 357 is then obtained by refluxing compound 356 with HONH$_2$-HCl in a MeOH-pyridine solution. Thus, compound 356 (0.05 g, 0.12 mmol) is dissolved in a mixture of pyridine (2 ml) and methanol (2 ml) and HONH$_2$-HCl (0.017 g, 0.24 mmol) is added. The mixture is refluxed for 1.5 hours and the mixture is diluted with ethyl acetate (50 ml) and washed with 5% HCl (3×15 ml) then by saturated sodium bicarbonate (3×15 ml) and then H$_2$O (3×15 ml). The organic layer is dried over magnesium sulphate, filtered and evaporated to dryness to yield compound 357 (0.052 g, 0.12 mmol, 99%) which is used in the next reaction without further purification. Product 357 (0.071 g, 0.16 mmol) is then dissolved in pyridine (13 mg) in acetic anhydride (3 ml), cooled to 0° C. and acetyl chloride (15.5 mg, 0.20 mmol) is added. The mixture is then heated for 8 hours at 100° C. H$_2$O (0.5 ml) is added and heating is continued for 30 minutes. The mixture is then cooled to room temperature, diluted with H$_2$O (10 ml), and extracted with CH$_2$Cl$_2$ (3×15 ml). The combined organic extracts are then washed with H$_2$O (2×10 ml). The organic layer is dried over magnesium sulphate, filtered and evaporated to dryness and the residue is purified by silica gel flash chromatography (2:1 hexane/ethyl acetate)

to give compound 358 (0.41 g, 0.086 mmol, 52%). The C3 ketone in 358 (0.020 g, 0.042 mmol) is then reduced with NaBH$_4$ (2.4 mg) in THF (2 ml) at room temperature for 1 hour. AcOH (2 drops) is added and the mixture is diluted with ethyl acetate (50 ml) and washed with saturated sodium bicarbonate (2×15 ml) then H$_2$O (2×50 ml). The organic layer is dried over magnesium sulphate, filtered and evaporated to dryness and the crude product 359 is dissolved in methanol (1.5 ml). NaOMe (10 mg) is added and the mixture is stirred at room temperature for 48 hours. Amberlite IR-120 ion exchange resin is added until pH 6. The mixture is filtered and evaporated to dryness and purified by silica gel flash chromatography (10:1 CHCl$_3$/MeOH) to give compound 360 (0.010 g, 0.028 mmol, 67% over two steps).

and the formation of blood clots that cause thrombosis and associated diseases. An effective amount of a compound or composition of the present invention is used to treat allergy, asthma, arthritis or thrombosis in a warm-blooded animal, such as a human. Methods of administering effective amounts of anti-allergy, anti-asthma, anti-arthritis and anti-thrombotic agents are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices. Generally, oral or intravenous administration is preferred for the treatment of arthritis and

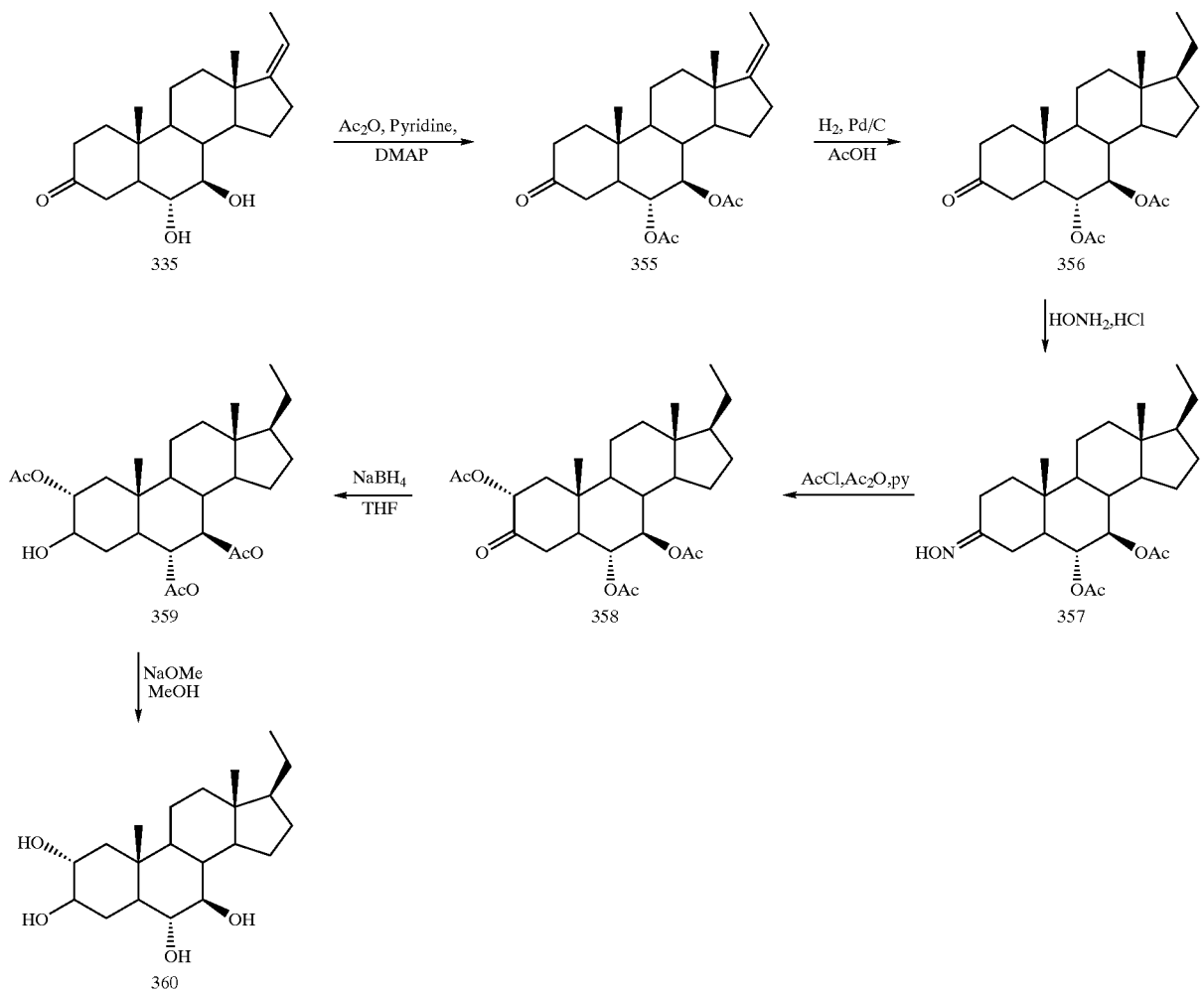

Scheme 91

The following examples are offered by way of illustration and not by way of limitation.

Utility Examples

The compounds described above have utility in treating allergy and asthma, arthritis and/or thrombosis. As used herein, "treating allergy and asthma, arthritis and/or thrombosis" refers to both therapy for allergy and asthma, arthritis and thrombosis, and for the prevention of the development of the allergic response, bronchoconstriction, inflammation thrombosis, while oral or inhalation/intranasal are preferred for asthma and allergy. The dosage amount and frequency are selected to create an effective level of the agent without harmful effects. It will generally range from a dosage of about 0.01 to 100 mg/kg/day, and typically from about 0.1 to 10 mg/Kg/day where administered orally or intravenously, for anti-allergy, anti-asthma, anti-arthritis or anti-thrombotic effects. Also, the dosage range will be typically from about 0.01 to 1 mg/Kg/day where administered intranasally or by inhalation for anti-asthma and anti-allergy effects.

Administration of compounds or compositions of the present invention may be carried out in combination with the administration of other agents. For example, it may be desired to administer a bronchodilator or a glucocorticoid agent for effects on asthma, a glucocorticoid for effects on arthritis, or an anti-histamine for effects on allergy. Non-steroid compounds may be co-administered with the steroids of the present invention, and/or non-steroid compounds may used in combination with the steroid compounds of the invention to provide a therapy for one or more of asthma, allergies, arthritis and thrombosis.

For example, provided below are several examples of the biological activity of various compounds described in Synthesis Examples, Sections 1–5.

Anti-thrombolytic Activity of Polyhydroxylated Steroids

Within the present invention, it was discovered that the polyhydroxylated steroids as well as intermediates described in previous sections inhibited the aggregation of platelets caused by platelet activating factor (PAF). PAF is a local mediator of thrombosis and prevention of the formation of blood clots has direct implication in the treatment of thrombosis and associated cardiovascular diseases. The assay system used to evaluate the ability of compounds to inhibit the aggregation of platelets in response to exogenous stimuli is indicative of anti-thrombotic or thrombolytic activity.

Platelets were isolated from rabbit blood and prepared at a density of 2.4×108 cells/ml in Tyrodes buffer (pH 7.2) containing $Ca^{2+}$. Platelets were incubated with each compound for 5 min at 37° C. prior to stimulation. Platelets were stimulated with 1 nM platelet activating factor (PAF; $EC_{75}$) in the presence of each of the compounds and aggregation was monitored for 5 min. Compounds were solubilized in dimethylsulfoxide (DMSO) and aggregation was measured as a percentage of the response to 1 nM PAF obtained in the presence of the appropriate concentration of DMSO. The degree of inhibition caused by each sample was calculated using the control response in the presence of DMSO equal to 100%.

Table 1 shows examples of some of the compounds that inhibit platelet aggregation in response to PAF.

TABLE 1

THE EFFECT OF VARIOUS COMPOUNDS ON THE AGGREGATION OF RABBIT PLATELETS STIMULATED WITH 0.1 NM PAF*

| Sample Number | % Inhibition at 80 µM |
|---|---|
| 7 | 12.3 |
| 8 | 11.6 |
| 165 | 51.2 |
| 236 | 100 |
| 241 | 93.1 |
| 246 | 21 |
| 330 | 20.9 |

*Platelets were incubated with 80 µM of each compound for 5 minutes prior to stimulation. Responses were measured as a percentage of the inhibition of the PAF-induced response obtained in the presence of the appropriate concentration of DMSO alone.

Effects of Compounds on the Release of Hexosaminidase From a Rat Mast Cell Line (RBL-2H3)

The anti-allergic effects of various polyhydroxylated steroids of the present invention were evaluated by measuring their effect on antigen-induced secretion of hexosaminidase from a passively sensitized rat mast cell line (RBL-2H3) and a murine mast cell line (MC/9). The ability of agents to inhibit the release of mast cell granule contents, e.g., histamine and hexosaminidase, is indicative of anti-allergy and/or anti-asthma activity.

Hexosaminidase is released from the mast cell granule along with histamine and other mediators during antigen challenge. RBL-2H3 and MC/9 cells were grown in culture and passively sensitized to dinitrophenol (DNP) using anti-human-DNP (IgE). Cells were incubated with each compound (25 µM) for 1 hour at 37° C. and then stimulated with 0.1 mg/ml DNP-HSA (antigen) for 15 min. Aliquots of the supernatant were removed and used to measure the amount of hexosaminidase released during challenge with the antigen. The amount of hexosaminidase present in the supernatant was determined colorimetrically by monitoring the enzymatic metabolism of p-nitrophenyl-N-acetyl-β-D-glucosaminide (p-NAG) over a period of 1 hour at 410 nm. The effect of each compound was determined as a percentage of the antigen-induced response (minus background release) obtained in the presence of DMSO alone, as set forth in Tables 2 and 3. These values were used to determine the degrees of inhibition of antigen-induced hexosaminidase release from the cells.

TABLE 2

THE EFFECT OF VARIOUS COMPOUNDS (EACH 25 µM) ON ANTIGEN-INDUCED RELEASE OF HEXOSAMINIDASE FROM PASSIVELY SENSITIZED RAT MAST CELLS (RBL-2H3) AND MOUSE MAST CELLS (MC/9)*

| | Percentage Inhibition (mean) | |
|---|---|---|
| Compound Number | RBL-2H3 Cells | MC/9 cells |
| 333 | 69 | 71 |
| 335 | 56 | 69 |
| 339 | 79 | 67 |
| 337 | 44 | 56 |
| 339 | 76 | 55 |
| 330 | 59 | 49 |
| 343 | 52 | 40 |
| 342 | 57 | 39 |
| 361 | ND | 13 |
| 331 | ND | 5 |
| 354 | 30 | 76 |
| 346 | 16 | 61 |

ND = not determined.

TABLE 3

THE EFFECT OF VARIOUS COMPOUNDS (EACH 25 µM) ON ANTIGEN-INDUCED RELEASE OF HEXOSAMINIDASE FROM PASSIVELY SENSITIZED RAT MAST CELLS (RBL-2H3)*

| | Percentage Inhibition (mean) RBL-2H3 Cells |
|---|---|
| 7 | 21.7 |
| 165 | 51.8 |
| 236 | 31 |
| 241 | 22 |
| 246 | 29.4 |
| 306 | 40.5 |
| 322 | 25.6 |
| 327 | 35.2 |
| 328 | 34.3 |
| 266 | −12.5 |
| 239 | 9.6 |
| 351 | 33.6 |
| 360 | 76.0 |

*Values represent the percentage inhibition produced by each compound compared to the response obtained in the presence of DMSO alone.

Effects of Selected Compounds on Allergen-induced Contraction of Ileum Smooth Muscle The ability of compounds to inhibit allergen-induced contraction of ileum from sensitized animals is indicative of antiallergic activity. Sensitized guinea pig ileum is particularly useful in measuring the immediate allergic response.

The guinea pig ileum has been used to evaluate the ability of compounds to inhibited allergen-induced histamine and mediator release causing smooth muscle contraction. Guinea pigs were sensitized by an intraperitoneal injection of 100 mg ovalbumin and an intramuscular injection of 50 mg ovalbumin on day 0, followed by a second intramuscular injection of 50 mg ovalbumin on day 1. Twenty one days after the initial immunization, the animals were found to be sensitized, in that an anaphylactic responce was obtained upon challenge with allergen. Segments of ileum were prepared and suspended, with muscle contractions being measured in the longitudinal plane, in Tyrode's buffer at 37° C. and aerated with 5% $CO_2$ in $O_2$. Tissues were suspended under a resting tension of 2 grams and isometric contractions were measured using force-displacement transducers coupled to a polygraph. Tissues were stimulated with 3 $\mu$M histamine 3 times to ensure reproducible contractions were obtained. Tissues were then incubated with each compound (30 $\mu$M) or 0.15% dimethylsulphoxide (DMSO) as a control, for 20 min, after which time the tissues were challenged with 100 $\mu$g/ml ovalbumin. The magnitude of the contraction induced by OA in the presence of each compound was expressed as a percentage of the contraction obtained to 3 $\mu$M histamine. The protective effects of the various compounds on OA-induced contraction of guinea pig ileum from sensitized animals are summarized in Table 4.

TABLE 4

THE EFFECT OF VARIOUS COMPOUNDS (EACH 30 $\mu$M) ON ANTIGEN-INDUCED CONTRACTION OF ILEUM FROM SENSITIZED GUINEA PIGS. ANTIGEN-INDUCED CONTRACTIONS WERE EXPRESSED AS A PERCENTAGE OF THE CONTRACTION INDUCED BY 3 $\mu$M HISTAMINE*.

| Compound Number | Percentage Inhibition |
| --- | --- |
| 330 | 70.0 |
| 221 | 60.7 |
| 338 | 64.0 |
| 7 | 54.0 |
| 333 | 63.0 |
| 343 | 48.9 |
| 336 | 79.3 |
| 342 | 28.3 |
| 339 | 40.6 |
| 335 | 30.7 |
| 337 | 50.7 |
| 165 | 27.0 |
| 251 | −10.5 (stim) |
| 361 | 55.0 |
| 331 | 14.5 |
| 339 | 36.3 |
| 346 | 62.5 |
| 334 | 74.0 |

TABLE 4-continued

THE EFFECT OF VARIOUS COMPOUNDS (EACH 30 $\mu$M) ON ANTIGEN-INDUCED CONTRACTION OF ILEUM FROM SENSITIZED GUINEA PIGS. ANTIGEN-INDUCED CONTRACTIONS WERE EXPRESSED AS A PERCENTAGE OF THE CONTRACTION INDUCED BY 3 $\mu$M HISTAMINE*.

| Compound Number | Percentage Inhibition |
| --- | --- |
| 266 | 17.4 |
| 351 | 43.6 |
| 360 | 50.5 |

*Values represent the mean percentage inhibition produced by each compound compared to the response obtained in the presence of DMSO alone, n = 3–4.

Effects of Selected Compounds on Allergen-induced Bronchoconstriction In Vitro and In Vivo The effects of a number of the compounds described herein on allergen-induced bronchoconstriction were evaluated for anti-asthma activity. The ability of a compound to inhibit allergen-induced decreases in lung function in sensitized guinea pigs in response to antigen-challenge is indicative of anti-asthma activity. In particular, the model system is useful in the evaluation of the potential effects of a compound in the treatment of the early asthmatic reaction (EAR) when severe bronchoconstriction occurs.

Guinea pigs were exposed to a nebulized solution of 1% ovalbumin (OA) in saline for 15 min. After 10 days the animals were found to be sensitized, i.e., the tracheal tissue responded with anaphylactic bronchospasm to further antigen (OA) challenge. Trachea from these animals were found to respond in a similar manner to the in vivo situation. Tracheal rings were prepared and bathed in Krebs-Henseleit solution at 37° C. and aerated with 5% $CO_2$ in $O_2$. Tissues were suspended under a resting tension of 2 g and isometric contractions were measured using force-displacement transducers coupled to a polygraph. Tissues were incubated with each compound or 0.1% dimethylsulfoxide (as a control) for 20 min, after which increasing concentrations of OA (0.001–100 $\mu$g/ml) were added to the tissue. After the final concentration of OA was added and the response was recorded, the tissues were stimulated with 100 $\mu$M methacholine which caused maximum contraction of the trachea. The magnitude of the contraction induced by OA in the presence of each compound was expressed as a percentage of the maximum contraction obtained using methacholine (100 $\mu$M). The protective effects of various compounds on OA-induced contraction of tracheal tissue are summarized in Tables 5–7.

TABLE 5

EFFECTS OF SELECTED COMPOUNDS (EACH 20 $\mu$M) ON ALLERGEN-INDUCED CONTRACTIONS OF ISOLATED TRACHEA* (STUDY 1)

| | $\mu$g/ml OA | | | | | | | | | |
| --- | --- | --- | --- | --- | --- | --- | --- | --- | --- | --- |
| | 0.001 | 0.003 | 0.01 | 0.03 | 0.1 | 0.3 | 1.0 | 3.0 | 10.0 | 30.0 |
| Ctrl | 2.9 | 7.7 | 11.4 | 17.4 | 19.7 | 26.4 | 30.9 | 37.2 | 43.6 | 46.8 |
| 241 | 8.5 | 12.6 | 17.1 | 25.8 | 31.0 | 33.4 | 36.3 | 34.4 | 35.0 | 37.0 |
| 236 | 1.9 | 5.6 | 5.6 | 5.6 | 11.1 | 16.7 | 39 | 28 | 39 | 41 |
| 145 | 0.8 | 6.2 | 5.9 | 7.6 | 8.3 | 13.6 | 14.8 | 20.0 | 28.0 | 31.0 |
| 246 | 2.6 | 4.0 | 6.5 | 9.7 | 12.2 | 15.3 | 20.0 | 21.0 | 23.0 | 22.0 |

*Values represent percentage contraction compared to that obtained with 100 $\mu$M methacholine (100%), Ctrl = control (0.1% DMSO)

TABLE 6

EFFECTS OF VARIOUS COMPOUNDS (EACH 20 μM) ON ALLERGEN-INDUCED CONTRACTIONS OF ISOLATED TRACHEA* (STUDY 2)

| | OA μg/ml | | | | |
|---|---|---|---|---|---|
| Sample | 0.01 | 0.1 | 1 | 10 | 100 |
| Ctrl | 0.95 | 9.0 | 25.7 | 44.7 | 54.6 |
| 326 | 0 | 10.25 | 23.4 | 43.9 | 49.1 |
| 327 | 0 | 0 | 9.1 | 27.3 | 40.9 |

*Values represent percentage contraction compared to that obtained with 100 μM methacholine (100%), Ctrl = control (0.1% DMSO).

TABLE 7

EFFECTS OF COMPOUND 330 (EACH 30 μM) ON ALLERGEN-INDUCED CONTRACTIONS OF ISOLATED TRACHEA* (STUDY 3)

| | OA μg/ml | | | | | |
|---|---|---|---|---|---|---|
| Sample | 0.001 | 0.01 | 0.1 | 1 | 10 | 100 |
| Ctrl | 6.0 | 12.0 | 26.0 | 41.0 | 54.0 | 59.0 |
| 330 | 0 | 1.90 | 9.00 | 17.5 | 26.0 | 30.0 |

*Values represent percentage contraction compared to that obtained with 100 μM methacholine (100%), Ctrl = control (0.1% DMSO).

In addition, the effect of compounds of the invention on lung function in vivo was determined in sensitized animals as follows:

Female Cam Hartley guinea pigs (350–400 g) are sensitized to ovalbumin by exposure of the guinea pigs to a nebulized solution of 1% ovalbumin in saline for 15 minutes. After 10–12 days, the animals are found to be acutely sensitized to the allergen (ovalbumin). Animals are treated by oral gavage, under light halothane anesthesia, with 300 μl polyethyleneglycol-200 (PEG) or 5 mg/Kg of test compound in 300 μl of PEG. Animals are treated once daily for 4 days with the final dose administered 2 hours prior to allergen challenge. Alternatively, compounds were delivered by inhalation, using a Hudson nebulizer driven by 6 psi oxygen, providing a single dose of 50 μg/Kg 20 min prior to challenge.

An animal is anaesthetized using ketamine (50 mg/ml; i.p.) and xylazine (10 mg/Kg; i.p.) and 1% halothane during the surgical procedure. A tracheostomy is performed and a water-filled esophageal cannula is inserted prior to positioning the animal in a body plethysmograph. The tracheal cannula is attached to a fixed tracheal cannula in the plethysmograph. Cardiac function is monitored using electrocardiography. The animal is paralyzed using pancuronium bromide (0.8 mg/Kg; i.m.) and ventilated with 3 ml tidal breaths using a Harvard small animal ventilator, at a frequency of 60 breaths per minute. Pulmonary resistance and dynamic lung compliance data are obtained from volume, flow and transpulmonary pressure signals using multipoint analysis.

Pulmonary function is continually monitored throughout the experiment and measurements of lung resistance and lung compliance are made at various time-points (e.g., 0, 1, 2, 3, 4, 5, 10, 20 and 30 min) following antigen challenge. Data is collected on a computer-linked physiological measurement system using DIREC Physiological recording software and analyzed using ANADAT software designed for lung mechanics measurements. This software was obtained from RHT-InfoDat Inc., Montreal, Quebec, Canada.

Once baseline resistance and compliance measurements are obtained, the animal is challenged with 6 breaths of saline. After 10 minutes, during which time no alterations in lung function should occur, the animal is challenged with 6 breaths of 2 or 3% ovalbumin in saline (as the antigen stimulus). Saline and antigen are delivered in each breath using a Hudson nebulizer. The protective effects of compound 330 administered orally on OA-induced contraction of tracheal tissue are summarized in Tables 8 and 9 below.

TABLE 8

THE EFFECT OF COMPOUND 330 (5 MG/KG/DAY FOR 4 DAYS; P.O.) ON ALLERGEN-INDUCED INCREASE IN LUNG RESISTANCE IN SENSITIZED GUINEA PIGS

| | Lung Resistance (cm $H_2O$/ml/sec) | |
|---|---|---|
| Time Interval after challenge | Control | 330 |
| Baseline | 0.287 ± 0.020 | 0.275 ± 0.036 |
| OA/10 s | 0.295 ± 0.024 | 0.260 ± 0.036 |
| 1 min | 0.982 ± 0.209 | 0.560 ± 0.101 |
| 2 min | 2.390 ± 0.728 | 0.845 ± 0.201 |
| 3 min | 2.627 ± 0.714 | 0.887 ± 0.160 (P < 0.06) |
| 4 min | 2.801 ± 1.042 | 0.778 ± 0.119* |
| 5 min | 2.514 ± 0.952 | 0.791 ± 0.139* |
| 10 min | 1.329 ± .209 | 0.661 ± 0.141* |
| 20 min | 1.352 ± 0.494 | 0.366 ± 0.046* |
| 30 min | 1.00 ± 0.434 | 0.340 ± 0.037* |

*Significant difference from control, $P < 0.05$.

TABLE 9

THE EFFECT OF COMPOUND 330 (5 MG/KG/DAY FOR 4 DAYS; P.O.) ON ALLERGEN-INDUCED DECREASES IN LUNG COMPLIANCE IN SENSITIZED GUINEA PIGS

| | Lung Compliance (ml/cm $H_2O$) | |
|---|---|---|
| Time Interval after challenge | Control | 330 |
| Baseline | 0.412 ± 0.053 | 0.318 ± 0.042 |
| OA/10 s | 0.573 ± 0.083 | 0.435 ± 0.041 |
| 1 min | 0.077 ± 0.016 | 0.182 ± 0.093 |
| 2 min | 0.029 ± 0.006 | 0.145 ± 0.092 |
| 3 min | 0.024 ± 0.003 | 0.133 ± 0.095 |
| 4 min | 0.023 ± 0.001 | 0.124 ± 0.088* |
| 5 min | 0.026 ± 0.002 | 0.125 ± 0.087* |
| 10 min | 0.042 ± 0.002 | 0.150 ± 0.082* |
| 20 min | 0.059 ± 0.007 | 0.184 ± 0.061* |
| 30 min | 0.077 ± 0.010 | 0.196 ± 0.061* |

*Significant difference from control, $P < 0.05$.

The protective effects of compound 330 administered by inhalation on OA-induced contraction of tracheal tissue are summarized in Tables 10–11 below.

TABLE 10

THE EFFECT OF COMPOUND 330 (50 μG/KG; INHALATION) ON ALLERGEN-INDUCED INCREASE IN LUNG RESISTANCE IN SENSITIZED GUINEA PIGS

| | Lung Resistance (cm $H_2O$/ml/sec) | |
|---|---|---|
| Time Interval after challenge | Control | 330 |
| Baseline | 0.257 ± 0.019 | 0.300 ± 0.025 |
| OA/10 s | 0.257 ± 0.046 | 0.288 ± 0.036 |
| 1 min | 0.557 ± 0.118 | 0.382 ± 0.033 |
| 2 min | 1.323 ± 0.344 | 0.420 ± 0.044* |

TABLE 10-continued

THE EFFECT OF COMPOUND 330 (50 μG/KG; INHALATION) ON ALLERGEN-INDUCED INCREASE IN LUNG RESISTANCE IN SENSITIZED GUINEA PIGS

| | Lung Resistance (cm H$_2$O/ml/sec) | |
|---|---|---|
| Time Interval after challenge | Control | 330 |
| 3 min | 1.987 ± 0.572 | 0.420 ± 0.051* |
| 4 min | 1.625 ± 0.248 | 0.455 ± 0.047* |
| 5 min | 1.395 ± 0.193 | 0.446 ± 0.124* |
| 10 min | 0.949 ± 0.165 | 0.436 ± 0.036* |
| 20 min | 0.589 ± 0.091 | 0.413 ± 0.076 |
| 30 min | 0.493 ± 0.067 | 0.412 ± 0.072 |

*Significant difference from control, P < 0.05.

TABLE 11

THE EFFECT OF COMPOUND 330 (50 μG/KG; INHALATION) ON ALLERGEN-INDUCED DECREASE IN LUNG COMPLIANCE IN SENSITIZED GUINEA PIGS

| | Lung Compliance (ml/cm H$_2$O) | |
|---|---|---|
| Time Interval after challenge | Control | 330 |
| Baseline | 0.515 ± 0.169 | 0.463 ± 0.129 |
| OA/10 s | 0.526 ± 0.042 | 0.565 ± 0.062 |
| 1 min | 0.095 ± 0.015 | 0.349 ± 0.059* |
| 2 min | 0.044 ± 0.010 | 0.213 ± 0.046* |
| 3 min | 0.031 ± 0.007 | 0.176 ± 0.045* |
| 4 min | 0.037 ± 0.009 | 0.145 ± 0.046* |
| 5 min | 0.047 ± 0.007 | 0.146 ± 0.031* |
| 10 min | 0.127 ± 0.053 | 0.138 ± 0.022 |
| 20 min | 0.096 ± 0.009 | 0.193 ± 0.054 |
| 30 min | 0.110 ± 0.010 | 0.181 ± 0.046 |

*Significant difference from control, P < 0.05.

The protective effects of compound 339 administered orally on OA-induced contraction of tracheal tissue are summarized in Tables 12–13 below.

TABLE 12

THE EFFECT OF COMPOUND 339 (5 MG/KG/DAY FOR 4 DAYS; P.O.) ON ALLERGEN-INDUCED INCREASE IN LUNG RESISTANCE IN SENSITIZED GUINEA PIGS

| | Lung Resistance (cm H$_2$O/ml/sec) | |
|---|---|---|
| Time Interval after challenge | Control | 339 |
| Baseline | 0.25 ± 0.008 | 0.249 ± 0.017 |
| OA/10 s | 0.261 ± 0.011 | 0.239 ± 0.013 |
| 1 min | 1.781 ± 0.737 | 0.326 ± 0.041* |
| 2 min | 3.079 ± 1.066 | 0.522 ± 0.187* |
| 3 min | 3.623 ± 0.806 | 1.102 ± 0.047* |
| 4 min | 1.699 ± 0.342 | 0.996 ± 0.380 |
| 5 min | 2.783 ± 1.010 | 1.014 ± 0.413 |
| 10 min | 1.115 ± 0.348 | 0.440 ± 0.099 |
| 20 min | 0.624 ± 0.178 | 0.296 ± 0.031 |
| 30 min | 0.465 ± 0.126 | 0.291 ± 0.037 |

*Significant difference from control, P < 0.05.

TABLE 13

THE EFFECT OF COMPOUND 339 (5 MG/KG/DAY FOR 4 DAYS; P.O.) ON ALLERGEN-INDUCED DECREASE IN LUNG COMPLIANCE IN SENSITIZED GUINEA PIGS

| | Lung Compliance (ml/cm H$_2$O) | |
|---|---|---|
| Time Interval after challenge | Control | 339 |
| Baseline | 0.548 ± 0.116 | 0.463 ± 0.026 |
| OA/10 s | 0.598 ± 0.129 | 0.442 ± 0.025 |
| 1 min | 0.026 ± 0.005 | 0.172 ± 0.027* |
| 2 min | 0.018 ± 0.002 | 0.088 ± 0.018* |
| 3 min | 0.016 ± 0.002 | 0.060 ± 0.017* |
| 4 min | 0.019 ± 0.002 | 0.050 ± 0.013 |
| 5 min | 0.021 ± 0.003 | 0.051 ± 0.011 |
| 10 min | 0.043 ± 0.005 | 0.084 ± 0.012* |
| 20 min | .074 ± 0.007 | 0.123 ± 0.015* |
| 30 min | 0.093 ± 0.010 | 0.150 ± 0.012* |

*Significant difference from control, P < 0.05.

The protective effects of compound 342 administered orally on OA-induced contraction of tracheal tissue are summarized in Tables 14–15 below.

TABLE 14

THE EFFECT OF COMPOUND 342 (5 MG/KG/DAY FOR 4 DAYS; P.O.) ON ALLERGEN-INDUCED INCREASE IN LUNG RESISTANCE IN SENSITIZED GUINEA PIGS

| | Lung Resistance (cm H$_2$O/ml/sec) | |
|---|---|---|
| Time Interval after challenge | Control | 342 |
| Baseline | 0.214 ± 0.010 | 0.212 ± 0.020 |
| OA/10 s | 0.204 ± 0.010 | 0.223 ± 0.020 |
| 1 min | 2.380 ± 0.83 | 0.453 ± 0.120* |
| 2 min | 4.241 ± 1.04 | 1.786 ± 0.82* |
| 3 min | 4.657 ± 1.21 | 1.930 ± 0.55* |
| 4 min | 4.088 ± 1.42 | 1.621 ± 0.36* |
| 5 min | 4.519 ± 1.65 | 1.4816 ± 0.32* |
| 10 min | 1.821 ± 0.38 | 1.002 ± 0.14* |
| 20 min | 0.979 ± 0.23 | 0.524 ± 0.08* |
| 30 min | 0.703 ± 0.24 | 0.354 ± 0.04 |

*Significant difference from control, P < 0.05.

TABLE 15

THE EFFECT OF COMPOUND 342 (5 MG/KG/DAY FOR 4 DAYS; P.O.) ON ALLERGEN-INDUCED DECREASE IN LUNG COMPLIANCE IN SENSITIZED GUINEA PIGS

| | Lung Compliance (ml/cm H$_2$O) | |
|---|---|---|
| Time Interval after challenge | Control | 342 |
| Baseline | 0.441 ± 0.034 | 0.444 ± 0.037 |
| OA/10 s | 0.509 ± 0.057 | 0.464 ± 0.031 |
| 1 min | 0.028 ± 0.007 | 0.154 ± 0.055* |
| 2 min | 0.027 ± 0.012 | 0.073 ± 0.038* |
| 3 min | 0.016 ± 0.004 | 0.044 ± 0.022* |
| 4 min | 0.017 ± 0.004 | 0.044 ± 0.022 |
| 5 min | 0.018 ± 0.004 | 0.038 ± 0.015 |
| 10 min | 0.034 ± 0.004 | 0.048 ± 0.005 |
| 20 min | 0.054 ± 0.005 | 0.084 ± 0.005 |
| 30 min | 0.074 ± 0.008 | 0.109 ± 0.006 |

*Significant difference from control, P < 0.05.

Effect of Selected Compounds on Allergen Induced Lung Inflammation

The ability of a compound to inhibit the allergen-induced accumulation of inflammatory cells such as eosinophils and neutrophils in the lavage fluid obtained from sensitized animals is indicative of anti-asthma activity. In particular, the model system is useful in the evaluation of the effects of compounds in the treatment of the late-phase response of asthma, when lung inflammation and the second phase of bronchoconstriction is apparent.

Male Brown Norway rats (200–250 g) are sensitized to ovalbumin by an intraperitoneal injection of 1 mg ovalbumin and 100 mg aluminum hydroxide in 1 ml of sterile saline. After 21 days the animals are found to be sensitized to ovalbumin. Animals are treated with drug or vehicle (0.3 ml PEG-200) once daily for 4 days by oral gavage. The animals are challenged by exposure, for a period of 60 minutes, to nebulized solution of 0.5% ovalbumin in saline generated using a Devillbis nebulizer. The final dose of drug is given 24 hours after challenge. Forty eight hours after challenge the animals are euthanized by an overdose of halothane and the lungs are lavaged with 7×2 mLs of sterile saline (room temperature). The recovered lavage fluid is placed on ice and centrifuged at 1200 rpm to separate the cells from the supernatant. The cells are exposed briefly to Tris/ammonium chloride, pH 7.3 to remove any red cells, and washed in phosphate buffered saline. Cytospins of each cell sample are prepared and stained for the presence of cells containing peroxidase and for the determination of the numbers of eosinophils and neutrophils. The numbers of inflammatory cells are expressed as a percentage of the total number of cells recovered in the lavage fluid. The protective effect of compound 330 on allergen-induced lung inflammation is summarized in Table 16.

TABLE 16

EFFECT OF COMPOUND 330 (5 MG/KG/DAY FOR 4 DAYS, P.O.) ON OVALBUMIN-INDUCED ACCUMULATION OF INFLAMMATORY CELLS IN THE LUNG LAVAGE FLUID OBTAINED FROM SENSITIZED BROWN NORWAY RATS#

| Treatment | Percentage Total Cells Recovered in Lavage Fluid | | |
|---|---|---|---|
| | Cells Stained Positive for Peroxidase | Eosinophils | Neutrophils |
| Control | 0.55 ± 0.27 | 0.69 ± 0.30 | 0.665 ± 0.31 |
| OA Alone | 36.03 ± 5.55 | 20.0 ± 2.65 | 11.58 ± 1.53 |
| Cpd 330 + OA | 5.65 ± 2.44* | 1.98 ± 0.78* | 6.16 ± 4.54 |

Drug was administered in 300 μL polyethyleneglycol-200 which was used as a vehicle. No-drug-treated animals received 300 μL polyethyleneglycol-200 alone.
*Significant difference from OA alone, $P < 0.05$.

Effect of Selected Compounds in the Allergic Sheep Model of Asthma

Effect of selected compounds in the allergic sheep model of asthma were studied.

The allergic sheep model was used as it exhibits the cardinal features associated with asthma. Such a model exhibits natural allergy, early (acute) bronchoconstriction, late phase bronchoconstriction, lung inflammation and bronchial hyperresponsiveness. The model is conscious, where the animals are breathing spontaneously, allowing measurement of airways bronchoconstriction and acute airway hyperresponsiveness.

Sheep which were naturally sensitized to *Ascaris suum* (30–40 Kg) were intubated with an endotracheal tube and a balloon catheter, positioned in the lower esophagus. Pleural pressure was estimated with the esophageal catheter, while later pressure was measured with a side-hole catheter advanced through and positioned distal to the tip of the endotracheal tube. Transpulmonary pressure differences between the trachea and pleural pressures were measured with a differential pressure transducer catheter system.

The proximal end of the endotracheal tube was connected to a Fleisch pneumotachograph in order to measure flow changes. Pulmonary resistance ($R_L$) was calculated from pressure measurements of transpulmonary pressure, respiratory volume (from digital integration of the flow signal) and flow by the mid-flow technique. $SR_L$ was calculated as $R_L V_{tg}$ ($V_{tg}$=thoracic gas volume).

Aerosols generated using a disposable nebulizer, were directed into a T-piece connected to a Harvard respirator and the tracheal tube in series. The aerosol delivery was controlled using a dosimeter system, consisting of a solenoid valve and compressed air (20 psi) activated at the start of each inspiratory cycle. Aerosols were delivered in tidal volumes of 500 ml at 20 Hz.

Selected compounds from the invention were dissolved as a stock solution in DMSO and diluted in saline. Animals received either, 400 μg/Kg of compound 30 min prior to challenge and 4 hours after challenge, or 400 μg/Kg of compound for 4 days with the last dose 2 hours before challenge. *Ascaris suum* extract was diluted in phosphate buffered saline to a concentration of 82000 protein nitrogen units/ml and delivered by aerosol over 20 min. Carbachol was dissolved in PBS to concentrations of 0.25, 0.5 1.0, 2.0, 4.0% wt/vol. Each animal served as its own control throughout the study.

Specific lung resistance ($SR_L$) was measured every 60 min for 8 hours after antigen challenge. Airways hyperresponsiveness to carbachol was measured 24 hours after the initial challenge.

The protective effects of compound 330 administered acutely (30 min prior to challenge and 4 hours after challenge; 400 μg/Kg) on specific lung resistance and hyperresponsiveness are summarized in Tables 17–18.

TABLE 17

EFFECT OF COMPOUND 330 (400 μG/KG 30 MIN PRIOR TO CHALLENGE AND 4 HRS AFTER CHALLENGE, BY INHALATION) ON ALLERGEN-INDUCED CHANGES IN SPECIFIC LUNG RESISTANCE IN *ASCARIS SUUM* SENSITIZED SHEEP#

| | Specific Lung Resistance (% Baseline) | |
|---|---|---|
| Time Interval after Challenge (hr) | Control | 330 |
| Baseline | 7 ± 10 | 2 ± 5 |
| −0.5 | 7 ± 10 | 0 ± 4 |
| Challenge (0) | 266 ± 33 | 268 ± 35 |
| 1 | 197 ± 51 | 117 ± 11 |
| 2 | 77 ± 21 | 49 ± 11 |
| 3 | 68 ± 36 | 32 ± 6 |
| 4 | 23 ± 7 | 20 ± 6 |
| 5 | 73 ± 12 | 14 ± 4* |
| 6 | 132 ± 29 | 14 ± 5* |
| 6.5 | 126 ± 15 | 18 ± 6* |
| 7 | 129 ± 16 | 10 ± 2* |
| 7.5 | 156 ± 13 | 17 ± 8* |
| 8 | 123 ± 27 | 5 ± 3* |

Drug was administered in 3 mLs (66% DMSO in saline). Vehicle alone had no effect. Animals were treated once 30 min prior to challenge and 4 hours post challenge.
*Significantly different from control, $P < 0.05$.

TABLE 18

EFFECT OF COMPOUND 330 (400 μG/KG 30 MIN PRIOR TO CHALLENGE AND 4 HOURS AFTER CHALLENGE, BY INHALATION) ON BRONCRIAL HYPERRESPONSIVENESS TO CARBACHOL IN *ASCARIS SUUM* SENSITIZED SHEEP#

| | $PC_{400}$ (Breath Units) Hyperresponsiveness | |
| --- | --- | --- |
| | Control | 330 |
| Baseline | 26.65 ± 3.08 | 26.01 ± 3.06 |
| Post-Challenge | 12.28 ± 1.49 | 22.79 ± 6.11* |

Drug was administered in 3 mLs (66% DMSO in saline). Vehicle alone had no effect. Animals were treated once 30 min prior to challenge and 4 hours post challenge. Hyperresponsiveness to carbachol was measured 24 hours after the initial challenge.
*Significantly different from control, P < 0.05.

Further studies demonstrated the protective effects of compound 330 administered for 4 days (400 μg/Kg) on specific lung resistance and hyperresponsiveness are summarized in Tables 19–20.

TABLE 19

EFFECT OF COMPOUND 330 (400 μG/KG/DAY FOR 4 DAYS, BY INHALATION) ON ALLERGEN-INDUCED CHANGES IN SPECIFIC LUNG RESISTANCE IN *ASCARIS SUUM* SENSITIZED SHEEP#

| | Specific Lung Resistance (% Baseline) | |
| --- | --- | --- |
| Time Interval after Challenge (hr) | Control | 330 |
| Baseline | 2.00 ± 2.00 | 5.25 ± 4.50 |
| −0.5 | 2.00 ± 2.00 | −3.75 ± 4.29 |
| Challenge (0) | 248.25 ± 85.71 | 126.00 ± 19.11 |
| 1 | 170.75 ± 58.62 | 34.00 ± 10.75 |
| 2 | 74.25 ± 17.10 | 11.50 ± 6.18* |
| 3 | 82.00 ± 6.82 | −15.00 ± 37.67* |
| 4 | 21.25 ± 5.41 | 4.00 ± 1.78* |
| 5 | 57.50 ± 7.51 | −4.50 ± 4.17* |
| 6 | 132.00 ± 9.68 | 7.75 ± 9.75* |
| 6.5 | 153.75 ± 21.93 | 5.50 ± 4.87* |
| 7 | 173.75 ± 21.74 | 10.75 ± 4.91* |
| 7.5 | 148.00 ± 20.96 | 4.00 ± 2.35* |
| 8 | 124.75 ± 28.53 | 3.25 ± 4.73* |

Drug was administered in 3 mLs (66% DMSO in saline). Vehicle alone had no effect. Animals were treated for 4 days with the final dose 30 min prior to challenge.
*Significantly different from control, P < 0.05.

TABLE 20

EFFECT OF COMPOUND 330 (400 μG/KG/DAY FOR 4 DAYS, BY INHALATION) ON BRONCHIAL HYPERRESPONSIVENESS TO CARBACHOL IN *ASCARIS SUUM* SENSITIZED SHEEP#

| | $PC_{400}$ (Breath Units) Hyperresponsiveness | |
| --- | --- | --- |
| | Control | 330 |
| Baseline | 25.1 ± 1.54 | 21.26 ± 2.75 |
| Post-Challenge | 11.9 ± 1.09 | 21.21 ± 3.10* |

Drug was administered in 3 mLs (66% DMSO in saline). Vehicle alone had no effect. Animals were treated for 4 days with the final dose 30 min prior to challenge. Hyperresponsiveness to carbachol was measured 24 hours after the initial challenge.
*Significantly different from control, P < 0.05.

Effects of Selected Compounds on Transcription Factors Involved in the Inflammatory Process The hallmark of a number of chronic inflammatory diseases is the activation of a number of genes known to be integral in maintaining the inflammation state. Among these are cytokines, chemokines, adhesion molecules, transcription factors and proteases. Pivotal to the induced expression of many of these pro-inflammatory molecules are a class of proteins called transcription factors. One family of transcription factors known to be key to a pro-inflammatory state is NF-κB. A number of clinical disease states are associated with elevated levels of activated NF-κB. These include atherosclerosis, cancers, infectious diseases, and various inflammatory based diseases including asthma, inflammatory bowel disease, arthritis, ischemia/perfusion and inflammatory skin conditions. It was discovered that compounds described in the invention caused inhibition of NF-κB activation caused by phorbol esters (activators of NF-κB).

Gel shift assays were used to examine the effect of selected compounds in the invention on the activation of NF-κB, by determining the level of binding of NF-κB to specific sites on DNA. Oligonucleotides used to measure binding of NF-κB were labeled by the following procedure. 5 μl NF-κB oligonucleotide (8.9 pmol), 2 μl 10×T4-polynucleotide kinase buffer, 10 units T4 polynucleotide kinase, and 1 ul γ-P-32-dATP (10 μCi) were made up to a final volume of 20 μl with $H_2O$. The reaction was incubated at 37° C. for 30 minutes. At this time the reaction was quenched with 2 μl 0.5 M EDTA and 2 1μl 3M NaOAc (pH 5.2). 2.5×vol of 100% EtOH was added and the resultant mixture centrifuged at 15,000 g (eppendorf microfuge) for 10 minutes. The pellet was then washed several times in 70% ethanol, air dried at room temperature for 10 minutes, and resuspended in double distilled $H_2O$ (final conc. of 0.75 pmol/2 μl). Cells (RBL-2H3 and A-549) were washed twice in phosphate buffered saline (PBS) at room temperature. They were scraped off the tissue culture dishes into 5 ml PBS using a cell scraper and centrifuged (1500 rpm at room temp; Beckman GPR centrifuge). Following the removal of the supernatant the cells were resuspended in 2×pellet volume of Buffer A (0.25M Sucrose, 20 mM Hepes (pH 7.9), 10 mM KCl, 1.5 mM $MgCl_2$, 0.5mM DTT, 0.5mM Spermidine, 0.15 mM Spermine). This was re-centrifuged and the cells resuspended in the same buffer at a concentration of $10^8$ cells/ml. The cells were allowed to incubate at room temperature for 5 minutes. Lysolecithin (10 mg/ml in Buffer A) was added to a final concentration of 400 μg/ml (4 μl/100 μl Buffer A) and the suspension was incubated with gentle inversion for no longer than 90 seconds. Cell lysis was rapidly stopped by the addition of twice the vol. of ice-cold Buffer A containing 3% BSA. Nuclei were collected by centrifugation at 4000 rpm for 1 minute at 4° C. in a microfuge. The supernatant was removed and the pellet resuspended in Buffer A containing 3% BSA before centrifugation at 30,000 g for 60 seconds at 4° C. (Beckman, TL-100). The nuclei were resuspended in ice-cold Buffer B (20 mM Hepes (pH 7.9), 25% v/v glycerol, 0.6 M $KCl_2$, 1.5 mM $MgCl_2$, 0.2 mM EDTA, 0.5 mM DTT, 0.5 mM PMSF) at approximately $10^7$ nuclei/ml. The nuclei were disrupted by sonication on ice with 2×five second pulses (40% intensity setting, MICROSON: Ultrasonic cell disrupter). The homogenate was gently stirred on ice for 30 minutes before centrifugation at 25,000 g at 4° C. in a Beckman TL-100. The supernatant was then removed and frozen at −70° C. if not used immediately. Determinations of NF-κB DNA binding activity were conducted as follows; 2 μl of 10×binding buffer {20 mM HEPES (pH 7.5), 50 mM KCl, 5 mM $MgCl_2$, 200 μg/mg BSA (Sigma #B-2185), 8% glycerol}, 0.4 μl Poly dI-dC (0.5 mg/ml stock), 2.0 μl $^{32}$P-labelled oligo were mixed with 5 μg of protein isolated from cell nuclei. The resulting mix was made up to a final volume of 20 μl with distilled H₂O. This was then incubated on ice for 5 minutes to allow binding to occur. A further incubation (20 to 30 minutes) at room temperature followed. Samples are then loaded onto a 4.5% acrylamide gel {6 ml (29:1) acrylamide:bis, 2 ml 5×TBE buffer, 800 μl 50% glycerol, 31 ml distilled H₂O, 150 μl 10% APS (ammonium persulphate), 40 μl TEMED}. Acrylamide gels were pre-run in 0.25×TBE buffer for 1.5 hrs (10 volts/cm), followed by a buffer change prior to loading and running of the actual samples.

The effect of selected compounds from the invention on NF-κB activity, as determined using the gel-shift binding assay, are shown in Table 21.

TABLE 21

EFFECT OF SELECTED COMPOUNDS ON NF-κB BINDING IN RBL-2H3 CELLS STIMULATED WITH TPA (0.1 μM)#

| Treatment | Percent Inhibition of Response to TPA (0.1 μM) |
|---|---|
| 165 (10 μM) | 54 |
| 330 (1 μM) | 66 |
| 333 (1 μM) | 34 |
| 339 (1 μM) | 65 |

Compounds or vehicle (0.1 % DMSO) were preincubated with cells (RBL-2H3) for 2 hours prior to stimulation with TPA. Cells were stimulated with 0.1 μM TPA for 2.5 hours to activate NF-κB. All values shown are as a percent inhibition of control (0.1 μM TPA in the presence of vehicle).

All publications and patent applications mentioned in this specification are herein incorporated by reference to the same extent as if each individual publication or patent application was specifically and individually incorporated by reference.

From the foregoing, it will be evident that, although specific embodiments of the invention have been described herein for purposes of illustration, various modifications may be made without deviating from the spirit and scope of the invention.

What is claimed is:

1. A compound of the formula:

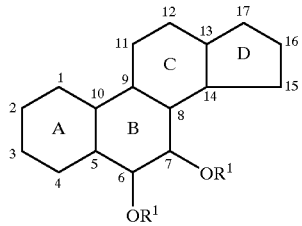

or pharmaceutically acceptable salts or solvates thereof, wherein:
each of C1, C2, C4, C11, C12, C15 and C16 is independently substituted according to any of (a) and (b):
(a) one of: =O, =C(R⁴)(R⁴), —C(R⁴)(R⁴)(C(R⁴)-(R⁴))$_n$— and —(O(C(R⁴)(R⁴))$_n$O)— wherein n ranges from 1 to about 6;
(b) two of: —X, —R⁴ and —OR¹, each independently selected;
C3 is substituted with one of =O or two of H, —X and —OR¹, each independently selected;
C5 is substituted with one of —X or R⁴;
C6 and C7 are each substituted with one of H, —X or —OR¹;
each of C8, C9 and C14 is independently substituted with one of —X, —R⁴ or —OR¹;
C10 and C13 are each independently substituted with one of H or methyl:
C17 is substituted with one hydrogen atom and one group selected from saturated C₁–C₃₀ hydrocarbyl groups and C₁–C₃₀ halogen substituted hydrocarbyl groups, excluding —CH(CH₃)(CH₂)₃CH(CH₃)₂;
the A, B, C and D rings are each fully saturated;
each R¹ is independently H or a protecting group such that —OR¹ is a protected hydroxyl group, where vicinal —OR¹ groups may together form a cyclic structure which protects vicinal hydroxyl groups, and where geminal —OR¹ groups may together form a cyclic structure which protects a carbonyl group, with the proviso that either or both of —OR¹ at C6 and C7 represents a carbonyl or protected carbonyl group;
R⁴ at each occurrence is independently selected from H and C₁₋₃₀ organic moiety that may optionally contain at least one heteroatom selected from the group consisting of boron, halogen, nitrogen, oxygen, silicon and sulfur, where two geminal R⁴ groups may together form a ring with the carbon atom to which they are both bonded; and
X represents fluoride, chloride, bromide and iodide.

2. A compound of claim 1 having a formula selected from:

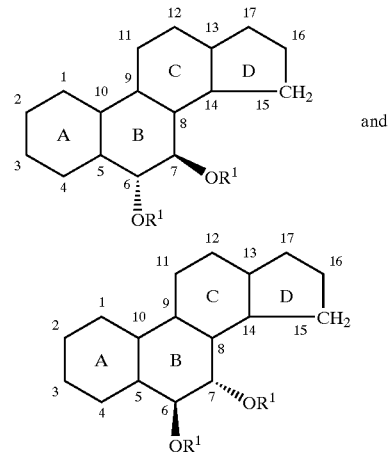

or pharmaceutically acceptable salts or solvates thereof, wherein:
each of C1, C2, C4, C11, C12, C15 and C16 is independently substituted according to any of (a) and (b):
(a) one of: =O, =C(R⁴)(R⁴), —C(R⁴)(R⁴)(C(R⁴)-(R⁴))$_n$— and —(O(C(R⁴)(R⁴))$_n$O)— wherein n ranges from 1 to about 6;
(b) two of: —X, —R⁴ and —OR¹, each independently selected;
C3 is substituted with one of =O or two of H, —X and —OR¹, each independently selected;
C5 is substituted with a hydrogen atom;
C6 and C7 are each substituted with one of H, —X or —OR¹;
each of C8, C9 and C14 is independently substituted with one of —X, —R⁴ or —OR¹;
C10 and C13 are each independently substituted with one of H or methyl;
C17 is substituted with one hydrogen atom and one group selected from C₁–C₃₀ saturated hydrocarbyl excluding —CH(CH₃)

$(CH_2)_3CH(CH_3)_2$, and $C_1$–$C_{30}$ hydroger substituted hydrecarbyl groups;

the A, B, C and D rings are each fully saturated;

each $R^1$ is independently H or a protecting group such that —$OR^1$ is a protected hydroxyl group, where —$OR^1$ groups bonded to adjacent carbon atoms may together form a cyclic structure which protects both hydroxyl groups;

$R^4$ at each occurrence is independently selected from H and $C_{1-30}$ organic moiety that may optionally contain at least one heteroatom selected from the group consisting of boron, halogen, nitrogen, oxygen, silicon and sulfur; where two geminal $R^4$ groups may together form a ring with the carbon atom to which they are both bonded; and X represents fluoride, chloride, bromide or iodide.

3. A compound of claim 1 having the formula:

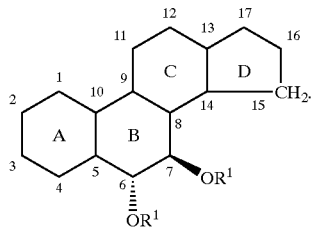

4. A compound of claim 1 having the formula

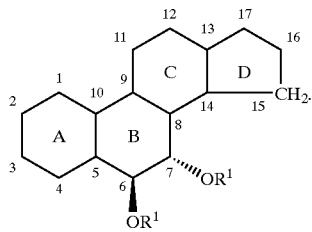

5. A compound of claim 1 wherein C10 and C13 are each substituted with methyl.

6. A compound of claim 1 wherein C11 and C13 are each substituted only with hydrogen.

7. A compound of claim 1 or claim 2 wherein C117 is substituted with a substituent selected from $C_1$–$C_7$ hydrocarbyl.

8. A compound of claim 1 wherein C3 is substituted with a substituent selected from halogen, hydroxyl and protected hydroxyl.

9. A compound of claim 1 wherein C6 and C7 are each substituted with hydrogen.

10. A compound of claim 1 wherein C6 and C7 are both substituted with hydroxyl groups.

11. A pharmaceutical composition comprising a compound of claim 1 in combination with a pharmaceutically acceptable carrier or diluent.

12. The composition of claim 11 wherein C17 is substituted with a hydrocarbyl group.

13. The composition of claim 11 wherein C17 is substituted with a $C_1$–$C_7$ alkyl group.

14. The composition of claim 11 wherein $R^4$ is hydrogen or $C_1$–$C_{10}$ alkyl.

15. The composition of claim 11 wherein C15 is substituted with two hydrogen atoms.

16. The composition of claim 11 wherein C5 is substituted with hydrogen.

17. The composition of claim 11 of wherein the hydrogen at C5 has the alpha configuration.

18. The composition of claim 11 wherein the —$OR^1$ group at C6 has the alpha configuration.

19. The composition of claim 11 wherein the —$OR^1$ group at C7 has the beta configuration.

20. The composition of claim 11 wherein the —$OR^1$ group at C6 has the alpha configuration and the —$OR^1$ group at C7 has the beta configuration.

21. The composition of claim 11 wherein at least one of C3 and C4 is bonded to an oxygen atom.

22. The composition of claim 11 wherein C10 is substituted with a methyl group.

23. The composition of claim 11 wherein C13 is substituted with a methyl group.

24. The composition of claim 11 wherein both C10 and C13 are substituted with methyl groups.

25. The composition of claim 11 wherein both C6 and C7 are bonded to hydrogen atoms.

26. The composition of claim 11 wherein at least one of C1, C2, C3, C4, C5, C8, C9, C10, C11, C12, C13, C14, C15 and C16 is substituted exclusively with hydrogen atoms.

27. The composition of claim 11 wherein C1 and C2 are substituted exclusively with hydrogen atoms.

28. The composition of claim 11 wherein C11 and C12 are substituted exclusively with hydrogen atoms.

29. The composition of claim 11 wherein C15 and C16 are substituted exclusively with hydrogen atoms.

30. The composition of claim 11 wherein the A ring does not contain a bicyclic structure.

* * * * *

UNITED STATES PATENT AND TRADEMARK OFFICE
CERTIFICATE OF CORRECTION

PATENT NO.   : 6,706,701 B1
DATED        : March 16, 2004
INVENTOR(S)  : Burgoyne, David L. et al.

It is certified that error appears in the above-identified patent and that said Letters Patent is hereby corrected as shown below:

Column 174,
Lines 55-65, the formula 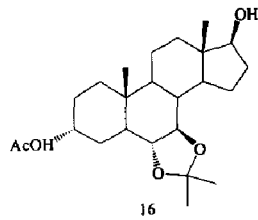 should read as: 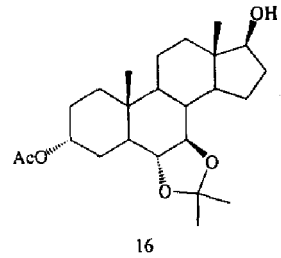

Column 175,
Lines 1-10, the formula 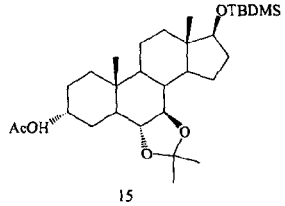 should read as: 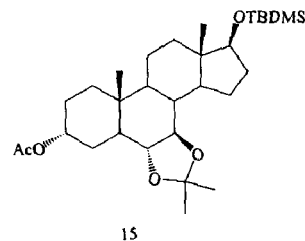

Column 207,
Line 1, "hydroger" should read as -- halogen --.
Line 2, "hydrecarbyl" should read as -- hydrocarbyl --.

Signed and Sealed this

First Day of March, 2005

JON W. DUDAS
*Director of the United States Patent and Trademark Office*